US008911831B2

(12) United States Patent
Messersmith et al.

(10) Patent No.: US 8,911,831 B2
(45) Date of Patent: *Dec. 16, 2014

(54) SURFACE INDEPENDENT, SURFACE-MODIFYING, MULTIFUNCTIONAL COATINGS AND APPLICATIONS THEREOF

(75) Inventors: Phillip B. Messersmith, Clarendon Hills, IL (US); Haeshin Lee, Chicago, IL (US); Andrea R. Statz, Evanston, IL (US); Bruce P. Lee, Madison, WI (US); Jeffrey L. Dalsin, Madison, WI (US); Daniel Sherman, Madison, WI (US)

(73) Assignee: Northwestern University, Evanston, IL (US)

( * ) Notice: Subject to any disclaimer, the term of this patent is extended or adjusted under 35 U.S.C. 154(b) by 152 days.

This patent is subject to a terminal disclaimer.

(21) Appl. No.: 12/793,653

(22) Filed: Jun. 3, 2010

(65) Prior Publication Data
US 2010/0330025 A1    Dec. 30, 2010

Related U.S. Application Data

(63) Continuation-in-part of application No. 11/068,298, filed on Feb. 28, 2005, now Pat. No. 8,815,793, and a continuation-in-part of application No. 11/179,218, filed on Jul. 11, 2005, now Pat. No. 7,858,679, and a continuation-in-part of application No. 11/875,237, filed on Oct. 19, 2007, now Pat. No. 8,541,060, and a continuation-in-part of application No. 11/972,008, filed on Jan. 10, 2008, now abandoned.

(51) Int. Cl.

| B05D 1/18 | (2006.01) |
|---|---|
| B05D 1/26 | (2006.01) |
| B05D 1/36 | (2006.01) |
| B05D 3/10 | (2006.01) |
| C08L 89/02 | (2006.01) |
| C23C 18/18 | (2006.01) |
| C23C 18/31 | (2006.01) |
| C09D 5/16 | (2006.01) |
| A61L 31/10 | (2006.01) |
| A61L 31/14 | (2006.01) |
| A61L 29/08 | (2006.01) |
| A61L 27/34 | (2006.01) |
| A61L 27/50 | (2006.01) |
| A61L 29/14 | (2006.01) |
| B82Y 30/00 | (2011.01) |
| B82Y 40/00 | (2011.01) |

(52) U.S. Cl.
CPC .......... C09D 5/1693 (2013.01); C23C 18/1844 (2013.01); C23C 18/31 (2013.01); C09D 5/1637 (2013.01); A61L 31/10 (2013.01); A61L 31/14 (2013.01); A61L 29/085 (2013.01); A61L 27/34 (2013.01); A61L 2400/18 (2013.01); A61L 27/50 (2013.01); A61L 29/14 (2013.01); B82Y 30/00 (2013.01); B05D 1/185 (2013.01); B05D 3/10 (2013.01); B82Y 40/00 (2013.01)
USPC ............ 427/402; 427/2.1; 210/702; 435/128; 524/17

(58) Field of Classification Search
None
See application file for complete search history.

(56) References Cited

U.S. PATENT DOCUMENTS

| 4,339,561 A | 7/1982 | Jacquet et al. |
|---|---|---|
| 4,496,397 A | 1/1985 | Waite |
| 4,585,585 A | 4/1986 | Waite |
| 4,615,697 A | 10/1986 | Robinson |
| 4,687,740 A | 8/1987 | Waite |
| 4,795,436 A | 1/1989 | Robinson |
| 4,808,702 A | 2/1989 | Waite |
| 4,908,404 A | 3/1990 | Benedict et al. |
| 4,978,336 A | 12/1990 | Capozzi et al. |
| 4,983,392 A | 1/1991 | Robinson |
| 5,015,677 A | 5/1991 | Benedict et al. |
| 5,024,933 A | 6/1991 | Yang et al. |
| 5,030,230 A | 7/1991 | White |
| 5,049,504 A | 9/1991 | Maugh et al. |
| 5,098,999 A | 3/1992 | Yamamoto et al. |
| 5,108,923 A | 4/1992 | Benedict et al. |
| 5,116,315 A | 5/1992 | Capozzi et al. |
| 5,156,956 A | 10/1992 | Motoki et al. |
| 5,192,316 A | 3/1993 | Ting |
| 5,197,973 A | 3/1993 | Pang et al. |
| 5,202,236 A | 4/1993 | Maugh et al. |
| 5,202,256 A | 4/1993 | Maugh et al. |
| 5,225,196 A | 7/1993 | Robinson |

(Continued)

FOREIGN PATENT DOCUMENTS

| DE | 196 43 007 A1 | 4/1998 |
|---|---|---|
| JP | 02191629 | 7/1990 |

(Continued)

OTHER PUBLICATIONS

Zeng, et al., "Synthesis and Characterization of DOPA-PEG Conjugates," Polymer Preprints, vol. 41, No. 1 (2000), pp. 989-990.*

(Continued)

Primary Examiner — Maury Audet
(74) Attorney, Agent, or Firm — Quarles & Brady, LLP

(57) ABSTRACT

The invention provides surface treatments that reduce or eliminate marine biofouling of various surfaces. A surface that is to be subjected to a marine environment can be treated with a mPEG-DOPA. The treated surface is thus rendered less susceptible to fouling of the surface.

21 Claims, 57 Drawing Sheets

(56) References Cited

U.S. PATENT DOCUMENTS

| | | | |
|---|---|---|---|
| 5,242,808 A | 9/1993 | Maugh et al. | |
| 5,260,194 A | 11/1993 | Olson | |
| 5,374,431 A | 12/1994 | Pang et al. | |
| 5,410,023 A | 4/1995 | Burzio | |
| 5,428,014 A | 6/1995 | Labroo et al. | |
| 5,487,739 A | 1/1996 | Aebischer et al. | |
| 5,490,980 A | 2/1996 | Richardson et al. | |
| 5,520,727 A | 5/1996 | Vreeland et al. | |
| 5,525,336 A | 6/1996 | Green et al. | |
| 5,549,904 A | 8/1996 | Juergensen et al. | |
| 5,563,047 A | 10/1996 | Petersen | |
| 5,574,134 A | 11/1996 | Waite | |
| 5,580,697 A | 12/1996 | Keana et al. | |
| 5,582,955 A | 12/1996 | Keana et al. | |
| 5,605,938 A | 2/1997 | Roufa et al. | |
| 5,618,551 A | 4/1997 | Tardy et al. | |
| 5,628,793 A | 5/1997 | Zirm | |
| 5,705,177 A | 1/1998 | Roufa et al. | |
| 5,705,178 A | 1/1998 | Roufa et al. | |
| 5,736,132 A | 4/1998 | Juergensen et al. | |
| 5,776,747 A | 7/1998 | Schinstine et al. | |
| 5,800,828 A | 9/1998 | Dionne et al. | |
| 5,817,470 A | 10/1998 | Burzio et al. | |
| 5,830,539 A | 11/1998 | Yan et al. | |
| 5,834,232 A | 11/1998 | Bishop et al. | |
| 5,858,747 A | 1/1999 | Schinstine et al. | |
| 5,935,849 A | 8/1999 | Schinstine et al. | |
| 5,939,385 A | 8/1999 | Labroo et al. | |
| 5,955,096 A | 9/1999 | Santos et al. | |
| 5,968,568 A | 10/1999 | Kuraishi et al. | |
| 5,985,312 A | 11/1999 | Jacob et al. | |
| 5,994,325 A | 11/1999 | Roufa et al. | |
| 6,010,871 A | 1/2000 | Takahara et al. | |
| 6,020,326 A | 2/2000 | Roufa et al. | |
| 6,022,597 A | 2/2000 | Yan et al. | |
| 6,083,930 A | 7/2000 | Roufa et al. | |
| 6,093,686 A | 7/2000 | Nakada et al. | |
| 6,129,761 A | 10/2000 | Hubbell | |
| 6,150,461 A | 11/2000 | Takei et al. | |
| 6,156,348 A | 12/2000 | Santos et al. | |
| 6,162,903 A | 12/2000 | Trowern et al. | |
| 6,235,313 B1 | 5/2001 | Mathiowitz et al. | |
| 6,267,957 B1 | 7/2001 | Green et al. | |
| 6,284,267 B1 | 9/2001 | Aneja | |
| 6,294,187 B1 | 9/2001 | Boyce et al. | |
| 6,306,993 B1 | 10/2001 | Rothbard et al. | |
| 6,309,669 B1 | 10/2001 | Setterstrom et al. | |
| 6,322,996 B1 | 11/2001 | Sato et al. | |
| 6,325,951 B1 | 12/2001 | Soper et al. | |
| 6,331,422 B1 | 12/2001 | Hubbell et al. | |
| 6,335,430 B1 | 1/2002 | Qvist | |
| 6,365,187 B2 | 4/2002 | Mathiowitz et al. | |
| 6,368,586 B1 | 4/2002 | Jacob et al. | |
| 6,417,173 B1 | 7/2002 | Roufa et al. | |
| 6,486,213 B1 | 11/2002 | Chen et al. | |
| 6,491,903 B1 | 12/2002 | Forster et al. | |
| 6,497,729 B1 | 12/2002 | Moussy et al. | |
| 6,506,577 B1 | 1/2003 | Deming et al. | |
| 6,537,546 B2 | 3/2003 | Echigo et al. | |
| 6,555,103 B2 | 4/2003 | Leukel et al. | |
| 6,565,960 B2 | 5/2003 | Koob et al. | |
| 6,566,074 B1 | 5/2003 | Goetinck | |
| 6,566,406 B1 | 5/2003 | Pathak et al. | |
| 6,635,274 B1 | 10/2003 | Masiz et al. | |
| 6,663,883 B1 | 12/2003 | Akiyama et al. | |
| 6,821,530 B2 | 11/2004 | Koob et al. | |
| 6,887,845 B2 | 5/2005 | Barron et al. | |
| 7,009,034 B2 | 3/2006 | Pathak et al. | |
| 7,208,171 B2 | 4/2007 | Messersmith et al. | |
| 7,300,991 B2 | 11/2007 | Nishimura et al. | |
| 7,858,679 B2 * | 12/2010 | Messersmith et al. | 524/17 |
| 8,541,060 B2 * | 9/2013 | Messersmith et al. | 427/402 |
| 2001/0043940 A1 | 11/2001 | Boyce et al. | |
| 2001/0049400 A1 | 12/2001 | Alli et al. | |
| 2002/0022013 A1 | 2/2002 | Leukel et al. | |
| 2002/0049290 A1 | 4/2002 | Vanderbilt | |
| 2002/0182633 A1 | 12/2002 | Chen et al. | |
| 2003/0009235 A1 | 1/2003 | Manrique et al. | |
| 2003/0012734 A1 | 1/2003 | Pathak et al. | |
| 2003/0039676 A1 | 2/2003 | Boyce et al. | |
| 2003/0065060 A1 | 4/2003 | Qvist et al. | |
| 2003/0069205 A1 | 4/2003 | Roufa et al. | |
| 2003/0087338 A1 * | 5/2003 | Messersmith et al. | 435/68.1 |
| 2003/0099682 A1 | 5/2003 | Moussy et al. | |
| 2003/0109587 A1 | 6/2003 | Mori | |
| 2003/0208888 A1 | 11/2003 | Fearing et al. | |
| 2004/0005421 A1 | 1/2004 | Gervase et al. | |
| 2004/0028646 A1 | 2/2004 | Gross et al. | |
| 2005/0032929 A1 | 2/2005 | Greener | |
| 2005/0288398 A1 * | 12/2005 | Messersmith et al. | 524/17 |
| 2006/0009550 A1 * | 1/2006 | Messersmith et al. | 524/17 |
| 2008/0149566 A1 * | 6/2008 | Messersmith et al. | 210/702 |
| 2008/0171012 A1 * | 7/2008 | Messersmith et al. | 424/78.09 |
| 2010/0330025 A1 * | 12/2010 | Messersmith et al. | 424/78.17 |

FOREIGN PATENT DOCUMENTS

| | | | | |
|---|---|---|---|---|
| WF | WO2006091226 | * | 8/2006 | A61K 38/00 |
| WO | WO 88/03953 | | 6/1988 | |
| WO | WO 92/10567 | | 6/1992 | |
| WO | WO 94/28937 | | 12/1994 | |
| WO | 9640090 | | 12/1996 | |
| WO | WO 97/34016 | | 9/1997 | |
| WO | WO 98/07076 | | 2/1998 | |
| WO | 9950394 | | 10/1999 | |
| WO | 0027802 A1 | | 5/2000 | |
| WO | WO 01/44401 A1 | | 6/2001 | |
| WO | WO 02/34764 A1 | | 5/2002 | |
| WO | 03008376 | | 1/2003 | |
| WO | WO 03/080137 A1 | | 10/2003 | |
| WO | WO 2004/042068 A2 | | 5/2004 | |
| WO | 2006091226 A2 | | 8/2006 | |

OTHER PUBLICATIONS

Li et al. (Electrochemical quartz crystal microbalance study on growth and property of the polymer deposit at gold electrodes during oxidation of dopamine in aqueous solutions, Thin Solid Films 497 (2006) 270-278) (also cited in r/t U.S. Appl. No. 11/875,273).*

PCT International Search Report and Written Opinion, PCT/US2007/081941, Feb. 28, 2008.*

PCT International Preliminary Report on Patentability, PCT/US2007/081941, Apr. 30, 2009.*

Dalsin et al: "Bioinspired antifouling polymers" Materials Today, Elsevier Science, Kidlington, GB, vol. 8, No. 9, Sep. 2005, pp. 38-46, ISSN: 1369-7021.*

Li, et al., Electrochemical Quartz Crystal Microbalance Study on Growth and Property of the Polymer Deposit at Gold Electrodes During Oxidation of Dopamine in Aqueous Solutions, Thin Solid Films, 2006, 497:270-278.

March, et al., March's Advanced Organic Chemistry, Reactions, Mechanisms, and Structure, Sixth Edition, John Wiley & Sons Inc., 2007, pp. 1703-1704.

Zhang, et al., A Novel Wood-Binding Domain of a Wood-Plastic Coupling Agent: Development and Characterization, J. Appl. Polym. Sci., 2003, 89:1078-1084.

United States Patent and Trademark Office, Office Action Summary and Detailed Action, U.S. Appl. No. 11/875,237, Apr. 1, 2011.

Applicant, Response to USPTO Apr. 1, 2011 Non-Final Office Action, U.S. Appl. No. 11/875,237, Jun. 14, 2011.

United States Patent and Trademark Office, Office Action Summary and Detailed Action, U.S. Appl. No. 11/875,237, Aug. 18, 2011.

Applicant, Response to USPTO Aug. 18, 2011 Non-Final Office Action, U.S. Appl. No. 11/875,237, Nov. 16, 2011.

United States Patent and Trademark Office, Office Action Summary and Detailed Action, U.S. Appl. No. 11/875,237, Jan. 5, 2012.

United States Patent and Trademark Office, Advisory Action Before the Filing of an Appeal Brief, U.S. Appl. No. 11/068,298, Mar. 11, 2011.

(56) References Cited

OTHER PUBLICATIONS

Applicant, Response to USPTO Mar. 11, 2011 Advisory Action Accompanying Request for Continued Examination, U.S. Appl. No. 11/068,298, Apr. 7, 2011.
United States Patent and Trademark Office, Office Action Summary and Detailed Action, U.S. Appl. No. 11/068,298, Jul. 11, 2011.
Applicant, Response to USPTO Jul. 11, 2011 Non-Final Office Action, U.S. Appl. No. 11/068,298, Dec. 6, 2011.
United States Patent and Trademark Office, Office Action Summary and Detailed Action, U.S. Appl. No. 11/068,298, Feb. 17, 2012.
Mexican Patent Office, Official Action, Application No. PA/a/2006/009785, Mar. 6, 2012.
State Intellectual Property Office of People's Republic of China, First Office Action, Application No. 200580006180.3, Aug. 7, 2009.
Applicant, Response to State Intellectual Property Office of People's Republic of China First Office Action, Application No. 200580006180.3, Feb. 22, 2010.
State Intellectual Property Office of People's Republic of China, Second Office Action, Application No. 200580006180.3, Aug. 16, 2010.
European Patent Office, Supplementary European Search Report, Application No. EP 05804747.3, Oct. 17, 2011.
Japanese Patent Office, Notification of Reasons for Rejection (Non-Final), Application No. 2007-500804, Oct. 5, 2010.
Applicant, Response to Japanese Patent Office Oct. 5, 2010 Notification of Reasons for Rejection (Non-Final), Application No. 2007-500804, Apr. 5, 2011.
Japanese Patent Office, Notification of Reasons for Rejection (Final), Application No. 2007-500804, Nov. 8, 2011.
Applicant, Response to Japanese Patent Office Nov. 8, 2011 Notification of Reasons for Rejection (Non-Final), Application No. 2007-500804, Jan. 19, 2012.
United States Patent and Trademark Office, Office Action Summary and Detailed Action, U.S. Appl. No. 11/875,237, Jul. 16, 2012.
Applicant, Response to U.S. Patent and Trademark Office Jul. 16, 2012 Non-Final Office Action, U.S. Appl. No. 11/875,237, Jan. 15, 2013.
Applicant, Response to U.S. Patent and Trademark Office Feb. 17, 2012 Final Office Action, U.S. Appl. No. 11/068,298, Jun. 13, 2012.
United States Patent and Trademark Office, Advisory Action, U.S. Appl. No. 11/068,298, Jul. 31, 2012.
Applicant, Response to U.S. Patent and Trademark Office Feb. 17, 2012 Final Office Action and Jul. 31, 2012 Advisory Action and Request for Continued Examination, U.S. Appl. No. 11/068,298, Aug. 14, 2012.
European Patent Office, Examination Report, EP Application No. 05804747.3, May 15, 2012.
Applicant, Response to European Patent Office May 15, 2012 Examination Report, EP Application No. 05804747.3, Nov. 15, 2012.
Response to May 27, 2009 Non-Final Office Action, U.S. Appl. No. 11/068,298, Nov. 24, 2009.
United States Patent and Trademark Office, Notice of Non-Compliant Amendment, U.S. Appl. No. 11/068,298, Mar. 5, 2010.
Response to Mar. 5, 2010 Notice of Non-Compliant Amendment, U.S. Appl. No. 11/068,298, Mar. 30, 2010.
United States Patent and Trademark Office, Office Action Summary and Detailed Action, U.S. Appl. No. 11/068,298, Jul. 9, 2010.
Amendments, U.S. Appl. No. 11/068,298, Jul. 20, 2010.
Amendment After Final Under 37 CFR Sec. 1.116, U.S. Appl. No. 11/068,298, Oct. 7, 2010.
Bain et al., Molecular-level Control over Surface Order in Self-Assembled Monolayer Films of Thiols on Gold. Science 1988, 240, (4848), 62-63.
Burdinski et al., Universal Ink for Microcontact Printing. Angwandte Chemie 2006, 45, 1-5.
Dalsin et al., Bioinspired Antifouling Polymers. Materials Today 2005, 8, 9 (38-46).
Desai et al., Surface-Immobilized Polyethylene Oxide for Bacterial Repellence. Biomaterials 1992, 13, (7), 417-420.

Evans et al., Iron Chelator, Exopolysaccharide and Protease Production in Staphylococcus-Epidermidis—a Comparative-Study of the Effects of Specific Growth-Rate in Biofilm and Planktonic Culture. Microbiology-Uk 1994, 140, 153-157.
Floriolli et al., Marine surfaces and the expression of specific byssal adhesive protein variants in Mytilus. Mar Biotechnol 2000, 2, 352-363.
Gristina, Biomaterial-Centered Infection—Microbial Adhesion Versus Tissue Integration. Science 1987, 237, (4822), 1588-1595.
Holl et al., Solid-State NMR Analysis of Cross-Linking in Mussel Protein Glue. Archives of Biochemistry and Biophysics 1993, 302, (1),255-258.
International Search Report, PCT/US2008/050721.
Jose et al., Vancomycin covalently bonded to titanium beads kills *Staphylococcus aureus*. Chemistry & Biology 2005, 12, (9), 1041-1048.
Pasche et al., Poly(I-lysine)graft-poly(ethylene glycol) assembled monolayers on niobium oxide surfaces: A quantitative study of the influence of polymer interfacial architecture on resistance to protein adsorption by ToF-SIMS and in situ OWLS. Langmuir 2003,19, (22), 9216-9225.
Waite, Reverse engineering of bioadhesion in marine mussels. Bioartificial Organs ii: Technology, Medicine, and Materials 1999, 875, 301-309.
Yu et al., Adhesion of Coagulase-Negative Staphylococci and Adsorption of Plasma-Proteins to Heparinized Polymer Surfaces. Biomaterials 1994,15, (10), 805-814.
Zhang et al., Reactive coupling of poly(ethylene glycol) on electroactive polyaniline films for reduction in protein adsorption and platelet adhesion. Biomaterials 2002, 23, (3), 787-795.
United States Patent and Trademark Office, Office Action Summary and Detailed Action, U.S. Appl. No. 11/280,107, May 16, 2006.
Response to May 16, 2006 Office Action, U.S. Appl. No. 11/280,107, Jul. 17, 2006.
United States Patent and Trademark Office, Office Action Summary and Detailed Action, U.S. Appl. No. 11/280,107, Oct. 6, 2006.
Response to Oct. 6, 2006 Office Action, U.S. Appl. No. 11/280,107, Jan. 8, 2007.
United States Patent and Trademark Office, Office Action Summary and Detailed Action, U.S. Appl. No. 11/280,107, Apr. 18, 2007.
Amendment and Reply to Apr. 18, 2007 Office Action Under 37 C.F.R. 1.116, U.S. Appl. No. 11/280,107, Jun. 16, 2007.
United States Patent and Trademark Office, Advisory Action Before the Filing of an Appeal Brief, U.S. Appl. No. 11/280,107, Oct. 19, 2007.
Request for Continued Examination and Amendment Accompanying Request for Continued Examination, U.S. Appl. No. 11/280,107, filed Dec. 13, 2007.
United States Patent and Trademark Office, Office Action Summary and Detailed Action, U.S. Appl. No. 11/280,107, Apr. 30, 2008.
Amendment and Response to Apr. 30, 2008 Non-Final Office Action, U.S. Appl. No. 11/280,107, Jul. 30, 2008.
United States Patent and Trademark Office, Issue Notification, U.S. Appl. No. 11/280,107, Nov. 17, 2009.
Preliminary Amendment, U.S. Appl. No. 10/199,960, Nov. 12, 2002.
United States Patent and Trademark Office, Office Action Summary and Detailed Action, U.S. Appl. No. 10/199,960, Dec. 14, 2004.
United States Patent and Trademark Office, Notice of Abandonment, U.S. Appl. No. 10/199,960, Jun. 30, 2005.
Chongsiriwatana et al., "Peptoids that Mimic the Structure, Function, and Mechansim of Helical Antimicrobial Peptides", PNAS, Feb. 26, 2008, vol. 105, No. 8, pp. 2794-2799.
Dalsin et al., Mussel adhesive protein mimetic polymers for the preparation of nonfouling surfaces. Journal of the American Chemical Society 2003, 125, (14), 4253-4258.
Dalsin et al., Protein resistance of titanium oxide surfaces modified by biologically inspired mPEG-DOPA. Langmuir 2005, 21, (2), 640-646.
Fuller et al., Procedure for Facile Synthesis of Amino-Acid N-Carboxyanhydrides. Biopolymers 1976, 15, (9), 1869-1871.
Fuller et al., Dopa-Containing Polypeptides .1. Improved Synthesis of High-Molecular-Weight Poly(L-Dopa) and Water-Soluble Copolypeptides. Biopolymers 1978, 17, (12), 2939-2943.

(56) References Cited

OTHER PUBLICATIONS

Gu et al., The role of microbial biofilms in deterioration of space station candidate materials. Int Biodeter Biodegr 1998, 41, (1), 25-33.
Haemers et al., Effect of Oxidation Rate on Cross-Linking of Mussel Adhesive Proteins. Biomacromolecules 2003, 4, 632-640.
International Search Report, International Patent Application No. PCT/US2009/052470, Jul. 31, 2009.
Kingshott et al., Effects of cloud-point grafting, chain length, and density of PEG layers on competitive adsorption of ocular proteins. Biomaterials 2002, 23, (9), 2043-2056.
Klug et al., In situ analysis of peptidyl DOPA in mussel byssus using rotational-echo double-resonance NMR. Archives of Biochemistry & Biophysics 1996, 333, (1), 221-4.
Lee et al., Single-Molecule Mechanics of Mussel Adhesion. Proceedings of the National Acadamy of Sciences 2006, 103, (35), 12999-13003.
Online-Medical Dictionary. "Amino acid". http://cancerweb.ncl.ac.uk/cgi-bin/omd?query=amino+acid. Nov. 13, 1997 (complete reference available online).
Ryu et al., A generalized approach to the modification of solid surfaces. Science 2005, 308, (5719), 236-239.
Statz et al., "Surface-Immobilized Antimicrobial Peptoids", Biofouling, Aug. 8, 2008, vol. 24, No. 6, pp. 439-448.
Waite, Adhesion a la Moule. Integrative and Comparative Biology 2002, 42, (6), 1172-1180.
Waite, Nature's underwater adhesive specialist. Int. J. Adhesion and Adhesives 7, 9 (1987).
Waite, Mussel Beards: A Coming of Age. Chem Ind, Sep. 2, 1991, 607-611.
Warner et al., Expression of multiple forms of an adhesive plaque protein in an individual mussel, Mytilus edulis. Mar Biol 1999, 134, (4), 729-734.
Wisniewski et al., Methods for reducing biosensor membrane biofouling. Colloids and Surfaces B-Biointerfaces 2000, 18, (3-4), 197-219.
Yu et al., Role of L-3,4-dihydroxyphenylanine in mussel adhesive proteins. J Am Chem Soc 1999, 121, (24), 5825-5826.
United States Patent and Trademark Office, Office Action Summary and Detailed Action, U.S. Appl. No. 11/972,008, Dec. 4, 2009.
Response to Dec. 4, 2009, NonFinal Office Action, U.S. Appl. No. 11/972,008, Jun. 3, 2010.
United States Patent and Trademark Office, Office Action Summary and Detailed Action, U.S. Appl. No. 11/972,008, Jul. 2, 2010.
United States Patent and Trademark Office, Office Action Summary and Detailed Action, U.S. Appl. No. 11/875,237, Jul. 29, 2010.
Response to Jul. 29, 2010 Restriction Requirement, U.S. Appl. No. 11/875,237, Aug. 23, 2010.
United States Patent and Trademark Office, Office Action Summary and Detailed Action, U.S. Appl. No. 11/179,218, Oct. 2, 2007.
Response to Oct. 2, 2007 Restriction and Election of Invention Requirement, U.S. Appl. No. 11/179,218, Nov. 28, 2007.
United States Patent and Trademark Office, Office Action Summary and Detailed Action, U.S. Appl. No. 11/179,218, Apr. 10, 2008.
Response and Response to Apr. 10, 2008 Non-Final Office Action, U.S. Appl. No. 11/179,218, Jul. 9, 2008.
United States Patent and Trademark Office, Notice of Non-Compliant Amendment, U.S. Appl. No. 11/179,218, Aug. 8, 2008.
Response to Aug. 8, 2008 Notice of Non-Compliant Amendment, U.S. Appl. No. 11/179,218, Sep. 3, 2008.
United States Patent and Trademark Office, Office Action Summary and Detailed Action, U.S. Appl. No. 11/179,218, Feb. 20, 2009.
Response to Feb. 20, 2009 Final Office Action, U.S. Appl. No. 11/179,218, May 19, 2009.
United States Patent and Trademark Office, Advisory Action Before the Filing of an Appeal Brief, U.S. Appl. No. 11/179,218, Jul. 22, 2009.
Request for Continued Examination and Amendment Accompanying Request for Continued Examination, U.S. Appl. No. 11/179,218, Aug. 19, 2009.
Supplemental Response to Feb. 20, 2009, Final Office Action, U.S. Appl. No. 11/179,218, Sep. 23, 2009.
United States Patent and Trademark Office, Office Action Summary and Detailed Action, U.S. Appl. No. 11/179,218, Dec. 11, 2009.
Response to Dec. 11, 2009 Non-Final Office Action, U.S. Appl. No. 11/179,218, Jun. 10, 2010.
Amendments, U.S. Appl. No. 11/179,218, filed Jun. 29, 2010.
United States Patent and Trademark Office, Office Action Summary and Detailed Action, U.S. Appl. No. 11/068,298, Apr. 9, 2007.
Amendment and Reply Under 37 C.F.R. Sec. 1.11 to Apr. 9, 2007 Office Action, U.S. Appl. No. 11/068,298, Jun. 1, 2007.
United States Patent and Trademark Office, Office Action Summary and Detailed Action, U.S. Appl. No. 11/068,298, Sep. 11, 2007.
Amendment and Reply After Final (Sep. 11, 2007), U.S. Appl. No. 11/068,298, Dec. 10, 2007.
United States Patent and Trademark Office, Advisory Action Before the Filing of an Appeal Brief, U.S. Appl. No. 11/068,298, Apr. 15, 2008.
United States Patent and Trademark Office, Interview Summary, U.S. Appl. No. 11/068,298, Apr. 18, 2008.
Request for Continued Examination and Amendment and Reply After Final Amendment Accompanying Request for Continued Examination, U.S. Appl. No. 11/068,298, May 12, 2008.
United States Patent and Trademark Office, Office Action Summary and Detailed Action, U.S. Appl. No. 11/068,298, Nov. 25, 2008.
Response to Nov. 25, 2008 Non-Final Office Action, U.S. Appl. No. 11/068,298, Feb. 25, 2009.
United States Patent and Trademark Office, Office Action Summary and Detailed Action, U.S. Appl. No. 11/068,298, May 27, 2009.
Advincula, "Surface Initiated Polymerization from Nanoparticle Surfaces," *J. Dispersion Sci. Technol.*, vol. 24, Nos. 3 & 4 (2003), pp. 343-361.
Ahmed, et al., "Synthesis and Application of Fluorescein-Labeled Pluronic Block Copolymers to the Study of Polymer-Surface Interactions," *Langmuir*, vol. 17, No. 2 (2001), pp. 537-546.
Alexandridis, P.; Nivaggioli, T.; Hatton, T. A., "Temperature Effects on Structural Properties of Pluronic P104 and F108 PEO-PPO-PEO Block Copolymer Solutions," *Langmuir*, vol. 11, No. 5 (1995), pp. 1468-1476.
Alexandridis, P., "Poly(ethylene oxide)-Poly(propylene oxide) Block Copolymer Surfactants," *Curr. Opin. Colloid Interface Sci.*, vol. 2, No. 5 (1997), pp. 478-489.
Alivisatos, P., "The use of nanocrystals in biological detection," *Nature Biotechnology*, vol. 22, No. 1 (2004), pp. 47-52.
Alleyne, Jr., et al., "Efficacy and biocompatibility of a photopolymerized, synthetic, absorbable hydrogel as a dural sealant in a canine craniotomy model," *J. Neurosurg.*, vol. 88 (1998), pp. 308-313.
Andreopoulos, et al., "Light-induced tailoring of PEG-hydrogel properties," *Biomaterials*, vol. 19 (1998), pp. 1343-1352.
Andrzejewska, et al., "The role of oxygen in camphorquinone-initiated photopolymerization," *Macromol. Chem. Phys.*, vol. 199 (1998), pp. 441-449.
Araujo, et al., "Interaction of Catechol and Gallic Acid with Titanium Dioxide in Aqueous Suspensions. 1. Equilibrium Studies," *Langmuir*, vol. 21 (2005), pp. 3470-3474.
Armstrong et al., "Scanning Microcalorimetric Investigations of Phase Transitions in Dilute Aqueous Solutions of Poly(oxypropylene)," *J. Phys. Chem.*, vol. 99 (1995), pp. 4590-4598.
Arnow, "Colorimetric Determination of the Component of 3, 4-Dihydroxyphemylalanine-Tyrosine Mixtures," *J. Biol. Chem.*, vol. 118 (1937), pp. 531-538.
Arzt et al., "From micro to nano contacts in biological attachment devices," *Proc. Nat. Acad. Sci. USA*, vol. 100 (2003), pp. 10603-10606.
Arzt, "Biological and artificial attachment devices: Lessons for materials scientists from flies and geckos," *Mater. Sci. Eng. C*, vol. 26 (2006), pp. 1245-1250.
Autumn et al., "Adhesive force of a single gecko foot-hair," *Nature*, vol. 405 (2000), pp. 681-685.
Autumn et al., "Evidence for van der Waals adhesion in gecko setae," *Proc. Nat. Acad. Sci. USA*, vol. 99 (2002), pp. 12252-12256.
Baird, et al. (2007), "Reduction of Incisional Cerebrospinal Fluid Leak Following Posterior Foss Surgery with the use of Duraseal,"

(56) References Cited

OTHER PUBLICATIONS

American Association of Neurosurgeons. Abstract retrieved Jul. 23, 2008, from AANS Abstract Center database. Available from: http://www.aans.org/library/article.aspx?ArticleId=42392.

Balsa-Canto, et al., "Reduced-Order Models for Nonlinear Distributed Process Systems and Their Application in Dynamic Optimization," Ind. Eng. Chem. Res., vol. 43 (2004), pp. 3353-3363.

Banerjee, et al., "Derivatives of 3, 4-Dihydroxyphenylalanine for Peptide Synthesis," J. Org. Chem., vol. 41, No. 18 (1976), pp. 3056-3058.

Barbakadze, et al., "Poly[3-(3, 4-dihydroxyphenyl)glyceric Acid], A New Biologically Active Polymer from Symphytum Asperum Lepech. and S. Caucasicum Bieb. (Boraginaceae)," Molecules, vol. 10 (2005), pp. 1135-1144.

Barichello et al., "Absorption of insulin from Pluronic F-127 gels following subcutaneous administration in rats," Int. J. Pharm., vol. 184 (1999), pp. 189-198.

Benedek, "End Uses of Pressure-Sensitive Products" in Developments in Pressure-Sensitive Products, Benedek (ed.), CRC Press: Boca Raton, FL (2006). pp. 539-596.

Bharathi, et al., "Direct synthesis of gold nanodispersions in sol-gel derived silicate sols, gels and films," Chem. Commun. (1997), pp. 2303-2304.

Bontempo, et al., "Atom Transfer Radical Polymerization as a Tool for Surface Functionalization," Adv. Mater., vol. 14, No. 17 (2002), pp. 1239-1241.

Boogaarts, et al., "Use of a novel absorbable hydrogel for augmentation of dural repair: results of a preliminary clinical study," Neurosurg., vol. 57 (2005), pp. 146-151.

Bromberg, "Novel Family of Thermogelling Materials via C—C Bonding between Poly(acrylic acid) and Poly(ethylene oxide)-b-poly(propylene oxide)-b-poly(ethylene oxide)," J. Phys. Chem. B, vol. 102 (1998), pp. 1956-1963.

Bromberg, "Self-Assembly in Aqueous Solutions of Polyether-Modified Poly(acrylic acid)," Langmuir, vol. 14 (1998), pp. 5806-5812.

Bromberg, "Temperature-responsive gels and thermogelling polymer matrices for protein and peptide delivery," Advanced Drug Reviews, vol. 31 (1998), pp. 197-221.

Brown, et al., "Micelle and Gel Formation in a Poly(ethylene oxide)/Poly(propylene oxide)/Poly(ethylene oxide) Triblock Copolymer in Water Solution. Dynamic and Static Light Scattering and Oscillatory Shear Measurements," J. Phys. Chem., vol. 95 (1991), pp. 1850-1858.

Bruinsma, et al., "Bacterial adhesion to surface hydrophilic and hydrophobic contact lenses," Biomaterials, vol. 22 (2001), pp. 3217-3224.

Bryant, et al., "Cytocompatibility of UV and visible light photoinitiating systems on cultured NIh/3T3 fobroblasts in vitro," J. Biomater. Sci. Polymer Edn, vol. 11, No. 5 (2000), pp. 439-457.

Burdick, et al., "Synthesis and Characterization of Tetrafunctional Lactic Acid Oligomers: a potential in Situ Forming Degradable Orthopaedic Biomaterial," J. Polym. Sci., Part A: Polym. Chem., vol. 39 (2001), pp. 683-692.

Burzio, et al., "Cross-Linking in Adhesive Quinoproteins: Studies with Model Decapeptides," Biochemistry, vol. 39 (2000), pp. 11147-11153.

Cabana, et al., "Study of the Gelation Process of Polyethylene Oxide$_a$—Polypropylene Oxide$_b$—Polyethylene Oxide$_a$ Copolymer (Poloxamer 407) Aqueous Solutions," J. Colloid Interface Sci., vol. 190 (1997), pp. 307-312.

Campbell, et al., "Evaluation of Absorbable Surgical Sealants: In vitro Testing," Confluent Surgical, Inc. (2005) White Paper. Available from: http://www.confluentsurgical.com/pdf/ds/6070_DuraSeal_Invitro_WP13-25.pdf.

Carmichael, et al., "Selective Electroless Metal Deposition Using Microcontact Printing of Phosphine—Phosphonic Acid Inks," Langmuir, vol. 20 (2004), pp. 5593-5598.

Chalykh, et al., "Pressure-Sensitive Adhestion in the Blends of Poly(N-vinyl pyrrolidone) and Poly(ethylene glycol) of Disparate Chain Lengths," J. of Adhes., vol. 78 (2002), pp. 667-694.

Chehimi, et al., "XPS investigations of acid-base interactions in adhesion. Part 3. Evidence for orientation of carbonyl groups from poly(methylmethacrylate) (PMMA) at the PMMA—glass and PMMA—SiO$_2$ interfaces," J. Electron. Spectrosc. Relat Phenom., vol. 63 (1993), pp. 393-407.

Chen, et al., "Temperature-Induced Gelation Pluronic-g-Poly(acrylic acid) Graft Copolymers for Prolonged Drug Delivery to the Eye," in Harris, et al. (eds.) Poly(ethylene glycol): Chemistry and Biological Applications. New York, NY: Oxford University Press USA, 1997. pp. 441-451.

Chen, et al., "Enzymatic Methods for in Situ Cell Entrapment and Cell Release," Biomacromolecules, vol. 4 (2003), pp. 1558-1563.

Collier, et al., "Enzymatic Modification of Self-Assembled Peptide Structures with Tissue Transglutaminase," Bioconjugate Chem., vol. 14 (2003), pp. 748-755.

Collier, et al., "Self-Assembling Polymer-Peptide Conjugates: Nanostructural Tailoring," Adv. Mater., vol. 16, No. 11 (2004), pp. 907-910.

Collins, et al., "Use of collagen film as a dural substitute: Preliminary animal studies," J. Biomed. Mater. Res., vol. 25 (1991), pp. 267-276.

Connor, et al., "New Sol-Gel Attenuated Total Reflection Infrared Spectroscopic Method for Analysis of Adsorption at Metal Oxide Surfaces in Aqueous Solutions. Chelation of TiO$_2$, ZrO$_2$, and Al$_2$O$_3$ Surfaces by Catechol, 8-Quinolinol, and Acetylacetone," Langmuir, vol. 11 (1995), pp. 4193-4195.

Cosgrove, et al., "Safety and efficacy of a novel polyethylene glycol hydrogel sealant for watertight dural repair," J. Neurosurg., vol. 106 (2007), pp. 52-58.

Cosgrove, "Safety and Efficacy of a Novel PEG Hydrogel Sealant (DuraSeal®) for Watertight Closure after Dural Repair," Presented at the Congress of Neurological Surgeons 55th Annual Meeting, Boston, MA, Oct. 2005. Available from: http://www.confluentsurgical.com/pdf/ds/CosgroveAbstractCNS2005.pdf.

Crescenzi, et al., "New Gelatin-Based Hydrogels via Enzymatic Networking," Biomacromolecules, vol. 3 (2002), pp. 1384-1391.

Creton, "Pressure-Sensitive Adhesives: An Introductory Course," MRS Bulletin, vol. 26, No. 6 (2003), pp. 434-439.

Crosby, et al., "Rheological properties and adhesive failure of thin viscoelastic layers," J. Rheol., vol. 46, No. 1 (2002), pp. 273-294.

Crosby, et al., "Controlling Polymer Adhesion with "Pancakes"," Langmuir, vol. 21 (2005), pp. 11738-11743.

Cruise, et al., "A Sensitivity Study of the Key Parameters in the Interfacial Photopolymerization of Poly(etheylene glycol) Dlacrylate upon Porcine Islets," Biotechnol. Bioeng., vol. 57, Issue 6 (1998), pp. 655-665.

Dai, et al., "Novel pH-Responsive Amphiphilic Diblock Copolymers with Reversible Micellization Properties," Langmuir 19 (2003). pp. 5175-5177.

Dalsin, et al., "Surface Modification for Protein Resistance Using a Biomimetic Approach," Mat. Res. Soc. Symp. Proc., vol. 774 (2002), pp. 75-80.

Dalsin, et al., "Antifouling Performance of Poly(ethylene glycol) Anchored onto Surfaces by Mussel Adhesive Protein Mimetic Peptides," Polymeric Materials Science and Engineering 90 (2004). pp. 247-248.

Davis, et al., "Polymeric microspheres as drug carriers," Biomaterials 9 (1), 1988. pp. 111-115.

Deible, et al., "Creating molecular barriers to acute platelet deposition on damaged arteries with reactive polyethylene glycol," J. Biomed. Maters. Res. 41 (1998). pp. 251-256.

Deming, "Mussel byssus and biomolecular materials," Current Opinion in Chemical Biology, 3 (1), 1999. pp. 100-105.

Deming, et al., "Mechanistic Studies of Adhesion and Crosslinking in Marine Adhesive Protein Analogs," Polym. Mater. Sci. Eng., 80 (1999). pp. 471-472.

Deruelle, et al., "Adhesion at the Solid—Elastomer Interface: Influence of the Interfacial Chains," Macromolecules, vol. 28 (1995), pp. 7419-7428.

(56) References Cited

OTHER PUBLICATIONS

Desai, et al., "In Vitro Evaluation of Pluronic F127-Based Controlled-Release Ocular Delivery Systems for Polocarpine," *J. Phar. Sci.*, 87 (2), 1998. pp. 226-230.
Dillow, et al., "Adhesion of $\alpha_5\beta_1$ receptors to biomimetic substrates constructed from peptide amphiphiles," *Biomaterials*, vol. 22 (2001), pp. 1493-1505.
Donkerwolcke, et al., "Tissue and bone adhesives—historical aspects," *Biomaterials* 19 (1998). pp. 1461-1466.
Dossot, et al., "Role of Phenolic Derivatives in Photopolymerization of an Acrylate Coating," *J. Appl. Polymer. Sci.*, 78 (2000). pp. 2061-2074.
Drumheller, et al., "Polymer Networks with Grafted Cell Adhesion Peptides for Highly Biospecific Cell Adhesive Substrates," *Anal. Biochem.*, vol. 222 (1994), pp. 380-388.
Elbert, et al., "Reduction of fibrous adhesion formation by a copolymer possessing an affinity for anionic surfaces," *J. Biomed. Mater. Res.*, vol. 42, Issue 1 (1998), pp. 55-65.
Elisseeff, et al., "Photoencapsulation of chondrocytes in poly(ethylene oxide)-based semi-interpenetrating networks," *J. Biomed. Mater. Res.*, vol. 51, Issue 2 (2000), pp. 164-171.
Erli, et al., "Surface pretreatments for medical application of adhesion," *BioMed. Eng. Online*, 2 (15), 2003. Available from: http://www.biomedical-engineering-online.com/content/2/2/15.
Fan et al., "Surface-Initiated Polymerization from $TiO_2$ Nanoparticle Surfaces through a Biomimetic Initiator: A New Route toward Polymer-Matrix Composites," *Comp. Sci. Tech.*, 66 (9), 2006. pp. 1195-1201.
Fang, et al., "Effect of Molecular Structure on the Adsorption of Protein on Surfaces with Grafted Polymers," *Langmuir*, vol. 18 (2002), pp. 5497-5510.
Faulkner, et al., "A New Stable Pluronic F68 Gel Carrier for Antibiotics in Contaminated Wound Treatment," *Am. J. Emerg. Med.*, 15 (1), 1997. pp. 20-24.
Feldstein, et al., "Molecular Design of Hydrophilic Pressure-Sensitive Adhesives for Medical Applications," in *Developments in Pressure-Sensitive Products*, I. Benedek (ed.). 2006, CRC Press: Boca Raton, FL. pp. 473-503.
Filpula, et al., "Structural and Functional Repetition in a Marine Mussel Adhesive Protein," *Biotechnol. Prog.* 6 (1990). pp. 171-177.
Fischer, et al., "In vitro cytotoxicity testing of polycations: influence of polymer structure on cell viability and hemolysis," *Biomaterials* 24 (2003). pp. 1121-1131.
Flanigan, et al., "Adhesive and Elastic Properties of Thin Gel Layers," *Langmuir*, vol. 15 (1999), pp. 4966-4974.
Flanigan, et al., "Structural Development and Adhesion of Acrylic ABA Triblock Copolymer Gels," *Macromolecules*, vol. 32 (1999), pp. 7251-7262.
Flood, et al., "Efficient Asymmetric Epoxidation of $\alpha,\beta$-Unstarudated Ketones Using a Soluble Triblock Polyethylene Glycol-Polyamino Acid Catalyst," *Org. Lett.*, vol. 3, No. 5 (2001), pp. 683-686.
Floudas, et al., "Hierarchical Self-Assembly of Poly($\gamma$-benzyl-L-glutamate)—Poly(ethylene glycol)—Poly($\gamma$-benzyl-L-glutamate) Rod—Coil—Rod Triblock Copolymers," *Macromolecules*, vol. 36 (2003), pp. 3673-3683.
Flory, et al., "Effect of Volume Exclusion on the Dimensions of Polymer Chains," *J. Chem. Phys.*, vol. 44, No. 6 (1966), pp. 2243-2248.
Floyd-Smith, et al., "Interferon Action: RNA Cleavage Pattern of a (2'-5')Oligoadenylate-Dependent Endonuclease," *Science*, vol. 212, No. 4498 (May 29, 1981), pp. 1030-1032.
Frank, et al., "Adhesion of *Mytilus edulis*Foot Protein 1 on Silica: Ionic Effects on Biofouling," *Biotechnol. Prog.* 18 (2002). pp. 580-586.
Fuchsbauer, et al., "Influence of gelatin matrices cross-linked with transglutaminase on the properties of an enclosed bioactive material using $\beta$-galactosidase as model system," *Biomaterials* 17 (1996). pp. 1481-1488.

Fujisawa, et al., "Kinetic Evaluations of the Reactivity of Flavonoids as Radical Scavengers," *SAR QSAR Environ. Res.*, Vo. 13, No. 6 (2002), pp. 617-627.
Geim, et al., "Microfabricated adhesive mimicking gecko foot-hair," *Nat. Materials* 2 (2003). pp. 461-463.
Ghosh, et al., "N,N'-Disuccinimidyl Carbonate: A Useful Reagent for Alkoxycarbonylation of Amines," *Tetra. Lett.* 33 (20), 1992. pp. 2781-2784.
Gidanian, et al., "Redox behavior of melanins: direct electrochemistry of dihydroxyindole-melanin and its Cu and Zn adducts," *J. Inorg. Biochem.* 89 (2002). pp. 54-60.
Green, et al., "A surface plasmon resonance study of albumin adssoption to PEO-PPO-PEO triblock copolymers," *J. Biomed. Res.* 42 (1998). pp. 165-171.
Gross, et al., "Amine Bindindg Sites in Acyl Intermediates of Transglutaminases," *J. Biol. Chem.* 242 (11) (1977). pp. 3752-3759.
Grotenhuis, et al., "Synthetic Dural Sealant for Prevention of Postoperative CSF Leakage," Presented at the American Association of Neurological Surgeons; Apr. 2003, San Diego, CA. Available from: http://www.confluentsurgical.com/pdf/ds/AbstractGrotenhuisAbstract.pdf.
Grotenhuis, et al., "A Novel Absorbable Hydrogel for Dural Repair: Results of a Pilot Clinical Study," Confluent Surgical, Inc. (2005) White Paper. Available from: http://www.confluentsurgical.com/pdf/ds/DuraSeal_Pilot_Study_WP4-7-05.pdf.
Grotenhuis, "Costs of postoperative cerebrospinal fluid leakage: 1-year, retrospective analysis of 412 consecutive nontrauma cases," *Surg. Neurol.*, vol. 64, No. 6 (2005), pp. 493-494.
Gu, et al., "Synthesis of Aluminum Oxide/Gradient Copolymer Composites by Atom Transfer Radical Polymerization," *Macromolecules* 35 (2002). pp. 8913-8916.
Guvendiren, et al., "Adhesion in Self-Assembled Hydrogels with High DOPA Content," *Proceedings of the 30th Annual Meeting of the Adhesion Society* (2007).
Guvendiren, et al., "Synthesis and Adhesion Properties of DOPA Incorporated Acrylic Triblock Hydrogels," *Proceedings of the 29th Annual Meeting of the Adhesion Society* (2006). pp. 277-279.
Hajjaji, et al., "Effect of N-Alkybetaines on the Corrosion of Iron in 1 M HCI Soluction," *Corrosion*, vol. 49, No. 4 (1993), pp. 326-334.
Hanawa, et al., "XPS Characterization of the Surface Oxide Film of 316L Stainless Steel Samples that were Located in Quasi-Biological Environments," *Mater. Trans., JIM*, vol. 43, No. 12 (2002), pp. 3088-3092.
Hansen, et al., "Enzymatic Tempering of a Mussel Adhesive Protein Film," *Langmuir* 14 (1998). pp. 1139-1147.
Harris, "Laboratory Synthesis of Polyethylene Glycol Derivatives," *JMS—Rev. Macromol. Chem. Phys.*, vol. C25, No. 3 (1985), pp. 325-373.
Harris (ed.), "Introduction to Biotechnical and Biomedical Applications of Poly(Ethylene Glycol)" in *Poly(Ethylene Glycol) Chemistry: Biotechnical and Biomedical Applications*, Plenum Press: New York, 1992. pp. 1-14.
Hennink, et al., "Novel crosslinking methods to design hydrogels," *Adv. Drug Deliver. Rev.*, vol. 54 (2002), pp. 13-36.
Hern, et al., "Incorporation of adhesion peptides into nonadhesive hydrogels useful for tissue resurfacing," *J. Biomed. Mater. Res.*, vol. 39, Issue 2 (1998), pp. 266-276.
Hillery, et al., "The effect of adsorbed poloxamer 188 and 407 surfactants on the intestinal uptake of 60-nm polystyrene particles after oral administratin in the rat," *Int. J. Pharm.* 132 (1996). pp. 123-130.
Ho, et al., "Nanoseparated Polymeric Networks with Multiple Antimicrobial Properties," *Adv. Mater.* 16 (12), 2004. pp. 957-961.
Hoffman, "Hydrogels for biomedical applications," *Adv. Drug Deliver. Rev.*, vol. 43 (2002), pp. 3-12.
Hohenadl, et al., "Two Adjacent N-terminal Glutamines of BM-40 (Osteonectin, SPARC) Act as Amine Acceptor Sites in Transglutaminase$_c$-catalyzed Modification," *J. Biol. Chem.* 270 (40), 1995. pp. 23415-23420.
Hrkach, et al., "Synthesis of Poly(L-lactic acid-*co*-L-lysine) Graft Copolymers," *Macromolecules*, vol. 28 (1995), pp. 4736-4739.

(56) References Cited

OTHER PUBLICATIONS

Hu, et al., "Protection of 3,4-dihydroxyphenylalanine (DOPA) for Fmoc solid-phase peptide synthesis," *Tetra. Lett.* 41 (2000). pp. 5795-5798.

Hu, et al., "Rational Design of Transglutaminase Substrate Peptides for Rapid Enzymatic Formation of Hydrogels," *J. Am. Chem. Soc.*, vol. 125, (2003), pp. 14298-14299.

Huang, et al., "Synthesis and Characterization of Self-Assembling Block Copolymers Containing Adhesive Moieties," *Polym. Prepr.* 42 (2), 2001. pp. 147-148.

Huang, et al., "Synthesis and Characterization of Self-Assembling Block Copolymers Containing Bioadhesive End Groups," *Biomacromolecules* 3 (2002). pp. 397-406.

Huang, et al., "Covalent Attachment of Novel Poly(ethylene glycol)—Poly(DL-lactic acid) Copolymeric Micelles to $TiO_2$ Surfaces," *Langmuir* 18 (2002). pp. 252-258.

Huang, et al., "Functionalization of Surfaces by Water-Accelerated Atom-Transfer Radical Polymerization of Hydroxyethyl Methacrylate and Subsequent Derivatization," *Macromolecules* 35 (2002). pp. 1175-1179.

Huang, et al., "Poly(L-lysine)-g-poly(ethylene glycol) Layers on Metal Oxide Surfaces: Surface-Analytical Characterization and Resistance to Serum and Fibrinogen Adsorption," *Langmuir*, vol. 17 (2001), pp. 489-498.

Huang, "Molecular aspects of muco- and bioadhesion: Tethered structures and site-specific surfaces," *J. Controlled Release*, vol. 65 (2000), pp. 63-71.

Huber, et al., "Resolving the nanoscale adhesion of individual gecko spatulae by atomic force microscopy," *Biol. Lett.* 1 (2005). pp. 2-4.

Huber, et al., "Evidence for capillarity contributions to gecko adhesion from single spatula nanomechanical measurements," *Proc. Nat. Acad. Sci. USA,* 102 (45), 2005. pp. 16293-16296.

Huin-Amargier, et al., "New physically and chemically crosslinked hyaluronate (HA)-based hydrogels for cartilage repair," *J. Biomed. Mater. Res.* 76A (2), 2006. pp. 416-424.

Hunter, "Molecular hurdles in polyfectin design and mechanistic background to polycation inducted cytotoxicity," *Adv. Drug Deliver. Rev.*, vol. 58 (2006). pp. 1523-1531.

Hutter, et al., "Calibration of atomic-force microscope tips," *Rev. Sci. Instrum.* 64 (7), Jul. 1993. pp. 1868-1873.

Hvidt, et al., "Micellization and Gelation of Aqueous Solutions of a Triblock Copolymer Studied by Rheological Techniques and Scanning Calorimetry," *J. Phys. Chem.* 98 (1994). pp. 12320-12328.

Hwang, et al., "Expression of Functional Recombinant Mussel Adhesive Protein Mgfp-5 in *Escherichia coli*," *Appl. Environ. Microbiol.* 70 (6), 2004. pp. 3352-3359.

Ikada, "Tissue Adhesives," in *Wound Closure Biomaterials and Devices,* Chu, et al. (eds.), CRC Press, Inc.: Boca Raton, FL, 1997. pp. 317-346.

International Search Report for PCT/US2003/034633; WO 2004/042068 A3 (May 21, 2005); Northwestern University (Applicant); Messersmith, et al. (inventors).

International Search Report for PCT/US2005/006418; WO 2005/118831 A3 (Dec. 15, 2005); Northwestern University (Applicant); Messersmith, et al. (inventors).

International Search Report for PCT/US2005/024642; WO 2006/091226 A3 (Aug. 31, 2006); Northwestern University (Applicant); Messersmith, et al. (inventors).

International Search Report for PCT/US/2005/041280; WO 2006/055531 A3 (May 26, 2006); Northwestern University (Applicant); Messersmith, et al. (Inventors).

International Search Report for PCT/US2007/075299; WO 2008/019352 A3 (Feb. 14, 2008); Nerites Corporation (Applicant); Lee (Inventor).

International Search Report for PCT/US2002/23005; WO 03/008376 A3 (Jan. 30, 2003); Northerwestern University (Applicant); Messersmith, et al. (inventors).

Ishihara, et al., "Photocrosslinkable chitosan as a dressing wound occlusion and accelerator in healing process," *Biomaterials*, vol. 23, No. 3 (2002), pp. 833-840.

Jackson, "Tissue sealants: Current status, future potential," *Nat. Med.*, vol. 2, No. 5, (May 1996), pp. 637-638.

Jackson, "Fibrin sealants in surgical practice: An overview," *Am. J. Surg.*, vol. 182 (2001), pp. 1S-7S.

Jänchen, et al., "Adhesion Energy of Thin Collagen Coatings and Titanium," *Surf. Interface Anal.*, vol. 27 (1999), pp. 444-449.

Jensen, et al., "Lipopeptides Incorporated into Supported Phospholipid Monolayers Have High Specific Activity at Low Incorporation Levels," *J. Am. Chem. Soc.*, vol. 126, No. 46 (2004), pp. 15223-15230.

Jeon, et al., "Protein-Surface Interactions in the Presence of Polyethylene Oxide," *J. Colloid. Interface Sci.*, vol. 142, No. 1 (1991), pp. 159-166.

Jewell, et al., "Pharmacokinetics of RheothRx Injection in Healthy Male Volunteers," *J. Phar. Sci.* vol. 86, No. 7 (1997), pp. 808-812.

Jo, et al., "Surface modification using silanated poly(ethylene glycol)s," *Biomaterials*, vol. 21 (2000), pp. 605-616.

Johnson, et al., "Surface Energy and Contact of Elastic Solids," *Proc. R. Soc. Lond., A*, vol. 324, No. 1558 (1971), pp. 301-313.

Jones, et al., "Controlled Surface-Initiated Polymerization in Aqueous Media," *Adv. Mater.*, vol. 13, No. 16 (2001), pp. 1256-121259.

Jones, et al., "In Situ forming biomaterials," *Oral Maxillofacial Surg. Clin. N. Am.*, vol. 14 (2002), pp. 29-38.

Kacher, et al., "DuraSeal MR and CT Imaging: Evaluation in a Canine Craniotomy Model,", 2006.

Kahlem, et al., "Peptides containing glutamine repeats as substrates for transglutaminase-catalyzed cross-linking: Relevance to diseases of the nervous system," *Proc. Natl. Acad. Sci. USA*, vol. 93 (Dec. 1996), pp. 14580-14585.

Kellaway, et al., "Oral Mucosal Drug Delivery," in *Oral Mucosal Drug Delivery*, Rathbone (ed.). 1996, Marcel Dekkers, Inc.: New York, NY. pp. 221-239.

Kenausis, et al., "Poly(L-lysine)-g-Poly(ethylene glycol) Layers on Metal Oxide Surfaces: Attachment Mechanism and Effects on Polymer Architecture on Resistance to Protein Adsoprtion," *J. Phys. Chem. B*, vol. 104 (2000), pp. 3298-3309.

Khudyakov, et al., "Kinetics of Photopolymerization of Acrylates with Functionality of 1-6," *Ind. Eng. Chem. Res.* 38 (1999). pp. 3353-3359.

Kirschenbaum, et al., "Sequence-specific polypeptoids: a diverse family of heteropolymers with stable secondary structure," *Proc. Natl. Acad. Sci. USA* 95 (1998). pp. 4303-4308.

Kitano, et al., "Resistance of zwitterionic telomers accumulated on metal surfaces against nonspecific adsorption of proteins," *J. Colloid Interface Sci.* 282 (2005). pp. 340-348.

Kolb, et al., "Click Chemistry: Diverse Chemical Function from a Few Good Reactions," *Agnew. Chem. Int. Ed.*, vol. 40 (2001), pp. 2005-2021.

Koob, et al., "Mechanical and thermal properties of novel polymerized NDGA-gelatin hydrogels," *Biomaterials*, vol. 24 (2003), pp. 1285-1292.

Korobkova, et al., "From molecular noise to behavioural variability in a single bacterium," *Nature* 428 (2004). pp. 574-578.

Kummert, et al., "The Surface Complexation of Organic Acids of Hydrous $\gamma$-$Al_2O_3$," *J. Colloid Interface Sci.*, vol. 75, No. 2 (Jun. 1980), pp. 373-385.

Laucournet, et al., "Catechol derivatives and anion adsorption onto alumina surfaces in aqueous media: influence on the electrokinetic properties," *J. Eur. Ceram. Soc.* 21 (2001). pp. 869-878.

LaVoie, et al., "Dopamine covalently modifies and functionally inactivates parkin," *Nature Med.* 11 (11), 2005. pp. 1214-1221.

Lee, et al., "Enzymatic and Non-Enzymatic Pathways to Formation of DOPA-Modified PEG Hydrogels," *Polymer Preprints* 42 (2), 2001. pp. 151-152.

Lee, et al., "Synthesis and Gelation of DOPA-Modified Poly(ethylene glycol) Hydrogels," *Biomacromolecules* 3 (2002). pp. 1038-1047.

Lee, et al., "Synthesis of 3,4-dihydroxyphenylalanine (DOPA) containing monomers and their co-polymerizations with PEG-diacrylate to form hydrogels," *J. Biomater. Sci. Polymer Edn*, 15 (4), 2004. pp. 449-464.

(56) References Cited

OTHER PUBLICATIONS

Lee, et al., "Rapid Gel Formation and Adhesion in Photocurable and Biodegradable Block Copolymers with High DOPA Content," *Macromolecules* 39 (2006). pp. 1740-1748.

Lee, et al., "Biomimetic Adhesive Polymers Based on Mussel Adhesive Proteins," in *Biological Adhesives*, Smith, et al. (eds.), Springer-Verlag: Berlin Heidelberg, 2006. pp. 257-278.

Lee, et al., "Bioadhesive-Based Dosage Forms: The Next Generation," *J. Pharm. Sci.* 89 (7) (2000). pp. 850-866.

Lee, et al., "Hydrogels for Tissue Engineering," *Chem. Rev.*, vol. 101, No. 7 (Jul. 2001), pp. 1869-1879.

Lemieux, et al., "Block and Graft Copolymers and Nanogel™ Copolymer Networks for DNA Delivery into Cell," *J. of Drug Targeting* 8 (2), 2000. pp. 91-105.

Li, et al., "Protein Adsortion on Oligo(ethylene glycol)-Terminated Alkanethiolate Self-Assembled Monolayers: The Molecular Basis for Nonfouling Behavior," *J. Phys. Chem. B* 109 (2005). pp. 2934-2941.

Li, et al., "Copper-Based Metallization for ULSI Applications," *MRS Bulletin* 18 (6), Jun. 1993. pp. 18-21.

Li, et al., "Chemical Modifications of Surface Active Poly(ethylene oxide)—Poly(propylene oxide) Triblock Copolymers," *Bioconj. Chem.* 7 (1996). pp. 592-599.

Li, et al., "Two-Level Antibacterial Coating with Both Release-Killing and Contact-Killing Capabilities," *Langmuir* 22 (24), 2006. pp. 9820-9823.

Long, et al., "A peptide that inhibits hydroxyapatite growth is in an extended conformation on the crystal surface," *Proc. Natl. Acad. Sci. USA* 95 (1998). pp. 12083-12087.

Lorand, et al., "Transglutaminases," *Mol. Cell. Biochem.*, vol. 58 (1984), pp. 9-35.

Love, et al., "Self-Assembled Monolayers of Thiolates on Metals as a Form of Nanotechnology," *Chem. Rev.* 105 (2005). pp. 1103-1169.

Lovich, et al., "Arterial heparin deposition: role of diffusion, convection, and extravascular space," *Am. J. Phsyiol.—Heart C.*, vol. 275 (1998), pp. 2236-2242.

Lu, et al., "Studies on the synthesis and antibacterial activities of polymeric quaternary ammonium salts from dimethylaminoethyl methacrylate," *Reactive & Functional Polymers* 67 (2007). pp. 355-366.

Lucast, "Adhesive considerations for developing stick-to-skin products," *Adhesives Age* 43 (2000). pp. 36, 38-39.

Luo, et al., "Surface-Initiated Photopolymerization of Poly(ethylene glycol) Methyl Ether Methacrylate on a Diethyldithiocarbamate-Mediated Polymer Substrate," *Macromolecules*, vol. 35 (2002), pp. 2487-2493.

Lyman, et al., "Characterization of the formation of interfacially photopolymerized thin hydrogels in contact with arterial tissue," *Biomaterials* 17 (1996). pp. 359-364.

Martin, et al., "Surface Structures of a 4-Chlorocatechol Adsorbed on Titanium Dioxide," *Environ. Sci. Technol.*, vol. 30 (1996), pp. 2535-2542.

Maugh, et al., "Recombinant bioadhesive proteins of marine animals anad their use in adhesive compositions," in Genex Corp. 1988: USA. pp. 196 (1987).

Matyjaszewski, et al., "Atom Transfer Radical Polymerization," *Chem. Rev.* 101 (2001). pp. 2921-2990.

McBride, "Adsorption and Oxidation of Phenolic Compounds by Iron and Manganese Oxides," *Soil Sci. Soc. Am. J.*, vol. 51 (1987), pp. 1466-1472.

McWhitrter, et al., "Siderophore-Mediated Covalent Bonding to Metal (Oxide) Surfaces during Biofilm Initiation by *Pseudomonas aeruginosa* Bacteria," *Langmuir*, vol. 19 (2003), pp. 3575-3577.

Meisel, et al., "Estimation of calcium-binding constants of casein phosphopeptides by capillary zone electrophoresis," *Anal. Chim. Acta* 372 (1998). pp. 291-297.

Mellott, et al., "Release of protein from highly cross-linked hydrogels of poly(ethylene glycol) diacrylate fabricated by UV polymerization," *Biomaterials*, vol. 22 (2001), pp. 929-941.

Merrifield, "Solid Phase Peptide Synthesis. I. The Synthesis of a Tetrapeptide," *J. Am. Chem. Soc.*, vol. 85 (Jul. 20, 1963), pp. 2149-2154.

Merrill, "Distinctions and Correspondences among Surfaces Contacting Blood," *Annals of the NY Acad. Sci.* 516 (1987). pp. 196-203.

Miron, et al., "A Simplified Method for the Preparation of Succinimidyl Carbonate Polyethylene Glycol for Coupling to Proteins," *Bioconj. Chem.* 4 (1993). pp. 568-569.

Morgan, et al., "Biochemical characterisation of polycation-induced cytotoxicity to human vascular endothelial cells," *Journal of Cell Science* 94 (3), 1989,. pp. 553-559.

Morikawa, "Tissue sealing," *Am. J. Surg.*, vol. 182 (2001), pp. 29S-35S.

Mougin, et al., "Construction of Cell-Resistant Surfaces by Immobilization of Poly(ethylene glycol) on Gold," *Langmuir*, vol. 20 (2004), pp. 4302-4305.

Mowery, et al., "Adhesion of Thermally Reversible Gels to Solid Surfaces," *Langmuir*, vol. 13 (1997), pp. 6101-6107.

Mrksich, et al., "Using Self-Assembled Monolayers that Present Oligo(ethylene glycol) Groups to Control the Interactions of Proteins with Surfaces," *American Chemical Society Symposium Series on Chemistry and Biological Applications of Polyethylene Glycol*, vol. 680 (1997), pp. 361-373.

Mukkamala, et al., "Hydrogel Polymers from Alkylthio Acrylates for Biomedical Applications," *Polymer Gels: Fundamentals and Applciations* 833 (2003). pp. 163-174.

Müller, et al., "Interaction of differentiated HL60 cells with poloxamer and poloxamine surface modified model drug carriers," *Eur. J. Phar. Sci.* 5 (1997). pp. 147-153.

Nakagawa, et al., "ENH, Containing PDZ and LIM Domains, Heart/Skeletal Muscle-Specific Protein, Associates with Cytoskeletal Proteins through the PDZ Domain," *Biocehm. Biophys. Res. Commun.* 272 (2000). pp. 505-512.

Nakayama, et al., "Newly Designed Hemostatic Technology Based on Photocurable Gelatin," *ASAIO J.*, vol. 41, No. 3 (1995), pp. M374-M378.

Nakayama, et al., "Photocurable Surgical Tissue Adhesive Glues Composed of Photoreactive Gelatin and Poly(ethylene glycol) Diacrylate," *J. Biomed. Mater. Res.*, vol. 48, Issue 4 (1999), pp. 511-521.

Nakayama, et al., "Development of high-performance stent: gelatinous photogel-coated stent that permits drug delivery and gene transfer," *J. Biomed. Mater. Res.*, vol. 57, Issue 4 (2001), pp. 559-566.

Nakonieczna, et al., "A New Convenient Route for the Synthesis of DOPA Peptides," *Liebigs Annalen der Chemie*, Issue 10 (1994). pp. 1055-1058.

Neff, et al., "A novel method for surface modification to promote cell attachment to hydrophobic substrates," *J. Biomed. Mater. Res.* 40 (1998). pp. 511-519.

Ninan, et al., "Adhesive strength of marine mussel extracts on porcine skin," *Biomaterials* 24 (2003). pp. 4091-4099.

Nishiyama, et al., "Effects of a structucural change in collagen upon binding to conditioned dentin studied by $^{13}C$ NMR," *J. Biomed. Mater. Res.*, vol. 29 (1995), pp. 107-111.

Nishiyama, et al., "Adhesion mechanisms of resin to etched dentin primed with N-methacryloyl glycine studied by $^{13}C$-NMR," *J. Biomed. Mater. Res.*, vol. 40 (1998). pp. 458-463.

Nishiyama, et al., "Adhesion of N-Methacryloyl-ω-Amino Acid Primers to Collagen Analyzed by $^{13}C$ NMR," *J. Dent. Res.*, vol. 80, No. 3 (2001), pp. 855-859.

Northen, et al., "A batch fabricated biomimetic dry adhesive," *Nanotechnology* 16 (8), 2005. pp. 1159-1166.

Northen, et al., "Meso-scale adhesion testing of integrated micro- and nano-scale structures," *Sensors and Actuators A* 130-131 (2006). pp. 583-587.

Nyström, et al., "Dynamic Light Scattering and Rheological Studies of Thermoreversible Gelation of a Poly(ethylene oxide)-Poly(propylene oxide)-Poly(ethylene oxide) Triblock Copolymer in Aqueous Solution," *Faraday Discuss.* 101 (1995). pp. 335-344.

Nyström, et al., "Dynamic Viscoelasticity of an Aqueous System of a Poly(ethylene oxide)—Poly(propylene oxide)—Poly(ethylene oxide) Triblock Copolymer during Gelation," *J. Phys. Chem.* 100 (1996). pp. 5433-5439.

(56) References Cited

OTHER PUBLICATIONS

O'Keefe, et al., "Poloxamer-188 as an Adjunct to Primary Percutaneous Transluminal Coronary Angioplasty for Acute Myocardial Infarction," *Am. J. Cardiol.* 78 (1996). pp. 747-750.

Okino, et al., "In situ hydrogelation of photocurable gelatin and drug release," *J. Biomed. Mater. Res.*, vol. 59, Issue 2 (2001), pp. 233-245.

Online Medical Dictionary. "Amino acid." Available from: http//cancerweb.ncl.ac.uk/cgi-bin/omd?query=amino+acid.

Ono, et al., "Photocrosslinkable chitosan as a biological adhesive," *J. Biomed. Mater. Res.*, vol. 49, Issue 2 (1999), pp. 289-295.

Ooka, et al., "Surface-Enhanced Raman Spectroscopy of DOPA-Containing Peptides Related to Adhesive Protein of Marine Mussel, *Mytilus edulis*," *Biopolymers (Biospectroscopy)*, vol. 57, Issue 2 (2000), pp. 92-102.

Orban, et al., "Cytomimetic Biomaterials. 4. In-Situ Photopolymerization of Phospholipids on an Alkylated Surface," *Macromolecules* 33 (2000). pp. 4205-4212.

Ostuni, et al., "A Survey of Structure—Property Relationships of Surfaces that Resist the Adsorption of Protein," *Langmuir* 17 (2001). pp. 5605-5620.

Palmer, et al., "Surfactant Administration Reduces Testicular Ischemia-Reperfusion Injury," *J. Urol.* 159 (1998). pp. 2136-2139.

Papov, et al., "Hydroxyarginine-containing Polyphenolic Proteins in the Adhesive Plaques of the Marine Mussel *Mytilus edulis*," *J. Biol. Chem.* 270 (34) (1995). pp. 20183-20192.

Pardo, et al., "Purification of Adhesive Proteins from Mussels," *Protein Expression and Purif.* 1 (2), 1990. pp. 147-150.

Parsons, "Characteristics of the amino acids as components of a peptide hormone sequence," in *Peptide Hormones*, University Park Press: 1976. pp. 1-7.

Pasche, et al., "Effects of Ionic Strength and Surface Charge on Protein Adsorption at PEGylated Surfaces," *J. Phys. Chem. B* 109 (2005). pp. 17545-17552.

Patel, et al., "Synthesis of Benzyl Esters of α-Amino Acids," *J. Org. Chem.* 30 (1965). pp. 3575-3576.

Peressadko, et al, "When Less is More: Experimental Evidence for Tenacity Enhancement by Division of Contact Area," *J. Adhes.* 80 (2004). pp. 247-261.

Perruchot, et al., "Synthesis of Well-Defined, Polymer-Grafted Silica Particles by Aqueous ATRP," *Langmuir*, vol. 17 (2001), pp. 4479-4481.

Pierpont, et al., "Transition Metal Complexes of *o*-Benzoquinone, *o*-Semiquinone, and Catecholate Ligands," *Coord. Chem. Rev.*, vol. 38 (1981), pp. 45-87.

Preul, et al., "A Unique Dual-Function Device: A Dural Sealant with Adhesion Prevention Properties,", 2006.

Preul, et al., "Use of a Novel Hydrogel Sealant in a Canine Dural Repair Model," Presented at the American Association of Neurological Surgeons; Apr. 2002, Chicago, IL. Available from: http://www.confluentsurgical.com/pdf/ds/Abstract0BNI_PreulAbstract.pdf.

Preul, et al., "Obtaining Watertight Closures of Duraplasty Onlay Grafts in a Craniotomy Preclinical Model," Confluent Surgical, Inc. (2005), 'White Paper.' Available from: http://www.confluentsurgical.com/pdf/LT-6000-034RevA-DuraSeal_duraplasty_study_white_paper.pdf.

Prime, et al., "Adsorption of Proteins onto Surfaces Containing End-Attached Oligo(ethylene oxide): A Model System Using Self-Assembled Monolayers," *J. Am. Chem. Soc.* 115 (1993). pp. 10714-10721.

Prucker, et al., "Polymer Layers through Self-Assembled Monolayers of Initiators," *Langmuir*, vol. 14 (1998), pp. 6893-6898.

Pyun, et al., "Synthesis of Polymer Brushes Using Atom Transfer Radical Polymerization," *Macromol. Rapid. Commun.* 24 (2003). pp. 1043-1059.

Rajh, et al., "Surface Restructuring of Nanoparticles: An Efficient Route for Ligand-Metal Oxide Crosstalk," *J. Phys. Chem. B*, vol. 106 (2002), pp. 10543-10552.

Ramakrishna, et al., "Effect of Particle Size on the Reactivity of Quantum Size ZnO Nanoparticles and Charge-Transfer Dynamics with Adsorbed Catechols," *Langmuir*, vol. 19 (2003), pp. 3006-3012.

Ranger, et al., "Pneumostasis of Experimental Air Leaks with a New Photopolymerized Synthetic Tissue Sealant," *Am. Surg.*, vol. 63, Issue 9 (1997), pp. 788-795.

Reed, et al., "A One-Step Synthesis of Monoprotected Polyethylene Glycol Ethers," *J. Org. Chem.*, vol. 65 (2000), pp. 5843-5845.

Rodríguez, et al., "Surface Complexation at the $TiO_2$ (anatase)/Aqueous Solution Interface: Chemisorption of Catechol," *J. Colloid Interface Sci.*, vol. 177 (1996), pp. 122-131.

Rodríguez-Hernández, et al., "High Branched Poly(L-lysine)," *Biomacromolecules*, vol. 4 (2003), pp. 249-258.

Ross-Murphy, "Rheological Characterization of Polymer Gels and Networks," *Polym. Gels Networks*, vol. 2 (1994), pp. 229-237.

Rozier, et al., Gelrite®: A novel, ion-activated, in situ gelling polymer for ophthalmic vehicles. Effect on bioavailability of timolol, *Int. J. Pharm.* 57 (2), 1989. pp. 163-168.

Ruel-Gariépy, et al., "In situ-forming hydrogels—review of temperature-sensitive systems," *Eur. J. Pharm. Biopharm.* 58 (2004). pp. 409-426.

Ruibal, et al., "The Structure of the Digital Setae of Lizards," *J. Morph.* 117 (1965). pp. 271-294.

Rzepecki, et al., "α, β-Dehydro-3,4-dihydroxyphenylalanine Derivatives: Potential Schlerozation Intermediates in Natural Composite Materials," *Arch. Biochem. Biophys.* 285 (1) (1991). pp. 17-26.

Rzepecki, et al., "Wresting the muscle from mussel beards: research and applications," *Mol. Mar. Biol. Biotech.* 4 (4) (1995). pp. 313-322.

Rzepecki, et al., "Bioadhesives: DOPA and Phenolic proteins as components of organic composite materials", *Principles of Cell Adhesion*, P.D. Richardson and M. Steiner (eds.), CRC Press, Boca Raton, FL. (1995). pp. 107-142142.

Saby, et al., "*Mytilus edulis* Adhesive Protein (MAP) as an Enzyme Immobilization Matrix in the Fabrication of Enzyme-Based Electrodes," *Electroanalysis* 10 (17) (1998). pp. 1193-1199.

Sanborn, et al., "In situ crosslinking of a biomimetic peptide-PEG hydrogel via thermally triggered activation of factor XIII," *Biomaterials*, vol. 23 (2002). pp. 2703-2710.

Sawada, et al., "Micropatterning of Copper on a Poly(ethylene terephthalate) Substrate Modified with a Self-Assembled Monolayer," *Langmuir* 22 (2006). pp. 332-337.

Sawhney, et al., "Interfacial photopolymerization of poly(ethylene glycol)-based hydrogels upon alginate-poly(*l*-lysine) microcapsules for enhanced biocompatibility," *Biomaterials*, vol. 14, No. 13 (1993), pp. 1008-1016.

Sawhney, et al., "Bioerodible Hydrogels Based on Photopolymerized Poly(ethylene glycol)-*co*-poly(α-hydroxy acid) Diacrylate Macromers," *Macromolecules*, vol. 26 (1993), pp. 581-587.

Schmolka, "Articifial Skin. I. Preparation and Properties of Pluronic F-127 Gels for Treatment of Burns," *J. Biomed. Mater. Res.* 6 (6) (1972). pp. 571-582.

Schnurrer, et al., "Mucoadhesive properties of the mussel adhesive protein," *Int. J. Pharm.* 141 (1996). pp. 251-256.

Sever, et al., "Synthesis of peptides containing DOPA (3.4-dihydroxyphenylalanine)," *Tetrahedron* 57 (2001). pp. 6139-6146.

Sever, et al., "Metal-Mediated Cross-Linking in the Generation of a Marine-Mussel Adhesive," *Angew. Chem. Int. Ed.*, vol. 43 (2004), pp. 448-450.

Shull, et al., "Fracture Mechanics Studies of Adhesion in Biological Systems," *Interface Sci.*, vol. 8 (2000), pp. 95-110.

Shull, "Contact mechanics and the adhesion of soft solids," *Mater. Sci. Eng.*, R 36 (2002). pp. 1-45.

Sichel, et al., "Relationship Between Melanin Content and Superoxide Dismutase (SOD) Activity in the Liver of Various Species of Animals," *Cell Biochem. Funct.* 5 (1987). pp. 123-128.

Sierra, "Fibrin Sealant Adhesive Systems: A Review of Their Chemistry, Material Properties and Clinical Applications," *J. Biomed. Appl.*, vol. 7 (1993), pp. 309-352.

Sitti, et al., "Synthetic Gecko Foot-Hair Micro/Nano-Structures as Dry Adhesives," *J. Adhes. Sci. Technol.*, vol. 17, No. 8 (2003), pp. 1055-1073. Available from: http://nanolab.me.cmu.edu/publications/papers/Sitti-JAST2003.pdf.

Skelhorne, et al., "Hydrogel Adhesives for Wound-Care Applications," *Medical Device Technology* (Nov. 2002). pp. 19-23.

(56) References Cited

OTHER PUBLICATIONS

Soriaga, et al., "Determination of the Orientation of Adsorbed Molecules at Solid-Liquid Interfaces by Thin-Layer Electrochemistry: Aromatic Compounds at Platinum Electrodes," *J. Am. Chem. Soc.* 104 (1982). pp. 2735-2742.

Sousa, et al., "Human Serum Albumin Adsorption on $TiO_2$ from Single Protein Solutions and from Plasma," *Langmuir*, vol. 20 (2004), pp. 9745-9754.

Sperinde, et al., "Synthesis and Characterization of Enzymatically-Cross-Linked Poly(ethylene glycol) Hydrogels," *Macromolecules* 30 (18) (1997). pp. 5255-5264.

Sperinde, et al., "Control and Prediction of Gelation Kinetics in Enzymatically Cross-Linked Poly(ethylene glycol) Hydrogels," *Macromolecules* 33 (2000). pp. 5476-5480.

Spolenak, et al., "Adhesion design maps for bio-inspired attachment systems," *Acta. Biomater.* 1 (2005). pp. 5-13.

Spotnitz, "History of Tissue Adhesives." In: Sierra, et al. (eds.), *Surgical Adhesives and Sealants: Current Technology and Applications*. Technomic Publishing Company, Inc.: Lancaster, PA (1997). pp. 3-11.

Spotnitz, "Commercial fibrin sealants in surgical care," *Am. J. Surg.* 182 (2001). pp. 8S-14S.

Statz, et al., "New Peptidomimetic Polymers for Antifouling Surfaces," *J. Am. Chem. Soc.*, vol. 127, No. 22 (2005), pp. 7972-7973.

Stevens, "Trace bio-organic constituents of gelatins—a review," *Food Australia*, vol. 44, No. 7 (1992), pp. 320-324.

Stile, et al., "Sequential robust design methodology and X-ray photoelectron spectroscopy to analyze the grafting of hyaluronic acid to glass substrates," *J. Biomed. Mater Res.*, vol. 61, Issue 3 (2002), pp. 391-398.

Stiles, et al., "Axisymmetric Adhesion Test to Examine the Interfacial Interactions between Biologically-Modified Networks and Models of the Extracellular Matrix," *Langmuir*, vol. 19 (2003), pp. 1853-1860.

Strausberg, et al., "Protein-based medical adhesives," *Trends in Biotechnology* 8 (2) (1990). pp. 53-57.

Strausberg, et al., "Development of a microbial system for production of mussel adhesive protein." In: *Adhesives from Renewable Resources*. Hemingway, et al. (eds.), ACS Symposium Series 385, American Chemical Society, Washington, D.C. (1989). pp. 453-464.

Sugumaran, et al., "Chemical- and Cuticular Phenoloxidase-Mediated Synthesis of Cysteinyl-Catechol Adducts," *Arch. Insect Biochem. Physiol.* 11 (2) (1989). pp. 127-137.

Sugumaran, "Unified Mechanism for Sclerotization of Insect Cuticle," *Adv. Insect. Physiol.*, vol. 27 (1998), pp. 229-334.

Sun, et al., "Improved antifouling property of zwitterionic ultrafiltration membrane composed of acrylonitrile and sulfobetaine copolymer," *J. of Memr. Sci.* 285 (2006). pp. 299-305.

Sun, et al., "The Nature of the Gecko Lizard Adhesive Force," *Biophys. J.* 89 (2005). pp. L14-L16.

Swerdloff, et al., "Solid phase synthesis of bioadhesive analogue peptides with trifluoromethanesulfonic acid cleavage from PAM resin," *Int. J. Peptide Protein Res.*, vol. 33 (1989), pp. 318-327.

Tae, et al., "Sustained release of human growth hormone from in situ forming hydrogels using self-assembly of fluoroalkyl-ended poly-(ethylene glycol)," *Biomaterials*, vol. 26 (2005), pp. 5259-5266.

Taira, et al., "Analysis of Photo-iniators in Visible-light-cured Dental Composite Resins," *J. Dent. Res.*, vol. 67, No. 1 (1988), pp. 24-28.

Tan, et al., "Surface modification of nanoparticles by PEO/PPO block copolymers to minimize interactions with blood components and prolong blood circulation in rats," *Biomaterials*, vol. 14, No. 11 (1993), pp. 823-833.

Tatehata, et al., "Model Polypeptide of Mussel Adhesive Protein. I. Synthesis and Adhesive Studies of Sequential Polypeptides $(X-Tyr-Lys)_n$ and $(Y-Lys)_n$," *J. Appl. Polym. Sci.*, vol. 76, No. 6 (2000), pp. 929-937.

Taylor, et al., "Polargraphic and Spectrophotometric Investigation of Iron(III) Complexation to 3,4-Dihydroxyphenylalanine-Containing Peptides and Proteins from *Mytilus edulis*," *Inorg. Chem.*, vol. 33 (1994), pp. 5819-5824.

Taylor, et al., "*trans-2,3-cis*-3,4-Dihydroxyproline, a New Naturally Occurring Amino Acid, is the Sixth Residue in the Tandemly Repeated Consensus Decapeptides of an Adhesive Protein from *Mytilus edulis*," *J. Am. Chem. Soc.*, vol. 116 (1994), pp. 10803-10804.

Taylor, et al., "Ferric Ion Complexes of a DOPA-Containing Adhesive Protein from *Mytilus edulis*," *Inorg. Chem.*, vol. 35 (1996), pp. 7572-7577.

Uyama, et al., "Surface Modification of Polymers by Grafting," *Advances in Polymer Science*, vol. 137 (1998), pp. 1-39.

Venkatraman, et al., "Skin adhesives and skin adhesion. 1. Transdermal drug delivery systems," *Biomaterials*, vol. 19 (1998), pp. 1119-1136.

Vörös, et al., "Optical grating coupler biosensors," *Biomaterials*, vol. 23 (2002), pp. 3699-3710.

Waite, "Evidence for a Repeating 3,4-Dihydroxyphenylalanine- and Hydroxyproline-containing Decapeptide in the Adhesive Protein of the Mussel, *Mytilus edulis* L.," *J. Biol. Chem.*, vol. 258, No. 5 (1983), pp. 2911-2915.

Waite, et al., "Assay of Dihdroxyphenylalanine (Dopa) in Invertebrate Structural Proteins," *Methods Enzymol.*, vol. 107 (1984), pp. 397-413.

Waite, "Nature's underwater adhesive specialist," *Chemtech*, vol. 17 (1987), pp. 692-697.

Waite, et al., "3,4-Dihydroxyphenylalanine in an Insoluble Shell Protein of *Mytilus edulis*," *Biochem. Biophys. Acta*, vol. 541 (1978), pp. 107-114.

Waite, et al., "Polyphosphoprotein from the Adhesive Pads of *Mytilus edulis*," *Biochemistry*, vol. 40 (2001), pp. 2887-2893.

Waite, et al., "The Bioadhesive of *Mytilus byssus*: A Protein Containing L-DOPA," *Biochem. & Biophy. Res. Comm.*, vol. 96, No. 4 (1980), pp. 1554-1561.

Waite, et al., "Mussel Adhesion: Finding the Tricks Worth Mimicking," *J. Adhes.*, vol. 81 (2005), pp. 297-317.

Waite, et al., "Polyphenolic Substance of *Mytilus edulis*: Novel Adhesive Containing L-Dopa and Hydroxyproline," *Science*, vol. 212, No. 4498 (1981), pp. 1038-1040.

Waite, "Precursors of Quinone Tanning: Dopa-Containing Proteins," *Methods Enzymol.*, vol. 258 (1995), pp. 1-21.

Wang, et al., "Facile synthesis of well-defined water-soluble polymers via atom transfer radical polymerization in aqueous media at ambient temperature," *Chem. Commun.* (1999), pp. 1817-1818.

Wang, et al., "Facile Atom Transfer Radical Polymerization of Methoxy-Capped Oligo(ethylene glycol) Methacrylate in Aqueous Media at Ambient Temperature," *Macromolecules*, vol. 33 (2000), pp. 6640-6647.

Wanka, et al., "The aggregation behavior of poly-(oxyethylene)-poly-(oxypropylene)-poly-(oxyethylene)-block-copolymers in aqueous solution," *Cooloid. Polym. Sci.*, vol. 268 (1990), pp. 101-117.

Watanabe, et al., "Bonding durability of photocured phenyl-P in TEGDMA to smear layer-retained bovine dentin," *Quint. Int.*, vol. 24, No. 5 (1993), pp. 335-342.

Webber, et al., "Effects of geometric confinement on the adhesive debonding of soft elastic solids," *Phys. Rev. E*, vol. 68 (2003), pp. 021805-1-to-021805-11.

Whitesides, "The origins and the future of microfluidics," *Nature*, vol. 442 (2006), pp. 368-373.

Yamada, "Chitosan Based Water-Resistant Adhesive. Analogy to Mussel Glue," *Biomacromolecules*, vol. 1 (2000), pp. 252-258.

Yamamoto, "Marine Adhesive Proteins and Some Biotechnological Applications," Biotechnol. *Genet. Eng. Rev.*, vol. 13 (1996), pp. 133-165.

Yamamoto, "Adhesive studies of synthetic polypeptides: A model for marine adhesive proteins," *J. Adhesion Sci. Tech.*, vol. 1, No. 2 (1987), pp. 177-183.

Yamamoto, "Synthesis and Adhesive Studies of Marine Polypeptides," *J. Chem. Soc. Perkin Trans.*, vol. 1 (1987), pp. 613-618.

Yamamoto, "Insolubilizing and adhesive studies of water-soluble synthetic model proteins," *Int. J. Biol. Macromol.*, vol. 12 (1990), pp. 305-310.

(56) References Cited

OTHER PUBLICATIONS

Yamamoto, et al., "Synthesis and Adhesives of Marine Adhesive Proteins of the Chilean Mussel *Aula comya ater*," *Biomimetics*, vol. 1, No. 3 (1992), pp. 219-238.

Yamamoto, et al., "Work of Adhesion of Synthetic Polypeptides Containing *L*-Lysine," *J. Colloid Interface Sci.*, vol. 156 (1993), pp. 515-517.

Yamamoto, et al., "Wettability and Adhesion of Synthetic Marine Adhesive Proteins and Related Model Compounds," *J. Colloid Interface Sci.*, vol. 176 (1995), pp. 111-116.

Yang, et al., "Physicochemical aspects of drug delivery and release from polymer-based colloids," *Curr. Opin. Colloid Interface Sci.*, vol. 5 (2000), pp. 132-143.

Young, et al., "Marine Animals and Adhesion." In: Allen (ed.), *Adhesion 6*. Applied Science Publishers: London and New Jersey, 1982. pp. 19-39.

Yu, et al., "Micellisation and Gelation of Triblock Copoly(oxyethylene/oxypropylene/oxyethylene), F127," *J. Chem. Soc., Faraday Trans.*, vol. 88, No. 17 (1992), pp. 2537-2544.

Yu, et al., "Synthetic Polypeptide Mimics of Marine Adhesives," *Macromolecules*, vol. 31 (1998), pp. 4739-4745.

Yurdumakan, et al., "Synthetic gecko foot-hairs from multiwalled carbon nanotubes," *Chem. Commun.*, vol. 30 (2005), pp. 3799-3801.

Zekorn, et al., "Biocompatibility and immunology in the encapsulation of islets of Langerhans (bioartificial pancreas)," *Int. J. Artif. Organs*, vol. 19, No. 4 (1996), pp. 251-257.

Zhan, et al., "Functionalization of Nano-Faujasite Zeolite with PEG-Grafted PMA Tethers Using Atom Transfer Radical Polymerization," *Macromolecules*, vol. 37 (2004), pp. 2748-2753.

Zhao, et al., "Polymer brushes: surface-immobilized macromolecules," *Prog. Polym. Sci.*, vol. 25 (2000), pp. 677-710.

Zuckermann, et al., "Efficient Method for the Preparation of Peptoids [Oligo(N-substituted glycines)] by Submonomer Solid-Phase Synthesis," *J. Am. Chem. Soc.*, vol. 114 (1992), pp. 10646-10647.

\* cited by examiner

D  Mefp5

SSEEYKGGYYPGNAYHYHSGG
SYHGSGYHGGYKGKYYGKA**KK
YYYKYKNSGKYKYLKKARKYHR
KGYKYYGSS

Y: DOPA
K: Lysine

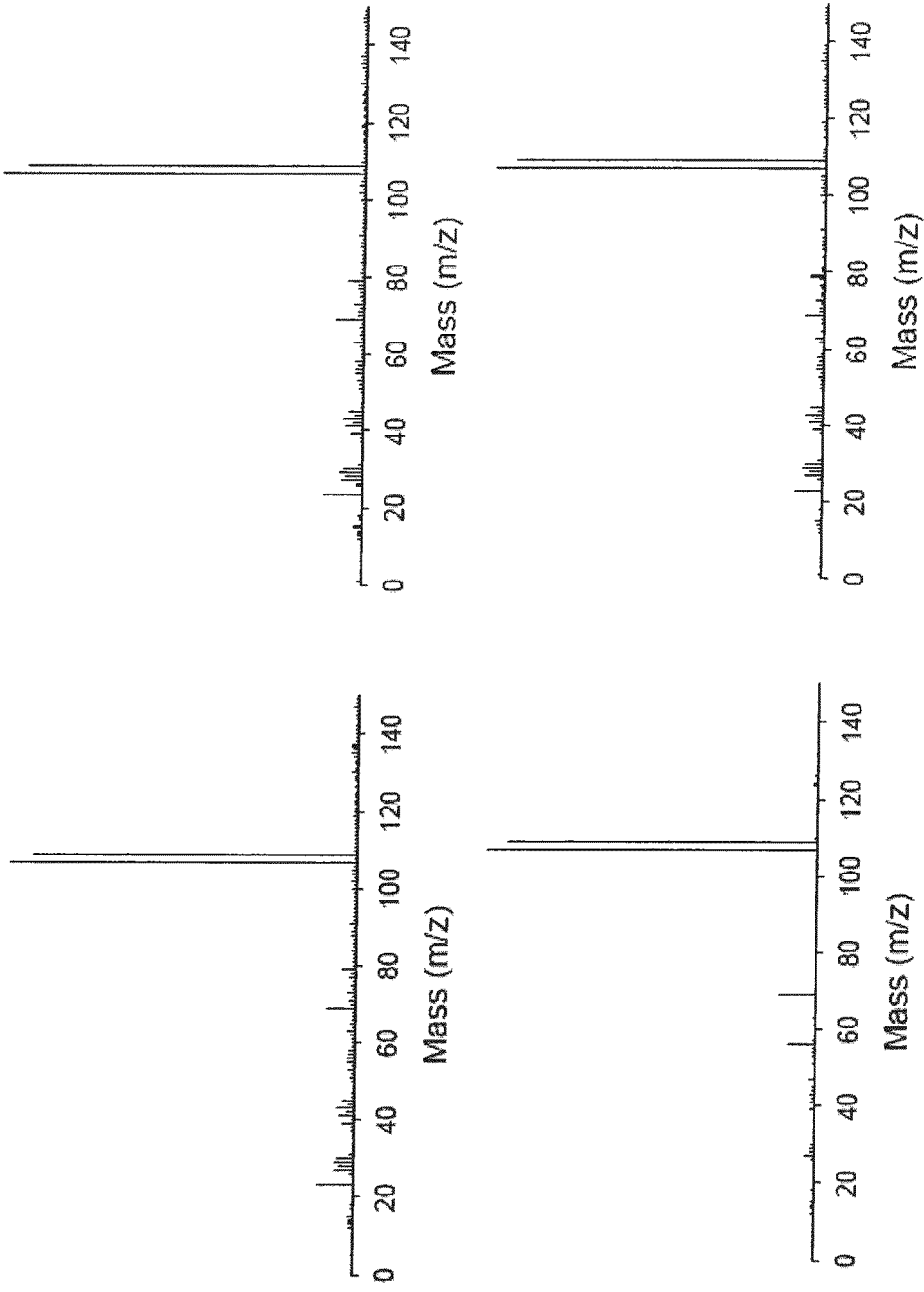

SURFACE INDEPENDENT, SURFACE-MODIFYING, MULTIFUNCTIONAL COATINGS AND APPLICATIONS THEREOF

CROSS REFERENCE TO RELATED APPLICATIONS

This application is a continuation-in-part of U.S. application Ser. No. 11/068,298 filed Feb. 28, 2005, U.S. application Ser. No. 11/179,218, filed Jul. 11, 2005 and issued as U.S. Pat. No. 7,858,679 on Dec. 8, 2010, U.S. application Ser. No. 11/875,237, filed Oct. 19, 2007 and U.S. application Ser. No. 11/972,008, filed Jan. 10, 2008, the contents of all of which are incorporated herein by reference in their entirety for all purposes.

STATEMENT REGARDING FEDERALLY SPONSORED RESEARCH

This invention was made with government support under DE14193 awarded by the National Institutes of Health. The government has certain rights in the invention.

FIELD OF THE INVENTION

This invention generally relates to polymeric coatings. More particularly, this invention relates to surface-independent, surface-modifying, multifunctional coatings, including compositions to reduce or prevent marine fouling (biofouling) of surfaces.

BACKGROUND OF THE INVENTION

Chemical modification of bulk material substrates plays a central role in modern chemical, biological and material sciences, as well as in applied sciences, engineering and technology. Methods for chemical modification of bulk material substrates have developed by interfacial chemistry using organothiol-metals, enediol-oxides, silane-oxides, and other physicochemical methods, in which the predominant purpose is to impose desired properties on non-functional substrates. Molecules utilized for surface modification mostly have bifunctional end groups in which one end anchors to substrates and the other end provides chemical functionality to the substrate surface.

The existing toolbox for functional modification of material/substrate surfaces includes methods such as self-assembled monolayer (SAM) formation, functionalized silanes, Langmuir-Blodgett deposition, layer-by-layer assembly, and genetically-engineered surface-binding peptides. Although widely implemented in research, these conventional methods have limitations for widespread practical use. For instance, chemical specificity between interfacial modifiers and substrates (e.g., alkanethiols on noble metals and silanes on oxides) is typically required, complex instrumentation is typically required, and the substrate size/shape (Langmuir-Blodgett deposition) is often limited, or multi-step procedures for implementation (layer-by-layer assembly and surface-binding genetically engineered peptides) are required. More importantly, the substrates available for conventional surface modification chemistry is the primary limitation.

Mussel Adhesives

Mussels represent a natural surface-independent adhesive. Mussels are promiscuous fouling organisms which attach to virtually all types of inorganic and organic substrates, including classically adhesion-resistant materials such as polytetrafluoroethylene (PTFE) (FIG. 1A). Mussels' adhesive versatility may lie in the amino acid composition of proteins found near the plaque-substrate interface (FIG. 1B-D), which is rich in 3,4-dihydroxy-L-phenylalanine (DOPA) and lysine amino acids. DOPA participates in reactions leading to bulk solidification of the adhesive and forms strong covalent and non-covalent interactions with substrates.

Dopamine is a small molecule compound that contains both catechol (DOPA) and amine (lysine) groups (FIG. 1E). Dopamine can be electro-polymerized onto conducting substrates (Y. Li, et al., *Thin Solid Films,* 497, 270, 2006).

Needed in the art of surface modification is a method of surface-independent modification of a substrate whereby specific functional moieties can be displayed on the surface.

Biofouling Compositions

As long as ships have plied the seas, biofouling has had an overwhelming economic impact for the marine industry. Traditional antifouling paints containing biocides such as cuprous oxide in combination with one or more co-biocides are generally effective in reducing fouling of marine surfaces, although their use is associated with significant concerns related to their environmental impact on non-target aquatic species.

Tributyltin-containing paints were found to be effective in reducing biofouling. However, the application of tributyltin-containing paints is no longer permitted under a ban imposed by the International Maritime Organization (IMO) and more environmentally friendly approaches to fouling control are being actively sought. Commercial non-toxic alternatives to traditional biocidal antifouling paints have been silicone elastomers known as "fouling-release" coatings, which reduce the adhesion strength of marine organisms, facilitating their hydrodynamic removal at high speeds. These coatings, however, are expensive, not completely effective against all marine fouling including slimes, and do not release macrofouling from slow-moving vessels.

Therefore, the environmental and functional limitations of existing antifouling coatings highlight the need for new marine antifouling technologies.

BRIEF SUMMARY OF THE INVENTION

In the present invention, it is shown that dopamine and related compounds can act as a powerful building block for thin polymer film deposition on virtually any bulk material surface wherein the deposited films are easily adaptable for a remarkable variety of functional uses. In one embodiment the deposition is spontaneous.

In one preferred embodiment, the present invention is a novel surface-independent, surface-modification method whereby substrates are modified to display at least one reactive moiety on the substrate surface by contacting at least a portion of the substrate with a surface-modifying agent (SMA). Because of the surface-independent nature of the present method, specific applications include diverse fields such as biocompatible coatings of medical devices, surface modifications of drug delivery carriers and tissue engineering scaffolds, biosensors, industrial and consumer coatings, semiconductors, surface catalysts and next generation electronic displays.

In a first embodiment, the present invention pertains to a method of modifying a substrate surface, the method comprising contacting at least a portion of the substrate with an alkaline solution under oxidative conditions, the solution comprising a surface-modifying agent (SMA) according to Formula I:

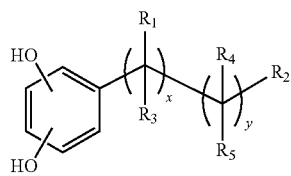

wherein each of $R_1$, $R_2$, $R_3$, $R_4$ and $R_5$ is independently selected from the group consisting of a thiol, a primary amine, a secondary amine, a nitrile, an aldehyde, an imidazole, an azide, a halide, a polyhexamethylene dithiocarbonate, a hydrogen, a hydroxyl, a carboxylic acid, an aldehyde, a carboxylic ester or a carboxamide, provided at least one of $R_1$, $R_2$, $R_3$, $R_4$ and $R_5$ is not a hydrogen atom; wherein x ranges from 0 to 10; wherein y ranges from 0 to 10, provided that x or y is at least 1; and wherein the substrate surface is modified. In a preferred embodiment, the SMA forms a polymeric coat on the substrate surface.

The SMA may also be selected from the group consisting of 3,4-dihydroxy-L-phenylalanine (DOPA), 3,4-dihydroxyphenylalanine methyl ester, dopamine, norepinephrine and epinephrine, and may be an aqueous solution.

In one embodiment of the SMA, x and y are both 1 and $R_1$ and $R_4$ form a double bond when eliminated. However, in alternative embodiments of the SMA, one of $R_1$ or $R_4$ is a halide, a hydroxyl or a thiol and one of $R_3$ or $R_5$ is a hydrogen atom, and $R_2$ is $NH_2$ or NHR, wherein R is an alkyl or aromatic group. In further alternate embodiments of the SMA, x is 1, y is 1, $R_1$ is a hydroxyl, $R_3$, $R_4$ and $R_5$ are hydrogen. In still further alternate embodiments of the SMA, x and y are each 1, each of $R_1$, $R_3$, $R_4$ and $R_5$ are hydrogen atoms, and $R_2$ is an $NH_2$ or NHR, where R is an alkyl or aromatic group; or, alternatively, one of $R_1$ or $R_4$ is a halide, a hydroxyl or a thiol and one of $R_3$ or $R_5$ is a hydrogen atom. In alternate embodiments of the SMA, x+y is at least 2, x+y is at least 3, and x+y ranges from 1 to 6. In alternate embodiments of the SMA, hydroxyls of the phenyl moiety are positioned at the 3 and 4 positions of the phenyl group relative to the side chain.

In a second embodiment, the invention relates to a method of modifying a substrate surface to provide a desired functionality, the method comprising contacting at least a portion of the substrate surface with an alkaline, aqueous solution under oxidative conditions, the solution comprising a SMA according to Formula I:

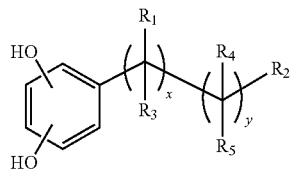

wherein each of $R_1$, $R_2$, $R_3$, $R_4$ and $R_5$ is independently selected from the group consisting of a thiol, a primary amine, a secondary amine, a nitrile, an aldehyde, an imidazole, an azide, a halide, a polyhexamethylene dithiocarbonate, a hydrogen, a hydroxyl, a carboxylic acid, an aldehyde, a carboxylic ester or a carboxamide, provided at least one of $R_1$, $R_2$, $R_3$, $R_4$ and $R_5$ is not a hydrogen atom; wherein x ranges from 0 to 10 and wherein y ranges from 0 to 10, provided that x or y is at least 1; wherein the substrate surface is modified; and contacting the surface-modified substrate with a reactive moiety, wherein the reactive moiety reacts with and is bound to the modified surface. The reactive moiety comprises nucleophiles or metals.

In a third embodiment, the invention provides a method of reducing amounts of metal in a fluid comprising the steps of contacting at least a portion of a substrate with an alkaline, aqueous solution under oxidative conditions, the solution comprising a SMA according to Formula I:

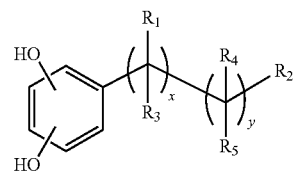

wherein each of $R_1$, $R_2$, $R_3$, $R_4$ and $R_5$ is independently selected from the group consisting of a thiol, a primary amine, a secondary amine, a nitrile, an aldehyde, an imidazole, an azide, a halide, a polyhexamethylene dithiocarbonate, a hydrogen, a hydroxyl, a carboxylic acid, an aldehyde, a carboxylic ester or a carboxamide, provided at least one of $R_1$, $R_2$, $R_3$, $R_4$ and $R_5$ is not a hydrogen atom; wherein x ranges from 0 to 10 and wherein y ranges from 0 to 10, provided that x or y is at least 1; contacting the surface-modified substrate with a reactive moiety, wherein the reactive moiety reacts with and is bound to the modified surface; and positioning the surface in a fluid with metal, whereby the modified surface binds at least a portion of the metal and wherein the reactive moiety is a metal.

In a fourth embodiment, the invention provides a method of modifying a substrate surface to form a biofouling-resistant, modified substrate surface, the method comprising the steps of contacting at least a portion of the surface of the substrate surface with an alkaline solution under oxidative conditions, the solution comprising a SMA according to Formula I:

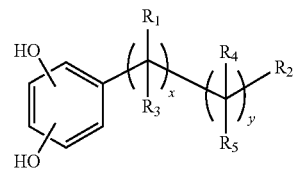

wherein each of $R_1$, $R_2$, $R_3$, $R_4$ and $R_5$ is independently selected from the group consisting of a thiol, a primary amine, a secondary amine, a nitrile, an aldehyde, an imidazole, an azide, a halide, a polyhexamethylene dithiocarbonate, a hydrogen, a hydroxyl, a carboxylic acid, an aldehyde, a carboxylic ester or a carboxamide, provided at least one of $R_1$, $R_2$, $R_3$, $R_4$ and $R_5$ is not a hydrogen atom; wherein x ranges from 0 to 10 and wherein y ranges from 0 to 10, provided that x or y is at least 1; and contacting at least a portion of the surface-modified substrate with a biofouling-resistant reactive moiety, wherein a biofouling-resistant, surface-modified substrate is formed. In one embodiment, the surface-modified substrate is part of a medical device, and the biofouling-resistant reactive moiety is selected from the group consisting of thiols, primary amines, secondary amines, nitriles, aldehydes, imidazoles, azides, halides, polyhexamethylene dithiocarbonate, hydrogen, hydroxyls, carboxylic acids, aldehydes, carboxylic esters or carboxamides.

In a fifth embodiment, the invention provides a kit for modifying a substrate surface, the kit comprising a SMA according to Formula I:

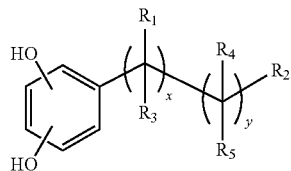

wherein each of $R_1$, $R_2$, $R_3$, $R_4$ and $R_5$ is independently selected from the group consisting of a thiol, a primary amine, a secondary amine, a nitrile, an aldehyde, an imidazole, an azide, a halide, a polyhexamethylene dithiocarbonate, a hydrogen, a hydroxyl, a carboxylic acid, an aldehyde, a carboxylic ester or a carboxamide, provided at least one of $R_1$, $R_2$, $R_3$, $R_4$ and $R_5$ is not a hydrogen atom; wherein x ranges from 0 to 10 and wherein y ranges from 0 to 10, provided that x or y is at least 1; and instructions for use. The surface-modifying agent may be in solution or in powdered form.

The kit may further comprise a reactive moiety selected from the group consisting of thiols, primary amines, secondary amines, nitriles, aldehydes, imidazoles, azides, halides, polyhexamethylene dithiocarbonate, hydrogen, hydroxyls, carboxylic acids, aldehydes, carboxylic esters or carboxamides and a substrate surface to be modified.

In the specification and in the claims, the terms "including" and "comprising" are open-ended terms and should be interpreted to mean "including, but not limited to . . . ." These terms encompass the more restrictive terms "consisting essentially of" and "consisting of."

The present invention also surprisingly provides surface treatments that reduce or eliminate marine fouling of various surfaces. A surface that is to be contacted with the marine environment can be easily treated with an mPEG-DOPA, as disclosed herein. The treated surface is thus rendered less susceptible to fouling of the surface.

Suitable mPEG-DOPAs include those where a L-3,4-dihydroxyphenylalanine (DOPA) unit is "pegylated" with a methoxyl terminated polyethylene glycol (mPEG) sidechain. Typically there are 1, 2 or 3 DOPA units contained within the mPEG-DOPA polymer. The mPEG portion of the mPEG-DOPA polymer has a polyethylene glycol repeat unit of about 113 units. The polyethylene glycol (PEG) repeat unit can vary from several units to a few hundred units, or from about 2 to about 300, from about 5 to about 250, from about 10 to about 200, from about 20 to about 150, and all integers and ranges there between.

A surface in need of treatment can simply be coated with a solution of the mPEG-DOPA antifouling polymer. Alternatively, a solution of the mPEG-DOPA antifouling polymer could be sprayed onto the surface, brushed onto the surface, etc. to effect a suitable treatment of the surface.

While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. Accordingly, the detailed descriptions are to be regarded as illustrative in nature and not restrictive.

BRIEF DESCRIPTION OF THE DRAWINGS

FIG. 1A. Photograph of a mussel attached to commercial polytetrafluoroethylene (PTFE). FIGS. 1B and C. Schematic illustrations of the interfacial location of Mefp-5 and a simplified molecular representation of characteristic amine and catechol groups. FIG. 1D. The amino acid sequence of Mefp-5. FIG. 1E Amine and catechol functional groups of dopamine. FIG. 1F. Schematic illustration of thin film deposition of polydopamine by dip-coating an object in an alkaline dopamine solution. FIG. 1G. Thickness evolution of polydopamine coating on Si as measured by AFM of patterned substrates. FIG. 1H. XPS characterization of twenty-five different polydopamine-coated substrates. The bar graph represents the intensity of characteristic substrate signal before (hatched) and after (filled) coating by polydopamine. The intensity of the unmodified substrate signal is in each case normalized to 100%. Substrates with characteristic XPS signals indistinguishable from polydopamine are marked by N.A. The circles represent the nitrogen-to-carbon ratio (N/C) after polydopamine coating.

FIG. 5. Time of flight secondary ion mass spectrometry (ToF-SIMS) analysis of polydopamine coating, suggested reaction, and organic ad-layer formation mechanisms.

FIG. 6A. The thickness evolution of a polydopamine-coated substrate as a function of dopamine coating time. Topological images of atomic force microscopy (AFM) measured a height difference between substrate (silicon) and the polydopamine-coated layer generated by photolithography. The bottom inset is 3D representation of actual AFM imaging of a 34 nanometers (nm) coating (6 hours (hr)). The top inset is the cross-section of a 19 nm polydopamine-coating (3 hr). FIG. 6B. ToF-SIMS on the polydopamine-coated substrate. The mass 445 m/z is the product of a fragmented polydopamine chain showing a trimer of 5,6-dihydroxlindole and leukodopaminechrome resulting from dopamine oxidation (refer to FIG. 12). The dehydroxylation ($\alpha$) followed by phenyl ring opening ($\beta$) indicates that a catechol moiety is the major component in the SMA-treated substrate.

FIG. 7A-C. Electroless copper deposition on polydopamine-coated nitrocellulose film (FIG. 7A); coin (FIG. 7B); and three-dimensional plastic object (FIG. 7C). FIG. 7D. Schematic representation of electroless metallization of photoresist-patterned polydopamine-coated substrates. Photoresist was removed before silver metallization (left) or after copper metallization (right). FIGS. 7E and F. Scanning Electron Microscopy (SEM) images showing micropatterns of silver on Si (FIG. 7E) and copper on a glass substrate (FIG. 7F).

FIG. 8. XPS and ToF SIMS characterization of silver ad-layer deposited on polydopamine-coated substrates by electroless metallization.

FIG. 12A. Total internal reflection fluorescence (TIRF) microscope images of a protein adsorption at a single molecule level. Significant amount of the surface adsorption of fluorophore-labeled proteins onto the unmodified glass surface was shown after 30 min (top). Protein adsorption resistance by PEG ($mPEG-NH_2$, 5 kDa) conjugated on polydopamine-coated glass substrates after continuous 30 min (middle left) and 48 hr (middle right) exposure to proteins. A proposed description of the surface chemistry for the protein inert substrates preparation (top schematic). Positive control experiments (bottom). Glass substrates were PEGylated by the standard silane chemistry and subsequent exposure to protein solutions for 30 min (bottom left) and 48 hr (bottom right) showing a defective surface. FIG. 12B. In vitro antifouling evaluation of various substrates (hatch). Short-term (4 hr) fibroblast adhesion test revealed significantly improved antifouling properties for all tested materials including oxides, metals, semiconductors, and polymers (solid). FIG. 12C. The XPS sulfur 2p (163 eV) signals on the polydopamine-coated glass substrate indicates successful interfacial PEG immobilization. Inset shows the high-resolution spectrum of the sulfur 2p region marked by the arrow in a survey scan.

FIG. 13A. Schematic illustration of alkanethiol monolayer (top right) and PEG polymer (bottom right) grafted on polydopamine-coated substrates. FIG. 13B. Pictures of water droplets on several unmodified (left), polydopamine-coated (middle), and alkanethiol-grafted substrates (right). Substrates investigated include organic polymers (PTFE, PC, and nitrocellulose (NC)), metal oxides ($SiO_2$ and $TiO_2$), and noble metals (Cu and Au). Contact angle values are shown in Table 3. FIG. 13C. NIH 3T3 fibroblast cell adhesion to unmodified glass and OEG6-terminated alkanethiol monolayer formed on polydopamine-coated glass. FIG. 13D-F. TIRF microscopy of Cy3 conjugated Enigma homolog protein adsorption to $mPEG-NH_2$-grafted polydopamine-coated glass (48 hr exposure to protein solution) (FIG. 13D), bare glass (30 min exposure) (FIG. 13E), and mPEG-silane immobilized on bare glass (48 hr exposure) (FIG. 13F). FIG. 13G. NIH 3T3 fibroblast cell adhesion to polydopamine-coated substrates after grafting with mPEG-SH (Pre-normalized data are available in Table 4).

FIG. 16A. Experimental scheme. The polydopamine-coated latex micro-bead was chemically conjugated to an E. coli flagella protein which enabled real-time monitoring of rotation of flagellum. FIG. 16B. Real-time images of counterclockwise rotation of single flagellum with a time resolution of 50 msec (starting from upper left). Spatially confined moving traces of the attached bead showed counterclockwise rotation of the flagellum. Notation of flagella rotational direction is opposite to the normal usage: flagellum rotates 'clockwise' from experimenter's point of view in this figure, which should be expressed as 'counterclockwise' rotation in bacterial chemotaxis. The rotational direction is determined from the bacterial point of view.

FIG. 17A. Representative scheme for hyaluronic acid (HA) conjugation to polydopamine-coated substrates. FIG. 17B. Adhesion of M07e cells on polydopamine-coated polystyrene (PS) increases with the HA solution concentration used during grafting. FIG. 17C. Bioactive HA ad-layers were formed on polydopamine-coated glass, tissue-culture PS, and indium tin oxide (ITO), as demonstrated by attachment of M07e cells. Competition with soluble HA (bar at the right end, PS+sol HA) confirmed that cell adhesion was due to grafted HA. FIG. 17D-F. Polydopamine-modified PS grafted with HA (0.5 mg/mL) retains bioactivity during long-term culture with M07e cells. Images taken after normal-force centrifugation show almost 100% attachment of expanding M07e cells at days 2 (FIG. 17D; 2760±390 cells/cm$^2$) and 4 (FIG. 17E; 5940±660 cells/cm$^2$). In the absence of HA, the polydopamine-coated substrates supported similar levels of M07e cell expansion at day 4, but did not support cell adhesion (610±630 cells/cm$^2$) (FIG. 17F).

DETAILED DESCRIPTION

I. In General

Figure 1:
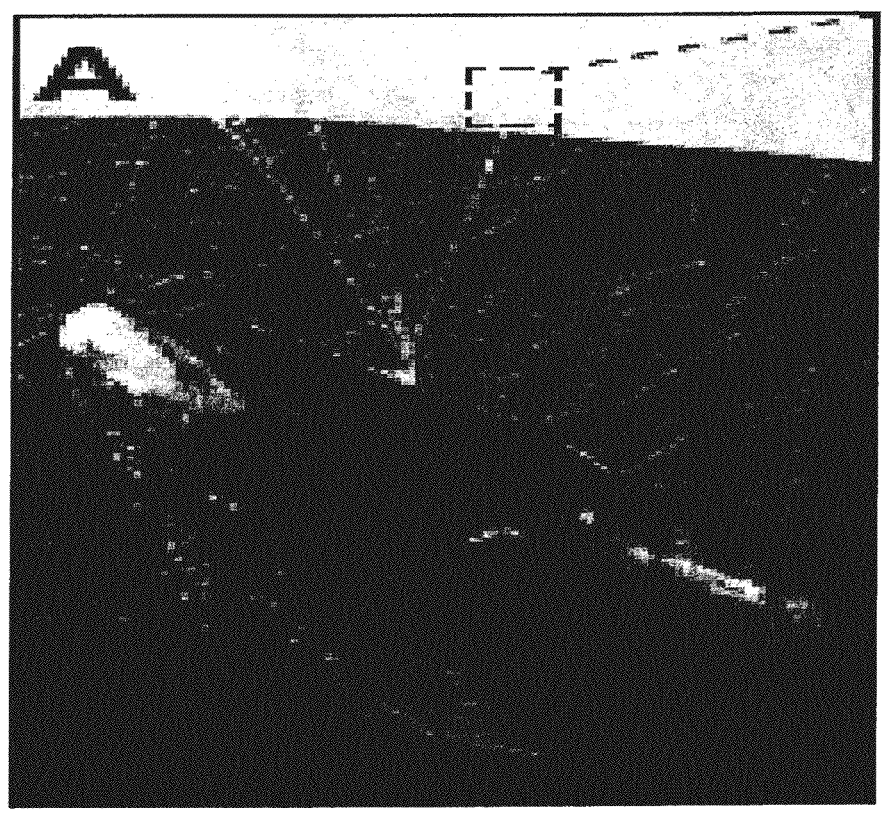
FIG. 1. Mussel-inspired surface-independent adhesive.
Figure 1:
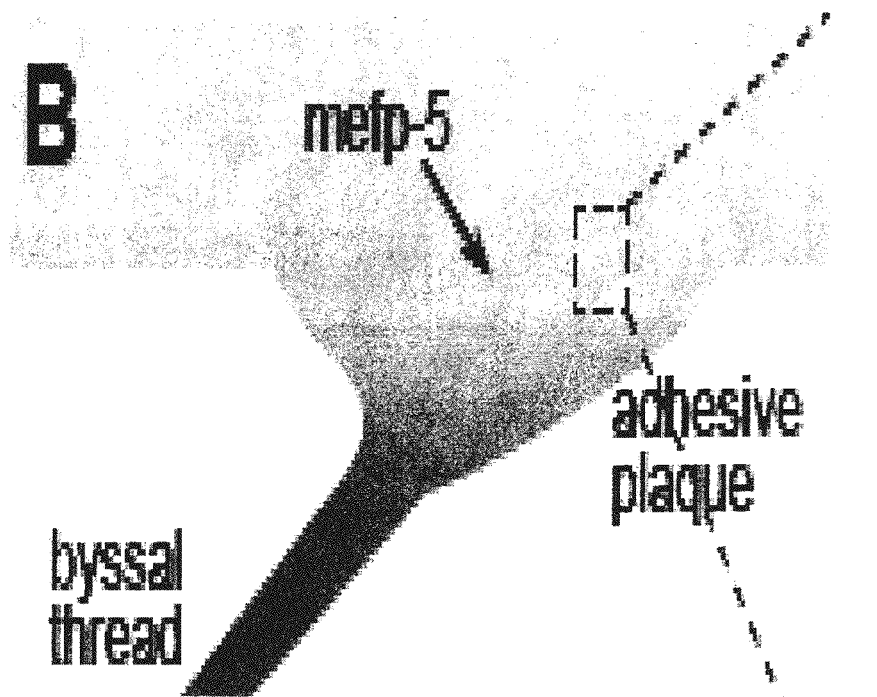
Figure 1:
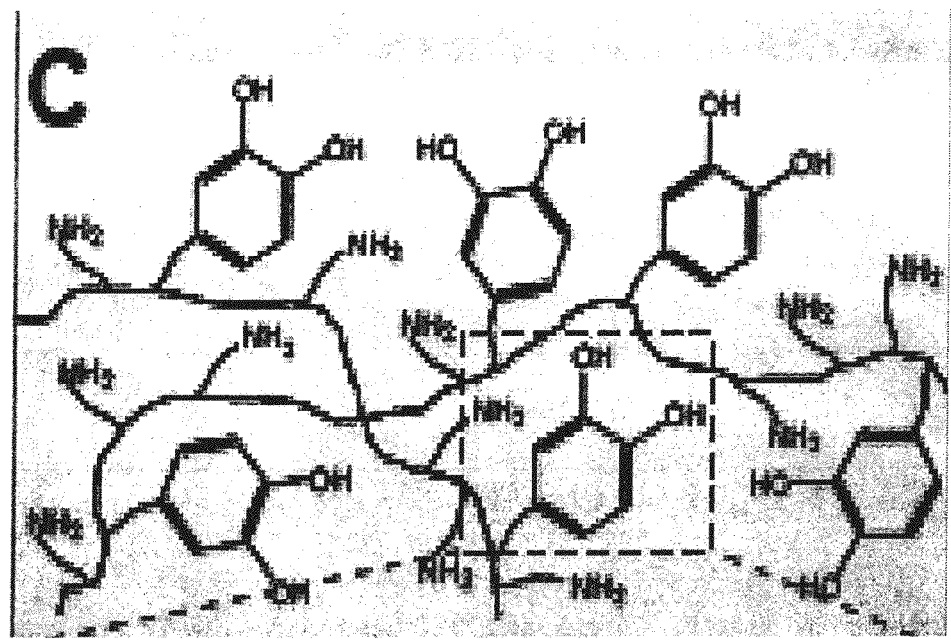
Figure 1:
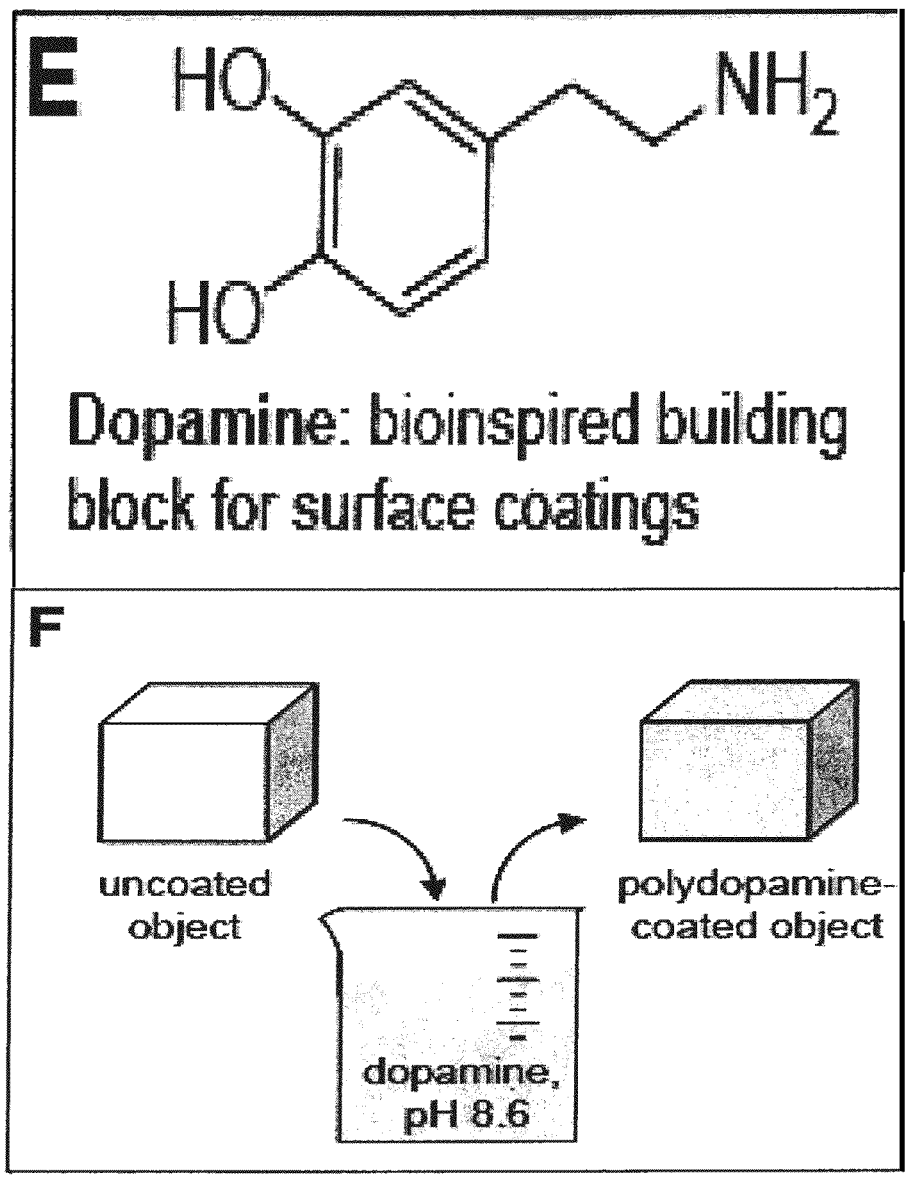
Figure 1:
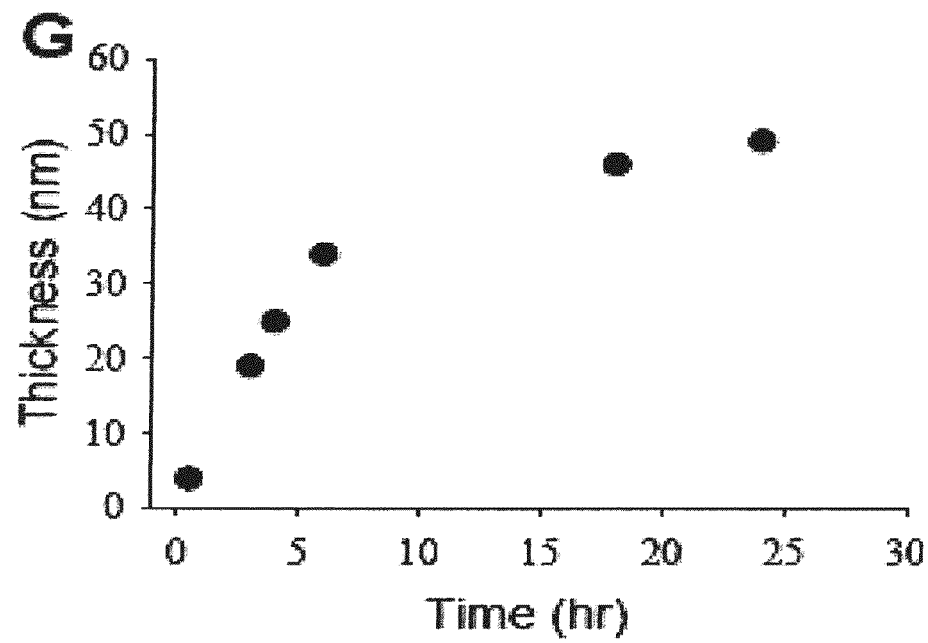
Figure 1:
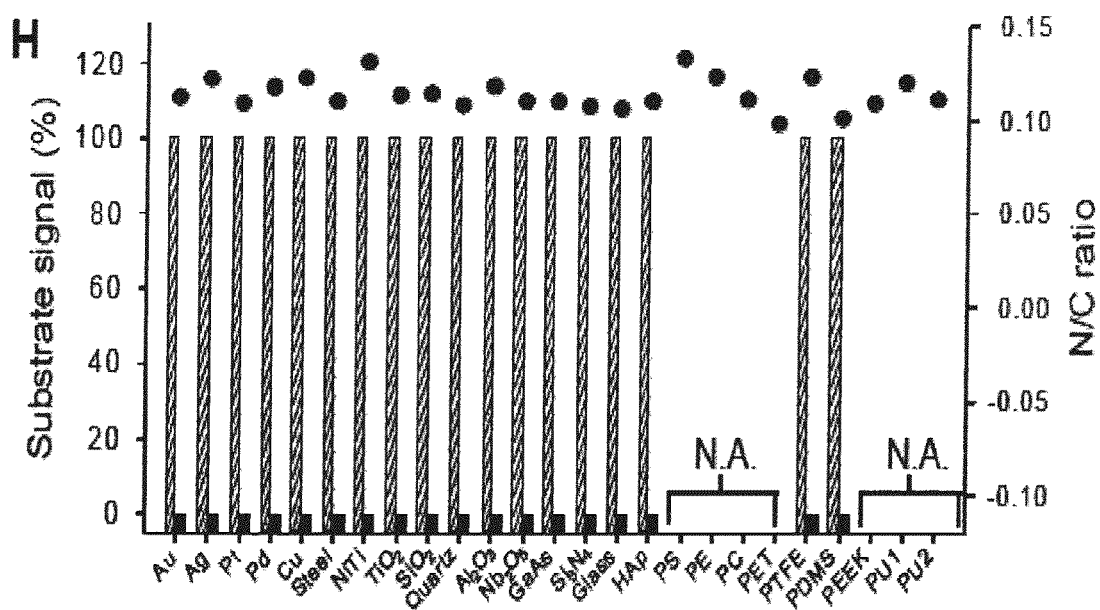

In the specification and in the claims, the terms "including" and "comprising" are open-ended terms and should be interpreted to mean "including, but not limited to . . . ." These terms encompass the more restrictive terms "consisting essentially of" and "consisting of."

As used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", "characterized by" and "having" can be used interchangeably.

Unless defined otherwise, all technical and scientific terms used herein have the same meanings as commonly understood by one of ordinary skill in the art to which this invention belongs. All publications and patents specifically mentioned herein are incorporated by reference in their entirety for all purposes including describing and disclosing the chemicals, instruments, statistical analyses and methodologies which are reported in the publications which might be used in connection with the invention. All references cited in this specification are to be taken as indicative of the level of skill in the art.

Nothing herein is to be construed as an admission that the invention is not entitled to antedate such disclosure by virtue of prior invention.

The present invention provides a novel, surface-independent, surface-modification method whereby substrates of all kinds are modified to support at least one functional ad-layer on the substrate's surface. In general, the method comprises contacting at least a portion of the substrate with a surface-modifying agent (SMA) to provide a surface modified to support at least one reactive moiety. The present invention's interfacial chemistry will be useful in important fields including biocompatible coatings of medical devices, surface modifications of drug delivery carriers and tissue engineering scaffolds, biosensors, biofouling-resistant, industrial and consumer coatings, semiconductors, metal removal, surface catalysts and next generation electronic displays.

The method comprises contacting at least a portion of a substrate with an alkaline solution under oxidizing conditions, the solution comprising a SMA according to Formula I:

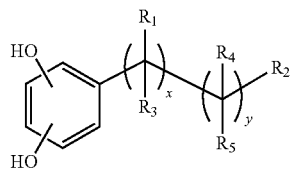

wherein each of $R_1$, $R_2$, $R_3$, $R_4$ and $R_5$ is independently selected from the group consisting of a thiol, a primary amine, a secondary amine, a nitrile, an aldehyde, an imidazole, an azide, a halide, a polyhexamethylene dithiocarbonate, a hydrogen, a hydroxyl, a carboxylic acid, an aldehyde, a carboxylic ester or a carboxamide, provided at least one of $R_1$, $R_2$, $R_3$, $R_4$ and $R_5$ is not a hydrogen atom; wherein x ranges from 0 to 10 and wherein y ranges from 0 to 10, provided that x or y is at least 1; and wherein the substrate surface is modified.

After contact with the Formula I solution, the substrate surface is modified. In a preferred embodiment the substrate surface is modified to comprise a polymeric coating. The SMA-treated surface may then be contacted with a reactive moiety to provide a SMA-treated surface having a functional ad-layer. The ad-layer can be tailored for specific applications and may include one or more ad-layers. For instance, in one embodiment, the SMA-treated surface may be modified to provide an ad-layer comprising at least one reactive moiety such as metals, nucleophiles and polymers.

In one embodiment, the present invention pertains to a method of modifying a substrate surface, the method comprising contacting at least a portion of the substrate with an alkaline solution under oxidative conditions, the solution comprising a SMA according to Formula I:

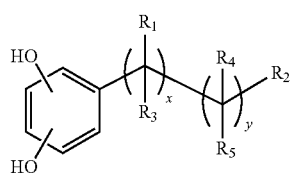

wherein each of $R_1$, $R_2$, $R_3$, $R_4$ and $R_5$ is independently selected from the group consisting of a thiol, a primary amine, a secondary amine, a nitrile, an aldehyde, an imidazole, an azide, a halide, a polyhexamethylene dithiocarbonate, a hydrogen, a hydroxyl, a carboxylic acid, an aldehyde, a carboxylic ester or a carboxamide, provided at least one of $R_1$, $R_2$, $R_3$, $R_4$ and $R_5$ is not a hydrogen atom; wherein x ranges from 0 to 10; wherein y ranges from 0 to 10, provided that x or y is at least 1; and wherein the substrate surface is modified. In one embodiment, wherein x and y are both 1, and where $R_1$ and $R_4$ form a double bond when eliminated. In one embodiment, $R_2$ is $NH_2$ or NHR, and R is an alkyl or aromatic group. In one embodiment, one of $R_1$ or $R_4$ is a halide, a hydroxyl or a thiol and one of $R_3$ or $R_5$ is a hydrogen atom. In one embodiment, x is 1, y is 1, $R_1$ is a hydroxyl and $R_3$, $R_4$ and $R_5$ are a hydrogen. In one embodiment, $R_2$ is a $NH_2$. In one embodiment, x and y are each 1 and each of $R_1$, $R_3$, $R_4$ and $R_5$ are hydrogen atoms. In one embodiment, $R_2$ is $NH_2$. In one embodiment, $R_2$ is $NH_2$ or NHR, and R is an alkyl or aromatic group. In one embodiment, one of $R_1$ or $R_4$ is a halide, a hydroxyl or a thiol and one of $R_3$ or $R_5$ is a hydrogen atom. In one embodiment, $R_2$ is an amine. In one embodiment, x+y is at least 2. In one embodiment, x+y is at least 3. In one embodiment, the hydroxyls of the phenyl moiety are positioned at the 3 and 4 positions of the phenyl group relative to the side chain.

In one embodiment, Formula I forms a polymeric coat on the substrate surface. In one embodiment, the surface-modifying agent is selected from the group consisting of 3,4-dihydroxy-L-phenylalanine (DOPA), 3,4-dihydroxyphenylalanine methyl ester, dopamine, norepinephrine, epinephrine and salts thereof. In one embodiment, the solution is aqueous and x+y ranges from 1 to 6.

In one embodiment, the invention relates to a method of modifying a substrate surface to provide a desired functionality, the method comprising contacting at least a portion of the substrate surface with an alkaline, aqueous solution under oxidative conditions, the solution comprising a surface-modifying agent according to Formula I:

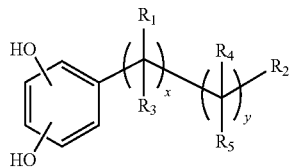

wherein each of $R_1$, $R_2$, $R_3$, $R_4$ and $R_5$ is independently selected from the group consisting of a thiol, a primary amine, a secondary amine, a nitrile, an aldehyde, an imidazole, an azide, a halide, a polyhexamethylene dithiocarbonate, a hydrogen, a hydroxyl, a carboxylic acid, an aldehyde, a carboxylic ester or a carboxamide, provided at least one of $R_1$, $R_2$, $R_3$, $R_4$ and $R_5$ is not a hydrogen atom; wherein x ranges from 0 to 10 and wherein y ranges from 0 to 10, provided that x or y is at least 1; and wherein the substrate surface is modified; and contacting the surface-modified substrate with a reactive moiety, wherein the reactive moiety reacts with and is bound to the modified surface. In one embodiment, the reactive moiety comprises a nucleophiles, such as a metal.

In one embodiment, the invention relates to a method of reducing amounts of metal in a fluid comprising the steps of contacting at least a portion of a substrate with an alkaline, aqueous solution under oxidative conditions, the solution comprising a SMA according to Formula I:

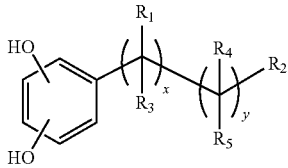

wherein each of $R_1$, $R_2$, $R_3$, $R_4$ and $R_5$ is independently selected from the group consisting of a thiol, a primary amine, a secondary amine, a nitrile, an aldehyde, an imidazole, an azide, a halide, a polyhexamethylene dithiocarbonate, a hydrogen, a hydroxyl, a carboxylic acid, an aldehyde, a carboxylic ester or a carboxamide, provided at least one of $R_1$, $R_2$, $R_3$, $R_4$ and $R_5$ is not a hydrogen atom; wherein x ranges from 0 to 10 and wherein y ranges from 0 to 10, provided that x or y is at least 1; contacting the surface-modified substrate with a reactive moiety, wherein the reactive moiety reacts with and is bound to the modified surface; and positioning the surface in a fluid with metal, whereby the modified surface binds at least a portion of the metal. In one embodiment, the reactive moiety is a metal.

In one embodiment, the invention relates to a method of modifying a substrate surface to form a biofouling-resistant, modified substrate, the method comprising the steps of contacting at least a portion of the substrate surface with an alkaline solution under oxidative conditions, the solution comprising a SMA according to Formula I:

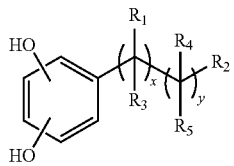

wherein each of $R_1$, $R_2$, $R_3$, $R_4$ and $R_5$ is independently selected from the group consisting of a thiol, a primary amine, a secondary amine, a nitrile, an aldehyde, an imidazole, an azide, a halide, a polyhexamethylene dithiocarbonate, a hydrogen, a hydroxyl, a carboxylic acid, an aldehyde, a carboxylic ester or a carboxamide, provided at least one of $R_1$, $R_2$, $R_3$, $R_4$ and $R_5$ is not a hydrogen atom; wherein x ranges from 0 to 10 and wherein y ranges from 0 to 10, provided that x or y is at least 1; and contacting at least a portion of the surface-modified substrate with a biofouling-resistant reactive moiety, wherein a biofouling-resistant, modified substrate surface is formed.

In one embodiment, the biofouling-resistant reactive moiety is selected from the group consisting of thiols, primary amines, secondary amines, nitriles, aldehydes, imidazoles, azides, halides, polyhexamethylene dithiocarbonate, hydrogen, hydroxyls, carboxylic acids, aldehydes, carboxylic esters or carboxamides. In one embodiment, the modified substrate surface is part of a medical device.

In one embodiment, the invention relates to a kit for modifying a substrate surface, the kit comprising a SMA according to Formula I:

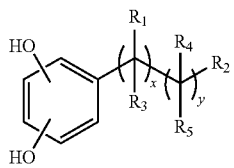

wherein each of $R_1$, $R_2$, $R_3$, $R_4$ and $R_5$ is independently selected from the group consisting of a thiol, a primary amine, a secondary amine, a nitrile, an aldehyde, an imidazole, an azide, a halide, a polyhexamethylene dithiocarbonate, a hydrogen, a hydroxyl, a carboxylic acid, an aldehyde, a carboxylic ester or a carboxamide, provided at least one of $R_1$, $R_2$, $R_3$, $R_4$ and $R_5$ is not a hydrogen atom; wherein x ranges from 0 to 10 and wherein y ranges from 0 to 10, provided that x or y is at least 1; and instructions for use.

In one embodiment, the kit further comprises a reactive moiety selected from the group consisting of thiols, primary amines, secondary amines, nitriles, aldehydes, imidazoles, azides, halides, polyhexamethylene dithiocarbonate, hydrogen, hydroxyls, carboxylic acids, aldehydes, carboxylic esters or carboxamides and a substrate surface to be modified. In one embodiment, the surface-modifying agent is in solution, while in other embodiments the surface-modifying agent is in powdered form.

These embodiments are described in more detail below.

II. Surface-Modifying Agents (SMAs)

In a preferred embodiment, the substrate surface is modified by contacting at least a portion of the substrate with a dilute, alkaline solution under oxidizing conditions, the solution comprising a SMA according to Formula I:

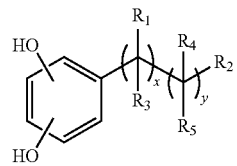

wherein each of $R_1$, $R_2$, $R_3$, $R_4$ and $R_5$ is independently selected from the group consisting of a thiol, a primary amine, a secondary amine, a nitrile, an aldehyde, an imidazole, an azide, a halide, a polyhexamethylene dithiocarbonate, a hydrogen, a hydroxyl, a carboxylic acid, an aldehyde, a carboxylic ester or a carboxamide, provided at least one of $R_1$, $R_2$, $R_3$, $R_4$ and $R_5$ is not a hydrogen atom; wherein x ranges from 0 to 10 and wherein y ranges from 0 to 10, provided that x or y is at least 1; and wherein the substrate surface is modified.

Dopamine.

In another preferred embodiment, the substrate surface is modified by contacting at least a portion of the substrate with a SMA wherein the SMA is dopamine or dopamine salts:

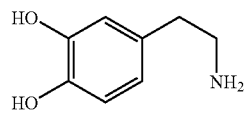

Figure 2A:
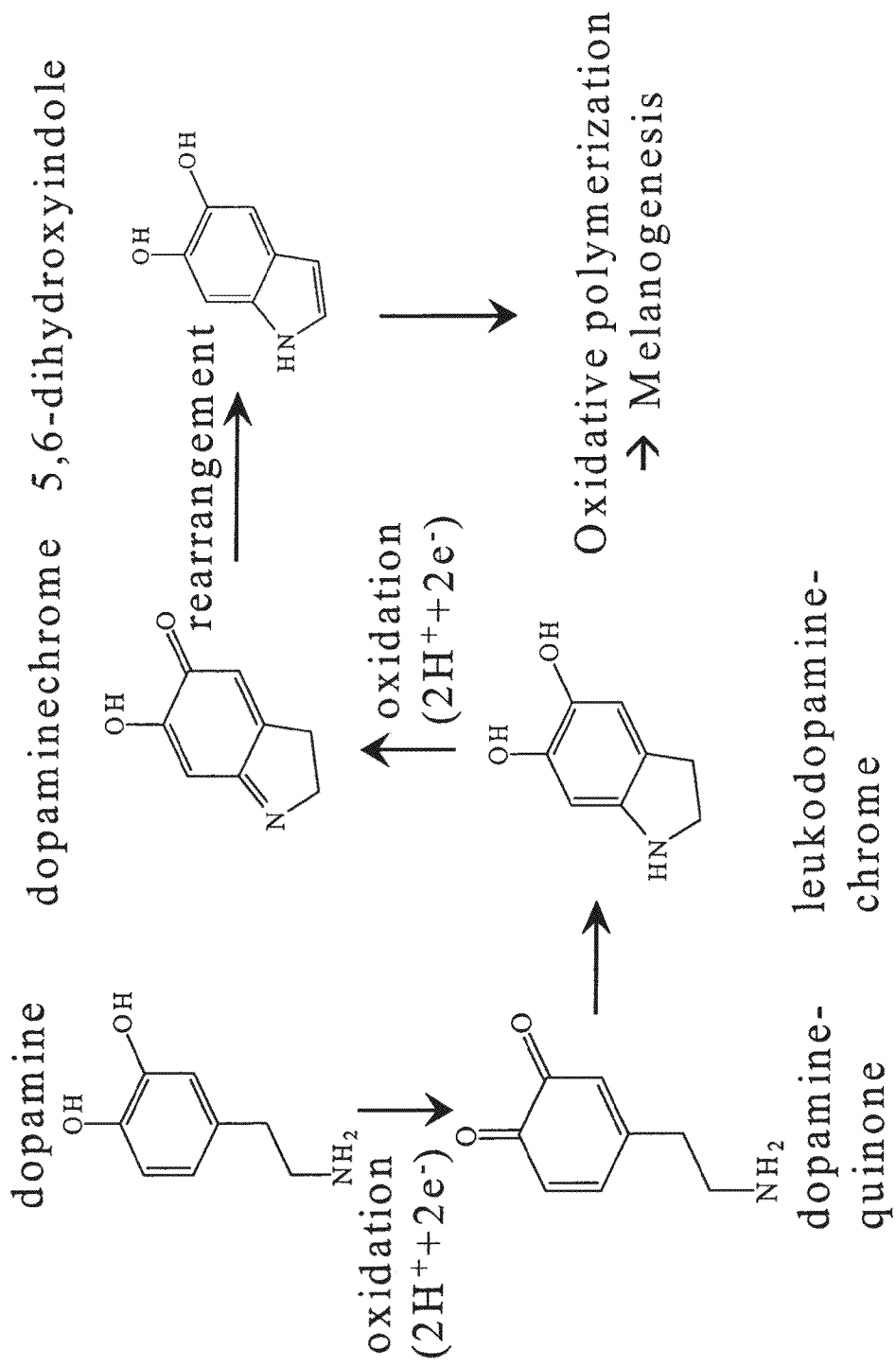
FIG. 2. Reaction schemes I (A) and II (B) of dopamine oxidation.
Figure 2B:
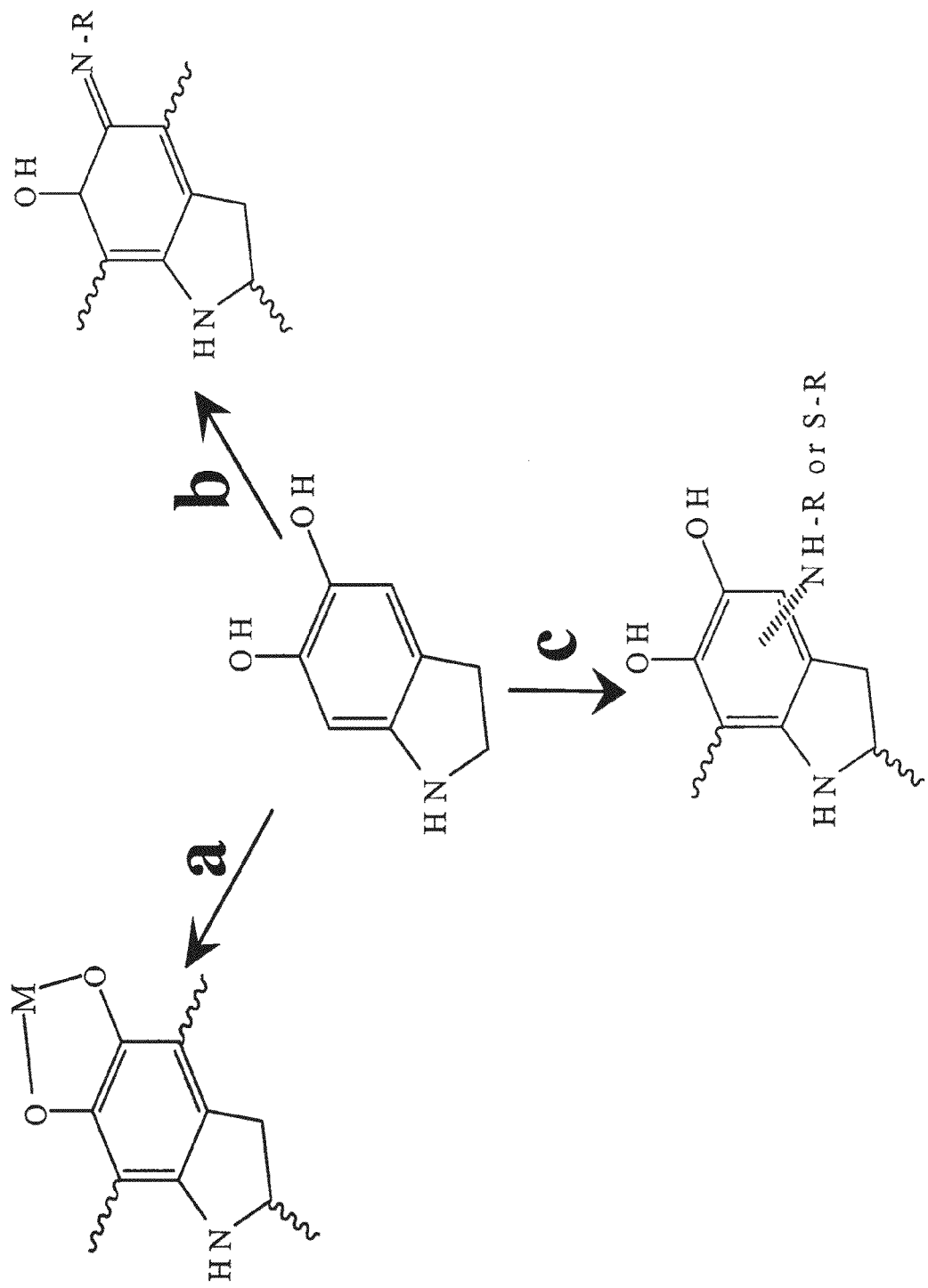

Substrates treated with dopamine are reactive with organic heteroatoms such as amine and thiol groups by Schiff base or Michael addition reactions (pathway "b," "c" reaction sequence II—FIG. 2B) and also strongly binds to various metals such as Fe, Cu, Hg, and Zn (pathway "a" of reaction sequence II—FIG. 2B). Thus our new concept of surface-independent, surface-modifying chemistry emerges: the self-polymerized multilayer nanofilm of dopamine provides multi-functionality due to chemical reactions or metal bindings at a top layer of a solid-liquid or solid-vapor interface whereas the bottom layer is attached to versatile organic and inorganic substrates. These very unique; current interface modifiers require chemical synthesis incorporating chemical orthogonality at each end.

In one preferred embodiment dopamine is used. When a substrate is contacted with dopamine, an adherent polydopamine polymeric film is coated on the substrate. Dopamine oxidation chemistry may be summarized by reaction sequence (I) in FIG. 2A. There, dopamine's dihydroxyl groups are deprotonated under oxidative conditions (neutral or alkaline), becoming dopamine-quinone. Rearrangement results in intra-molecular cyclization which reproduces dihydroxyl groups from quinone.

The second oxidation generates dopamine-chrome which quickly rearranges to form a stable phenyl ring structure creating an additional double bond in the 5-membered ring (5,6-dihydroxyindole). The third oxidation starts inter-molecular cross-linking due to the full unsaturated nature of indole forming polymer both in solution and on the substrate. Norepinephrine.

In another preferred embodiment, the substrate surface is modified by contacting at least a portion of the substrate with a SMA wherein the SMA is norepinephrine or norepinephrine salts:

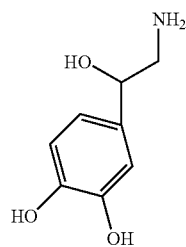

Norepinephrine is a neurotransmitter found in the brain which has an additional hydroxyl group in the carbon spacer of dopamine.

Other preferred SMAs include 3,4-dihydroxy-L-phenylalanine (DOPA), 3,4-dihydroxy-L-phenylalanine methyl ester, epinephrine and salts thereof.

The alkaline solution of SMA of the present invention can also include additives such as fillers, pigments, wetting agents, viscosity modifiers, stabilizers, anti-oxidants or cross-linking agents. The SMA can be cross-linked if desired. If desired, the SMA solution can include various adjuvants such as small particle fillers, surface active agents, UV absorbers, photo-initiators, colorants and indicators.

The surface-independent, surface-modification method of the present invention comprises contacting at least a portion of the substrate surface with a SMA under oxidative conditions to form a surface-modified substrate surface having at least one reactive moiety on the substrate's surface. The method comprises contacting at least a portion of the substrate with an alkaline solution under oxidizing conditions, the solution comprising a SMA according to Formula I:

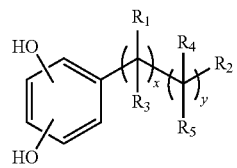

wherein each of $R_1$, $R_2$, $R_3$, $R_4$ and $R_5$ is independently selected from the group consisting of a thiol, a primary amine, a secondary amine, a nitrile, an aldehyde, an imidazole, an azide, a halide, a polyhexamethylene dithiocarbonate, a hydrogen, a hydroxyl, a carboxylic acid, an aldehyde, a carboxylic ester or a carboxamide, provided at least one of $R_1$, $R_2$, $R_3$, $R_4$ and $R_5$ is not a hydrogen atom; wherein x ranges from 0 to 10 and wherein y ranges from 0 to 10, provided that x or y is at least 1; and wherein the substrate surface is modified.

By "dilute," we mean that the concentration of SMA is 0.01 mg/ml-100 mg/ml, preferably ranging from about 0.05 mg/ml or higher.

By "alkaline," we mean that the pH value of the solution ranges from 7.1 to 12, with a preferred pH ranging from 7.5 to 10, with a further preferred pH ranging from 7.5 to 8.5. An alkaline solution triggers polymerization of SMAs onto the substrate surface.

By "solution," we mean both aqueous and non-aqueous solvents, including miscible solutions of water and organic solvents such as acetone, chloroform, dichloromethane, methanol, ethanol, isopropanol, dimethylformamide, dimethylsulfoxide and hexane. Preferably, the solution is made just prior to contacting the substrate, although the solution may be stored for at least brief periods of time before use.

By "under oxidative conditions," we mean alkaline pH of aqueous solutions and non-aqueous solvents with dissolved oxygen or organic bases such as triethylamine. In alternative embodiments, solutions comprising oxidants such as hydrogen peroxide, sodium periodate, tertiary butylhydroperoxide, organic peroxides, quinones including benzoquinones, napthoquinones, anthraquinones, nitroaryl compounds, metal oxidants including $Cu^{2+}$, $Fe^{3+}$, $Co^{3+}$ and $Mn^{3+}$, phenols, indoles, aminobenzenes and more can be used to initiate polymerization via oxidization of the SMA.

By "contacting," we mean exposing at least a portion of the substrate to the SMA for a period of time ranging from 1 minute to 24 hours and a range of temperatures from 0° C. to 100° C. In a preferred embodiment, the substrate is exposed to the SMA for a period of time ranging from 2 hrs to 18 hrs, preferably for 5 hrs to 15 hrs, even more preferably for 8 hrs to 12 hrs.

In a preferred embodiment the entire substrate is immersed or dipped in the SMA solution. The examples below illustrate preferred contacting methods. However, a variety of techniques can be employed to contact the substrate surface with the SMA solution including, without limitation, swabbing, dip coating, spin coating, die coating, ink jet coating, spraying, screen printing (e.g., rotary screen printing), gravure printing, photolithographic printing and flexographic printing, microcontact printing, nanolithography.

On contact, the substrate surface is preferably modified so as to provide a substrate surface having at least one reactive moiety. In a preferred embodiment, the reactive moiety comprises a smooth, continuous polymeric coating on the substrate surface, the polymeric coating having a substantially constant thickness. As a general guide, the polymeric coating exists on the substrate surface in a thickness ranging from about 1 to 1000 nm, preferably ranging from about 1 to 100 nm, more preferably ranging from about 5 to 50 nm, and even more preferably ranging from about 10 to 50 nm.

IV. Substrates

The method comprises contacting at least a portion of the substrate with the SMA described above.

By "substrate," we mean any inorganic or organic substrate. For instance, the substrate can be an organic solid, an inorganic solid, or a combination of organic and inorganic solids that provides a surface for receiving the adherent polymer. Suitable organic or inorganic substrates may also be fibrous, filamentous, meshes, porous or solvent-swollen (e.g. hydrogel or organogel) objects. Preferably, care is taken when selecting the substrate so that there will be an adequate degree of adhesion between the substrate and the SMA.

Suitable inorganic substrates include but are not limited to inorganic substrates such as quartz, glass, silica and other oxides or ceramics such as alumina, indium tin oxide, lithium tantalate (LiTaO3), lithium niobate (LiNbO3), gallium arsenide (GaAs), silicon carbide (SiC), langasite (LGS), zinc oxide (ZnO), aluminum nitride (AlN), aluminum oxide ($Al_2O_3$), silicon (Si), silicon nitride (Si3N4), and lead zirconium titanate ("PZT"), titanium oxide ($TiO_2$), niobium oxide ($Nb_2O_5$); and metals or alloys such as aluminum, copper, gold, silver and steel. Other suitable inorganic substrates include, without limitation, mica, diamond and nickel titanium (NiTi).

Suitable organic substrates include but are not limited to organic substrates such as thermoplastics including polyesters (e.g., polyethylene terephthalate or polyethylene naphthalates), polyacrylates (e.g., polymethyl methacrylate or "PMMA"), poly(vinyl acetate) ("PVAC"), poly(vinylbutyral) ("PVB"), poly(ethyl acrylate) ("PEA"), poly(diphenoxyphosphazene) ("PDPP"), polycarbonate ("PC"), polypropylene ("PP"), high density polyethylene ("HDPE"), low density polyethylene ("LDPE"), polysulfone ("PS"), polyether sulfone ("PES"), polyurethane ("PUR"), polyamide ("PA"), poly(dimethylsiloxane) ("PDMS"), polyvinyl chloride ("PVC"), polyvinylidene fluoride ("PVdF"), polystyrene ("PSy") and polyethylene sulfide; and thermoset plastics such as cellulose derivatives, polyimide, polyimide benzoxazole and polybenzoxazole. Other suitable organic substrates include, without limitation, graphite, carbon nanotubes, fullerenes, graphene, poly(glycolic acid), poly(lactic acid), and poly(lactic-co-glycolic acid) and Teflon®.

Untreated Substrates.

The method of the present invention can be used on substrates in any condition (see Examples 2 and 3). For instance, substrates having existing coatings such as paint, oil, grease, protectants and the like can be used without any additional pre-treatments or cleaning.

Pre-Treated Substrates.

In another embodiment, the substrate can instead or in addition to be pretreated to enhance surface-modification. Preferred pretreatments include but are not limited to electron and ion beam irradiation, electrical discharge in the presence of a suitable reactive or non-reactive atmosphere (e.g., plasma, glow discharge, corona discharge, dielectric barrier discharge or atmospheric pressure discharge); chemical pretreatment (e.g., with a low solids solution of polyvinylidene dichloride or with a solvent-borne mixture of a polyester resin and an aziridine cross-linker); flame pretreatment; ultraviolet light pretreatment with or without ozone pretreatment; and incorporating functional polymers into the substrate when a polymeric substrate is employed. In an alternative embodiment, the present invention provides a method of enhancing coatings on artificially or naturally damaged/altered substrates.

V. Reactive Moiety

The surface-independent, surface-modifying biocoating of the present invention provides an amazingly versatile platform for secondary reactions, allowing one to tailor specific reactive moieties to substrates for diverse functional uses. For instance, the SMA-treated substrates of the present invention are conformal and chemically reactive with a wide variety of organic and inorganic species such as metal ions, thiols, primary amines, secondary amines, nitriles, aldehydes, imidazoles, azides, halides, polyhexamethylene dithiocarbonate, hydrogen, hydroxyls, carboxylic acids, aldehydes, carboxylic esters or carboxamides. Thus, secondary reactions between the SMA-treated substrates and such reactive moieties can be exploited to impart specific functionalities to the surface-modified substrate.

The oxidative pathways for adding the secondary reactions are set forth in reaction sequence II in FIG. 2B. There, pathway 'a' represents various metal bindings of dopamine. The metal 'M' can be titanium (Ti), iron (Fe), copper (Cu), zinc (Zn), silver (Ag), or many others. Pathway 'b' is Schiff base and 'c' is Michael addition reactions which were used for the interfacial reactions with PEG-amine, PEG-thiol, and proteins (flagella).

Current applications for SMA-treated substrates having a reactive moiety are many and include, without limitation, applications for anti-biofouling surfaces; medical devices for catheters, stents, artificial bones, teeth, and dialysis tubes; semiconductors for bio-MEMS, and sensors; and metal nanoparticles and quantum dots for sensors, diagnostics, and cellular imaging.

Thus, in an alternate embodiment of the invention, a method of applying a reactive moiety to a SMA-treated substrate is provided. The method comprises contacting at least a portion of a substrate with an alkaline solution under oxidizing conditions, the solution comprising a SMA to form a substrate having a modified surface and then contacting the SMA-treated substrate with a reactive moiety to form a functional ad-layer on the SMA-treated substrate.

By "reactive moiety" we mean to include any reactive moiety including metals, nucleophiles and polymers. Specifically, we include thiols, primary amines, secondary amines, nitriles, aldehydes, imidazoles, azides, halides, polyhexamethylene dithiocarbonate, hydrogen, hydroxyls, carboxylic acids, aldehydes, carboxylic esters or carboxamides.

By "ad-layer" we mean an additional layer of reactive compounds which binds to the modified surface of the SMA-treated substrate and alters the functionality of the substrate.

Electroless Metallization.

In this embodiment, one would preferably treat a surface with an SMA as described above and then expose the treated surface to metal solutions to form an adherent metal film. Example 5, below, describes the dip-coating of an SMA-treated substrate in a silver nitrate and copper (II) chloride solution. In general, one would wish to expose the SMA-treated substrate to a solution of 10-500 mM metal, pH 3-8, and 20-70° C.

Nucleophile Addition.

In this embodiment, one would preferably contact a substrate with an SMA as described above and then expose the SMA-treated substrate to nucleophile. By "nucleophile" we mean an electron-rich species with a tendency to be attracted to the nuclear charge of an electron-poor species, the electrophile. Important nucleophiles include primary and secondary amines, thiols, azides, nitriles, aldehydes, imidazoles, azides, polyhexamethylene dithiocarbonate, hydrogen, hydroxyls, carboxylic acids, aldehydes, carboxylic esters or carboxamides, etc.

A partial list of important nucleophiles can be seen in Table 1:

TABLE 1

| Cl$^-$ | Br$^-$ | I$^-$ | |
|---|---|---|---|
| | HO$^-$ | *R—OH | *RO$^-$ |
| H$_2$S | HS$^-$ | *R—SH | *R—S$^-$ |
| —NH$_2$ | N$_3^-$ | $^-$C≡N | *R—C≡C$^-$ |

*R can be anything.

Suitable nucleophiles may comprise parts of more complex molecules, such as proteins or nucleic acids. For instance, Example 9 describes labeling surfaces with flagella. Example 10 describes fibroblast adhesion to surfaces, Example 11 describes adding hyaluronic acid to surfaces and Example 13 describes addition of histidine to surfaces. In general, macromolecules containing the nucleophiles described above react to SMA-treated substrates.

Polymer Grafting.

In this embodiment, one would preferably contact a substrate with an SMA as described above and then expose the SMA-treated substrate to polymers including any synthetic polymers that contain nucleophiles as described above. For example, in the case of poly(ethylene glycol) (PEG), NH$_2$-PEG-NH$_2$, methoxy-PEG-NH$_2$, methoxy-PEG-SH, SH-PEG-SH, branched-PEG-NH2, and branched-PEG-SH are the polymer structures reacting to SMA-treated surfaces. For instance, Example 8 describes grafting PEG to SMA-treated surfaces. However, alternative forms of polymeric grafting are also envisioned, including free radical graft polymerization, atom-transfer radical polymerization, plasma polymerization/deposition, plasma treatment and surface irradiation, and cationic and anionic monomer or oligomer additions.

Metal Scavenging.

In this embodiment, the amount of metal ions in a fluid can be reduced by binding to SMA-treated substrates. By "reducing" we mean any reduction in the amount of metal ions in solution, preferably to below maximum contaminant levels (MCL) or other established benchmarks for all metals. The method comprises contacting at least a portion of a substrate with an alkaline, aqueous solution comprising Formula I. One then positions the surface-modified substrate in a solution with metal, whereby the surface-modified substrate reduces the amount of metal in the solution. The method can be performed in either flow-through or batch mode. See Example 12 below for a preferred example.

VI. Kits

In an alternate embodiment of the invention, a kit for modifying a substrate's surface is provided. In one embodiment, the kit comprises a dilute, alkaline solution comprising a SMA according to Formula I, and, optionally, a substrate to be modified, and instructions for use. In a preferred embodiment, the kit comprises a powdered form of at least one SMA, wherein the powdered SMA is hydrated by the user and for immediate contacting with the substrate. For example, dopamine powder can be provided for dissolving in a provided alkaline solution.

In an alternate embodiment, the kit comprises an SMA formulated, delivered and stored as a liquid in a nonoxidizing condition, for example at a low pH. In this case the user would neutralize the liquid SMA to pH>7 for subsequent contacting with the substrate. For example, dopamine dissolved in acidic water can be provided for users to add base (NaOH) and substrates for coating.

In another alternative embodiment, a reactive moiety is also included, wherein a user can modify the SMA-treated substrate to include a reactive moiety.

By "substrate" we mean any substrate described above, including any substrate wherein having at least one reactive moiety on the surface would be useful.

By "instructions for use" we mean a publication, a recording, a diagram, or any other medium of expression which is used to communicate the usefulness of the invention for one of the purposes set forth herein. The instructional material of the kit can, for example, be affixed to a container which contains the present invention or be shipped together with a container which contains the invention. Alternatively, the instructional material can be shipped separately from the container or provided on an electronically accessible form on a internet website with the intention that the instructional material and the SMA solution and substrate be used cooperatively by the recipient.

VII. Applications for SMA-Treated Substrates

Photolithography.

SMA-treated substrates can be used for subsequent photolithography micropatterning and photoresist etching. Photolithography is a process used to selectively apply very precise geometric patterns onto substrates. Typically only very clean, flat substrates can be used for photolithography. However, SMA-treated substrates allow virtually any substrate to be modified for use with photolithography, greatly expanding the types of materials which can be used in applications requiring very small, very precise patterns including drug delivery carriers, micro- and nano-wires for photonics, peptide arrays, protein arrays, oligonucleotide arrays, electronic circuitry and integrated electronic chips, electronic displays and the like.

SMA-Assisted Electroless Metallization.

SMA-treated substrates can be used to accept adherent and uniform metal coatings by electroless metallization. Metals are often used as synthetic catalysts for chemical reactions with accelerated turn-over rates, such as platinum catalysts used to facilitate reactions of aromatic conversion or branched isomers from straight alkane chains. Copper layers on substrates such as metals, semiconductors, and polymers are important for various electronic and packaging technologies, particularly in copper deposition on synthetic organic substrates for flexible printed circuit, electromagnetic interference shielding of display panels, and multichip module packing. However, current approaches can be applied for only one or a few types of substrates and often involve complicated multi-step procedures. The present invention therefore describes a method of modifying the surface of any substrate to include a metal coating for use as, among other things, synthetic catalysts, semiconductors, display panels, surface-metallization of cantilever- or beam-based sensor devices, and carbon nanotubes.

Further, SMA-treated substrates can be used to accept electroless metal deposition combined with conventional lithography processes to yield micropatterned metal-deposition on SMA-treated substrates. This provides an aqueous, cost-effective and surface-independent preparation process that does not require toxic Pd/Sn colloids for catalysis, yielding substrates useful in, for example, electronic circuit fabrication.

Biofouling.

SMA-treated substrates can be used to provide biofouling-resistant substrate for use in medical and dental devices and implants, watercraft hulls, off-shore and on-shore structures of manmade or natural composition, water treatment facilities, liquid handling or movement structures such as pipelines and chemical treatment facilities, food processing surfaces, and construction and housing materials. By "biofouling" we mean the nonspecific adsorptions of macromolecules, cells, proteins, bacteria, algae and other organisms and their byproducts at solid-liquid or solid-air interfaces, often resulting in adverse effects on performance, safety, and longevity of, for instance, medical devices and sensors. By "resistant" we mean substrates modified so as to prevent the nonspecific adsorptions of macromolecules, cells, proteins, bacteria, algae and other organisms and their byproducts at solid-liquid or solid-air interfaces associated with biofouling. Currently, surface immobilization of polyethylene glycol (PEG or PEGylation) has been the most popular approach for non-fouling surface preparation, but anchoring PEG molecules in a surface independent manner remains a major challenge.

Biosensors.

SMA-treated substrates can be used to immobilize proteins and DNA on substrates for use in diagnosis, therapy of disease and experimental tools for research in tissue and cellular proteomics and genomics. Immobilizing proteins and DNAs on substrates has revolutionized throughput of medical diagnostics and biological research for library screening and gene expressions. So called protein and DNA chips require chemical conjugations of biomacromolecules (DNA and proteins) onto substrates. Glass has dominated in this area due to its optical transparency and low cost. However, efforts have been made to develop bioconjugate chemistry onto portable substrates such as paper for convenient diagnostic purposes. Thus the versatile SMA-treated substrates and method thereof presented herein can be applied to develop portable diagnostic kits including biosensors, functional genomics, proteomics, and metabolomics, or hospital/clinic-base diagnostic devices or their components.

Self-Assembled Monolayers.

Figure 5A:
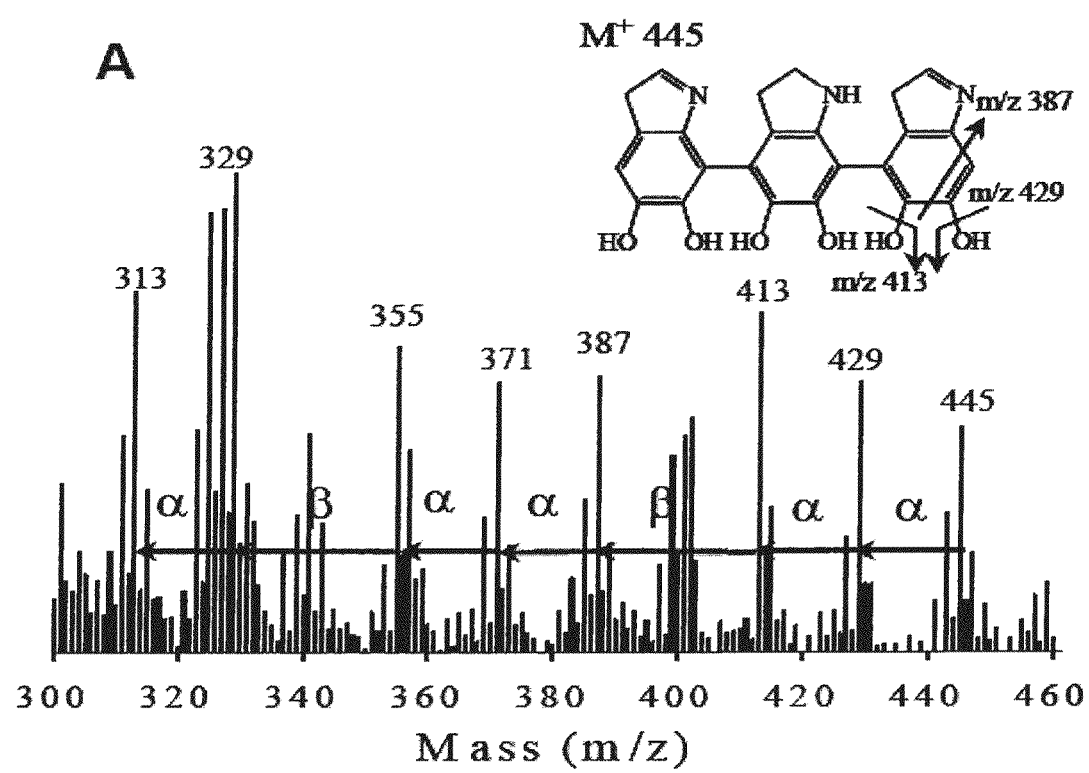
FIG. 5A. ToF-SIMS spectra of polydopamine-coated glass. The mass spectrum showed a trimer of 5,6-dihydroxyindole, possibly fragmented from a long-chain polymer of similar composition. The characteristic pattern of fragmentation suggests liberation of two hydroxyl groups and a portion of the phenyl group, identifying each subunit as derived from dopamine polymerization.
Figure 5B:
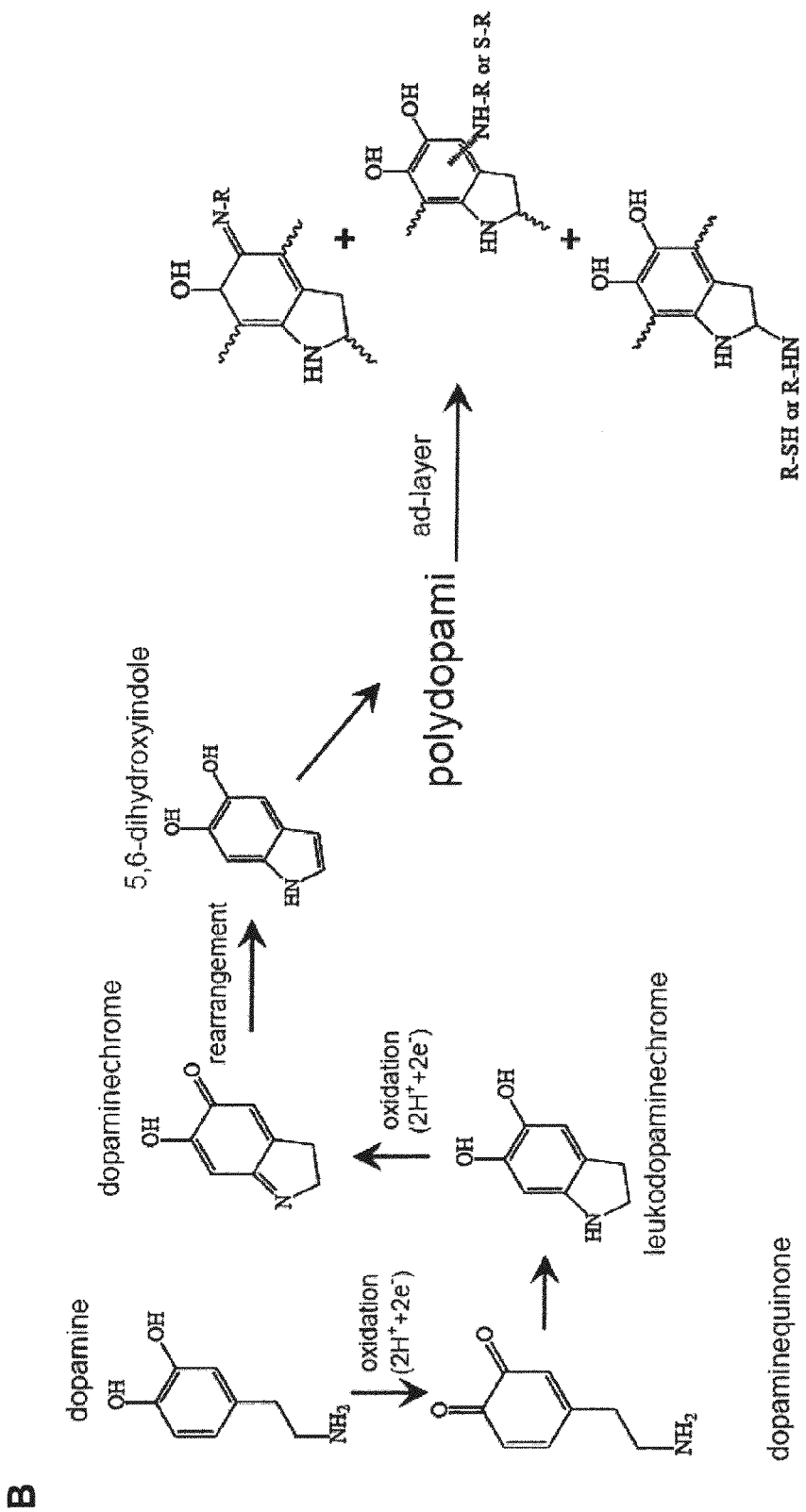
FIG. 5B. Possible structural evolution and polymerization mechanisms of dopamine, as well as suggested reaction mechanisms for organic ad-layer formation on polydopamine-coated substrates. Under an oxidative condition (e.g. alkaline pH, oxidants, etc.) dihydroxy group protons in dopamine are deprotonated, becoming dopamine-quinone, which subsequently rearranges via intramolecular cyclization to leukodopaminechrome. Further oxidation and rearrangement leads to 5,6 dihydroxyindole, whose further oxidation causes inter-molecular cross-linking to yield a polymer that is structurally similar to the bio-pigment melanin. The polydopamine-coated substrate subsequently reacts with a variety of molecules via Shiff-base (top) and Michael addition chemistries.
Figure 13:
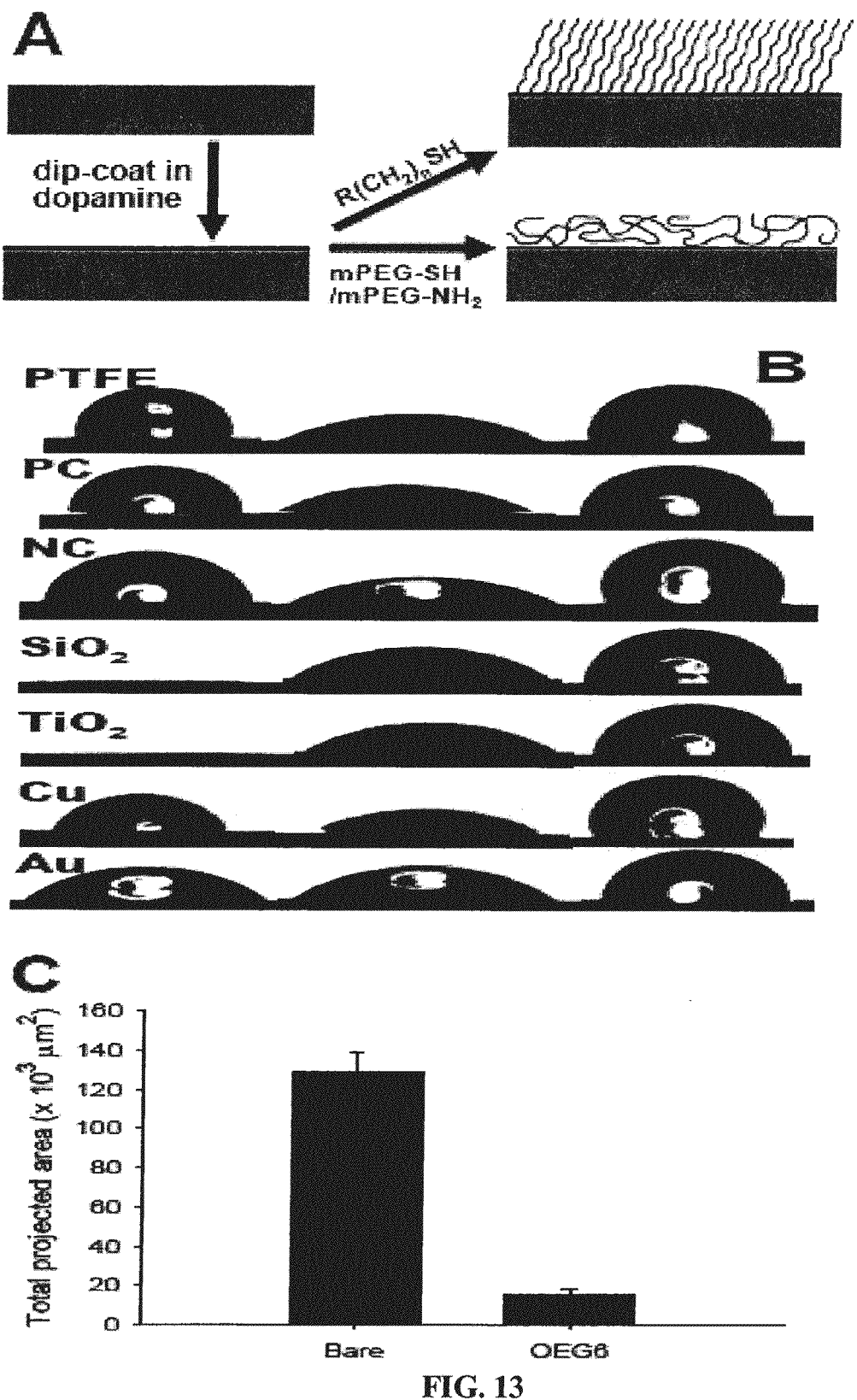
FIG. 13. Polydopamine-assisted grafting of various organic molecules onto polydopamine-coated substrates.
Figure 13:
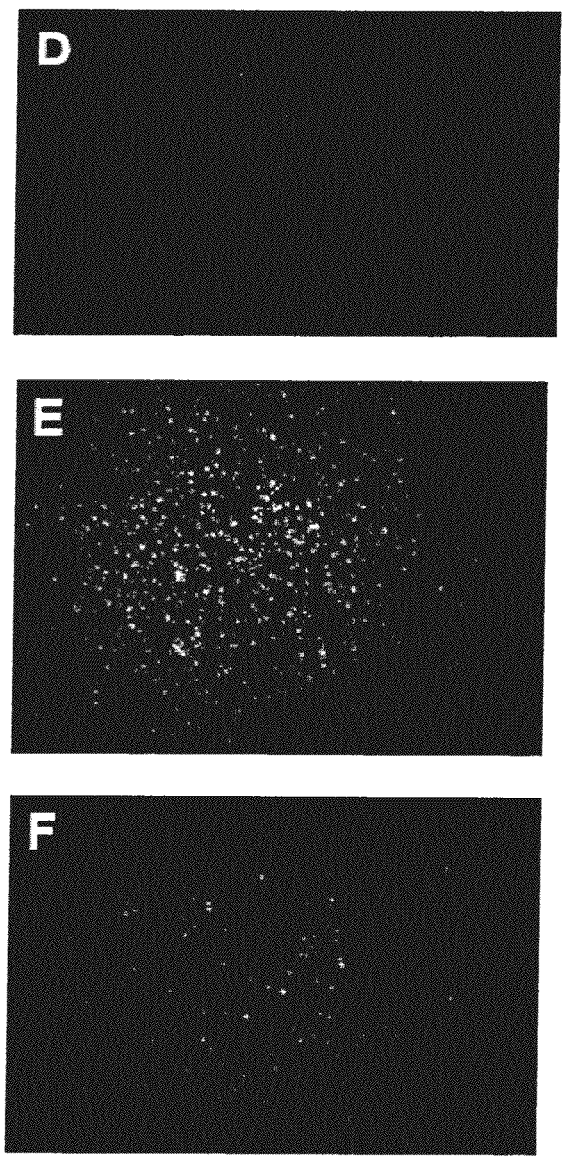

SMA-treated substrates can be used to support a variety of reactions with organic species for creating functional organic ad-layers. For example, under oxidizing conditions, catechols react with thiols and amines via Michael addition or Schiff base reactions (FIG. 5B). Thus, immersing SMA-treated substrates into a thiol- or amine-containing solution provides a convenient route to organic ad-layer deposition through thiol- and amine-catechol adduct formation (FIG. 13A). The following examples demonstrate methods for depositing organic ad-layers in the form of alkanethiol monolayers, synthetic polymers, and biopolymer coatings.

Polymeric Grafting.

SMA-treated substrates can be used to support polymeric ad-layers, including PEG, hyalurinic acid (HA), polyethylenimine, heparine, chitosan, or any other moiety described above. For example, PEG-grafted, SMA-treated substrates can be used for fouling-resistant substrates, and HA-immobilized surface is useful in hematopoietic cell cultures. Polymer ad-layers were grafted onto SMA-treated substrates in a method according to the present invention, wherein the secondary reactive moiety comprises thiol- or amine-functionalized polymers, thus yielding bioresistant and/or biointeractive substrates. Alternative forms of polymeric grafting are also envisioned, including free radical graft polymerization, atom-transfer radical polymerization, plasma polymerization/deposition, plasma treatment and surface irradiation, and cationic and anionic monomer or oligomer additions.

Protein Labeling.

SMA-treated substrates can be used to support protein ad-layers such as flagella, antibodies for diagnostic devices as well as therapeutic proteins and peptides for therapeutic purposes. For instance, flagella-labeled substrates are useful in chemotaxis and cellular network studies. Currently, the only approach for single flagella-labeling has been the physical adsorption of flagella antibody on micro-bead substrates and subsequent incubation in the presence of bacteria. By taking advantage of the chemical reactivity of SMA-treated substrates to flagella proteins, a general route for bacteria-independent flagella labeling is proposed, thereby providing a useful labeling technique for research in areas such as food science, bacterial chemotaxis, internal (stomach and intestine) medicine.

Biofouling.

The present invention surprisingly provides surface treatments that reduce or eliminate marine biofouling of various surfaces. A surface that is to be contacted with the marine environment can be easily treated with an mPEG-DOPA, as disclosed herein. The treated surface is thus rendered less susceptible to fouling of the surface.

The term "biofouling" is known in the art and refers to the attachment of an organism or organisms to a surface in contact with water for a period of time. There are several organisms that cause biofouling and many different types of surfaces affected by it. Biofouling occurs worldwide in various industries, from offshore oil and gas industries, to fishing equipment, to cooling systems. One of the most common biofouling sites is on the hulls of ships, where barnacles are often found. One problem of growth on a ship is the eventual corrosion of the hull, leading to the ship's deterioration. If left unattended, organic growth can increase the roughness of the hull, thereby decreasing its maneuverability and increasing drag. Drag increases a ship's fuel consumption and in turn has economic and environmental consequences, as increased fuel consumption leads to increased output of greenhouse gases. Economic losses are tremendous, as fuel accounts for up to 50% of marine transportation costs.

Biofouling is found everywhere. Parts of a ship other than the hull are affected as well: heat exchangers, water-cooling pipes, propellers, even the ballast water. Heating and cooling system biofouling might also be found in power stations or factories. Biofouling is a complex process that often begins with the production of a biofilm.

A biofilm is a film made of bacteria, such as *Thiobacilli* or other microorganisms that forms on a material when conditions are conducive for growth. Nutrient availability is an important factor as bacteria require dissolved organic carbon, humic substances and uronic acid for optimum biofilm growth. Biofilms do not have to contain living material; they may instead contain such once living material as dead bacteria and/or secretions. Bacteria are not the only organisms that can create this initial site of attachment (sometimes called the slime layer); diatoms, seaweed, and their secretions are also culprits. Coral reef diatoms' attachment depends on pH, and as in the Achnanthes and Stauronesis diatoms, the molecular structure of the organism.

The growth of a biofilm can progress to a point where it provides a foundation for the growth of seaweed, barnacles, and other organisms. In other words, microorganisms such as bacteria, diatoms, and algae form the primary slime film to which the macroorganisms such as mollusks, seasquirts, sponges, sea anemones, bryozoans, tube worms, polychaetes and barnacles attach.

Barnacles, encrusting bryozoans, mollusks, tube worms, and zebra mussels create a type of fouling known as calcareous (hard) fouling, while organisms such as algae, slimes and hydroids make up non-calcareous (soft) fouling.

The term "mPEG-DOPA" or "mPEG-DOPA polymer" is intended to include polymers prepared by the general process of described in detail in "Protein resistance of titanium oxide surfaces modified by biologically inspired mPEG-DOPA", Langmuir, 21, 640-646 (2005) by Dalsin et al. Briefly, mono-, di-, and tri-DOPA peptides (DOPA$_{1-3}$) were synthesized in solution from Boc/TBDMS-protected DOPA using standard carbodiimide chemistry. DOPA and DOPA peptides were deprotected and subsequently coupled to activated methoxy-PEG in the presence of 0.1 M sodium tetraborate buffer. The resulting polymer conjugate was characterized by MALDI-MS and $^1$H NMR.

As noted above, the mPEG-DOPA polymer can be applied to a surface in any manner known by a person skilled in the art. The substrate can be painted, sprayed, dipped, washed, etc. with the polymer. The polymer can be included in a paint or other suitable carrier used, for example, in the marine industry.

The term "paint" is known in the art and is intended to include any liquid, liquifiable, or mastic composition which after application to a substrate in a thin layer is converted to an opaque solid film. Typically, the opaque coating is prepared with a binder, liquids, additives, and pigments. The paint is applied in liquid form and upon drying provides a continuous film that protects and improves the appearance of the substrate.

Suitable carriers that can be used with the mPEG-DOPA polymers to treat a substrate include solvents or solvent systems that dissolve, suspend or emulsify the polymer in such a manner that the polymer can be applied to a substrate surface, thus effectively coating the substrate. After removal of the solvent(s), typically by drying, the mPEG-DOPA remains on the substrate.

Application of the mPEG-DOPA polymer to the substrate prevents, eliminates or, at a minimum, reduces the development of the growth of one or more organisms that result in biofouling of a surface.

The following paragraphs enumerated consecutively from 1 through 9 provide for various aspects of the present invention. In one embodiment, the present invention provides a method to decrease or prevent biofouling of a surface comprising the step of treating a surface with an mPEG-DOPA such that biofouling is decreased or prevented. The surface may be a ship hull, and the biofouling may be due to algae, diatoms or combinations thereof.

In one embodiment, the mPEG-DOPA has a formula comprising:

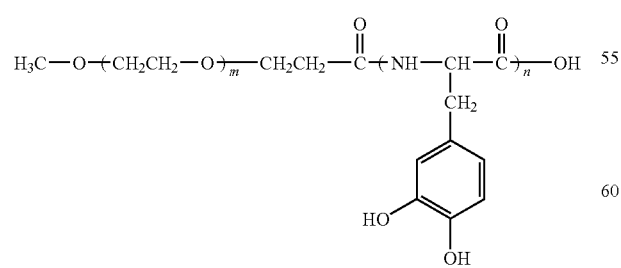

wherein n is an integer from 1 to about 100, in particular, 2 or 3; and m is between about 2 and about 300. In one embodiment, n is 1, 2 or 3.

In one embodiment, the mPEG-DOPA is

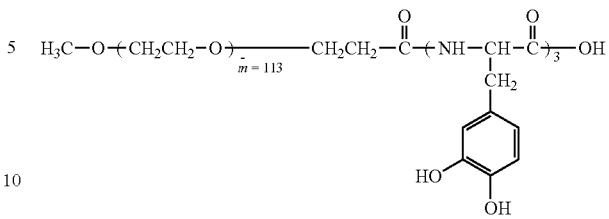

and may be provided in a carrier such as paint.

VIII. Examples

The invention will be further described with reference to the following non-limiting Examples. It will be apparent to those skilled in the art that many changes can be made in the embodiments described without departing from the scope of the present invention. Thus the scope of the present invention should not be limited to the embodiments described in this application, but only by embodiments described by the language of the claims and the equivalents of those embodiments. Unless otherwise indicated, all percentages are by weight.

The following examples describe various new and useful embodiments of the present invention. While the examples refer to substrates treated with dopamine, it is envisioned that any SMA according to Formula I will also be useful in the methods described herein.

General Methods and Materials.

Materials and substrate preparation. Platinum, silver, copper, and palladium (Alfa Aesar, Ward Hill, Mass.), sapphire ($Al_2O_3$, Rubicon Tech Inc. IL), quartz (MTI crystal, MA), stainless steel, NiTi, Si (MEMC electronics, Italy), Carbothane®, Tecoflex®, polycarbonate and polyethylene terephthalate (PET) (McMaster Carr Inc, Chicago, Ill.), poly(styrene) (Sigma), glass (Fischer scientific), polydimethysiloxane (PDMS, Sylgard 184, Dow corning), GaAs (University Wafer, Boston, Mass.), and silicon nitride (generous donation by Dr. Keun-Ho Kim and Prof. H. Espinosa, Northwestern University) were cleaned ultrasonically in 2-propanol for ten minutes before use. Titanium (20-50 nm) and gold (20 nm deposited onto 5 nm Ti) substrates were prepared by electron beam deposition (Edwards FL400, Boc Edwards, Sussex, UK) on Si-wafers. PDMS (Dow Corning) was prepared by mixing 10 parts of backbone and 1 part of curing agent and cured at 100° C. for 2 hrs.

Example 1

SMA Solution

As shown herein, simple immersion of virtually any substrate in a dilute alkaline aqueous solution of dopamine buffered to a pH typical of marine environments (pH>7.5) results in spontaneous deposition of a reactive moiety on the substrate surface. In the case of dopamine, the substrate surface forms a thin adherent polymer film (FIG. 1F-1H). Atomic force microscopy (AFM) indicated that the polymer film thickness was a function of the immersion time and reached a value of up to 50 nm after twenty-four hours (FIG. 1G). X-ray photoelectron spectroscopy (XPS) analysis of twenty-five diverse materials coated for three hours or more revealed the absence of signals unique to the substrate (solid bars, FIG.

Figure 3:
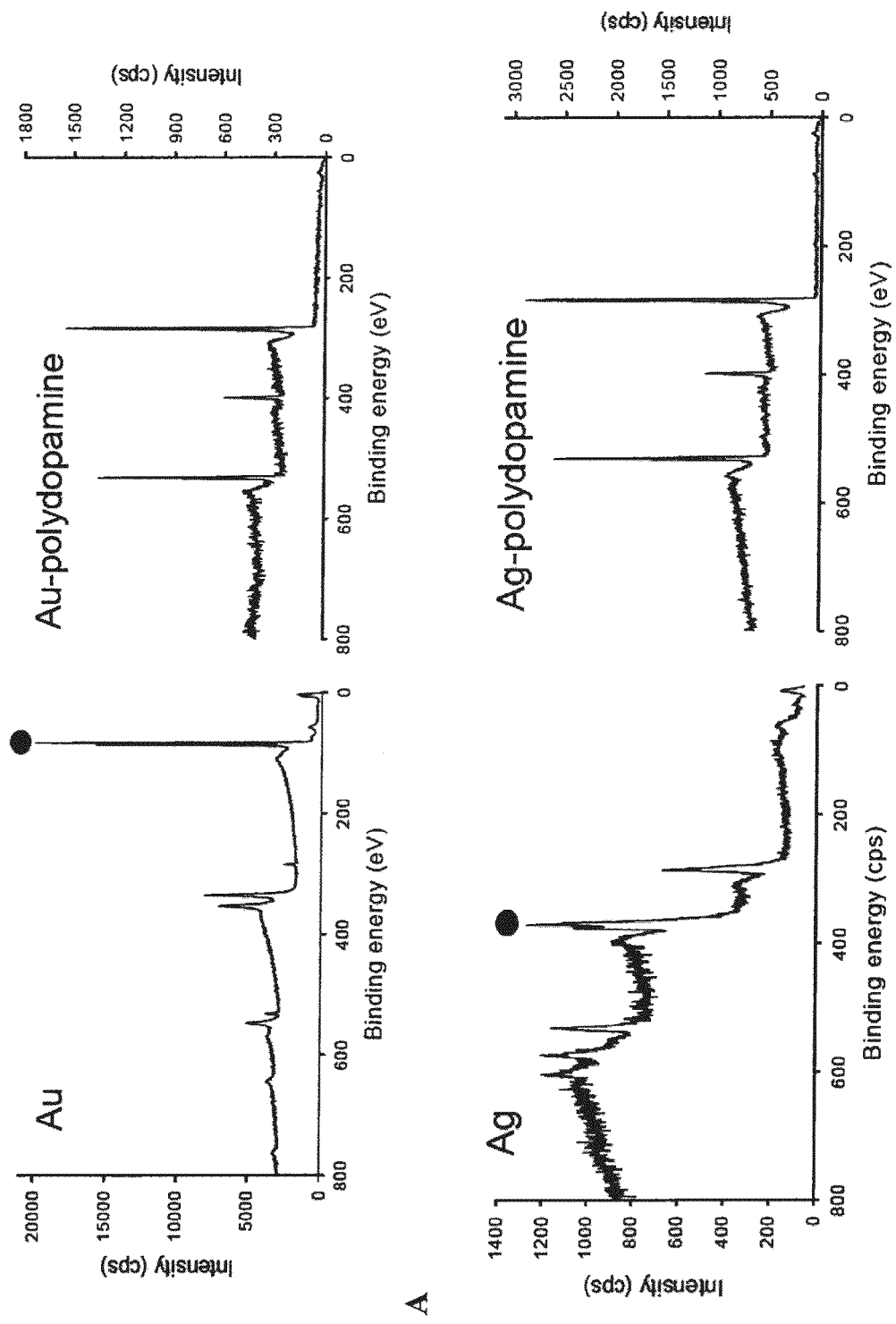
FIG. 3. X-ray Photoelectron Spectroscopy (XPS) characterization of polydopamine-coated substrates. XPS spectral changes of twenty-five substrates (A-Y) before (left column) and after (right column) polydopamine coating. The characteristic XPS substrate signals for unmodified substrates (left) were marked by filled circles, which were completely suppressed after polydopamine coating (right). Instead, carbon (~285 eV), nitrogen (399.5 eV), and oxygen (532.5 eV) photoelectron peaks (in order from low to high binding energy) were observed. The area ratio of nitrogen-to-carbon was determined for twenty-five different substrates, and those values are shown in FIG. 1H (circles). Substrate XPS peaks used in the experiments are summarized in Table 2.
Figure 3:
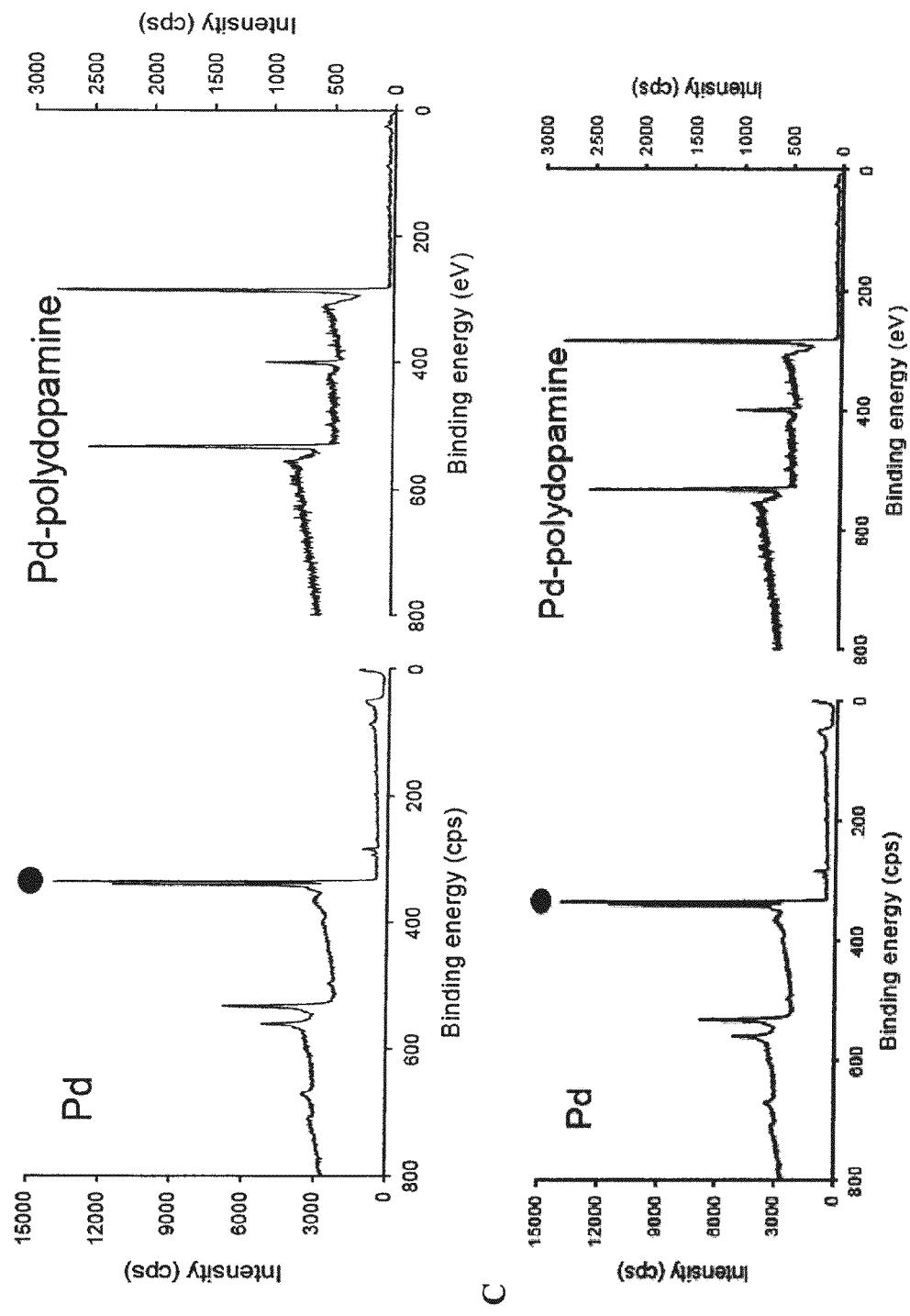
Figure 3:
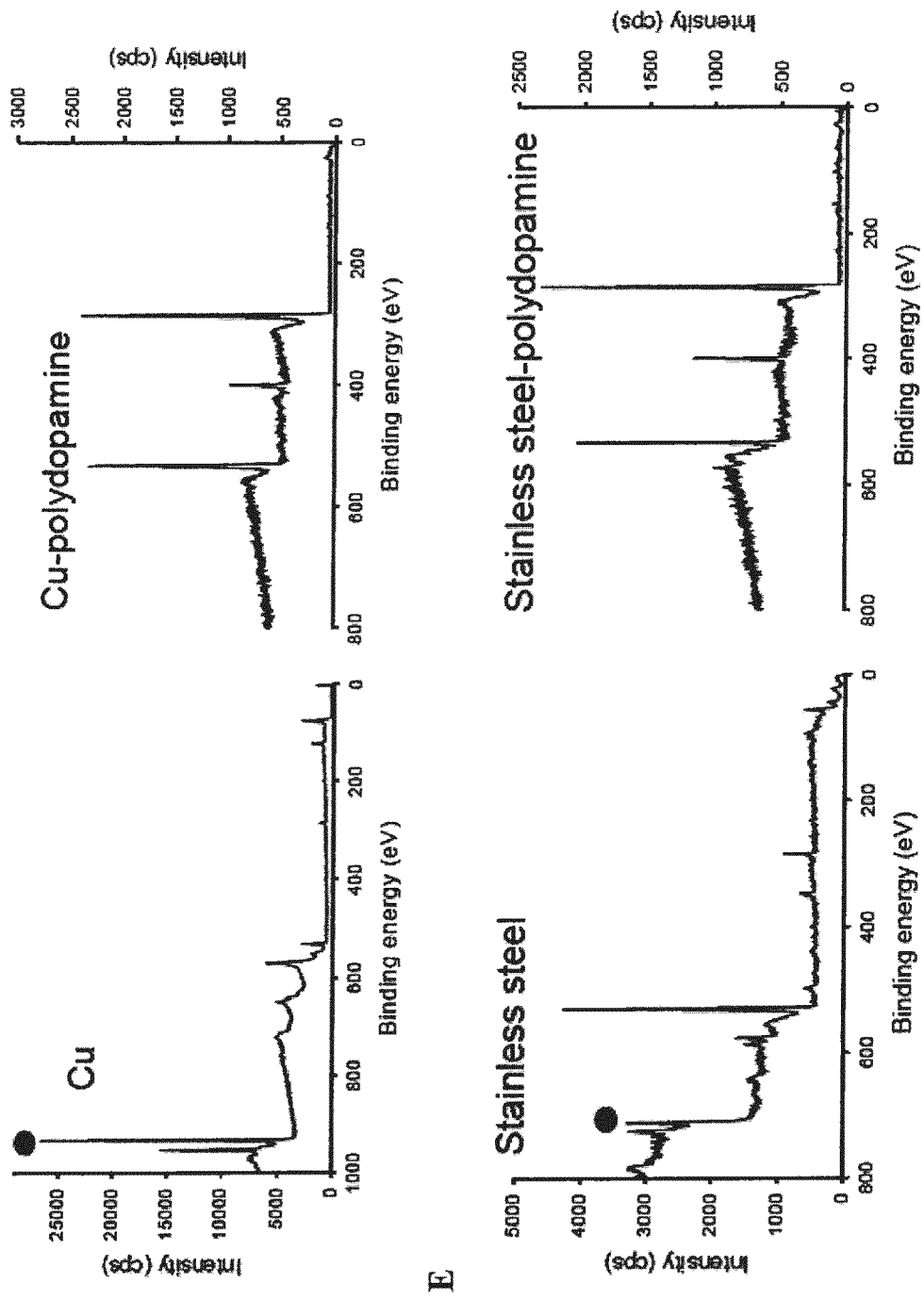
Figure 3:
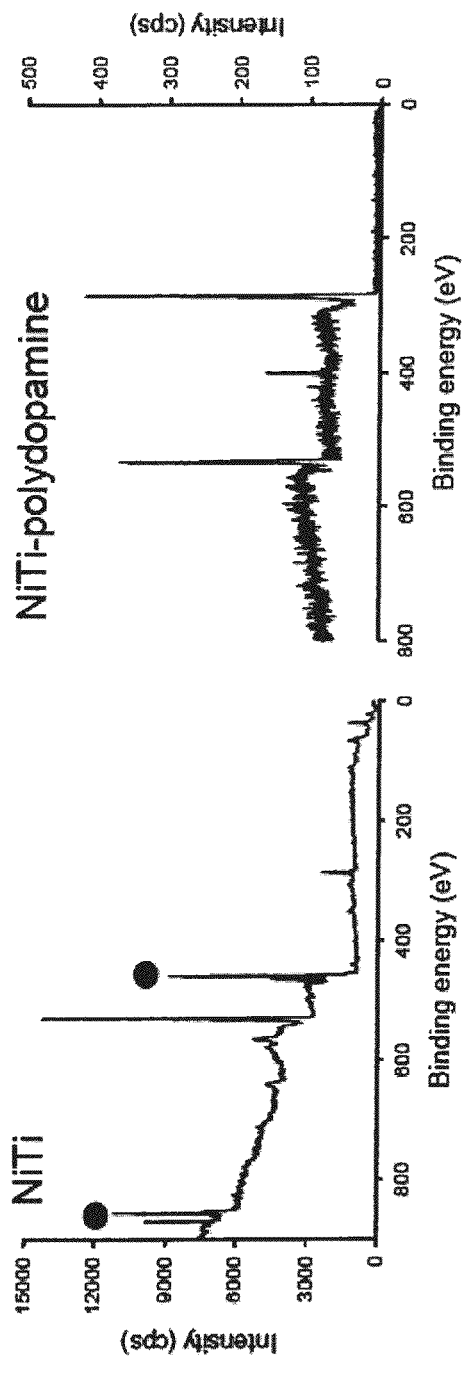
Figure 3:
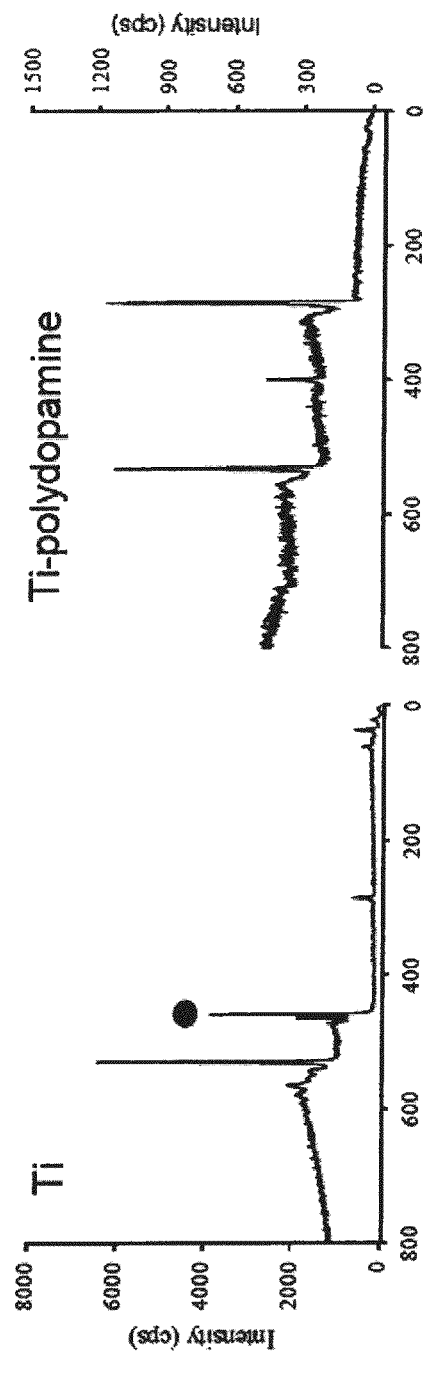
Figure 3:
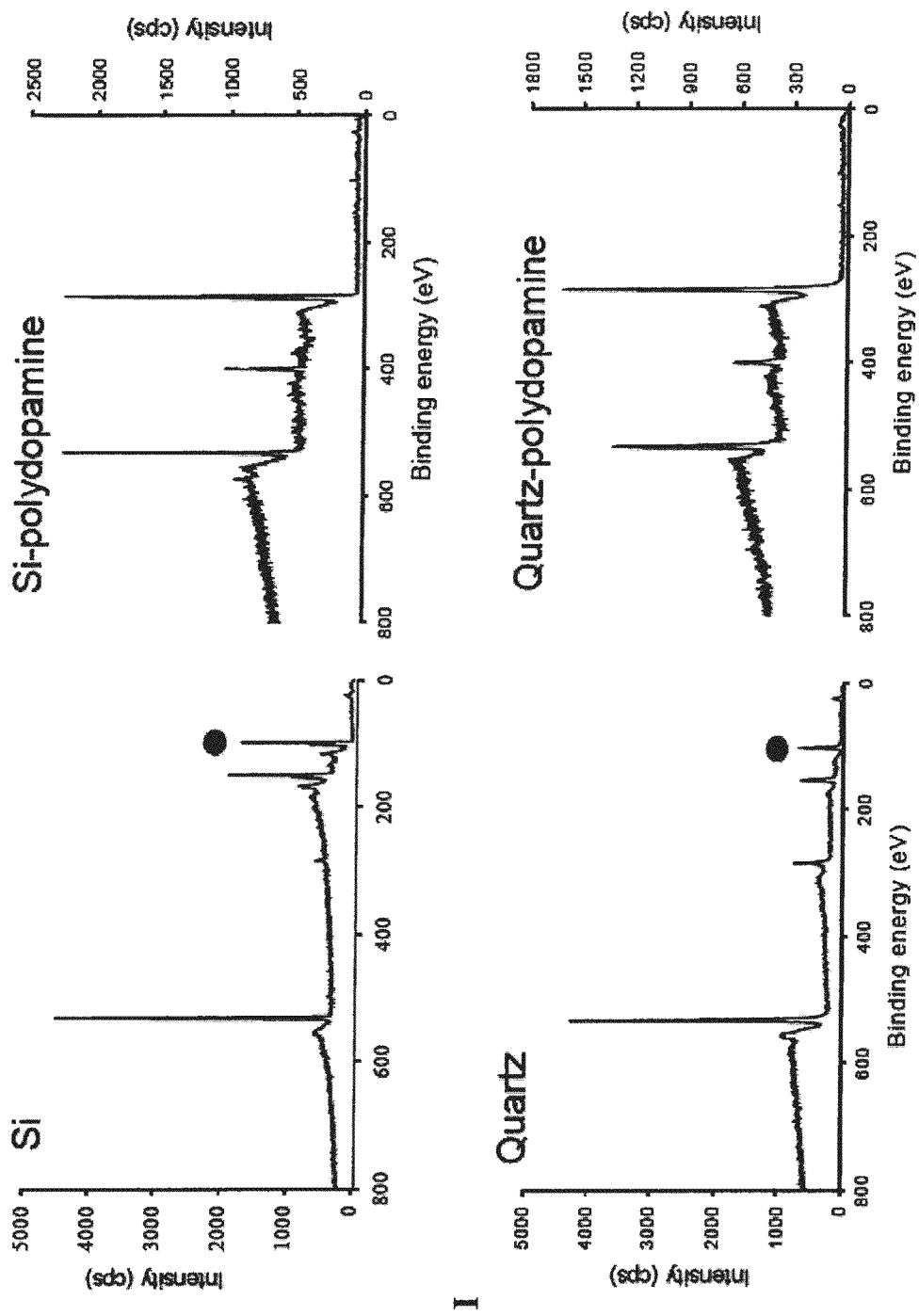
Figure 3:
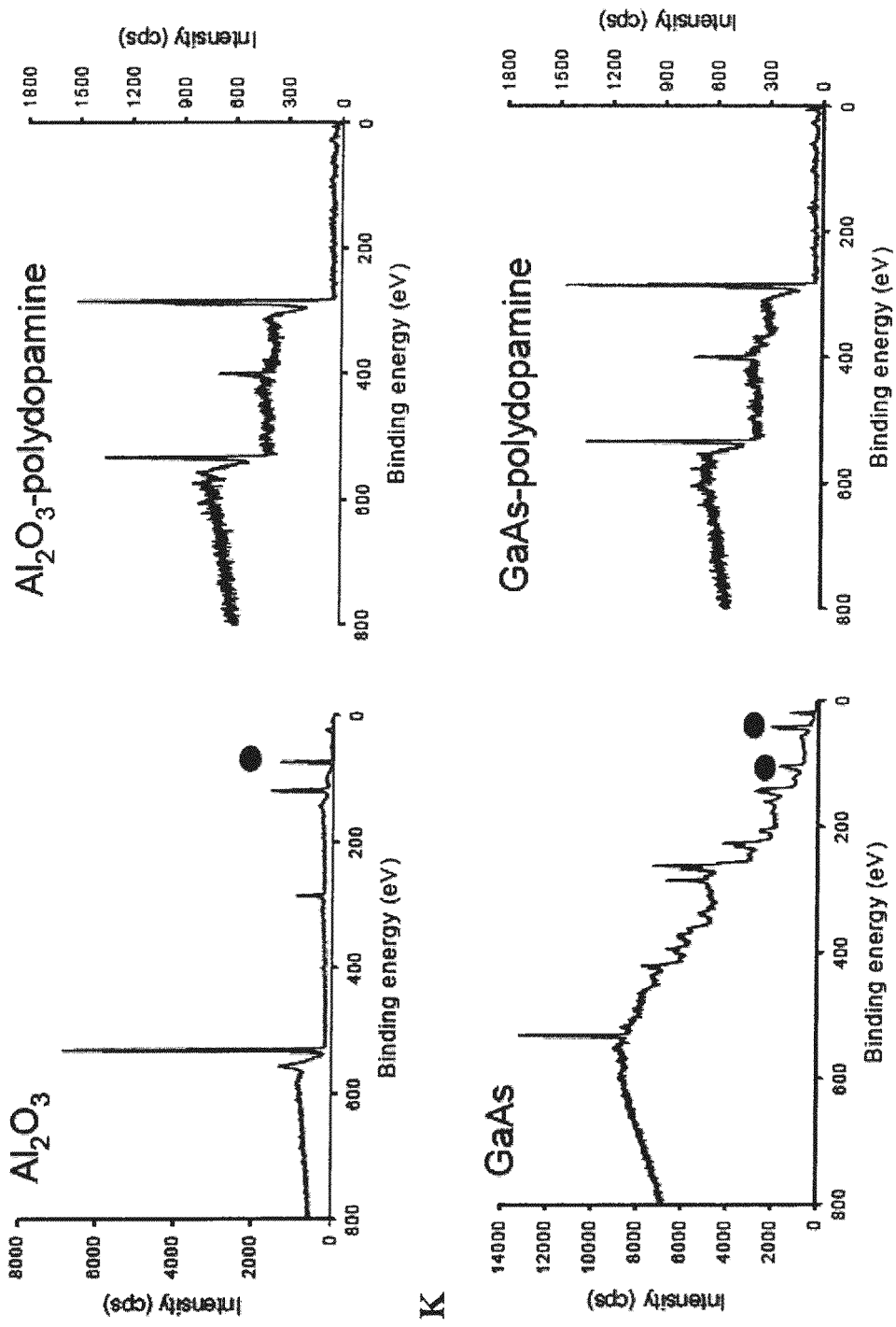
Figure 3:
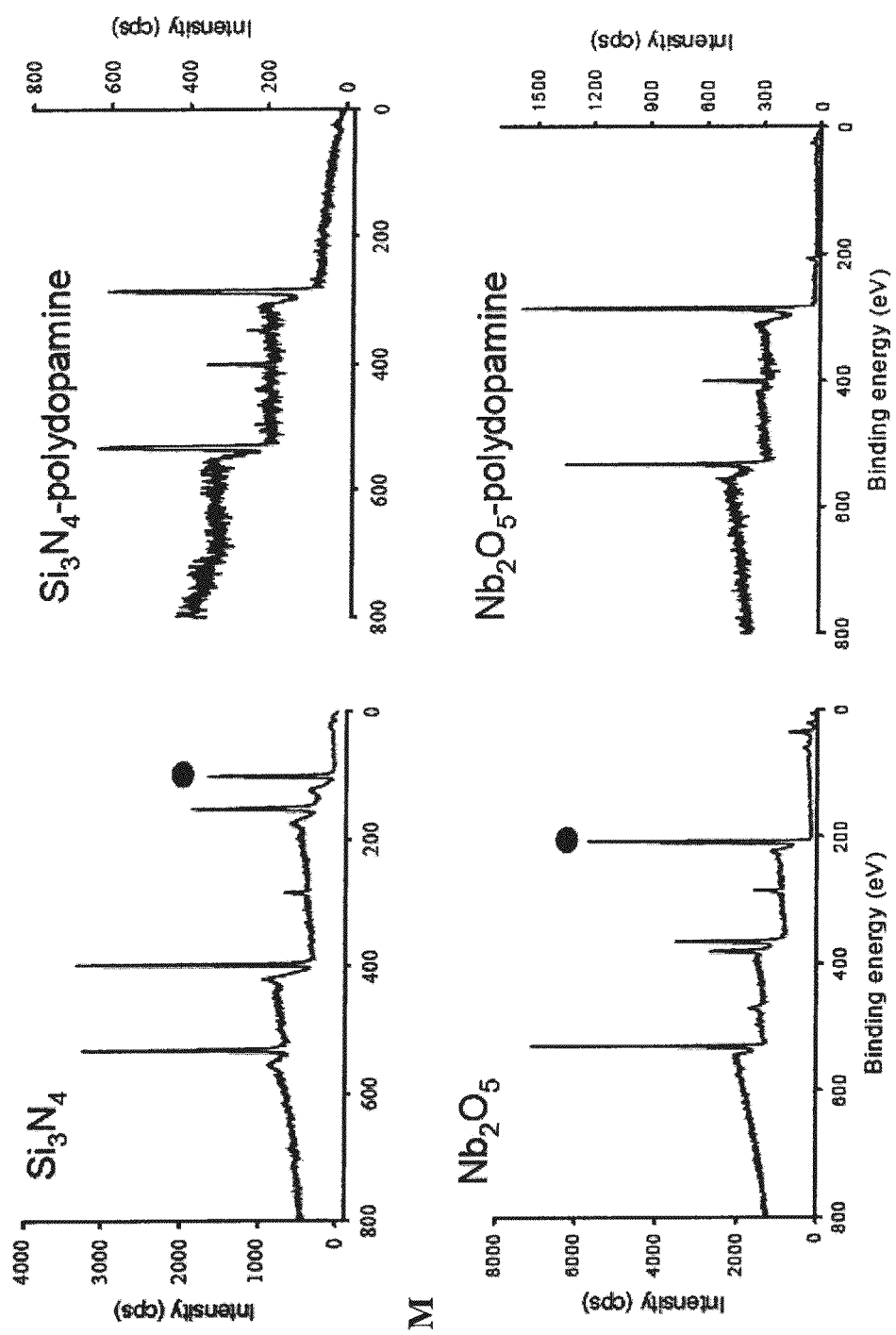
Figure 3:
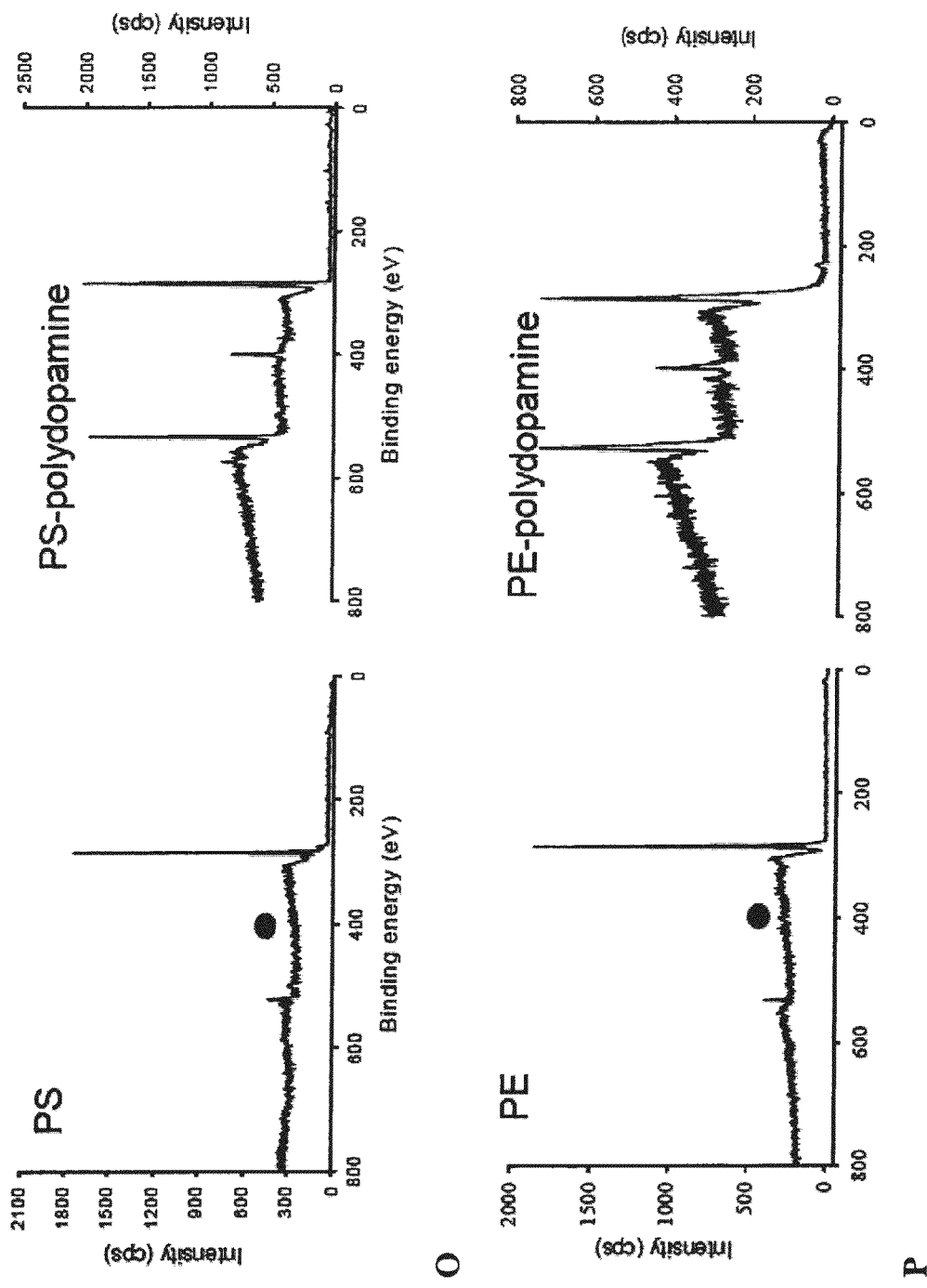
Figure 3:
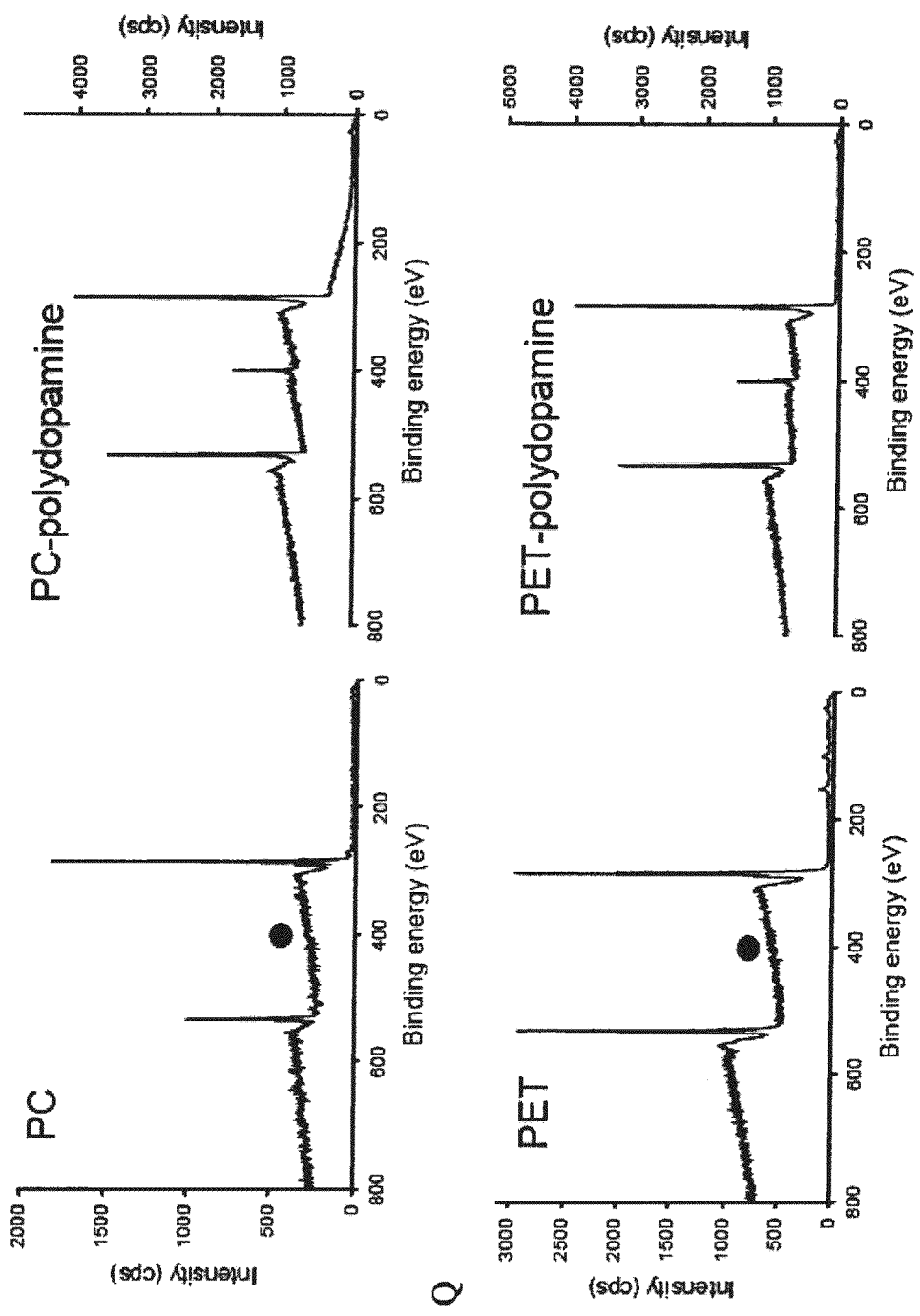
Figure 3:
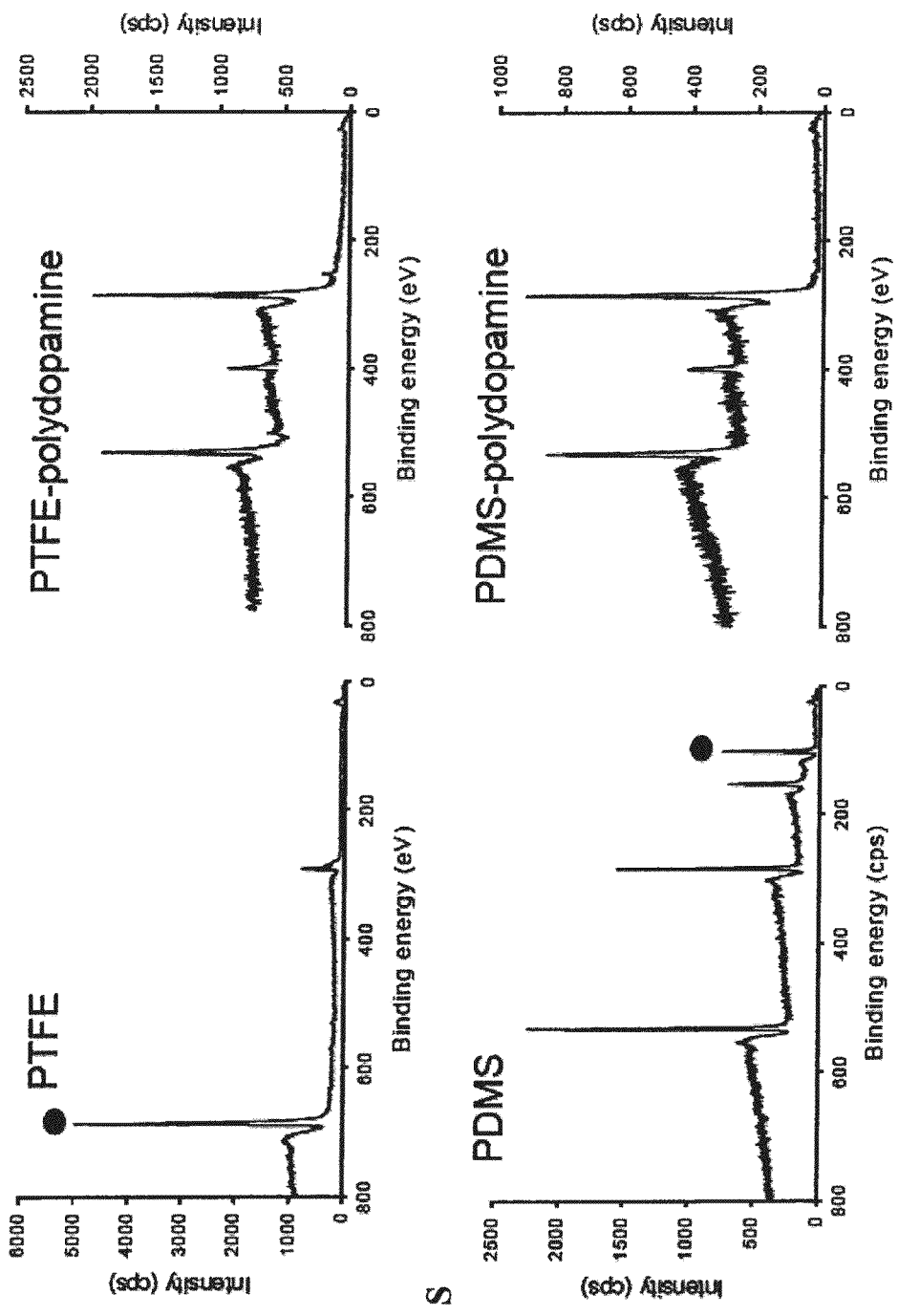
Figure 3:
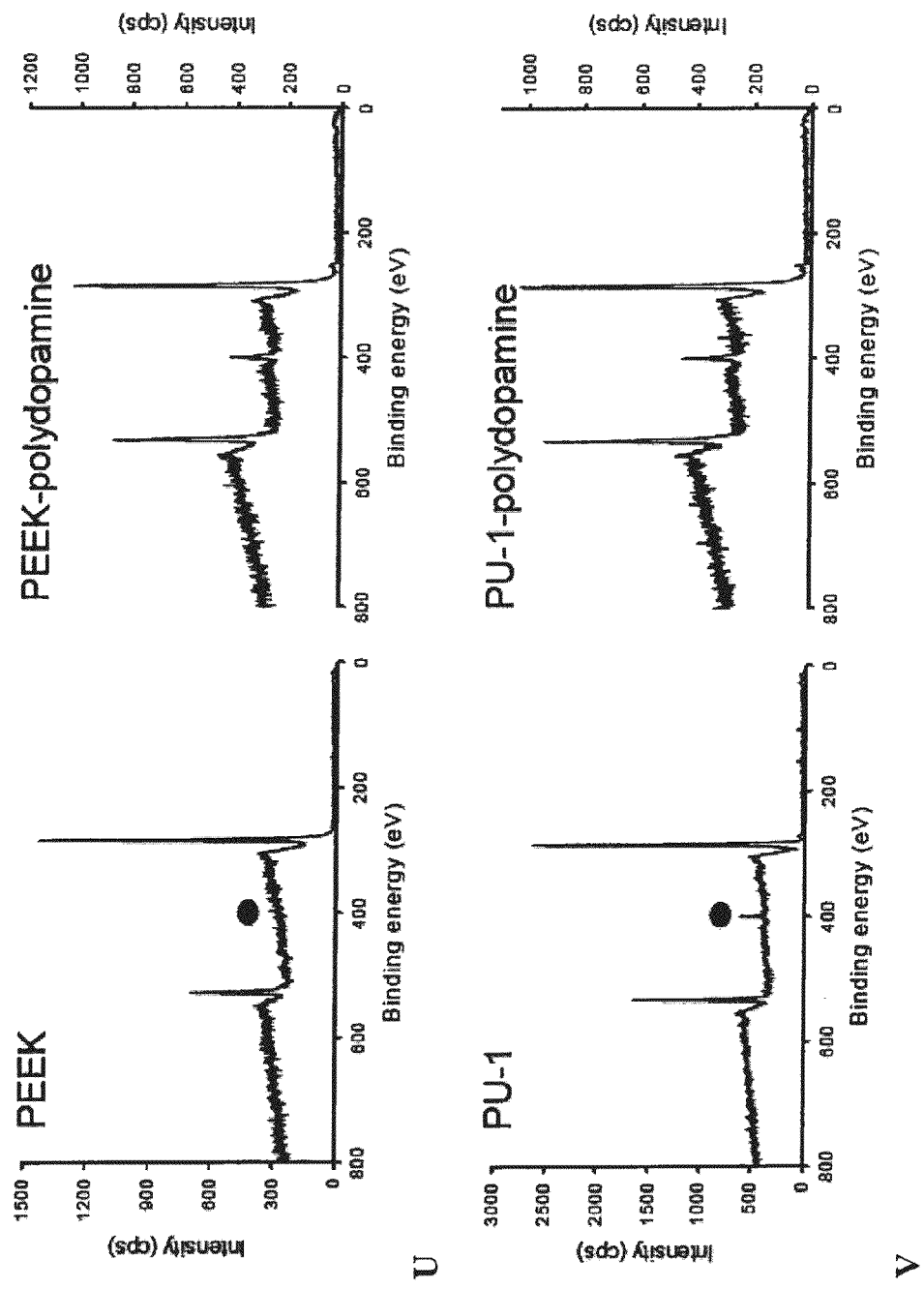
Figure 3:
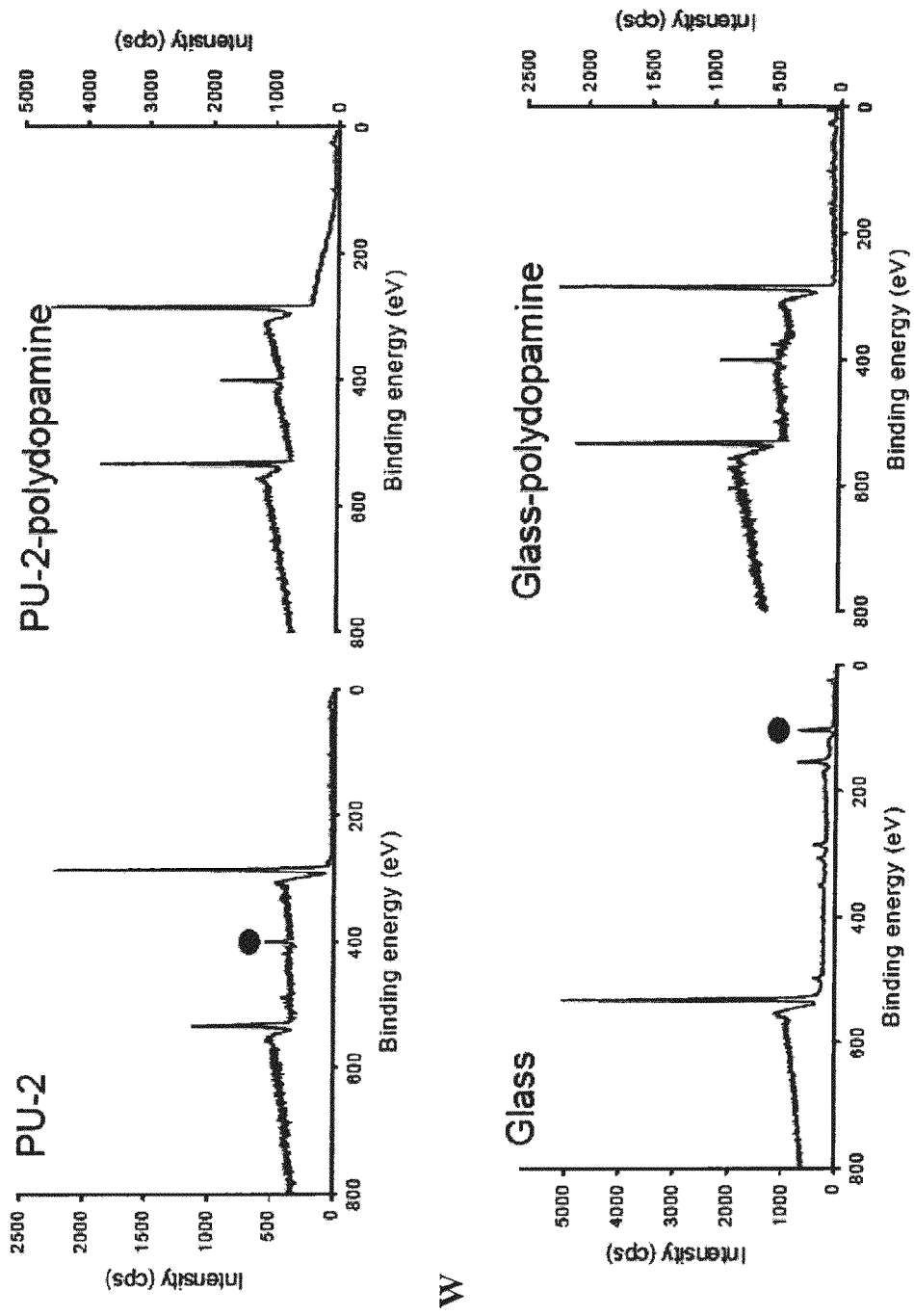
Figure 3:
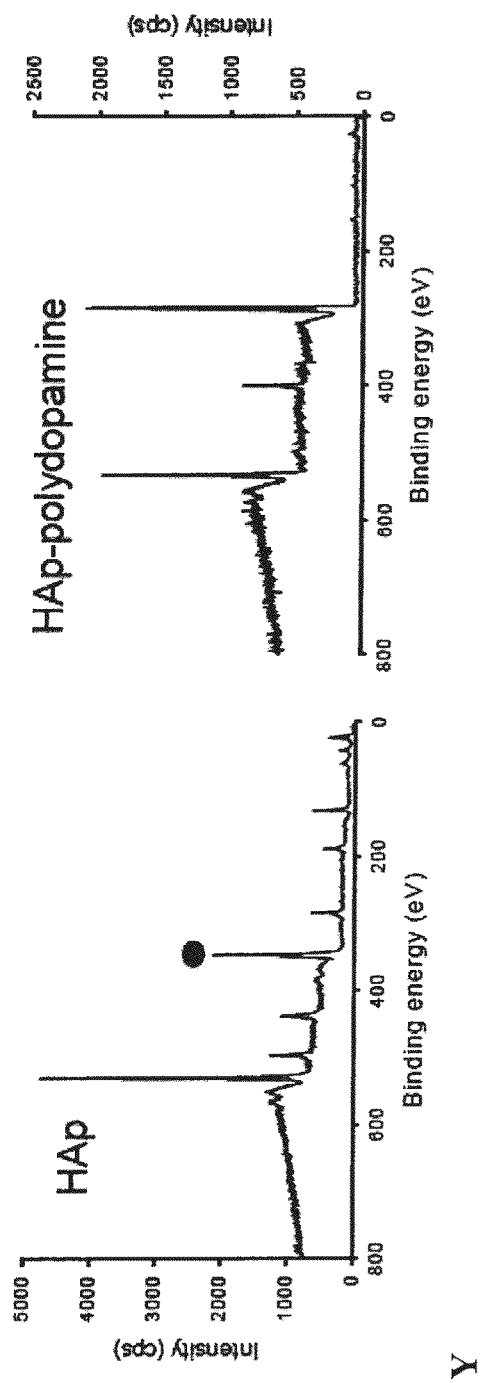

1H, and FIG. 3), indicating the formation of a polymer coating of 10 nm or more in thickness.

Figure 4:
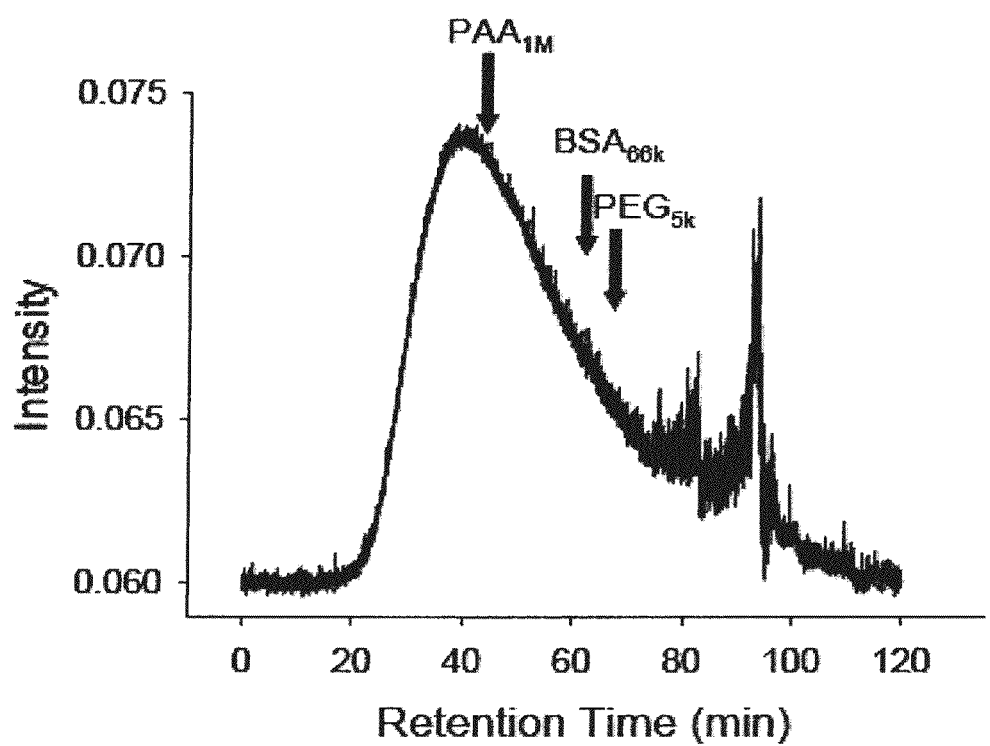
FIG. 4. Preliminary GPC analysis of dopamine solution after incubation for 60 hours at room temperature. Mobile phase buffer: 50 mM sodium phosphate, 100 mM NaCl, pH 6.5 with a flow rate of 0.3 mL/minutes (min). The sample was filtered before injection (pore size—0.8 microns (m) and the retention times of molecular weight standards are indicated by the arrows. The broad peak at a retention time (40 min) correlates to polydopamine at an approximate molecular weight of about several million Dalton based on molecular weight standards (PEG, 5 kDa, Bovine Serum Albumin (BSA), 66 kDa, and polyacrylic acid (PAA), 1 MDa). A second peak at an elution time of 80 min indicates oligomer formation, and a third peak found at the retention time of 95 min is due to a contaminant in the GPC system.

The atomic composition of the SMA-treated substrate varied little (circles, FIG. 1H), suggesting that the composition of the SMA coating was independent of the substrate. The nitrogen-to-carbon signal ratio (N/C) of 0.1-0.13 is similar to the theoretical value for dopamine (N/C=0.125), implying that the coating is derived from dopamine polymerization. Gel permeation chromatography (FIG. 4) and time-of-flight secondary-ion mass spectrometry (ToF-SIMS) (FIG. 5) also suggest that dopamine polymerization caused the thin adherent film to form on the substrates.

SMA was found both in solution and on the substrate, with ToF-SIMS clearly revealing signals corresponding to dihydroxyphenyl-containing polymer fragments. Although the exact mechanism is unknown at this time, it is likely to involve oxidation of the catechol to a quinone followed by polymerization in a manner reminiscent of melanin formation, which occurs through polymerization of structurally similar compounds (FIG. 5).

Dopamine (2 mg/mL) was dissolved in 10 mM Tris-HCl (pH 8.5), and substrates were dipped into the solution. pH-induced oxidation changes the solution color to dark brown. Stirring and/or vertical sample orientation were necessary to prevent non-specific microparticle deposition on substrates. The polydopamine-coated substrates were rinsed with ultra-pure water and dried by nitrogen gas before storage or treated as described below for ad-layer formation. Substrates coated in this manner remain stable on inorganic substrates unless scratched, treated by ultrasound, or dipped in a strong acid solution (<pH 1). Coatings on some organic substrates such as latex beads, Sephadex™ resins and some commercial plastics remain stable even in the presence of 1 N HCl combined with ultrasound.

Figure 24:
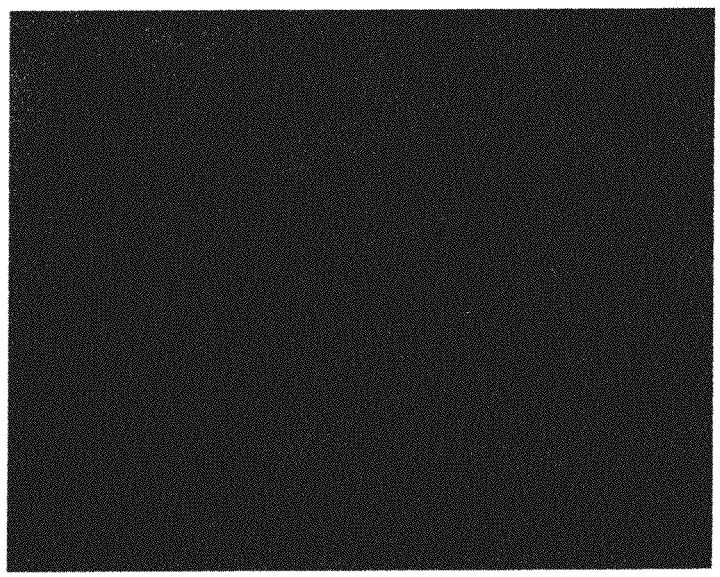
FIG. 24. Different conditions (pH and concentration of dopamine) for polydopamine coating on polystyrene substrates.

In another example, different conditions (pH and concentration of dopamine) for polydopamine coating on polystyrene surfaces were used. At a fixed concentration of 2 mg of dopamine per milliliter of 10 mM Tris buffer, the polydopamine coating was tested as a function of pH (7.4, 8.5 and 10). Also, at a fixed pH of 8.5, dopamine concentration was varied from 0.05 to 2 mg/ml (coating time was 15 hrs for all samples) to test the coating capability (FIG. 24).

All conditions resulted in successful polydopamine coatings except for the coating in the 0.05 mg of dopamine per milliliter of Tris, pH 8.5.

Incubating dopamine solution at room temperature for several days (i.e., greater than three days) prior to immersing the substrates did not produce surface discoloration (to dark-brown) typical of polydopamine coatings, indicating that the coating did not occur or was too thin to observe visually. Furthermore, the modification reaction appears to be prevented under anaerobic conditions, since purging of dopamine solution with argon resulted in dramatically reduced solution color change and coating formation on immersed substrates.

Analyzing polydopamine molecular weight in solution was performed on a Dawn EOS (Wyatt Technology, Santa Barbara, Calif.) GPC system using a mobile phase buffer (50 mM sodium phosphate, 100 mM NaCl, pH 6.5, flow rate of 0.3 mL/min) and Shodex-OH columns. The sample was filtered before injection (pore size 0.8 wn).

Example 2

SMA-Treated Substrates

Under oxidative conditions (e.g., pH>7.5), a dilute alkaline aqueous solution of dopamine surprisingly modifies substrate surfaces to include reactive, adherent polydopamine nanofilms. Virtually all natural and synthetic substrates including, without limitation, noble metals (Au, Ag, Pt and Pd), metals with native oxide substrates (Cu, stainless steel, NiTi shape memory alloy), oxides (TiO$_2$, NiTt, SiO$_2$, quartz, Al$_2$O$_3$, and Nb$_2$O$_5$), semiconductors (GaAs and Si$_3$N$_4$), ceramics (glass and hydroxyapatite (HAp), and synthetic polymers (polystyrene (PS), polyethylene (PE), polycarbonate (PC), polyethylene terephthalate (PET), polytetrafluoroethylene (PTFE), polydimethylsiloxane (PDMS), polyetheretherketone (PEEK), and polyurethanes (Carbothane® (PU1) and Tecoflex® (PU2))) (FIG. 1H) were effectively modified using the SMA-treatment of the present invention.

To date, over twenty-five substrates were successfully modified by a dilute, alkaline solution comprising dopamine using an aqueous one-pot process. Potentially any substrate known to man, including various composite materials, can be used in this process. For instance, x-ray photoelectron spectroscopy (XPS) analysis showed that substrate signals such as Si2p, Ti2p, and Au4d were completely suppressed by the SMA-treated substrates as described in Example 1 (Table 1). Instead, carbon, oxygen, and nitrogen signals were detected after the modification with a similar atomic composition of a nitrogen to carbon ratio (experimental N/C=0.09-0.13, theoretical N/C$_{dopamine}$=0.125) irregardless of substrates. Unavoidable carbon contamination in ambient conditions lowered the N/C ratio in XPS.

Table 2 illustrates the substrates and corresponding atoms (binding energy and orbital) used as characteristic substrate peaks for XPS characterization (as asterisk indicates synthetic, polymeric substrates without unique XPS signals except for carbon, nitrogen and oxygen.) The presence of the reactive moiety (in the case of dopamine, the reactive moiety formed is an adherent polymeric film) on the substrates was confirmed by the appearance of N1s signal after SMA-treatment, as shown in FIG. 3 (399.5 eV for PS, 399.1 eV for PE, 399.7 eV for PC, 399.6 eV for PET, and 399.8 eV for PEEK). The reactive moiety on PU-1,2 was confirmed by the nitrogen-to-carbon ratio after coating due to the presence of substrate nitrogen).

TABLE 2

| Substrate | Binding energy (eV) (photoelectron orbital) |
|---|---|
| Au | 84.1/84.9 (Au4f$_{7/2,5/2}$) |
| Ag | 369.9/373.9 (Ag3d$_{5/2,3/2}$) |
| Pt | 71.1/74.7 (Pt4f$_{7/2,5/2}$) |
| Cu | 952.5/932.5 (Cu2p$_{1/2,3/2}$) |
| Pd | 335.1/340.5 (Pd3d$_{5/2,3/2}$) |
| Stainless steel | 740.0/723.0 (Fe2P$_{3/2,1/2}$) |
| 110$_2$ | 456.5/462.4 (112p$_{3/2,1/2}$) |
| NiTi | 854.1/870.9 (Ni2p$_{3/2,1/2}$) |
| Quartz, Glass | 103(quartz), 102(glass) (Si2p) |
| SiO$_2$, Si$_3$N$_4$ | 99.2/99.8 (Si2p$_{3/2,1/2}$) |
| Al$_2$O$_3$ | 118.6 (Al$_{2s}$) |
| GaAs | 41.7, 106.5 (As3d$_{3/2}$ Ga3p$_{1/2}$) |
| PDMS | 102.2 (Si2p) |
| Nb2O5 | 207/209.5 (Nb3d$_{5/2,3/2}$) |
| PTFE | 686.1 (F1s) |
| PS* | 284.7 (C1 s) |
| PE* | 284.8 (C1 s) |
| PC* | 284.7 (C1s) |
| PET* | 284.7 (C1s) |
| PEEK* | 284.8 (C1 s) |
| HAp | 346.5/350.2 (Ca2P$_{3/2,1/2}$) |

Surface Characterization.

XPS spectra were obtained using an Omicron ESCALAB (Omicron, Taunusstein, Germany) with a monochromatic Al Ka (1486.8 eV) 300-W X-ray source, a flood gun to counter charging effects, and ultrahigh vacuum (~$10^{-9}$ torr). The take-off angle was fixed at 45° except as otherwise mentioned. High-resolution scans were acquired to calculate the chemical compositions of the substrates. Time-of-flight secondary ion mass spectroscopy (Physical Electronics, Eden Prairie, Minn.) was used to characterize the atomic composition of polydopamine coatings and metal ad-layers (copper and silver). The mass spectrometer was equipped with a Ga ion gun operated at 15 keV with a raster size of typically 100-200 p.m. Multi-mode atomic force microscopy (Veeco Inc., Santa Barbara, Calif.) was used for imaging (tapping-mode using Si-cantilever, Veecoprobes, resonance frequency=210-240 kHz)).

Total Internal Reflection Fluorescence (TIRF) Microscopy.

Detailed experimental procedures have been described elsewhere (Qu et al. *Proc. Natl. Acad. Sci. USA* 101, 11298 (2004)). Briefly, an Olympus 1×71 inverted fluorescence microscope (Melville, N.Y.) and a 60× objective (Olympus, N.A.=1.45 oil immersion) were used for single-molecule adsorption images. A 532-nm laser (New Focus 3951-20, 20 mW power, San Jose, Calif.) was used as a light source. An O.D. equals one neutral density filter was used for most experiments. The incident laser power was roughly 0.5 mW, illuminating a circular region of 40 1.1 m in diameter. After excitation, the emitted photons were collected by a filter cube (Chroma Q560LPBS, HQ585/40M, Rockingham, Vt.), magnified by a 3.3× eyepiece and detected by a TEcooled and frame-transfer CCD (Andor, DV435-BV, South Windsor, Conn.). The protein used in this experiment was Cy3 conjugated Enigma homolog (Enh). The protein was dissolved in 50 mM phosphate buffer pH 7.0 (11.IM) and experiments performed at room temperature (exposure time=33 msec).

Example 3

Untreated Substrates

In this example, substrates were tested to determine if substrates could be modified according to the present invention in an untreated condition. Accordingly, the following demonstrates that SMA-treated substrates that have not been cleaned (i.e., are used as received) can be modified to include at least one reactive moiety.

Figure 26:
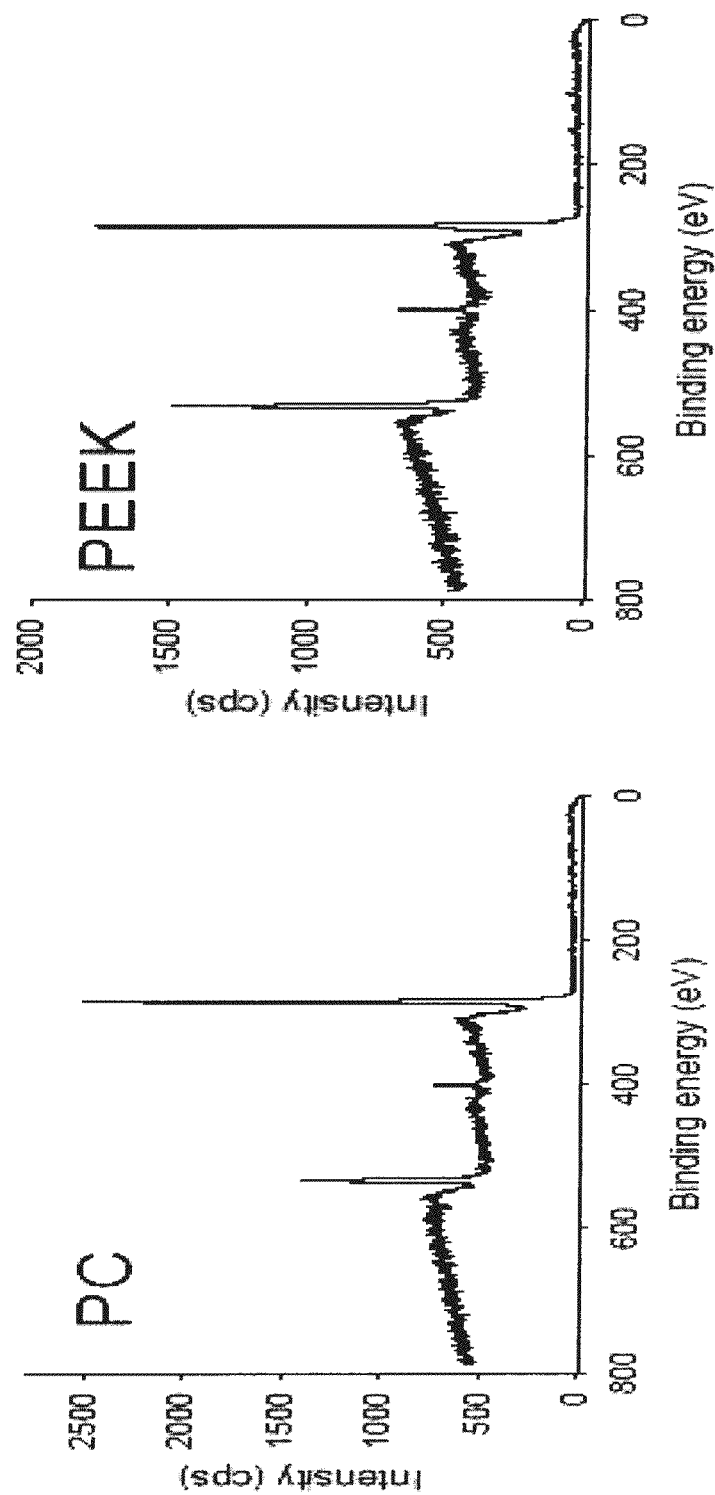
FIG. 26. XPS data to determine SMA-treatment on untreated substrates PC (A) and PEEK (B).
Figure 27:
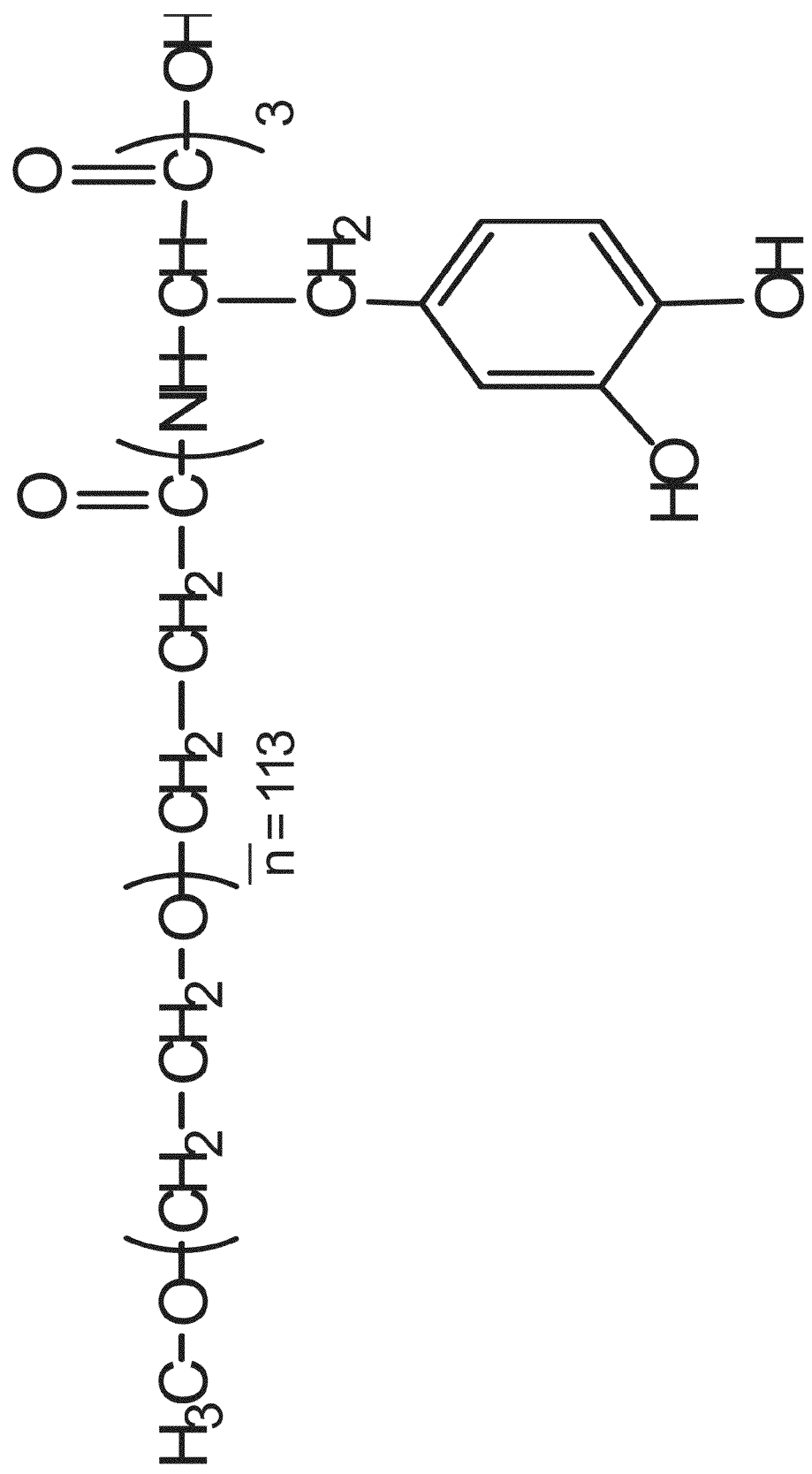
FIG. 27. Mussel adhesive-inspired mPEG-DOPA3 for reduction of marine fouling.

Substrates PEEK and PC were contacted with dopamine in a dilute, alkaline solution (2 mg/mL dopamine dissolved in 10 mM Tris; pH 8.5) for 5 hrs. XPS was used to determine the efficacy of the SMA-treated substrates. The presence of N1s signals (approximately 400 eV) (see FIGS. 26A-B) indicated successful polydopamine coating on unclean substrates (bare substrates do not show N1s).

These results indicate that substrates may be modified according to the present invention, even when such substrates are covered in paint, oil, grease, rust, protectant and the like.

Example 4

Photolithography

Figure 6:
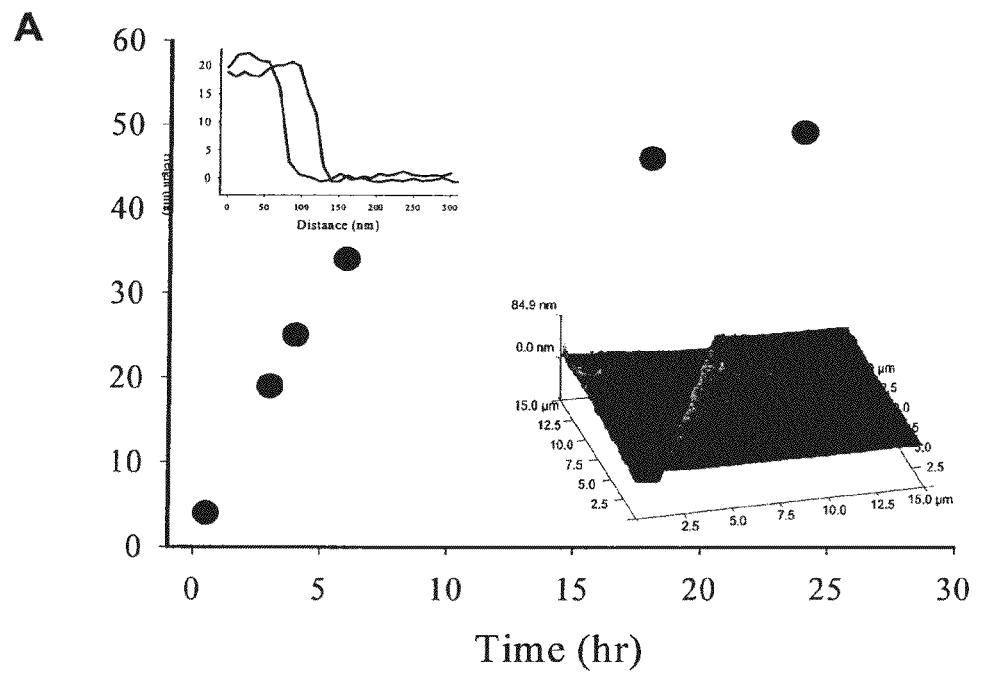
FIG. 6. Characterization of a surface-independent polydopamine-coated substrate.
Figure 6:
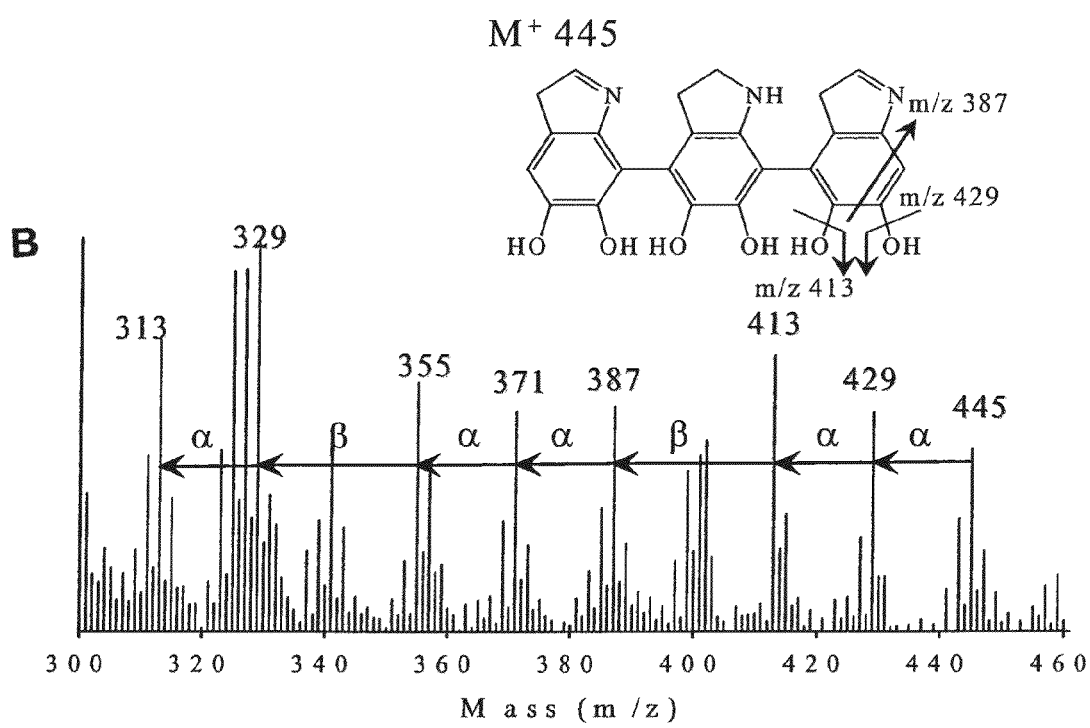

Dopamine's heterogeneous oxidative polymerization causes a substrate treated with dopamine to form a reactive moiety on the surface in the form of an adherent polymeric film. The polymeric film evolves in thickness as analyzed by photolithography micropatterning as a function of time and subsequent photoresist etching. This experiment resulted in substrates modified to include locally patterned thin films of dopamine, and the thickness was assessed by atomic force microscopy (AFM) (FIG. 6A inset). The coating thickness increased in a time-dependent manner and evolved up to 50 nm after one day (FIG. 6A).

The chemical identity of the polydopamine coating was analyzed by time of flight secondary ion mass spectrometry (ToF-SIMS). This technique relies on the ionization of chemical species ($2^{nd}$ ions) adsorbed on substrates which become fragmented molecules by incident primary ion beam ($Ga^+$), and the ionized molecules are analyzed in time-of-flight detectors. ToF-SIMS clearly proved the existence of polymerized dopamine (i.e., melanin ad-layers) by showing a fragmented trimer of 5,6-dihydroxlindole and leukodopaminechrome ($M^+445$, FIG. 6B), which are monomeric units generated by the sequential oxidation of dopamine (reaction sequence (I)—FIG. 2A). The ToF-SIMS results also showed interesting cleavage patterns: twice dehydroxylation (.OH-phenyl→OH phenyl→OH phenyl) and ring opening (.$C_6H_6$→$C_2H_2$+$C_4H_4$) providing unambiguous evidence of diol and phenyl ring content in the adsorbed layers.

Photoresist (Microposit S-1818, Shipley, Marlborough, Mass.) was spin-cast at 4000 rpm for 50 sec and then baked for 1 mM at 95° C. Utilizing a contact mask aligner (Q2000, Quintel Corp. San Jose, Calif.), the photoresist was exposed to UV (345 nm) light for six seconds and was subsequently developed for forty sec (MF-CD-26, Shipley, Mass.). Polydopamine coating was applied to the patterned substrates for three to six hours as described above. Finally, photoresist was removed by immersion in N-methyl-pyrrolidinone (NMP) for five to ten seconds. The coating thickness (FIG. 3) was measured by AFM on patterned substrates.

Example 5

SMA-Assisted Electroless Metallization

Figure 7:
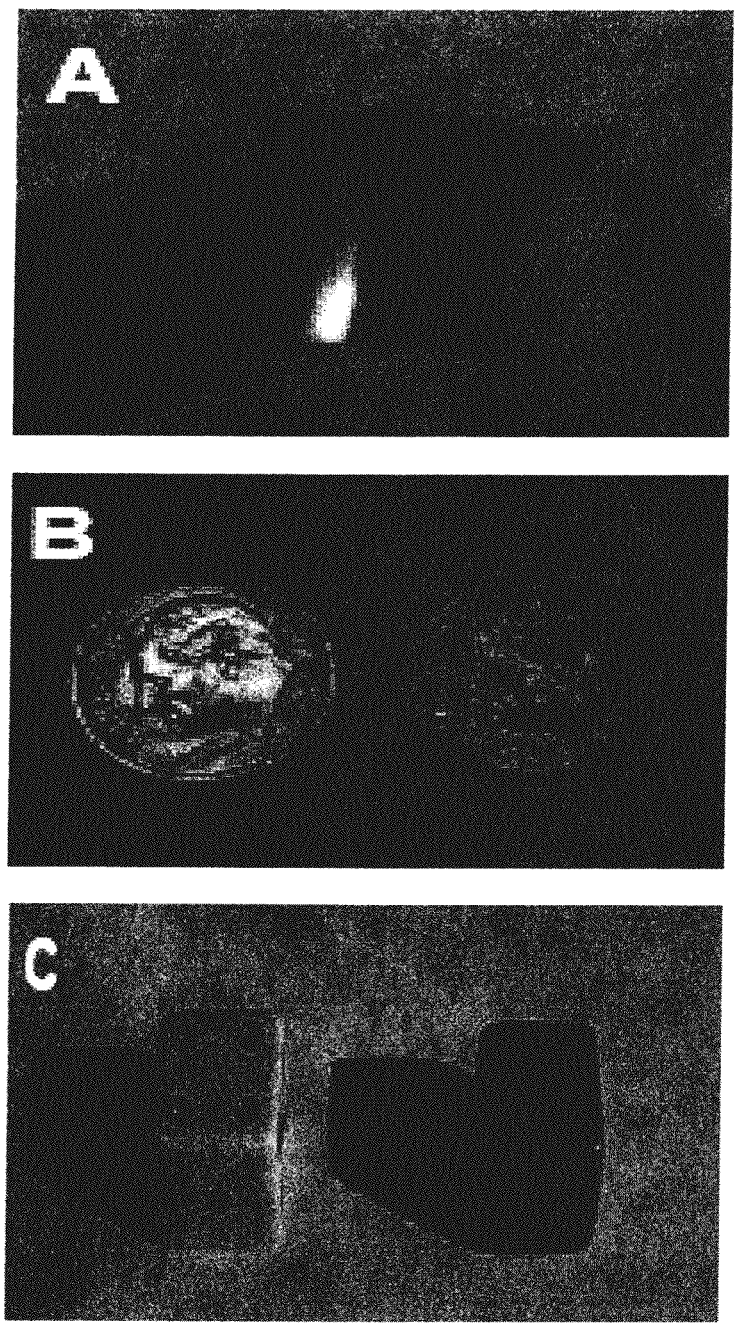
FIG. 7. Polydopamine-assisted electroless metallization of substrates.
Figure 7:
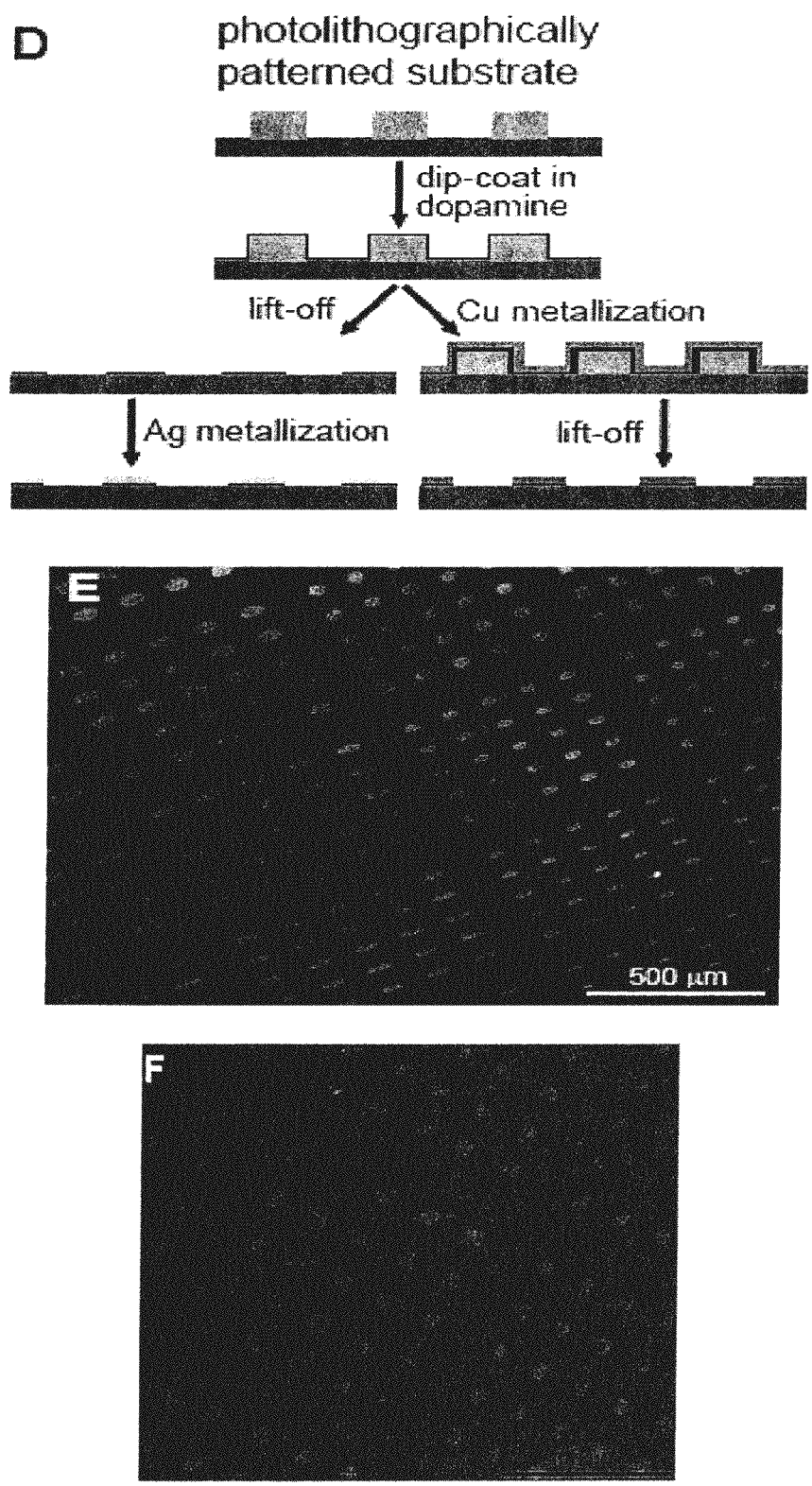
Figure 8A:
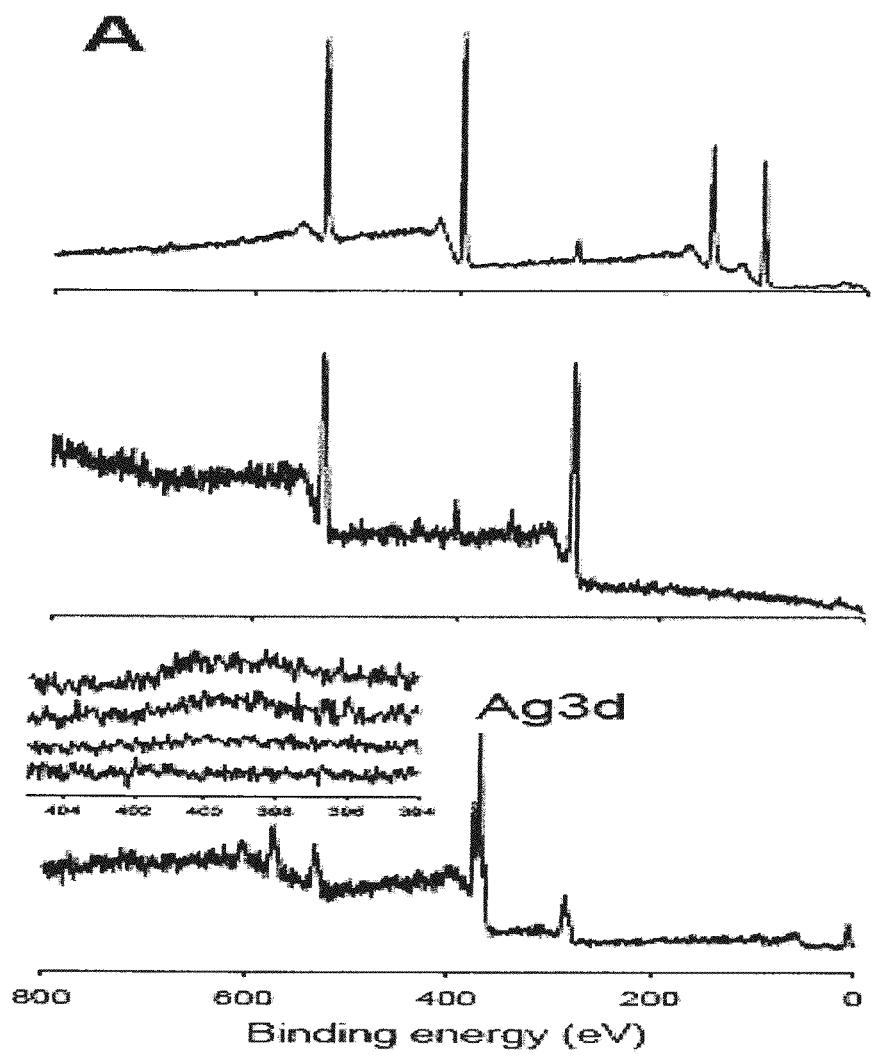
FIG. 8A. XPS spectra taken at each step of surface modification. (Top) Clean unmodified silicon nitride exhibited Si (2p=101.5 eV), N (1s=397.5 eV), and 0 (1s=532.5 eV) peaks. (Middle) Polydopamine-coated silicon nitride exhibited C, N, and 0 signals characteristic of polydopamine (Bottom) The silver metal layer formed on polydopamine-coated silicon nitride, showing strong metallic Ag peaks ($3d_{512}$=368.6 eV; $3d_{312}$=374.7 eV) and minor hydrocarbon contamination. Inset: Angle-dependent (60, 45, 30, and 20 degrees from top to bottom). XPS showed no nitrogen is at take-off angles of 30 deg or less, confirming metallic silver ad-layer formation on top of polydopamine FIG. 8B. Electroless silver deposition on various substrates. Silver on glass (top left), gold (top right), Ti (bottom left), and PEEK (bottom right) showed nearly identical ToF-SIMS spectra in which two strong silver isotope peaks at 106.8 (theoretical 106.9) and 108.8 (theoretical 108.9) m/z were observed.
Figure 9:
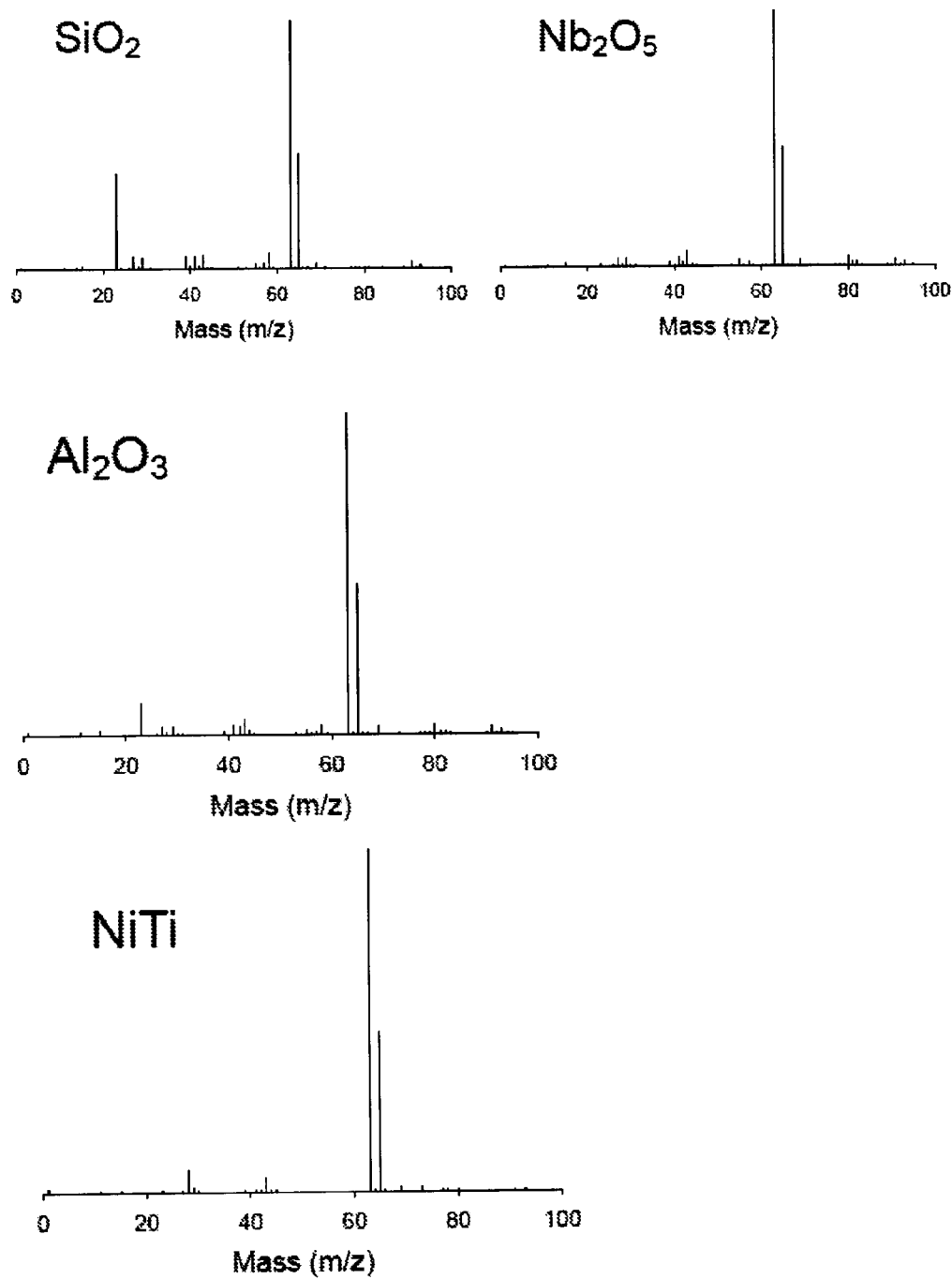
FIG. 9. ToF-SIMS characterization of copper ad-layer deposited by electroless metallization onto diverse polydopamine-coated substrates. All ToF-SIMS mass spectra were similar regardless of underlying substrates (62.9 and 64.9 m/z with an isotopic ratio of roughly 100% (62.9 m/z) to 40% (64.9 m/z)), indicating successful metallic copper deposition in a substrate-independent manner. The peak at 23 m/z was $Na^+$ contamination.
Figure 9:
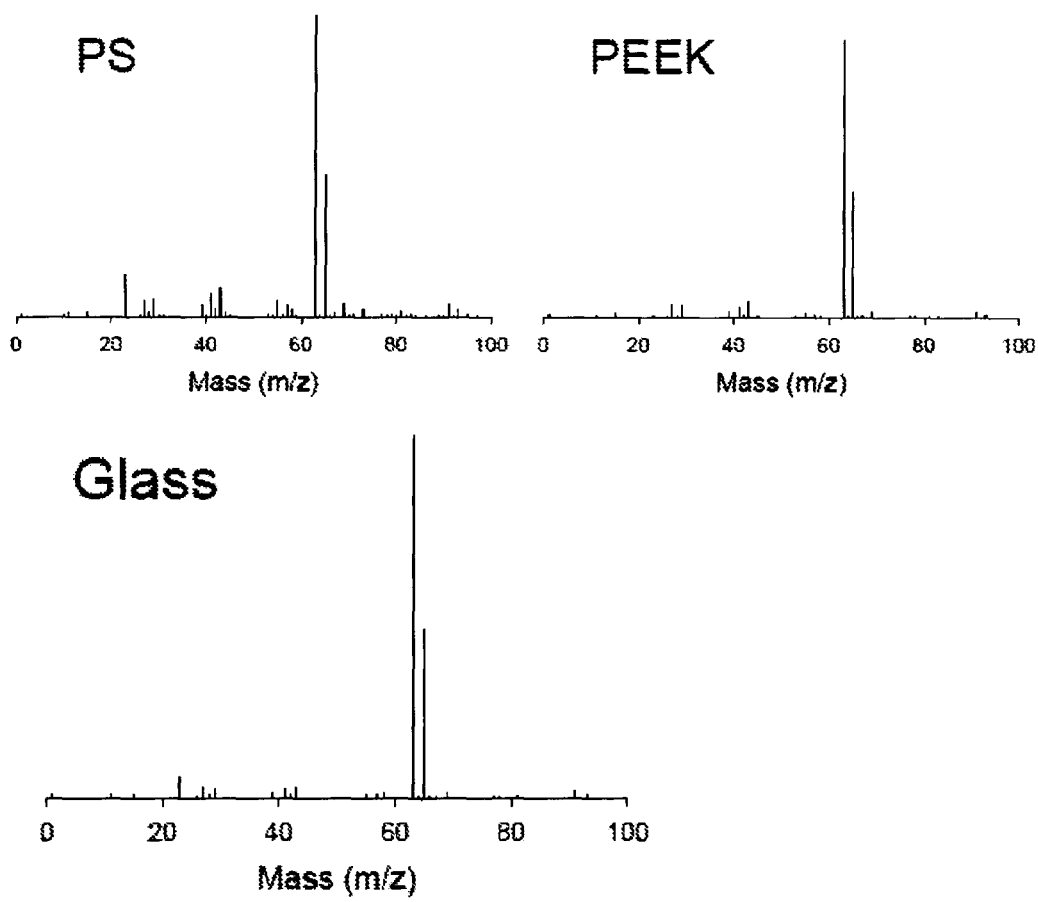
Figure 10:
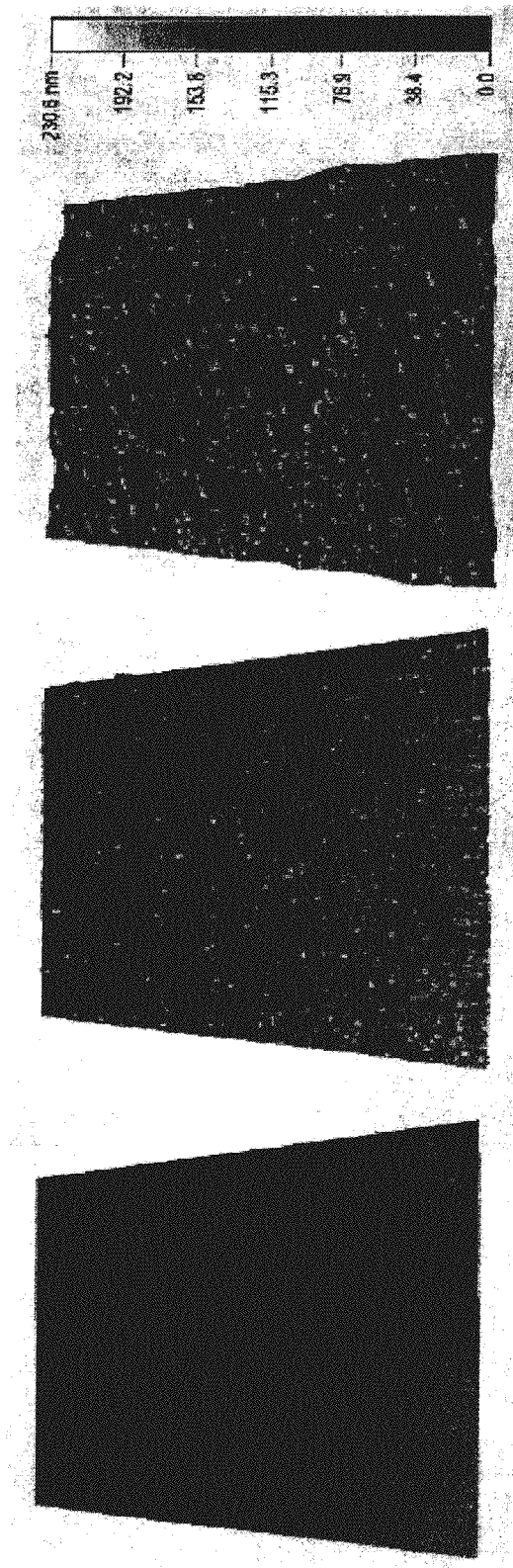
FIG. 10. Roughness analysis of polydopamine- and metallized polydopamine-coated substrates. The root mean square (RMS) roughness of $Nb_2O_5$, polydopamine-coated $Nb_2O_5$, and Cu-polydopamine-coated $Nb_2O_5$ was measured by AFM. The RMS roughness was 0.2 nm for bare $Nb_2O_5$ (left), 3.4 nm for polydopamine-coated $Nb_2O_5$ (middle), and 31.7 nm for Cu-polydopamine-coated $Nb_2O_5$ (right).

The metal binding ability of catechols present in the SMA's of the present invention was exploited to deposit adherent and uniform metal coatings onto substrates by electroless metallization. Silver and copper metal films were deposited on substrates by dip-coating SMA-treated substrates into silver nitrate and copper (II) chloride solutions, respectively (FIG. 7). Metal film deposition and roughness was confirmed by XPS and ToF-SIMS analysis, which demonstrated successful metal film deposition on a number of ceramic, polymer and metal substrates including nitrocellulose, coinage metals, commercial plastics, silicon nitride, glass, gold, titanium, Si, polycarbonate, polystyrene, PEEK, gold, niobium oxide, aluminum oxide, and nickel-titanium (FIGS. 8-10).

Metal coatings were also successfully applied in this manner to SMA-treated substrates including flexible polymer substrates and bulk objects with complex shapes (FIG. 7A-C), as well as flat substrates in which the SMA was patterned using standard photolithography techniques (FIG. 7D-F). Unlike many other approaches to electroless metallization, the use of (immobilized) colloidal metal seed particles was unnecessary for spontaneous formation of adherent metal films.

Surface-Independent Silver Deposition.

Silver has long been recognized as an anti-bacterial agent suitable for medical devices. Using the present invention, any underlying SMA-treated substrate can be modified to have silver metal layers. In the case of dopamine, silver metal layers can be formed solely by the redox power of the dopamine layer without a reducing agent. This implies that the underlying polydopamine coating on the substrate oxidizes during metal ion reduction. SMA-treated substrates were dipped into a 50 mM aqueous silver nitrate solution for eighteen hours (room temperature). Substrates were then washed with ultrapure water and dried with $N_2$ gas.

A series of XPS spectra showed clearly differentiated signals from silicon nitride (FIG. 8A, top), the polydopamine coating (middle), and electroless silver metallization afterward (bottom, reaction in 50 mM silver nitrate in water at room temperature) indicating layer by layer deposition at each step. Strong silver peaks ($Ag_{3d}$ 368.9 eV red line, FIG. 8A) were detected, completely suppressing a nitrogen signal from the underlying dopamine layer at a take-off angle of 20° (bottom inset).

Due to the surface-independent nature of the SMA-treated substrates described herein, virtually any substrate can be modified to include silver metallization. For instance, in addition to modifying silicon nitride, silver metal was successfully deposited on several representative substrates (FIG. 8B, glass (top left), gold (top right), Ti (bottom left) and PEEK (bottom right)). This was confirmed by the characteristic isotopic pattern (106.9 and 108.9 m/z) of silver mass in ToF SIMS.

In addition to the bulk electroless deposition, micropatterned silver deposition was acquired by photolithography followed by polydopamine-coating and silver metallization. The resulting silver pattern demonstrates that the metallization process described herein can be incorporated into conventional lithography processes. Additionally, the method described above provide an aqueous, cost effective and surface-independent preparation process that does not require toxic Pd/Sn colloids for catalysis. The method presented herein thus represents a significant advance in electroless silver deposition.

Surface-Independent Electroless Copper Metallization.

Using the method described herein, electroless copper metal plating was achieved on virtually all substrates, and was especially successful with synthetic polymer substrates. For instance, polyethylene terephthalate (PET) has been used for a substrate for flexible displays, an important commercial substrate for future electronic devices. Integrated copper circuit on PET substrates will supply power to organic light emitting diodes (OLED). Contacting PET substrates with dopamine followed by electroless copper plating is a simple and cost-effective method potentially revolutionizing integrated circuits.

The enediol group in dopamine has a strong affinity to various metals including copper so bound copper ions on the polydopamine-coated substrate act as seeds for subsequent metallization. Under a reducing condition, metal copper was successfully deposited on various substrates: Si, $Al_2O_3$, $Nb_2O_5$, NiTi, polystyrene, polycarbonate, polyetheretherketone, glass, and gold (FIG. 7). A micropatterning process was also developed to demonstrate a potential usage of circuit board applications on a hard substrate (glass, FIG. 7C) and a flexible substrate (cellulose acetate, FIG. 7D).

Figure 11:
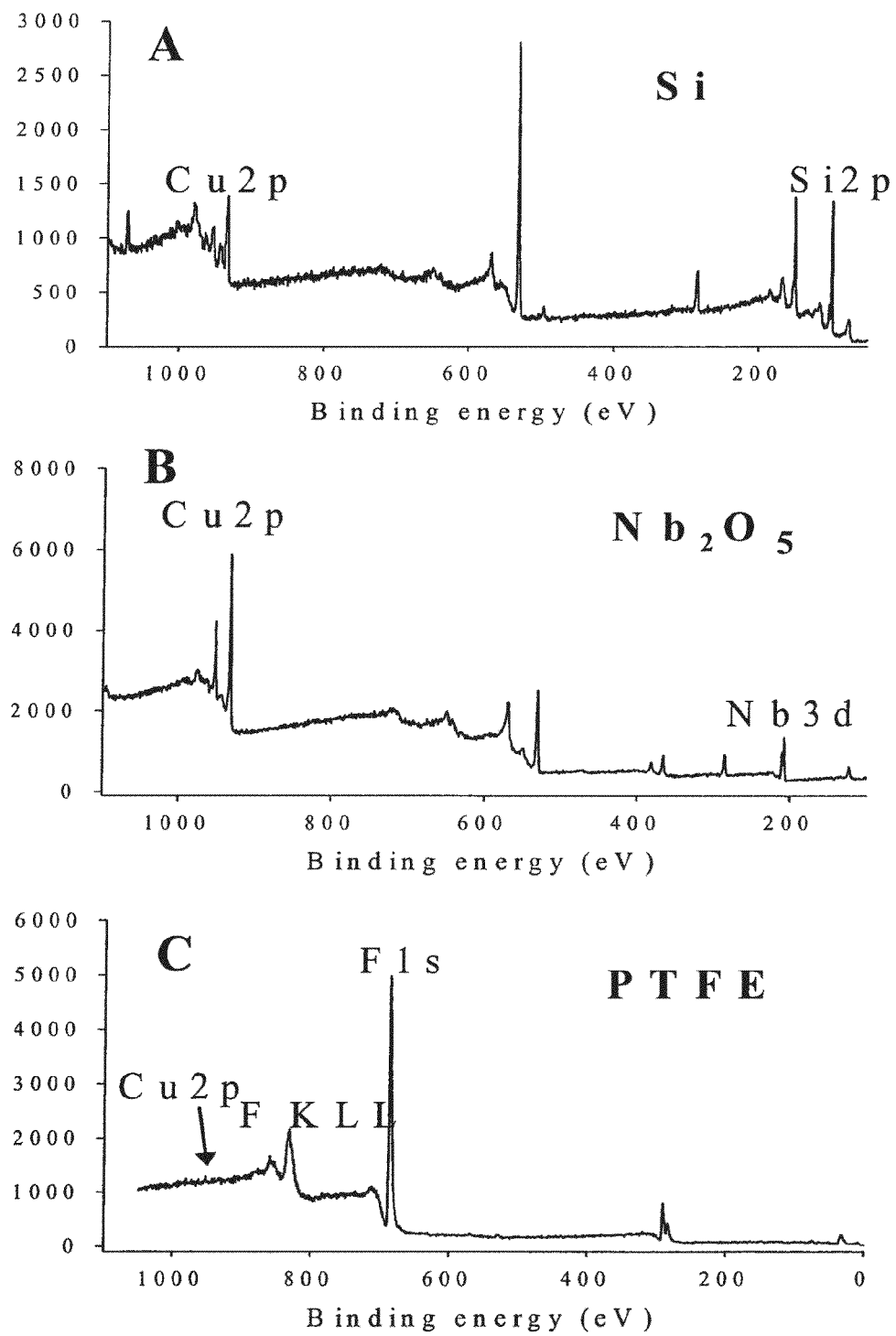
FIG. 11. Copper metallization in the absence of polydopamine-coated substrates. Copper metallization became inefficient without immobilized copper ions on polydopamine-coated substrates. Each tested substrate, silicon (A), niobium oxide (B), and polytetrafluoroethylene (PTFE) (C) showed different preferences for copper metallization without the polydopamine-coating. Metallic copper was barely detected on PTFE similar to unmodified substrates. Although the niobium oxide substrate exhibited good affinity to a copper layer, the niobium signals indicating that the Cu layer was not perfect. Silicon wafer revealed poor adhesion for newly formed metallic Cu layers showing a substrate Si2p signal.

The electroless copper deposition became ineffective without the SMA treatment, indicating the SMA-treated, substrate-bound copper plays a critical role in metallization. Substrates without SMA treatment showed strong substrate peaks: Si2p (103.3 eV) on Si, Nb (202.4 eV) on $Nb_2O_5$, and F1s (685 eV) on polytetrafluoroethylene indicating partial or no metallization (FIG. 11). SMA-treated substrates were metallized through immersion in copper (II) or silver salt solutions.

For electroless copper plating, a solution of 50 mM ethylenediaminetetraacetic acid (EDTA), 50 mM copper(II) chloride ($CuCl_2$), and 0.1 M boric acid ($H_3BO_3$) was prepared in ultrapure water, and the pH was adjusted to 7.0 using 1 N of NaOH. This solution can be stored in a refrigerator for future use. Immediately before use, 0.1 M dimethylamine-borane (DMAB) was added to the copper plating solution, after which the SMA-treated substrates were placed in the solution for two to three hours at 30° C. Substrates were then washed with ultrapure water and dried with $N_2$ gas.

Example 6

Biofouling and Biosensor Applications

Interfacial amino- or cysteinyl-dopamine coupling was performed by transferring pre-SMA-treated substrates to a monofunctional PEG solution (2 mg/mL methoxy-PEG-thiol or amine 5k (mPEG-SH, mPEG-$NH_2$) 10 mM Tris pH 8.5 50° C.). This simple two-step (SMA-treatment followed by PEGylation) aqueous chemistry successfully achieved universally-protein resistant substrates. The protein resistance capabilities were visualized at a resolution of a single molecule level using total internal reflection fluorescence (TIRF) microscopy.

Figure 12:
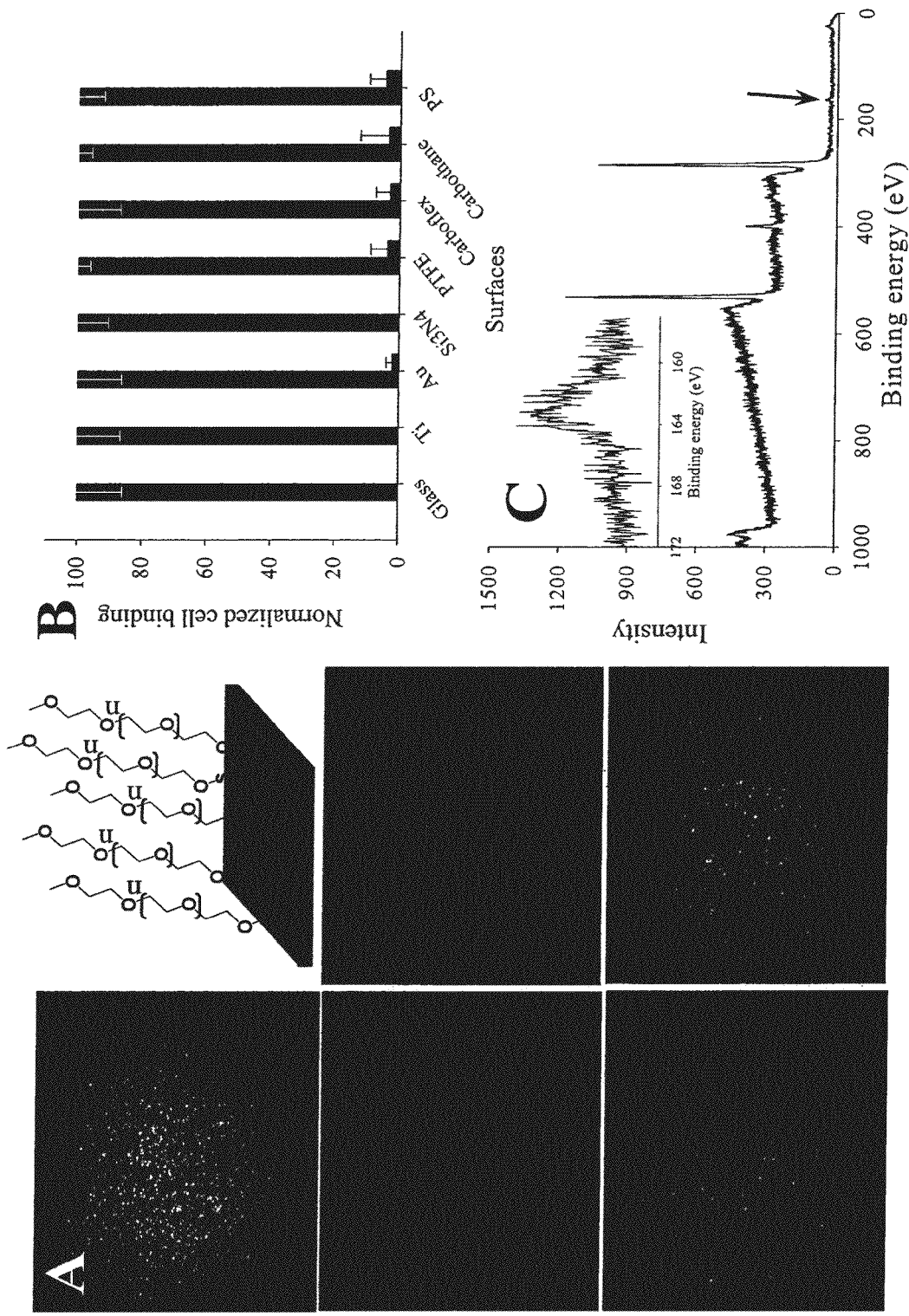
FIG. 12. Preparing surface-independent non-fouling (i.e., protein resistant) substrates.

Unmodified glass substrates upon exposure to proteins showed massive adsorption after 30 minutes (FIG. 12A, top), which was significantly improved by the traditional silane-PEG modification (bottom panel). However, long-term fouling resistance failed under the continuous exposure of a protein solution for 48 hrs (bottom right). SMA-treated substrates modified in a secondary reaction to contain PEG (mPEG-$NH_2$, 5 kDa) exhibited excellent antifouling properties showing incredible short- (30 min) and long-term (48 hrs) stability with virtually no defect (middle left and right respectively).

In the focal area, only fourteen proteins were detected on the SMA-treated, PEG-modified glass substrate, whereas approximately 400 proteins were adsorbed on silane-PEG modified substrates after 48 hrs. This demonstrates the enormously advantages of the present invention.

The proteins resolved by TIRF microscopy correspond to 0.01 pg/$cm^2$ which is below the lowest limit (approximately 1 ng/$cm^2$) of common surface analytical tools such as surface plasma resonance spectroscopy or optical waveguide light spectroscopy. Thus, PEGylated non-fouling substrates can be prepared in a surface-independent way. For non-transparent substrates, the four-hour fibroblast binding assay was used instead of TIRF microscopy (see Example 10). Also, the assay of cell binding resistance is an important criterion to examine antifouling performance of substrates in vitro.

All substrates tested, including oxide (Ti), metal (Au), semiconductor ($Si_3N_4$), polymer (polytetrafluoroethylene (PTFE), polyurethanes (Tecoflex®, Carbothane®)) and ceramic (glass) substrates exhibited excellent antifouling properties (FIG. 3B). The thiol end group of the PEG chain (mPEG-SH, 5 kDa) in this experiment was used for an elemental probe in X-ray photoelectron spectroscopy (XPS). Sulfur 2p (163 eV) orbital signal was clearly observed (FIG. 12C), demonstrating successful interfacial PEG conjugations.

Example 7

SMA-Assisted SAM Formation

For alkanethiol ad-layer formation, 5 mM of dodecanethiol (Sigma-Aldrich, Milwaukee, Wis.), 1-mercapto-11-undecyl tri(ethylene glycol) (OEG3-C11-SH), or OEG6-C11-SH (Asemblon Inc, Redmond, Wash.) was dissolved in dichloromethane (DCM) which was pre-equilibrated by bubbling with He or $N_2$. SMA-treated substrates (SMA according to Formula II) were subsequently added followed by triethylamine (final concentration 10 mM). After five hours or more (typically overnight reaction for eighteen hours), the SMA-treated substrates were rinsed by either DCM or ethanol and dried with nitrogen.

An alkanethiol monolayer was spontaneously formed through simple immersion of the SMA-treated substrates (FIG. 13B). Monolayer formation on the polydopamine sublayer is believed to involve reaction between terminal thiol groups and the catechol/quinone groups of the polydopamine coating of the substrate in a manner analogous to the reaction between thiols and noble metal films in the formation of conventional SAMs. Alkanethiol monolayers formed by this approach (referred to herein as "pseudo-SAMs" or "pSAMs") appear to be functionally similar to conventionally formed SAMs.

Figure 14:
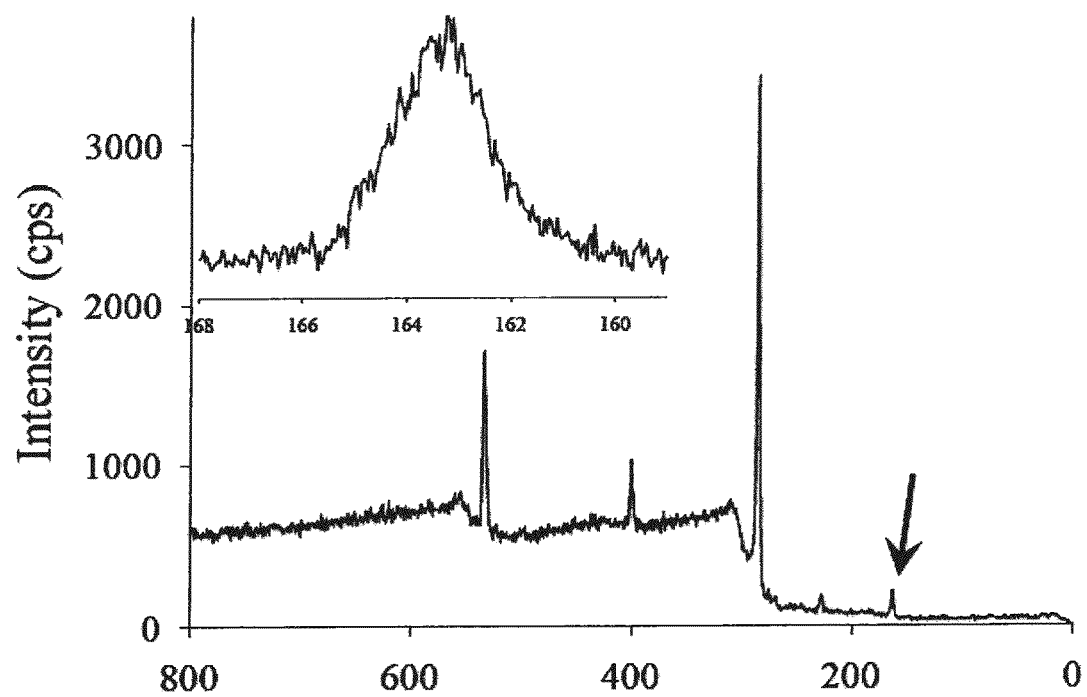
FIG. 14. XPS analysis of self-assembled monolayer formed on polydopamine-coated polycarbonate. XPS survey spectrum after reaction between dodecanethiol and polydopamine-coated polycarbonate. Arrow represents the sulfur 2p (163 eV) signal derived from the surface immobilized dodecanethiol molecules. Inset shows the high-resolution spectrum of the sulfur 2p region marked by the arrow.

For example, spontaneous formation of pSAMs using methyl-terminated alkanethiol (C12-SH) was suggested by water contact angles of greater than 100° (FIG. 13B, Table 3) and XPS spectra revealing the presence of sulfur in the modified substrates (FIG. 14). Table 3 describes the evolution of contact angles of SAMs formed on various polydopamine-coated substrates. $0_{stat}$ and $0_{stat}$ are advancing and static contact angles, respectively. The average contact angles of poly-dopamine-coated and SAM-formed substrates are shown in the last row. pSAMs were formed in this way on at least seven different materials including several ceramics and polymers.

TABLE 3

|  | Bare $0_{adv}$ ($0_{stat}$) | Polydopamine $0_{adv}$ ($0_{stat}$) | SAM $0_{adv}$ ($0_{stat}$) |
| --- | --- | --- | --- |
| PTFE | 115 (106) | 60 (49) | 111 (102) |
| PC | 103 (96) | 54 (42) | 104 (96) |
| NC | 95 (84) | 53 (41) | 118 (106) |
| $SiO_2$ | 21 (<10) | 66 (54) | 101 (92) |
| $TiO_2$ | 22 (<10) | 63 (51) | 103 (94) |
| Cu | 88 (78) | 55 (43) | 119 (109) |
| Au | 68 (54) | 57 (46) | 101 (90) |
| Average | — | 58 (47) | 108 (98) |

Example 8

PEG Grafting

Figure 15:
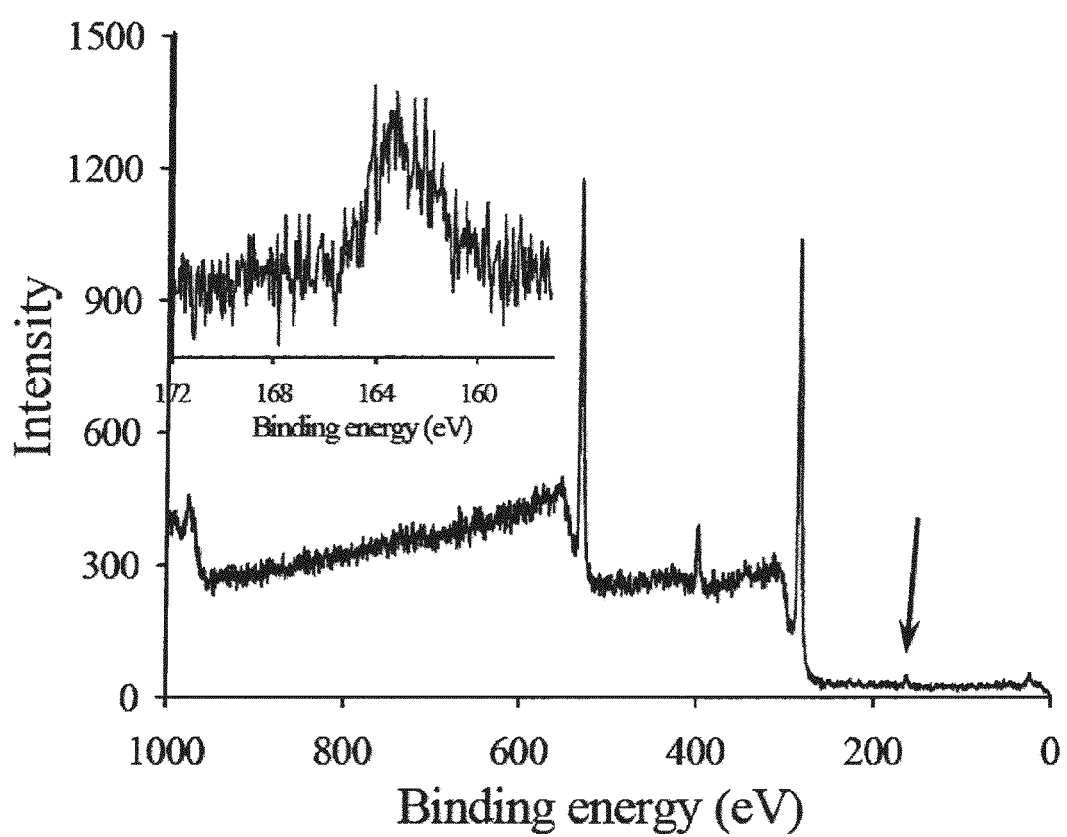
FIG. 15. XPS analysis of PEG grafted onto polydopamine-coated glass. XPS survey spectrum after reaction between mPEG-SH and polydopamine-coated glass. Arrow represents the sulfur 2p (163 eV) signal derived from the surface-immobilized mPEG-SH molecules. Inset shows the high-resolution spectrum of the sulfur 2p region marked by the arrow.

In this example, at least a portion of a substrate was contacted with dopamine to form a reactive, SMA-treated substrate which was contacted with a secondary reactive moiety to form fouling-resistant surfaces. Specifically, fouling-resistant substrates were made by covalently grafting amine- or thiol-terminated methoxy-poly(ethylene glycol) (mPEG-$NH_2$ or mPEG-SH in 10 mM Tris, pH 8.5, 50° C.) to the polydopamine-coated substrate surface (FIG. 15).

For PEG grafting, 5 mg/mL of methoxy-poly(ethylene glycol)-thiol (mPEG-SH, 5 kDa, SunBio, Ahn-Yang, South Korea) or methoxy-poly(ethylene glycol)-amine (mPEG-$NH_2$, 5 kDa, Nektar, San Carlos, Calif.) was dissolved in 10 mM Tris pH 8.0 or sodium phosphate buffer pH 8.0. The buffer used for mPEG-SH was vacuum degassed for more than one hour to prevent oxidation (—S—S—) between thiol groups.

mPEG-$NH_2$-modified, polydopamine-coated glass substrates exhibited substantial reduction in nonspecific protein adsorption compared to uncoated glass, and also outperformed glass substrates modified by a silane-terminated PEG in terms of fouling resistance after two days of continuous exposure to protein solution (FIG. 13D-F). Similarly, mPEG-SH grafting onto a variety of polydopamine-coated substrates led to dramatic reduction of fibroblast cell attachment compared to the unmodified substrates (FIG. 13G, Table 4). The polydopamine coating itself was supportive of fibroblast cell adhesion at a level similar to bare substrates (for example, the total area of attached cells on polydopamine modified $SiO_2$ ($46 \pm 1.4 \times 10^3$ $m^2$) was similar to unmodified $SiO_2$ ($55 \pm 8.6 \times 10^3$ $m^2$)), leading to the conclusion that the observed decrease in cell adhesion was due to the grafted mPEG-SH.

Example 9

SMA-Treated Substrates Having Flagella Labeling

Figure 16:
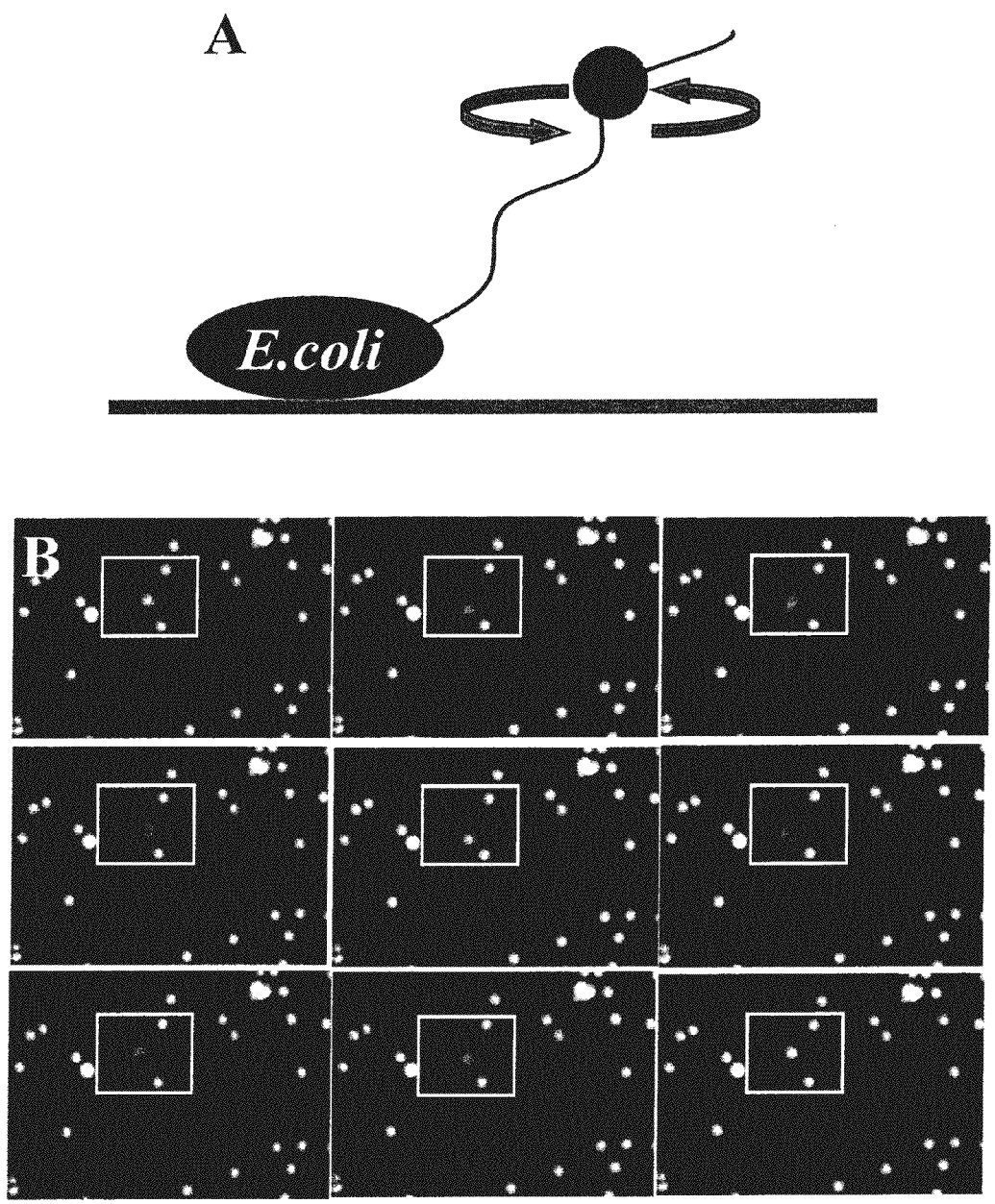
FIG. 16. Chemically 'active' coating targeting cellular proteins for the study of bacterial chemotaxis.

In this example, latex beads were contacted with an aqueous, alkaline solution of dopamine as described in Example 1. The latex beads (1 m in diameter) were spread onto pre-adsorbed E. coli, resulting in one bead attached to a flagella protein (presumably via N-terminus and lysine residues) as evidenced by the counterclockwise rotation of the flagella (FIG. 16, box). The dots represent an individual bead non-specifically adsorbed onto the glass surface showing no spatial movement.

Example 10

Short-Term (4 hr) Fibroblast Adhesion

NIH 3T3 fibroblasts (ATCC, Manassas, Va.) were maintained at 37° C. with 5% $CO_2$ in Dulbecco's Modified Eagle's medium (DMEM, Cellgro, Herndon, Va.) containing 10% fetal bovine serum (FBS, ATCC, Manassas, Va.) and 100 μg/ml of penicillin and 100 Wm' of streptomycin. Trypsinized cells were resuspended in DMEM with 10% FBS and then counted for sub-cultures and/or seeded onto the test substrates at a cell density of $5.0 \times 10^3$ cells/$cm^2$. After 4 hrs, cells were stained with 2.5 pM Calcein-AM (Molecular Probes) in complete PBS for one hour at 37° C. culture. Cell attachment was quantified by acquiring nine images from random locations of each substrate using a fluorescence microscope (Olympus BX-40, $2_{ex}$=549 nm, $X_{em}$=565 nm) equipped with a CCD camera (Roper Scientific, Trenton, N.J.). Finally, the resulting images were processed using Metamorph software (Universal Imaging, Downington, Pa.).

Figure 17:
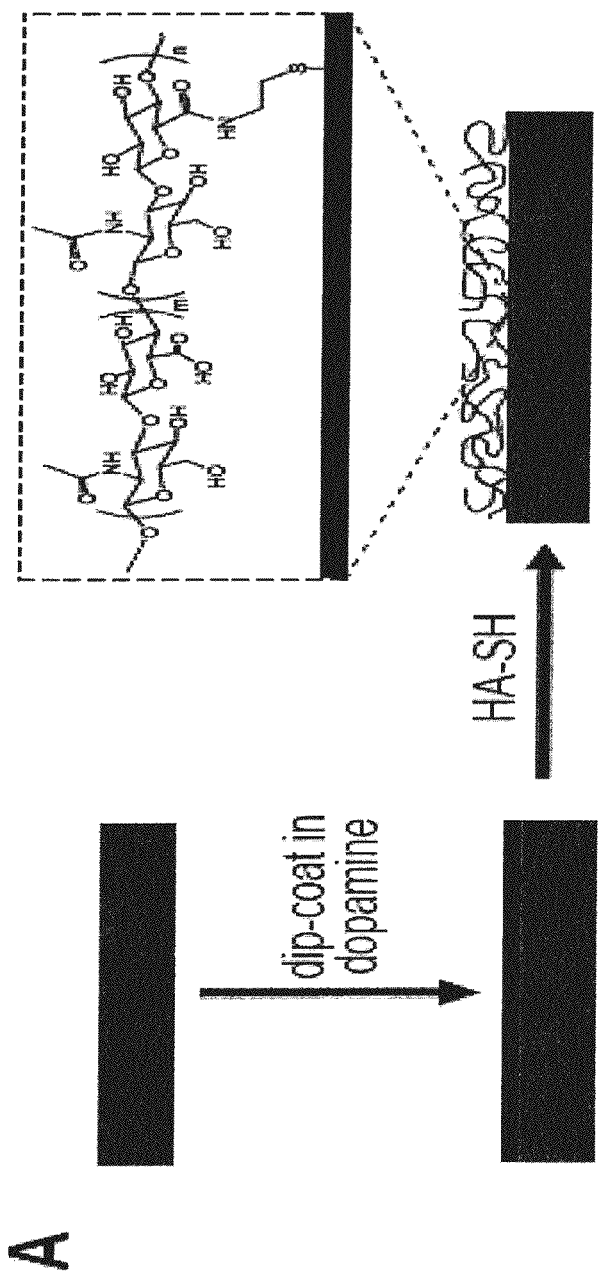
FIG. 17. Polydopamine-assisted grafting of a biomacromolecule for biospecific cell interaction.
Figure 17:
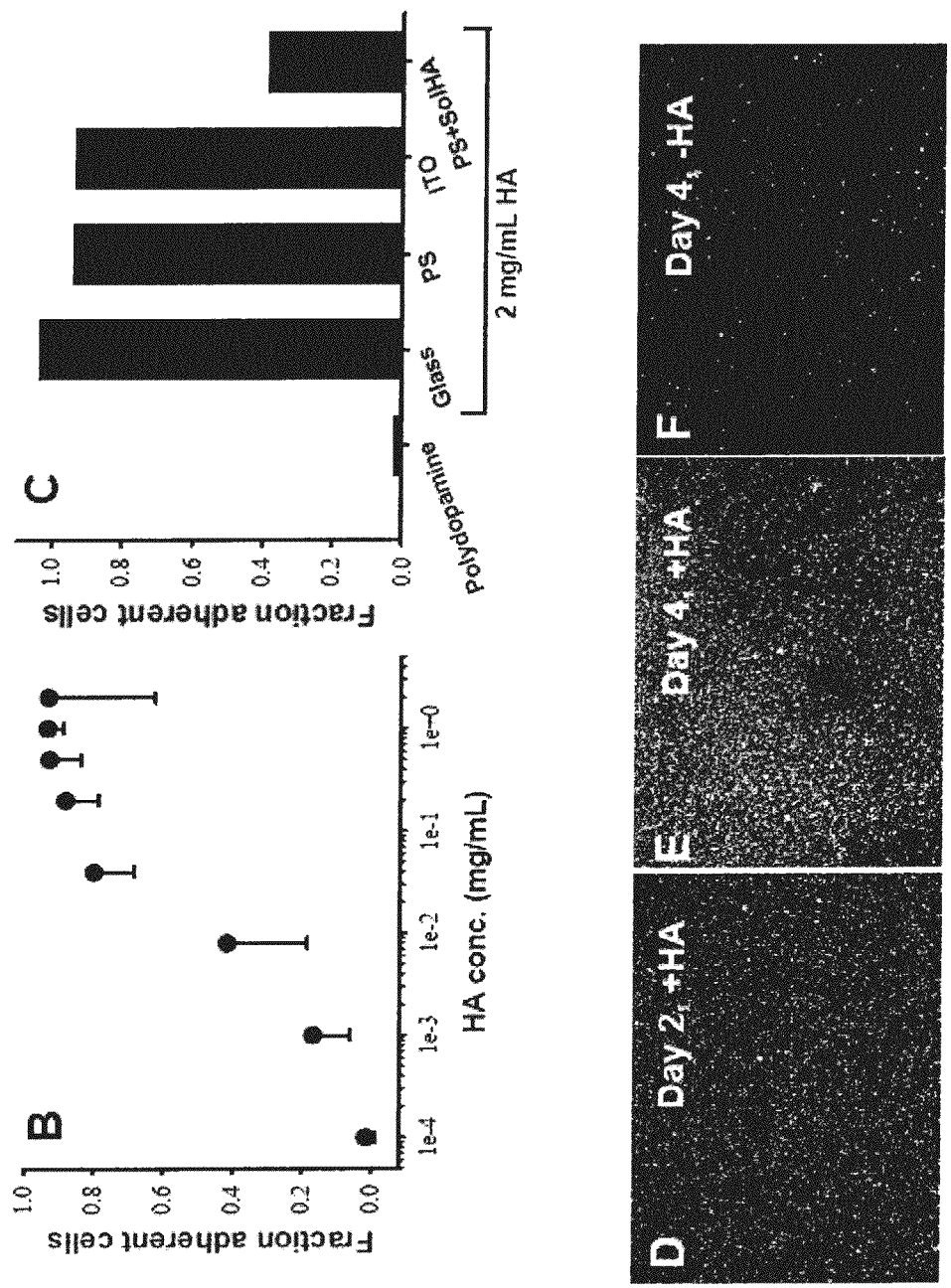

Ad-layers of the glycosaminoglycan hyaluronic acid (HA) were added to SMA-treated substrates prepared according to Example 1 for specific biomolecular interactions. HA/receptor interactions are important for physiological and pathophysiological processes including angiogenesis, hematopoietic stem cell commitment and homing, and tumor metastasis. Partially thiolated HA was grafted onto a variety of SMA-treated substrates (FIG. 17) and HA ad-layer bioactivity was measured via adhesion of the human megakaryocytic M07e cell line. Unlike fibroblasts, M07e cells did not adhere to polydopamine but did adhere to HA-grafted polydopamine-coated substrates in a dose dependent manner (FIG. 17B).

TABLE 4

| Substrates | # of cells (bare) | # of cells (PEG-polydopamine) |
| --- | --- | --- |
| Glass | 68.7 ± 14 | 0 ± 0 |
| $TiO_2$ | 72.1 ± 13 | 0 ± 0 |
| Au | 62.9 ± 14 | 1.3 ± 1 |
| $Sl_3N_4$ | 57.1 ± 9 | 0 ± 0 |
| PTFE | 7.8 ± 4 | 0.2 ± 0.4 |
| PU1 | 16.9 ± 13 | 0.6 ± 0.7 |

TABLE 4-continued

| Substrates | # of cells (bare) | # of cells (PEG-polydopamine) |
|---|---|---|
| PU2 | 15.1 ± 4 | 0.6 ± 1.3 |
| PS | 23.6 ± 8 | 1.1 ± 1.6 |

Example 11

SMA-Assisted Grafting of Hyaluronic Acid

Figure 18:
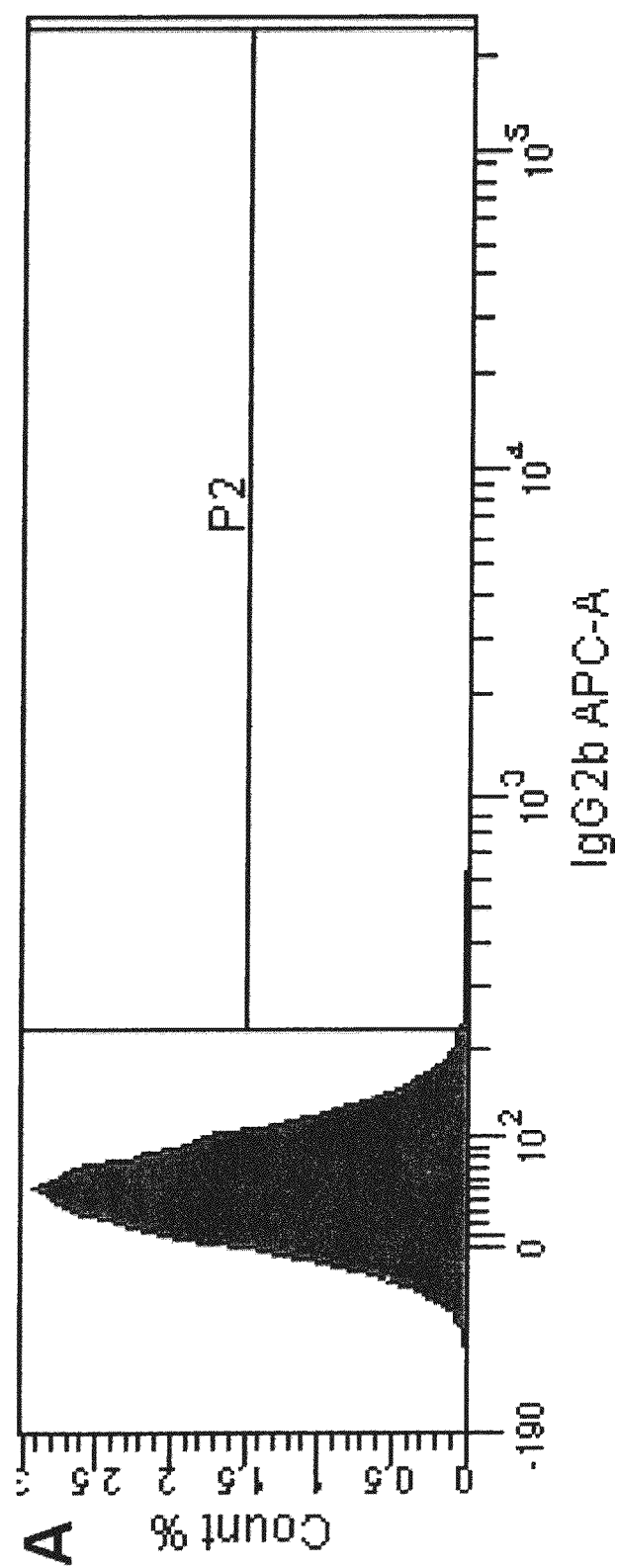
FIG. 18. Flow cytometry analysis of CD44 levels on M07e cells. M07e cells were stained with either isotype control-APC (A) or anti-CD44-APC (B) antibodies to determine the surface expression of CD44 receptors. The fraction of cells expressing CD44 was determined by quantifying the number of cells within the sample having fluorescence intensity greater than isotype-control-stained cells (P2=99.4% for CD44-APC stained cells). Data are representative of two independent experiments.
Figure 18:
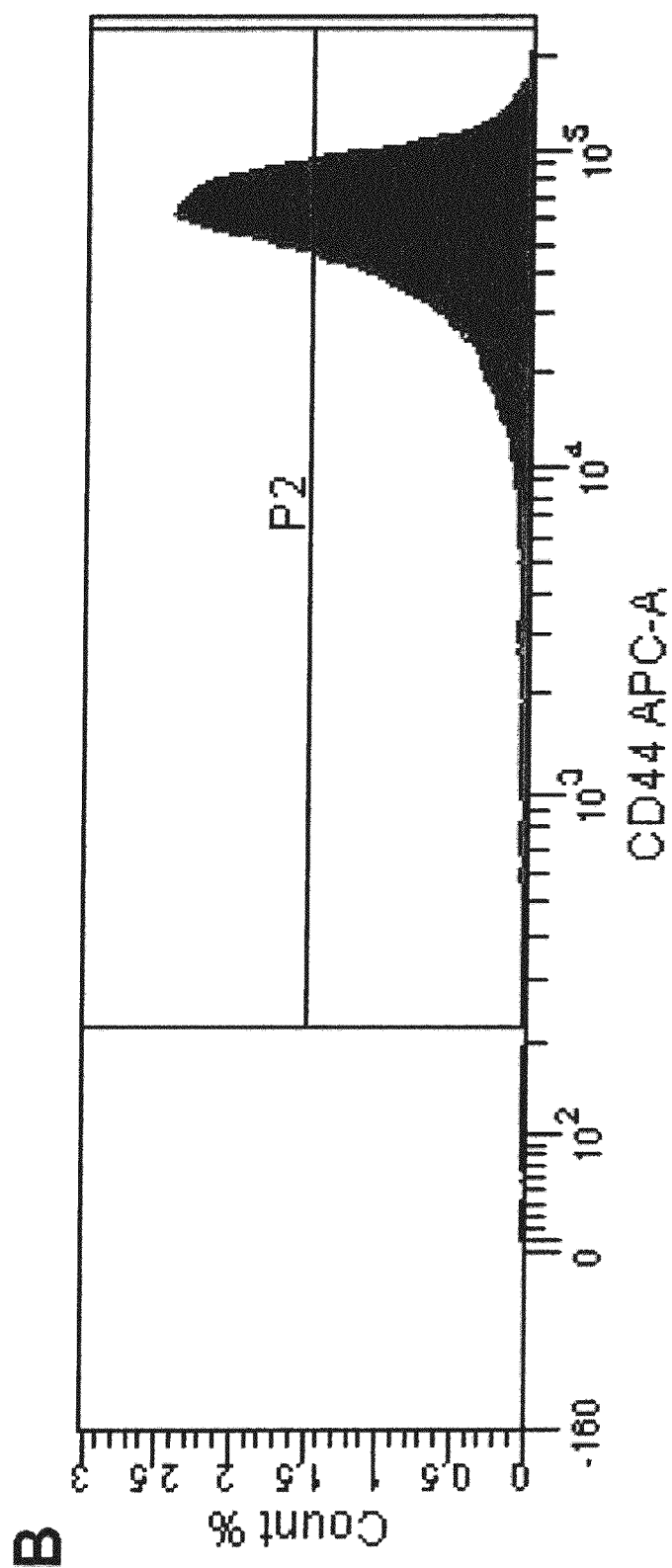
Figure 19:
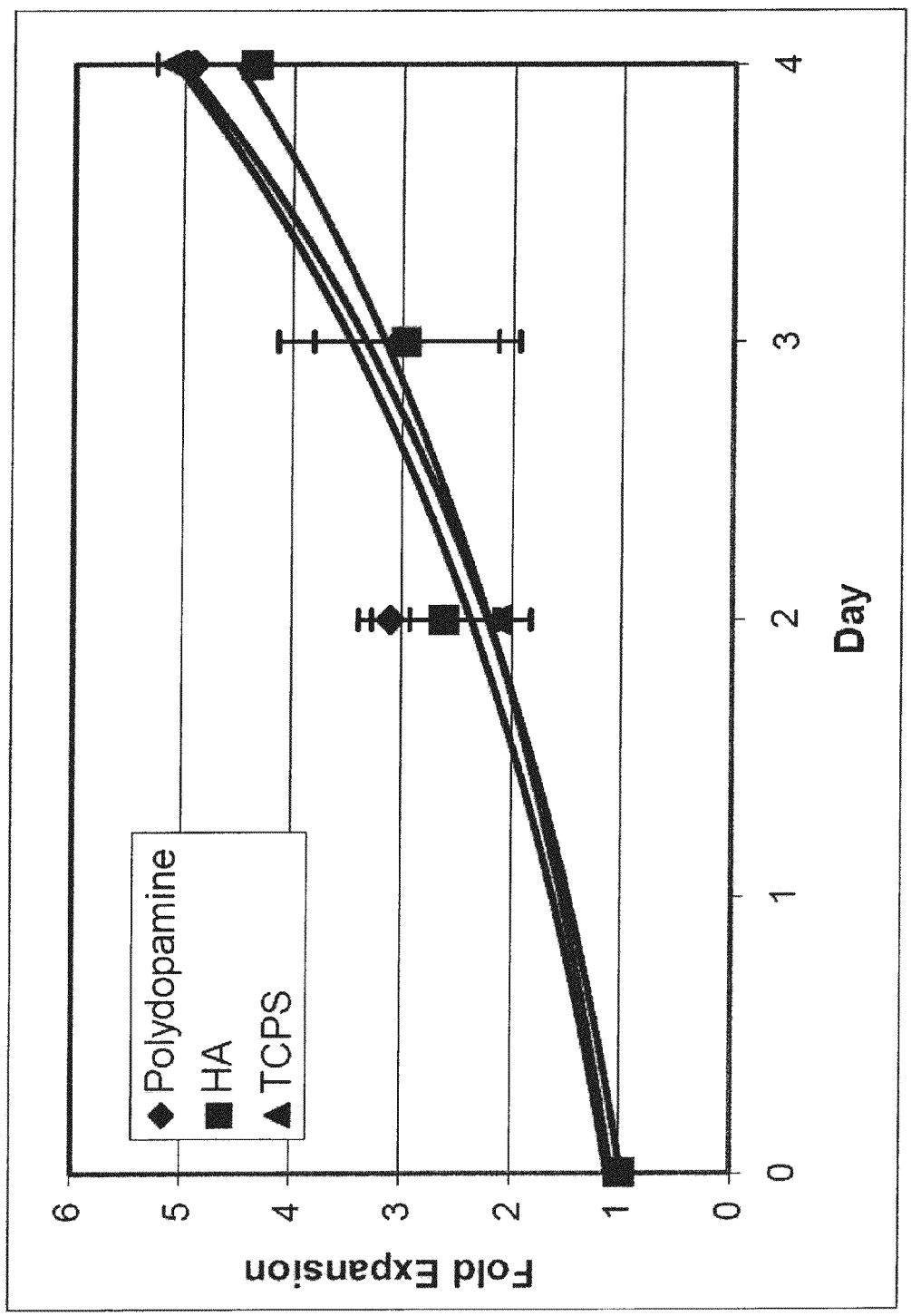
FIG. 19. M07e cell expansion on TCPS, polydopamine, and HA-polydopamine substrates. Similar cell expansion was observed on all three substrates. Curves are best-fit exponential and error bars show standard deviation. Represents average of thirteen experiments/timepoints.

Together with decreased binding in the presence of soluble HA (FIG. 17C), these findings are consistent with expression of the HA receptor CD44 by M07e cells (FIG. 18). Polydopamine and HA-grafted polydopamine-coated substrates were biocompatible as evidenced by similar levels of M07e cell expansion compared to tissue culture polystyrene, although only the HA-grafted polydopamine-coated substrates supported cell adhesion (FIG. 17OD-F; FIG. 19).

17 kDa HA (Lifecore, Chaska, Minn.) was thiolated using a previously published protocol (Lee et al., *Macromolecules* 39, 23 (2006)). The modified HA had approximately 50% substitution (by NMR) with thiol groups. Thiolated HA (0.001-2 mg/mL in de-oxygenated 10 mM Tris buffer, pH 8.0) was reacted with polydopamine-coated substrates for typically overnight to yield HAfunctionalized substrates. HA-tethered, polydopamine-coated glass or indium-tin oxide (ITO) substrates were attached to a bottomless sixteen-well chamber slide (Nunc, Rochester, N.Y.) via the injection of a self-curing silicone rubber (Silastic® Dow Corning) gasket. For TCPS, standard ninety six-well plates were used, and the polydopamine coating and HA ad-layer formation steps were performed sequentially in each well. (Please note that the polydopamine coating and HA ad-layer formation can also be performed simultaneously in each well.)

M07e Cell Culture.

M07e cells (DMSZ, Germany) were adapted to grow in IMDM (Sigma) supplemented with 2.5% FBS (Hyclone), 10 ng/mL GM-CSF (Berlex Laboratories), and 1 mg/mL gentamicin sulfate (Sigma). Cells were maintained in exponential growth phase between $5\times10^5$ and $1\times10^6$ cells/mL. Normal-force cell adhesion assays were performed as previously described (Jensen et al., *J. Am. Chem. Soc.* 126, 15223 (2004)). Briefly, M07e cells were stained with 5 ti·g/mL Calcein AM in PBS and incubated in normal growth media on substrates for two hours prior to removing non-adherent cells by inverted centrifugation at 30 rcf in sealed bags filled with PBS. Image analysis of pre- and post-spin images was used to calculate the percent cell adhesion. Substrates for extended cell culture were sterilized with short-wave UV light for thirty minutes prior to seeding cells in normal growth medium at a density of 3.75×105 cells/mL. Adhesion was measured on days 2 and 4 using the normal-force cell adhesion assay. However, in this case the cells were stained directly in the wells via addition of 40 uL of Calcein AM (diluted to 5 pg/mL PBS) thirty minutes prior to pre-centrifugation imaging. For HA competition, soluble 17 kDa HA was incubated with M07e cells for thirty minutes at 37° C. prior to loading onto HA-grafted, polydopamine-coated wells. For the M07e cell expansion assay, cell density was measured by total nuclei counts in a solution of hexadecyltrimethylammoniumbromide (Sigma; 30 g/L), sodium chloride (8.33 g/L) and EDTA (366.25 mg/L) with a Coulter Multisizer.

Flow Cytometry Analysis of CD44 Levels on M07e Cells.

To determine the expression levels of the HA receptor CD44, M07e cells were washed with PBS containing 1 g/L sodium azide and 0.5% bovine serum albumin. Allophycocyanin (APC)-conjugated mouse anti-human-CD44 antibody or APCconjugated isotype control mouse-$IgG_{2b}$,x antibody (Becton Dickinson) were incubated with the cells for thirty minutes at room temperature. After washing, cells were analyzed on a Becton Dickinson LSRII flow cytometer using FACSDiva software (Becton Dickinson).

Example 12

SMA-Assisted Metal Removal

Twenty mg of dopamine hydrochloride and 1 g of beads were added to 20 ml of pH 8 10 mM Tris buffer. The solution was put on the rocker for three hours for dopamine coating. A column of SMA-treated beads was prepared according to Example 1 and DI water was used to remove excess dopamine hydrochloride. 4.5 ml of metal solution was added to the column. The solution was put on the rocker for certain time to react, and then the filtrate was collected. The concentration of the filtrate was measured using ICP-AES.

Results can be seen in Table 5. Cr, Hg, and Pb showed great affinity for binding to polydopamine-coated beads. Cu showed relatively weak binding. Cd, Ba, and Se showed no affinity for binding. The last three tests on Cr, Hg, and Pb were conducted to see if the SMA-treated beads of the present invention could effectively remove the metal ions at low concentration, and the metal ion concentrations after binding can fall below the MCLs. When measuring such low concentrations, detection limit of the metal ion with ICP-AES and reliability of the data should be considered. ICP-MS can also be used to measure low concentrations. Generally, it falls within the detection limit when it shows a clear intensity peak for a certain concentration of metal ion. Further, the data is reliable when a fit standard can be generated.

For Cr, the data show that its concentration after binding fell below the MCL. The intensity peak for the sample was clear. Thus, polydopamine-coated beads effectively removed Cr to below the MCL. For Pb, the data show that its concentration after binding, although very close, did not fall below the MCL. Further experiments were conducted to test the accuracy of this data.

Hg is the most difficult metal species for ICP-AES to accurately measure the concentration. In ICP-AES, their intensity peaks tend to fluctuate even for the same sample. When measuring fractions of ppm, slight changes in intensity can lead to relatively large change in the calculated concentration. Overall, the data presented herein illustrate that polydopamine-coated substrates can be used to remove metals such as Cr, Hg and Pb from water. An increase in the amount of polymer in the polymeric-coated substrate may likely to reduce the final concentration to below the MCL values for each.

TABLE 5

| Metal (reaction time[1]) | Conc. of added metal solution (ppm) | Conc. without Binding[2] | Conc. Measured (ppm) | MCL[3] (ppm) |
|---|---|---|---|---|
| Cu (overnight) | 10 | 5 | 4.16 | 1.3 |
| Pb (overnight) | 10 | 5 | 2.42 | 0.015 |
| Hg (2 hr) | 10 | 5 | 1.1 | 0.002 |
| Hg (overnight) | 10 | 5 | 1.01 | 0.002 |
| Cr (1 hr) | 10 | 5 | 0.57 | 0.1 |
| Cd (1 hr) | 10 | 5 | 4.85 | 0.005 |
| Se (1 hr) | 10 | 5 | 5.22 | 0.05 |
| Ba (1 hr) | 10 | 5 | 5.22 | 2 |

TABLE 5-continued

| Metal (reaction time[1]) | Conc. of added metal solution (ppm) | Conc. without Binding[2] | Conc. Measured (ppm) | MCL[3] (ppm) |
|---|---|---|---|---|
| Cr (1 hr) | 1 | 0.5 | 0.02 | 0.1 |
| Pb (1 hr) | 1 | 0.5 | 0.031 | 0.015 |
| Hg (1 hr) | 1 | 0.5 | 0.17 | 0.002 |

[1]Reaction time indicates Step 4 in the procedure.
[2]"Concentration without Binding" was obtained from a prediction that 1 g of beads hold about 4.5 mL of water and additional 4.5 mL of metal solution should make the overall concentration half the concentration of the added metal solution.
[3]MCL stands for Maximum Contaminant Level for drinking water set by U.S. Environment Protection Agency.

Example 13

SMA-Treated Substrates Surface Conjugation of Poly-L-Histidine

Figure 20:
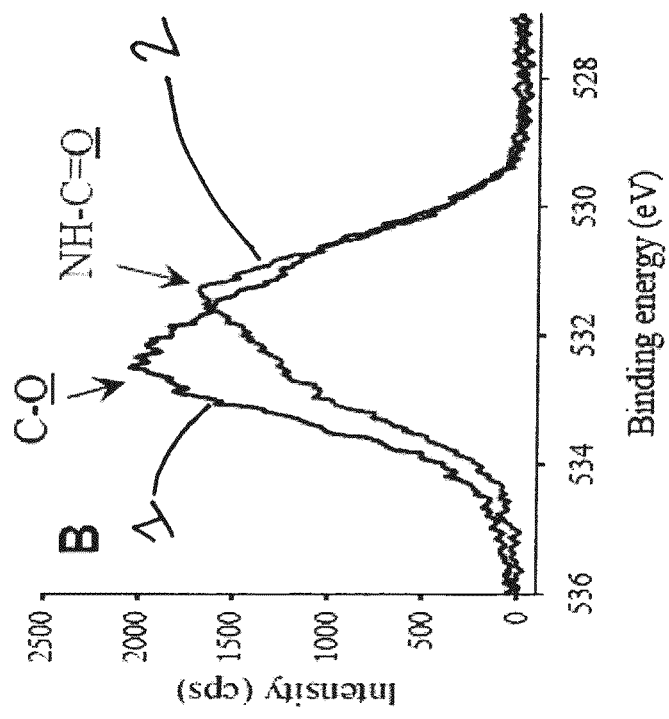
FIG. 20. High resolution x-ray photoelectron spectroscopy (XPS) analysis of C1s region (A) and O1s (B) of polydopamine-coated SiOx substrate after secondary reaction of pHis at pH 4.0 (1) and 6.8 (2).
Figure 20:
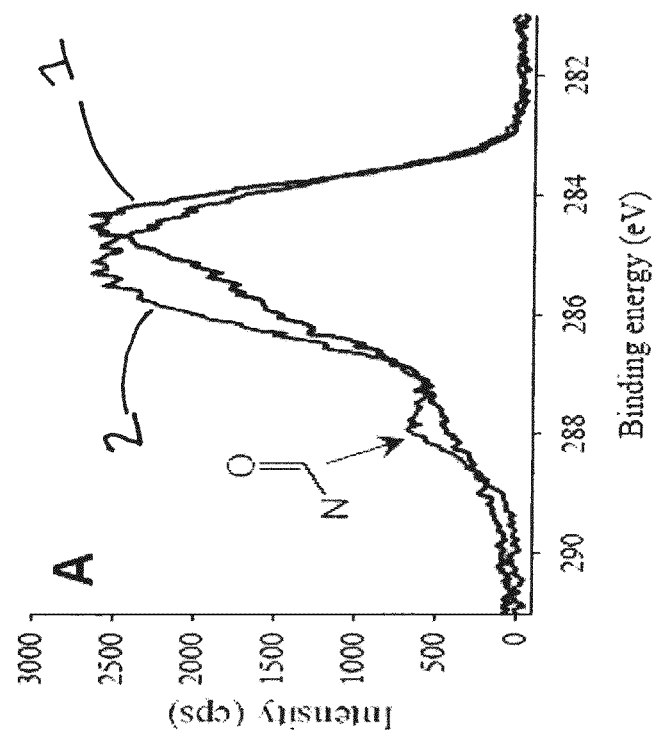

Poly-histidine (0.5 mg/mL, Sigma, $M_w$=12,000) (pHis) was dissolved in acetate/phosphate/tris buffers with various pHs. Subsequently, polydopamine-coated substrates (prepared according to Example 1) were immersed in pHis-containing solutions buffered at various pHs (4.0 and 6.8) for 4 hrs. As shown in FIG. 11A, pHis surface reaction was pH-dependent; the surface carbon composition of the polydopamine-coated silicon wafer reacted with pHis at low pH showed the absence of a peptide carbon (O═C—NH) signal, whereas the peptide carbon was appeared in XPS from the surface immersed in the pHis-containing neutral buffer (pH=6.8), indicating that the deprotonated nitrogen in imidazole rings is chemically reactive toward polydopamine layers. Likewise, a new oxygen signal from peptide bonds (approximately 531 eV) was detected at the polydopamine-coated silicon substrate reacted with pHis at pH 6.8 (FIG. 20B).

Figure 21:
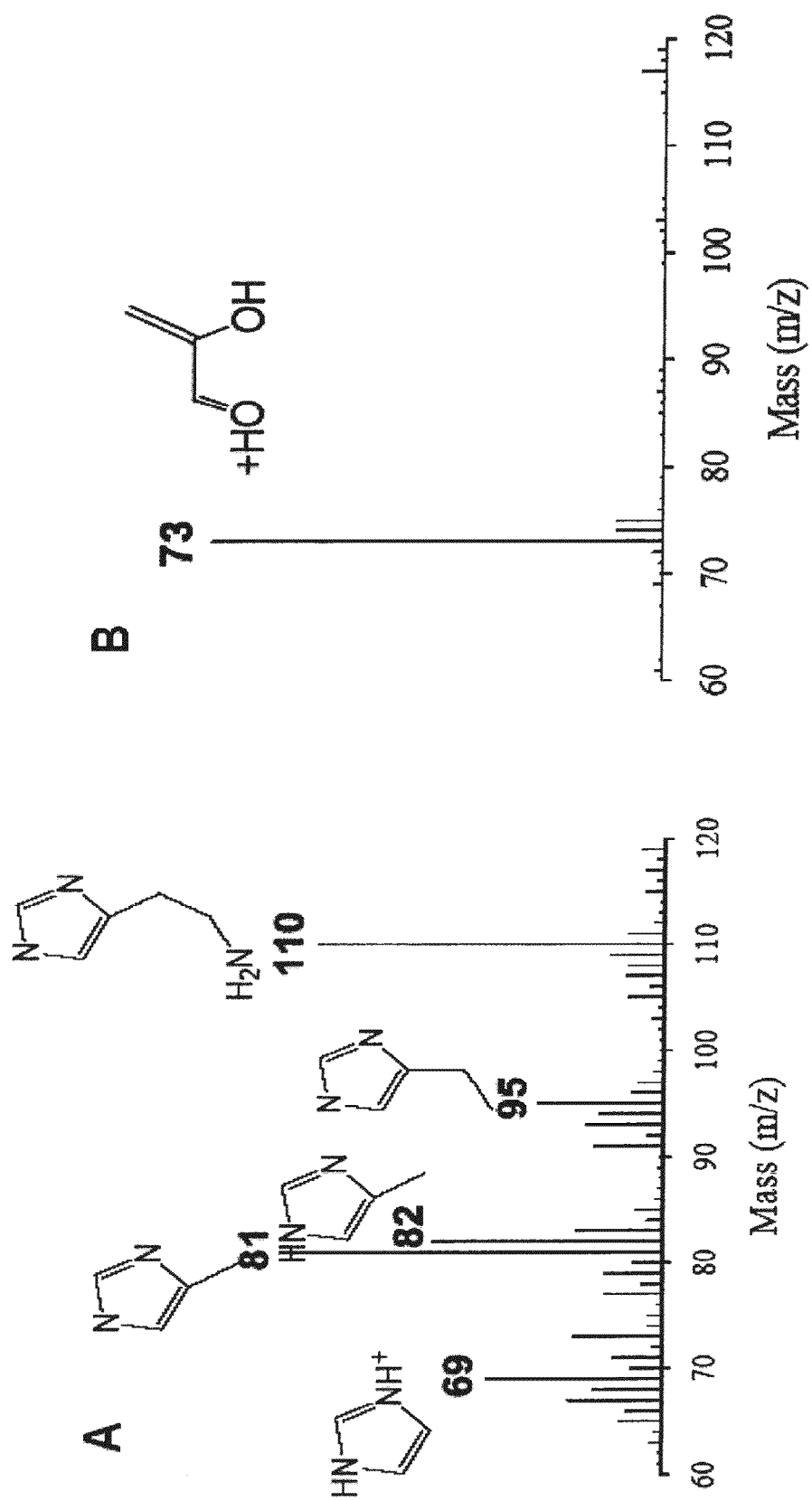
FIG. 21. ToF-SIMS analysis of pHis-polydopamine-coated silicon substrate (A); Polydopamine-coated substrate (B).

The pHis-conjugated polydopamine-coated silicon surface previously characterized in XPS (pH 6.8 sample) was used for time-of-flight secondary ion mass spectrometry (ToF SIMS) analysis. As shown in FIG. 21A, peaks (m/z=69, 81, 82, 95, and 110) detected from the pHis immobilized surface are reminiscent of imidazole-containing structures, which were not detected in the polydopamine-coated surface (FIG. 21B).

Figure 22:
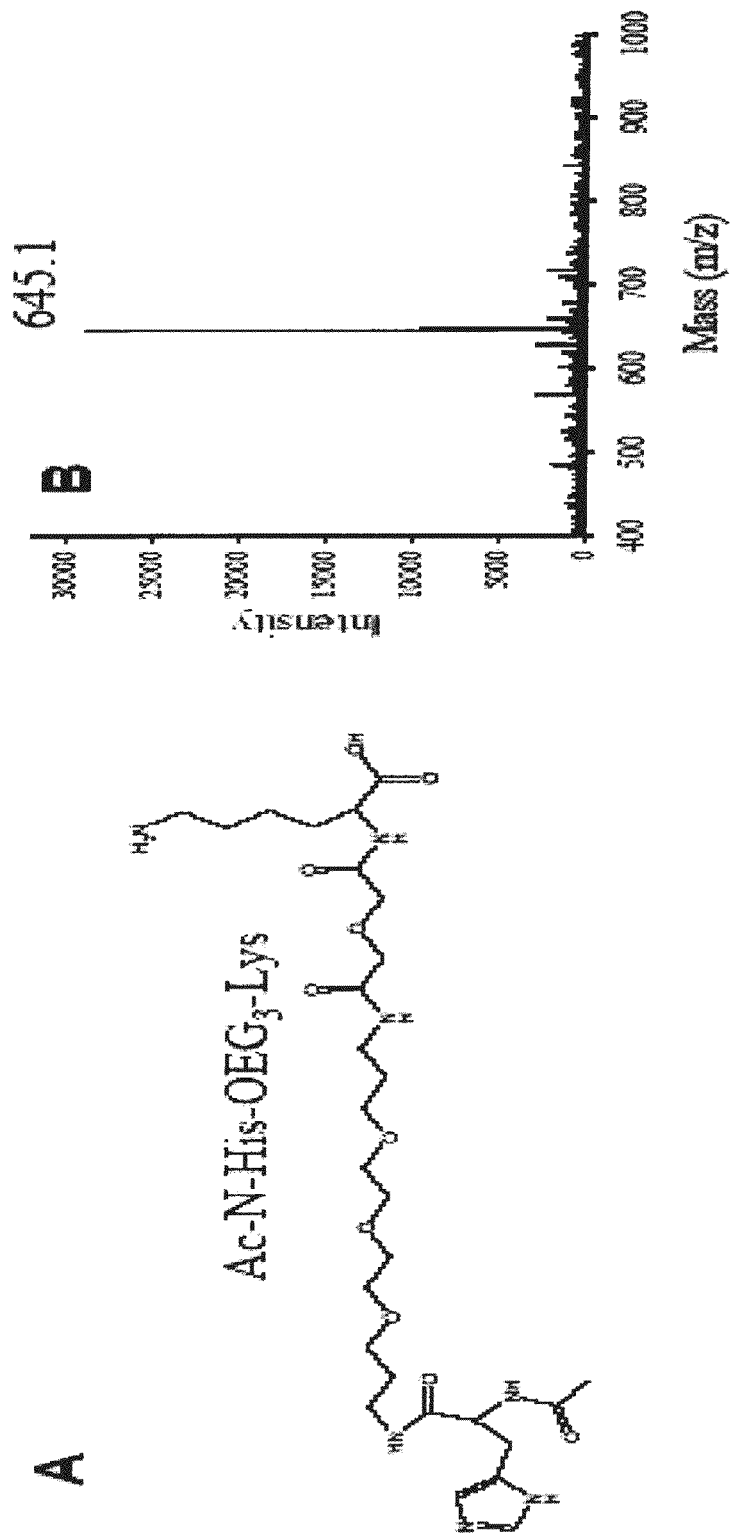
FIG. 22. Hetero-bifunctional Ac-N-His-OEG$_3$-Lys (A); Matrix Assisted Laser Desorption/Ionization Time of Flight mass spectrometry (MALDI-ToF MS) spectra after synthesis and purification of Ac-N-His-OEG$_3$-Lys (B).

Due to the difference in pKa of imidazole's secondary amine (approximately 6) and lysine's -primary amine (approximately 10), it can be hypothesized that the corresponding amine group from each side chain might exhibit different reactivity onto polydopamine-coated substrates depending on reaction buffer pHs. A heterobifunctional molecule, N-acetyl-histidine-oligo(ethylene glycol)-lysine (Ac-N-His-OEG3-Lys), was designed and synthesized by using a standard Fmoc solid-phase peptide synthesis method (FIG. 22A). Matrix-assisted laser desorption/ionization time-of-flight (MALDI TOF) mass spectrometry showed the successful synthesis of Ac-N-His-OEG3-Lys (m/z=645.1) (FIG. 22B).

The Ac-N-His-OEG3-Lys molecule (hereafter His-Lys) can be covalently immobilized via either secondary amine of imidazole (polydopamine-His) or -amine of lysine (polydopamine-Lys) side chain, which significantly impacts the orientation of the -primary amine or imidazole groups with respect to the substrate surface. The -primary amine is exposed to an aqueous solvent if histidine reacts with a polydopamine layer, or is alternatively not exposed to the solvent as a result of lysine reaction with the polydopamine layer, and the predominant orientation may therefore be controlled by the pH of the medium during reaction as shown in the following example where N-hydroxysuccinimidyl biotin and subsequent peroxidase-conjugated streptavidin coupling was used to determine the orientation of His-Lys molecules.

Figure 23:
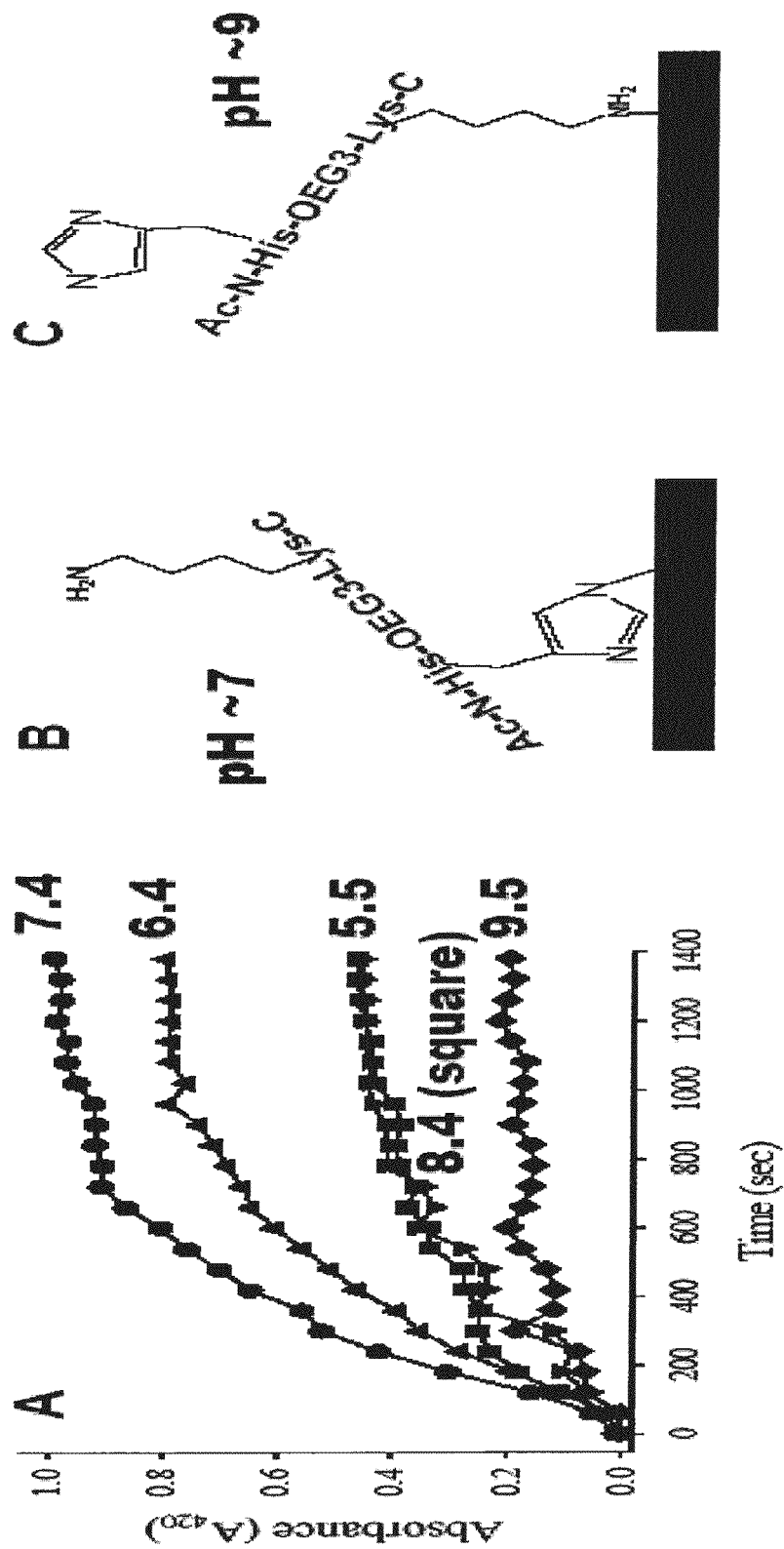
FIG. 23. Peroxidase activities monitored at 420 nm as a function of pH (A); Polydopamine-His configuration allowed biotinylation which serves as a platform for streptavidin-peroxidase immobilization at mild acidic and neutral pHs (B); Polydopamine-Lys orientation prevented biotinylation/streptavidin-peroxidase immobilization, resulting in low peroxidase activities at alkaline pHs (C).

Surface coupling reactions of His-Lys molecules (0.1 mM) dissolved in 10 mM acetate/phosphate-/tris co-buffer, (pH 5.5, 6.4, 7.4, 8.4, and 9.5) for 5 hrs followed by biotinylation (10 mM) (4 hrs, in 10 mM phosphate buffer pH 7.8) were performed. The colorimetric enzyme assay for peroxidase resulted in pH-dependent enzyme activities (FIG. 23A), demonstrating preferential orientation of His-Lys molecules covalently immobilized on polydopamine-coated substrates (FIGS. 23B-C). The enzyme activity was monitored by the colorimetric product, purpurogallin, at 420 nm in which pyrogallol and hydrogen peroxide were used as substrates.

10 mg/mL of pyrogallol in 0.1 M phosphate buffer (pH 6.0) and a dilute hydrogen peroxide solution (1:74=$H_2O_2$:$H_2O$, v/v) were prepared as substrates for peroxidase. The peroxidase reaction was triggered by the vertical insertion of the enzyme-immobilized polydopamine surface to a quartz cuvette. Composition of the substrate solution is as follows: 2.0 mL of phosphate buffer, pH 6.0, 0.3 mL of pyrogallol solution, pH 6.0, and 0.2 mL of hydrogen peroxide solution.

Example 14

Norepinephrine-Treated Substrates

Inspired by the surface-independent coating ability of dopamine, a structural derivative of dopamine, norepinephrine, was also tested and found to exhibit the versatile surface-modifying property. A wide range of substrates (noble metals, oxides, polymers, semiconductors, and ceramics) were treated with norepinephrine (15-20 hrs, 2 mg of norepinephrine per milliliter of 10 mM tris, pH 7.5 or higher and non-aqueous solvents such as chloroform, dichloromethane, methanol, ethanol, (iso)-propanol, dimethylformamide, dimethylsulfoxide, hexane, etc.), and subsequently the substrates were rinsed with water. Contact angle of each substrate was measured before (hatch) and after (solid) norepinephrine coating (FIG. 25).

Figure 25:
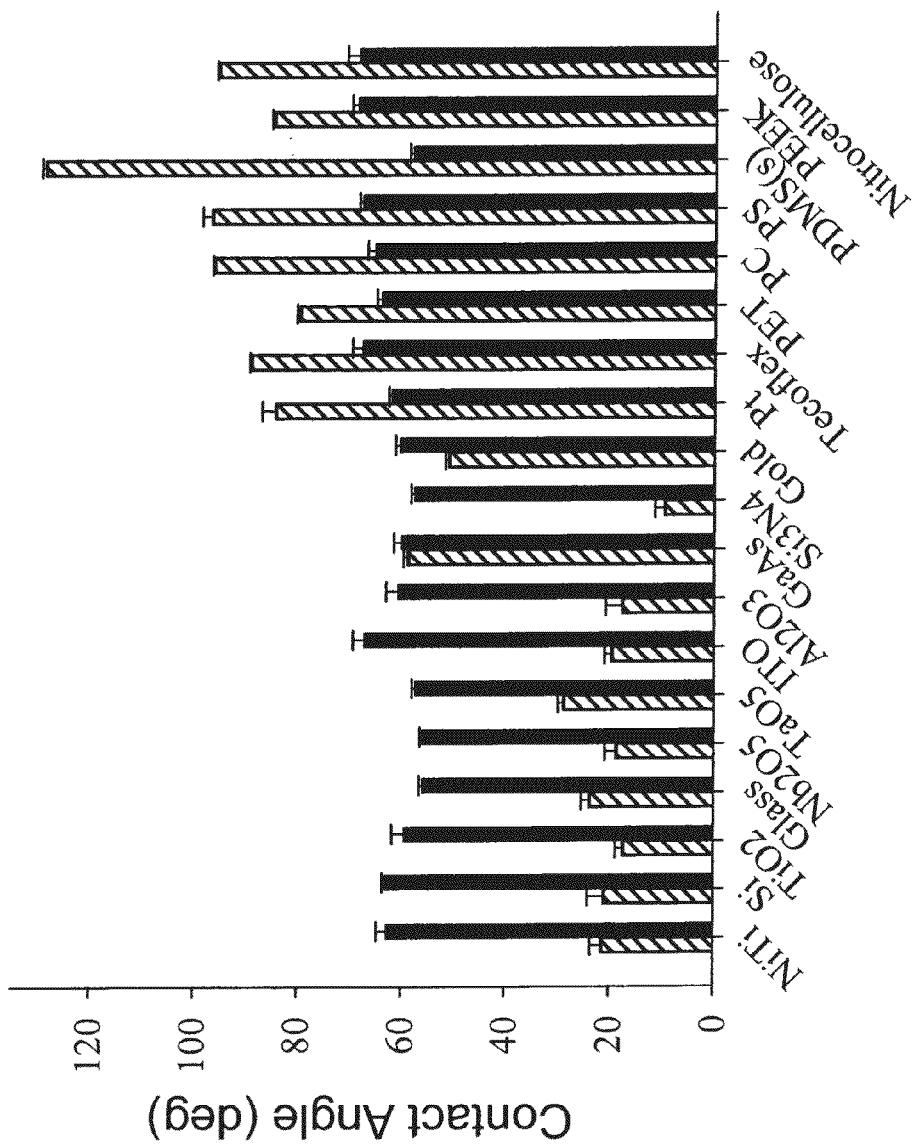
FIG. 25. Contact angle of each substrate was measured before (solid) and after (hatch) norepinephrine coating. The contact angle after coating was relatively consistent, indicating successful norepinephrine coating, whereas the contact angles of bare materials varied from hydrophilic (approximately 10°) to hydrophobic (approximately 130°).

As shown in FIG. 25, the contact angle after coating was relatively consistent (approximately 60°) indicating successful norepinephrine coating, whereas the contact angles of bare materials varied from hydrophilic (approximately 10°) to hydrophobic (approximately 130°).

The marine antifouling and fouling-release performance of titanium surfaces coated with a bio-inspired polymer was investigated. The polymer consisted of methoxy-terminated poly(ethylene glycol) (mPEG) conjugated to the adhesive amino acid L-3,4-dihydroxyphenylalanine (DOPA). Biofouling assays for the settlement and release of the diatom *Navicula perminuta* and settlement, growth and release of zoospores and sporelings (young plants) of the green alga *Ulva linza* were carried out. Results were compared to glass, a poly(dimethylsiloxane) elastomer (Silastic T2) and uncoated Ti. The mPEG-$DOPA_3$ modified Ti surfaces exhibited a substantial decrease in attachment of both cells of the diatom *Navicula perminuta* and zoospores of the green seaweed *Ulva linza* as well as the highest detachment of attached cells under flow compared to control surfaces. The superior performance of this polymer over a standard silicone fouling-release coating in diatom assays and approximately equivalent performance in zoospore assays demonstrate that this polymer can be effective in marine antifouling and fouling-release applications.

In summary, marine antifouling and fouling-release properties of titanium surfaces modified with mPEG-$DOPA_3$ were evaluated and compared to glass, glass coated with a poly (dimethylsiloxane) elastomer (PDMSE), and unmodified titanium. Settlement (adhesion) and fouling-release were assayed with the diatom *Navicula perminuta* and zoospores of the green alga *Ulva linza*. The release of sporelings (young plants) of *Ulva* was also determined. A substantial decrease in attachment of both *Navicula* cells and *Ulva* zoospores onto mPEG-DOPA$_3$-modified Ti surfaces was observed compared to all control surfaces. Furthermore, detachment of the adhered organisms under flow was highest on mPEG-DOPA$_3$ modified Ti surfaces, with removal of over 80% of *Ulva linza* spores and nearly 100% removal of *Navicula perminuta*.

Example 15

Biofouling Compositions

Materials and Methods.

Synthesis of mPEG-DOPA$_{1-3}$ has been described in detail in a previous communication (Dalsin et al., 2005 noted above). Briefly, di-, and tri-DOPA peptides (DOPA$_{2-3}$) were synthesized in solution from Boc/TBDMS-protected DOPA using standard carbodiimide chemistry. DOPA and DOPA peptides were deprotected and subsequently coupled to activated methoxy-PEG in the presence of 0.1 M sodium tetraborate buffer. The resulting polymer conjugate was characterized by MALDI-MS and $^1$H NMR.

Borosilicate glass microscope slides were purchased from Fisher Scientific. 2-propanol and the buffer N-morpholinopropanesulfonic acid (MOPS) were purchased from Aldrich (Milwaukee, Wis.). Water used for all experiments was purified with a Millipore water treatment apparatus (≥18.2 MΩ cm, total organic content ≤5 ppb). Artificial seawater was made with 'Tropic Marin' sea salt (Aquarientechnik GmbH). Guillard's F2 medium for diatom culture and enriched seawater medium for *Ulva* sporelings were made using artificial sea water supplemented with appropriate nutrients (Guillard R R L, Ryther J H (1962) Studies on marine planktonic diatoms. 1. *Cyclotella nana Hustedt* and *Detonula confervacea* (Cleve). *Can J Microbiol*, 8, 229-239).

Surface Preparation and Modification.

Glass microscope slides (75 mm×25 mm) were cleaned ultrasonically for ten minutes in 2-propanol, and then dried under a stream of N$_2$. Slides were further cleaned with a 3-min O$_2$ plasma exposure at ≤150 Torr and 100 W (Harrick Scientific, Ossining, USA) and then coated with a 20 nm thick layer of Ti by electron beam evaporation (Edwards Auto306; <10$^{-5}$ Torr). Prior to polymer adsorption, the Ti-coated slides were cleaned as above and then modified with mPEG-DOPA$_3$ by simple dip-coating in 1.0 mg ml$^{-1}$ mPEG-DOPA$_3$ in 0.6 M K$_2$SO$_4$ buffered to pH 6.0 with 0.1 M MOPS at 50° C. for 24 hours (Dalsin et al., 2005). After modification, slides were rinsed extensively with ultrapure H$_2$O and dried in a stream of filtered N$_2$. Slides modified with a coating of poly (dimethylsiloxane) elastomer (PDMSE; Silastic T2, Dow Corning) were used as a standard foul-release surface. The preparation of these surfaces has been described elsewhere (Hoipkemeier-Wilson L, Schumacher J, Carman M, Gibson A, Feinberg A, Callow M, Finlay J, Callow J, Brennan A (2004) Antifouling potential of lubricious, micro-engineered, PDMS elastomers against zoospores of the green fouling alga *Ulva* (*Enteromorpha*). *Biofouling*, 20, 53-63). Acid-washed glass slides and unmodified Ti-coated glass slides were included in assays as controls. All test and control surfaces were equilibrated in artificial seawater (ASW) at pH 8.0 in the dark for one hour prior to the start of bioassays.

Surface Characterization.

Modification of Ti-coated slides with mPEG-DOPA$_3$ was confirmed by contact angle measurements, ellipsometry thickness measurements as well as x-ray photoelectron spectroscopy (XPS). The wettability of surfaces before and after modification was measured using a contact angle goniometer (Ramé-Hart, Mountain Lakes, N.J.). Advancing and receding contact angles were measured for ultrapure water on the surfaces using an auto pipetting system (Ramé-Hart, Mountain Lakes, N.J.). Three measurements were made for each surface and the mean and standard deviation were reported. A M-2000 spectroscopic ellipsometer (J. A. Woollam, Lincoln, Nebr.) was used to measure mPEG-DOPA$_3$ polymer thickness on Ti-coated silicon wafer substrates; glass substrates could not be used for ellipsometry measurements because a reflective surface is required for this technique. Measurements were made at 65°, 70° and 75° using wavelengths from 193-1000 nm. The spectra were fit with multilayer models in the WVASE32 software (J. A. Woollam). Optical properties of the bare substrate were fit using a standard TiO$_2$ model, while properties of the polymer layer were fit using a Cauchy model ($A_n$=1.45, $B_n$=0.01, $C_n$=0). The obtained ellipsometric thicknesses represent the "dry" thickness of the polymer under ambient conditions. The average thickness of three substrates is reported with standard deviation.

Survey and high resolution XPS spectra were collected on an Omicron ESCALAB (Omicron, Taunusstein, Germany) configured with a monochromated Al K$_\alpha$ (1486.8 eV) 300-W X-ray source, 1.5 mm circular spot size, a flood gun to counter charging effects, and an ultrahigh vacuum (<10$^{-8}$ Torr). The takeoff angle, defined as the angle between the substrate normal and the detector, was fixed at 45°. Substrates were mounted on standard sample studs by means of double-sided adhesive tape. All binding energies were calibrated using the C(1s) carbon peak (284.6 eV). Analysis consisted of a broad survey scan (50.0 eV pass energy) and high-resolution scans (26.0 eV pass energy) at 275-295 eV for C(1s), 450-470 eV for Ti(2p) and 520-540 eV for O(1s). Curve fitting was performed using CasaXPS software with a Shirley background subtraction; atomic compositions of the surfaces were determined by normalizing peak areas using atomic sensitivity factors (Dalsin et al., 2005, noted above).

Experimental Organisms.

Cultures of the diatom *Navicula perminuta*, originally isolated by Dr. Richard. Wetherbee (The University of Melbourne; Melbourne, Australia), were grown in F2 medium (Guillard & Ryther, 1962) at 18° C. with a 16 h: 8 h, light: dark cycle. Reproductive thalli of the green macroalga *Ulva linza* (syn. *Enteromorpha linza*) (Hayden H S, Blomster J, Maggs C A, Silva P C, Stanhope M J, Waaland J R (2003) Linnaeus was right all along: *Ulva* and *Enteromorpha* are not distinct genera. *European Journal of Phycology*, 38, 277-294) were collected from Wembury Beach, Devon, England (50° 18' N; 4° 02' W). Zoospores were released in ASW and prepared for assays as described by Callow et al. (Callow M E, Callow J A, Pickett-Heaps J D, Wetherbee R (1997) Primary adhesion of *Enteromorpha* (Chlorophyta, Ulvales) propagules: Quantitative settlement studies and video microscopy. *Journal of Phycology*, 33, 938-947).

Settlement and Adhesion Strength of *Navicula*.

*Navicula* was cultured in F2 medium contained in 250 ml conical flasks for three days until log-phase growth was achieved. Cells were washed in fresh medium (3×) before harvesting and diluting to give a suspension with a chlorophyll a content of approximately 0.3 µg ml$^{-1}$. Cells were settled on 6 slides of each treatment in individual dishes containing 10 ml of suspension at ~20° C. Cells fall through the water column by gravity, thus a similar number of cells will settle onto all surfaces. After 2 h the slides were very gently washed in seawater to remove cells that had not properly attached. Three slides of each treatment were fixed in 2.5% glutaraldehyde in sea water, desalted by washing in 50:50 seawater:distilled water, followed by distilled water and dried before counting. The density of cells attached to the surface was counted on each of three replicate slides using a fluorescent microscope. On each slide, 30 fields of view (0.17 mm$^2$) taken at 1 mm intervals along the centre were counted to provide cell attachment data.

The remaining three replicate slides were used to evaluate the strength of diatom attachment. This was achieved by exposure to a shear stress of 20 Pa in a specially designed water channel, originally described by Schultz et al. (Schultz M P, Finlay J A, Callow M E, Callow J A (2000) A turbulent channel flow apparatus for the determination of the adhesion strength of microfouling organisms. *Biofouling*, 15, 243-251 and Schultz M P, Finlay J A, Callow M E, Callow J A (2003) Three models to relate detachment of low form fouling at laboratory and ship scale. *Biofouling*, 19 (supplement), 17-26) and subsequently modified with a higher capacity pump (Finlay J A, Callow M E, Ista L K, Lopez G P, Callow J A (2002) The influence of surface wettability on the adhesion strength of settled spores of the green alga *Enteromorpha* and the diatom *Amphora*. *Integrative and Comparative Biology*, 42, 1116-1122). After exposure to flow the slides were fixed in glutaraldehyde and processed for counting as described above. The number of cells remaining attached was compared with unexposed control slides to determine % removal under flow.

Settlement and Adhesion Strength of *Ulva*.

Procedures fully described elsewhere (e.g. Chaudhury et al. (2005) *Biofouling*, 21, 41-48) were used. In brief, 10 ml of a zoospore suspension containing 1×10$^6$ spores ml$^{-1}$ were added to individual compartments of Quadriperm dishes, each containing one slide. The slides were incubated in the dark for 1 h, and then gently washed in seawater to remove zoospores that were still motile and hence unattached. The density of zoospores attached to the surface was counted on each of three replicate slides using an image analysis system attached to a fluorescent microscope. Spores were visualized by autofluorescence of chlorophyll and counts were reported for 30 fields of view (0.17 mm$^2$) on each slide to provide settlement data as above.

Slides settled with zoospores for 1 h were subsequently exposed to a shear stress in the water channel used for *Navicula* assays. The water channel was run at maximum flow velocity creating a wall shear stress of 53 Pa. The number of spores remaining attached was compared with unexposed control slides.

Growth and Adhesion of *Ulva* Sporelings.

Spores were allowed to settle on test surfaces as described above. After 1 hour the seawater in the mPEG-DOPA$_3$ dishes was only partially changed (over 66%) so that the level of water did not fall below that of the slide surface, which could have resulted in the removal of weakly attached spores. Sporelings (young plants) were cultured in enriched seawater medium in individual (10 ml) wells in polystyrene dishes under illuminated conditions inside a growth cabinet at 18° C. with a 16:8 light:dark cycle (photon flux density 330 µmol m$^{-2}$s$^{-1}$). The medium was refreshed every 2 days. After an 8-day culture period, the sporeling biomass on half of each slide was removed by scraping with a razor blade, and the chlorophyll extracted in dimethyl sulphoxide (Pettitt et al. (2004) *Biofouling*, 20, 299-311). The amount of chlorophyll a present was determined spectrophotometrically using the equations of Jeffrey & Humphrey (Jeffrey et al. (1975) *Biochemie Und Physiologic Der Pflanzen*, 167, 191-194). The remaining half slides of biomass (from above) were exposed to a shear stress of 53 Pa in the water channel as for the spore test. The biomass remaining in the samples was analyzed for chlorophyll a content as described above.

Results.

Surface Characterization.

Thorough characterization of mPEG-DOPA$_3$ modified Ti substrates has been reported previously (Dalsin et al., 2005); selected experiments were repeated here in order to confirm similar results on Ti-coated glass substrates. Advancing ($\theta_a$) and receding ($\theta_r$) contact angles for all substrates are reported in Table 6. Surfaces modified with mPEG-DOPA$_3$ exhibited an advancing contact angle of 33°±3° and a receding contact angle of 26°±2° for ultrapure water. These results were within the range of contact angle measurements reported for OEG-containing surfaces, confirming the presence of PEG (Branch et al. (2001) *Biomaterials*, 22, 1035-1047; Sharma et al. (2004) *Langmuir*, 20, 348-356). The dry adsorbed polymer thickness was measured using spectroscopic ellipsometry; an average thickness of 31.4±5.1 Å was measured for mPEG-DOPA$_3$ on Ti-coated substrates.

TABLE 6

Advancing and receding water contact angles

| | Water contact angles (deg) | |
|---|---|---|
| | advancing | receding |
| Glass | <15 | <15 |
| PDMSE[a] | 115 ± 4 | 69 ± 2 |
| Ti Control | 24 ± 6 | 15 ± 4 |
| mPEG-DOPA$_3$ | 33 ± 3 | 26 ± 2 |

[a]As reported in Hoipkemeier-Wilson et al.

Figure 28:
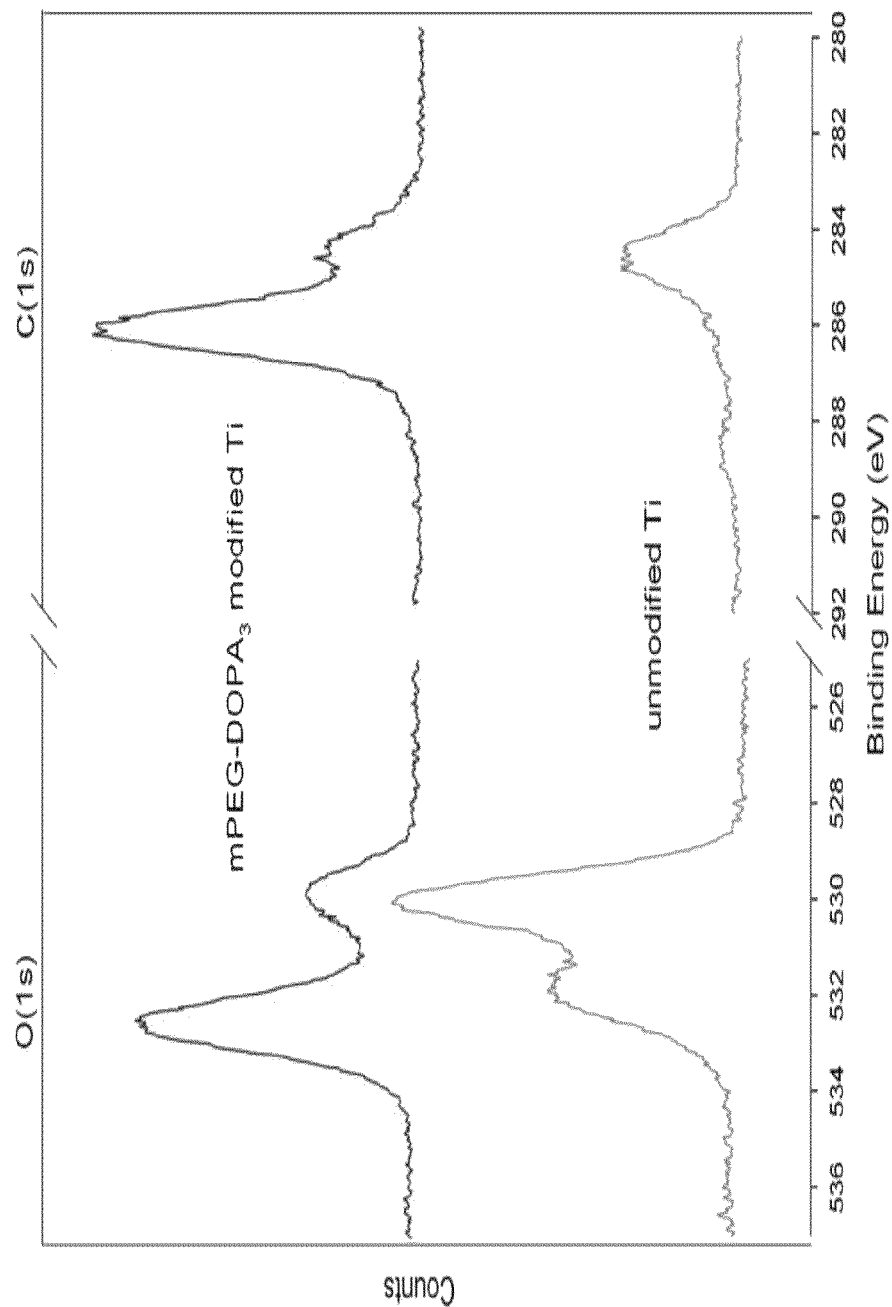
FIG. 28. XPS analysis indicates the presence of adsorbed mPEG-DOPA3 on modified Ti surfaces. High-resolution O(1s) (left) and C(1s) (right) XPS spectra of modified (top) and unmodified (bottom) Ti substrates.

High-resolution XPS spectra were acquired from unmodified Ti and mPEG-DOPA$_3$ modified Ti substrates; atomic compositions of the substrates are reported with corresponding binding energies in Table 7. The unmodified Ti substrates exhibited strong peaks for titanium and oxygen, as expected for the clean oxide layer; a weaker signal for carbon, most likely from hydrocarbon contamination, was also detected. The mPEG-DOPA$_3$ modified Ti substrates exhibited weaker signals for titanium and oxygen and stronger signals for carbon. The C1s spectra were further resolved into three components: C—C (284.6 eV), C—O (286.0 eV), and C=O (288.0 eV). The C—C component was attributed to the DOPA side chain, and NC=O is for the peptide amide bond. The large increase in the C—O component for the mPEG-DOPA$_3$ modified substrates indicated the presence of the PEG ether carbons. The high resolution O(1s) and C(1s) spectra for mPEG-DOPA$_3$ modified Ti and unmodified Ti are shown in FIG. 28. Collectively, these results confirm the presence of a thin coating of mPEG-DOPA$_3$ on the substrates used in biofouling experiments.

TABLE 7

Quantitative analysis of XPS data for substrates.
Atomic Composition [atom %] (binding energies [eV])

| Substrate | Ti | O | | | C | | |
|---|---|---|---|---|---|---|---|
| | | $TiO_2$ | TiOH | C—O, $H_2O$ | C—C, C—H | C—O | C=O |
| Bare Ti | 26.3 | 40.7 | 10.1 | 6.4 | 12.7 | 2.6 | 1.2 |
| | (458.6) | (530.0) | (531.5) | (532.3) | (284.6) | (286.4) | (288.5) |
| mPEG-DOPA$_3$ | 5.5 | 22.5 | 2.3 | 22.5 | 10.1 | 35.8 | 1.3 |
| | (460.4) | (529.9) | (531.1) | (532.6) | (284.6) | (286.3) | (288.0) |

Settlement and Attachment Strength of *Navicula*.

Diatoms adhered at approximately equal densities on the glass, PDMSE, and titanium control surfaces. On the mPEG-DOPA$_3$ coated slide, however, the number of cells attached was significantly lower compared to any of the other surfaces (one-way analysis of variance $F_{3, 356}$=267 P<0.05) (FIG. 3). Since diatoms settle through the water column and onto surfaces under the influence of gravity, initially there would have been as many cells per unit area in contact with the mPEG-DOPA$_3$ slide as the other surfaces. However, the low observed cell density on the mPEG-DOPA$_3$ surface indicates that most of the cells that initially attached were lost at the rinsing stage, demonstrating very weak attachment strength to this surface, perhaps a result of the steric hindrance of the PEG chains.

Figure 29:
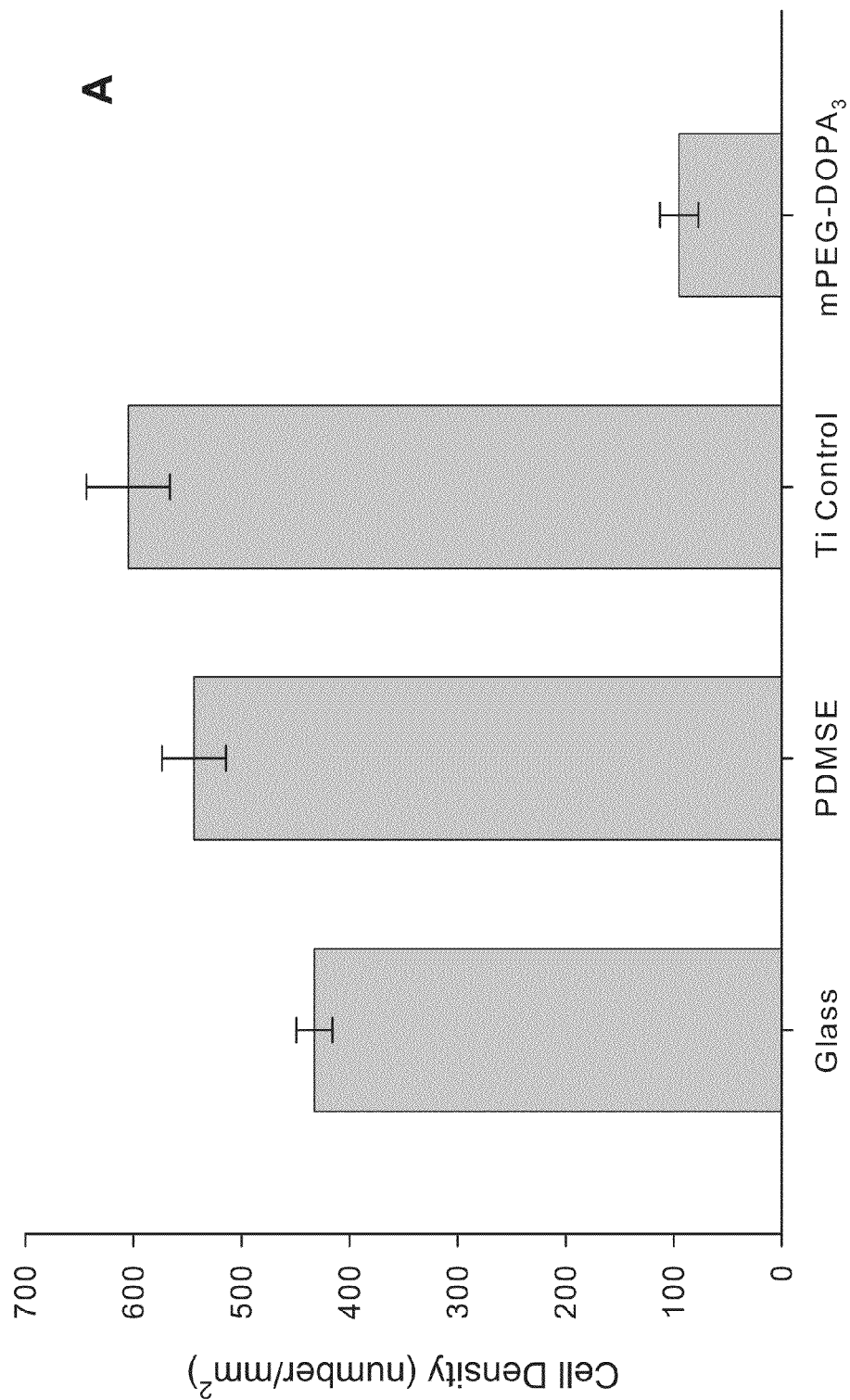
FIG. 29. Settlement (A) and release (B) of *Navicula* on control and mPEG-DOPA3 coated slides. PDMSE is Silastic T2. Each point is the mean from 90 counts on 3 replicate slides. Bars represent 95% confidence limits. For removal of attached cells slides were exposed to a wall shear stress of 20 Pa.
Figure 29:
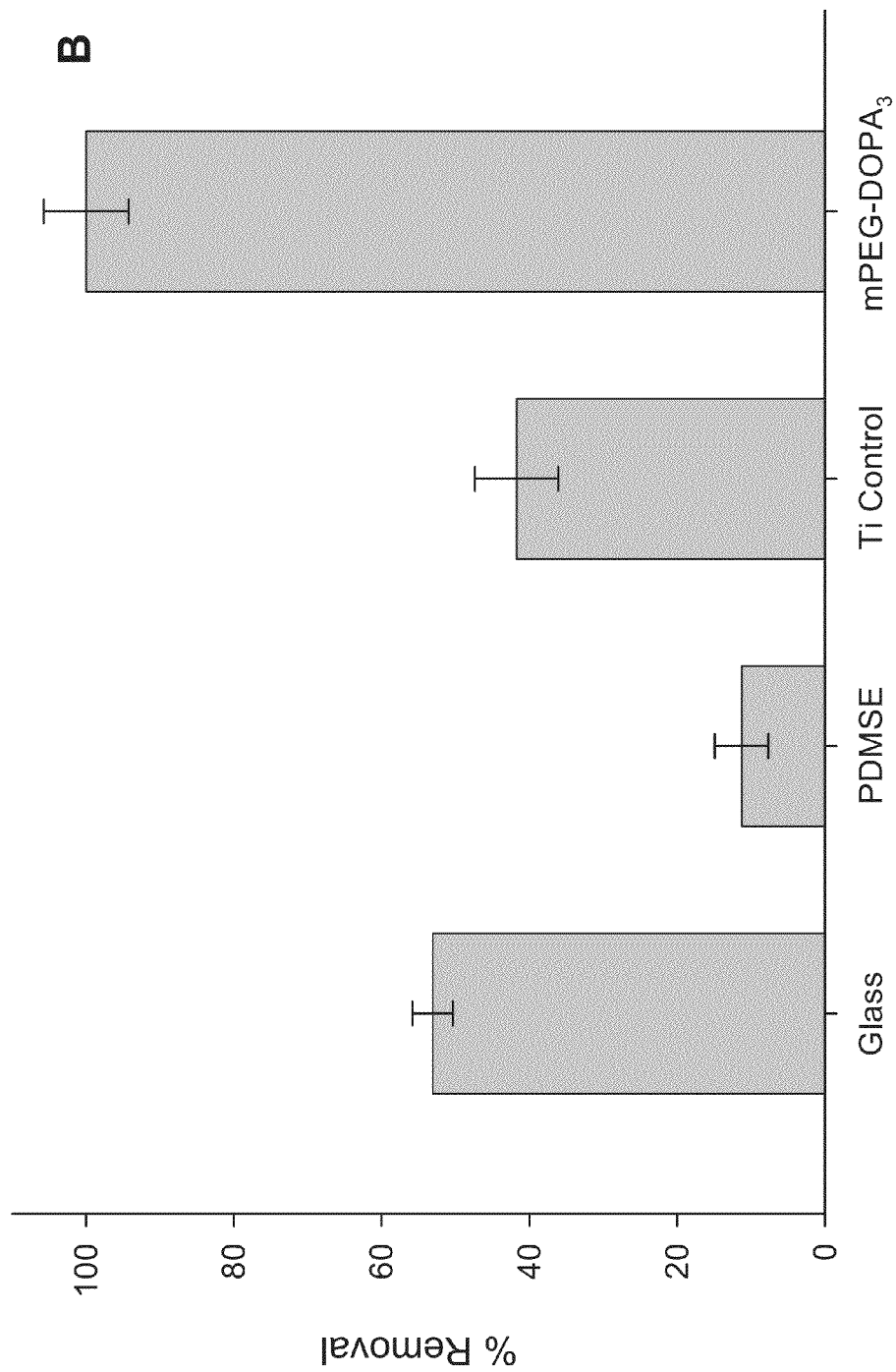

Removal of cells under shear (20 Pa) from the titanium control was similar to that from glass (approx. 40-50%), whereas removal from the PDMSE standard was low (approx. 10%). The latter result is expected as it is well documented that diatoms adhere strongly to fouling release silicone elastomers (Terlizzi et al. (2000) *Biofouling*, 15, 327-342; Holland et al. (2004) *Biofouling*, 20, 323-329; Holm et al. (2004) *Biofouling*, 20, 219-226). By contrast, detachment of the relatively few attached diatoms from the mPEG-DOPA$_3$ surfaces was almost total (one-way analysis of variance on arc-sine transformed data $F_{3, 356}$=342 P<0.05) (FIG. 29). The high level of diatom release from these surfaces further demonstrated very weak interaction between the organisms and the PEG surface.

Settlement and Attachment Strength of *Ulva* Zoospores.

Figure 30:
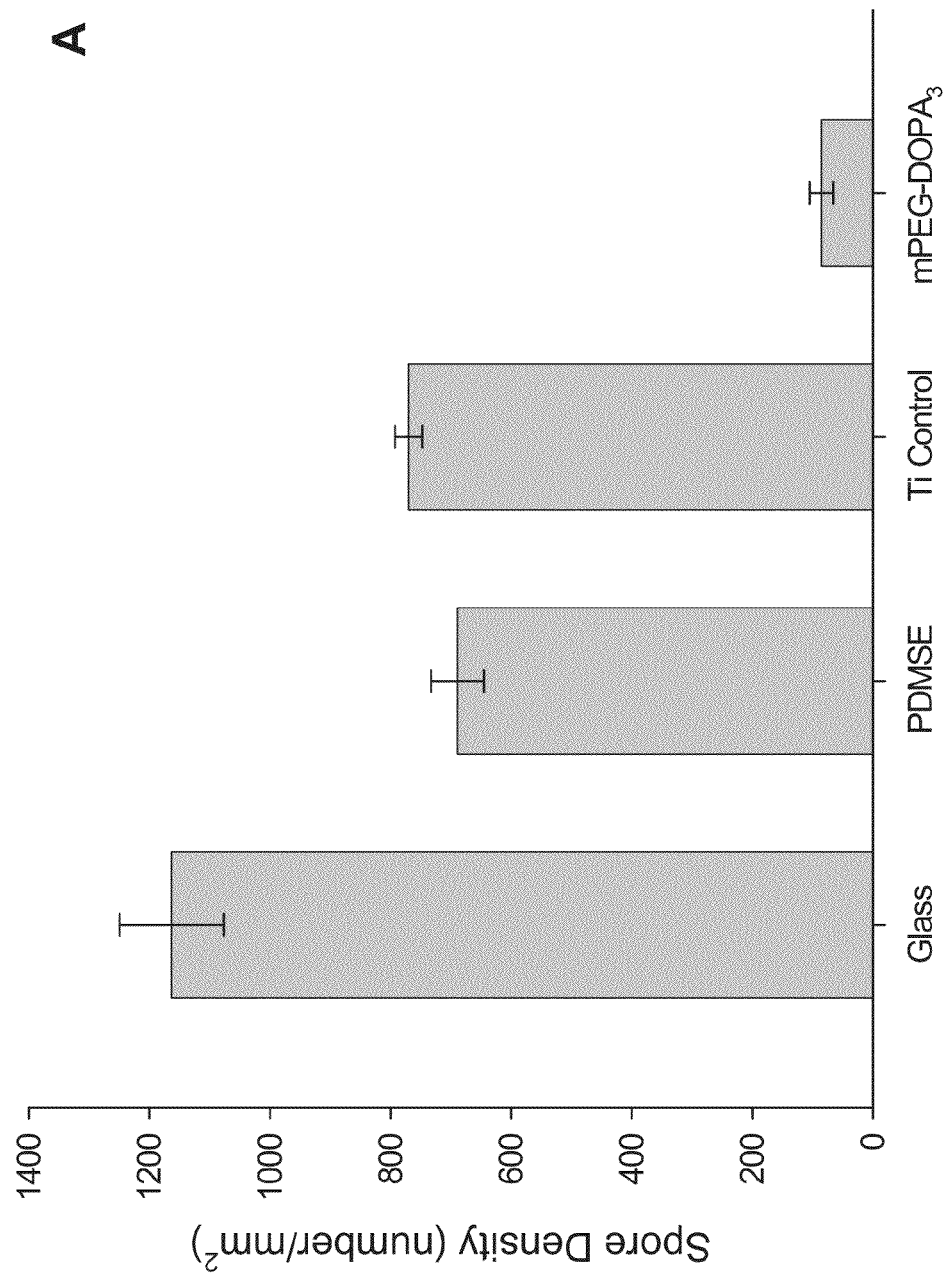
FIG. 30. Settlement (A) and release (B) of *U. linza* spores on control and mPEG-DOPA3 coated slides. PDMSE is Silastic T2. Each point is the mean from 90 counts on 3 replicate slides. Bars show 95% confidence limits. For removal of attached cells slides were exposed to a wall shear stress of 53 Pa.
Figure 30:
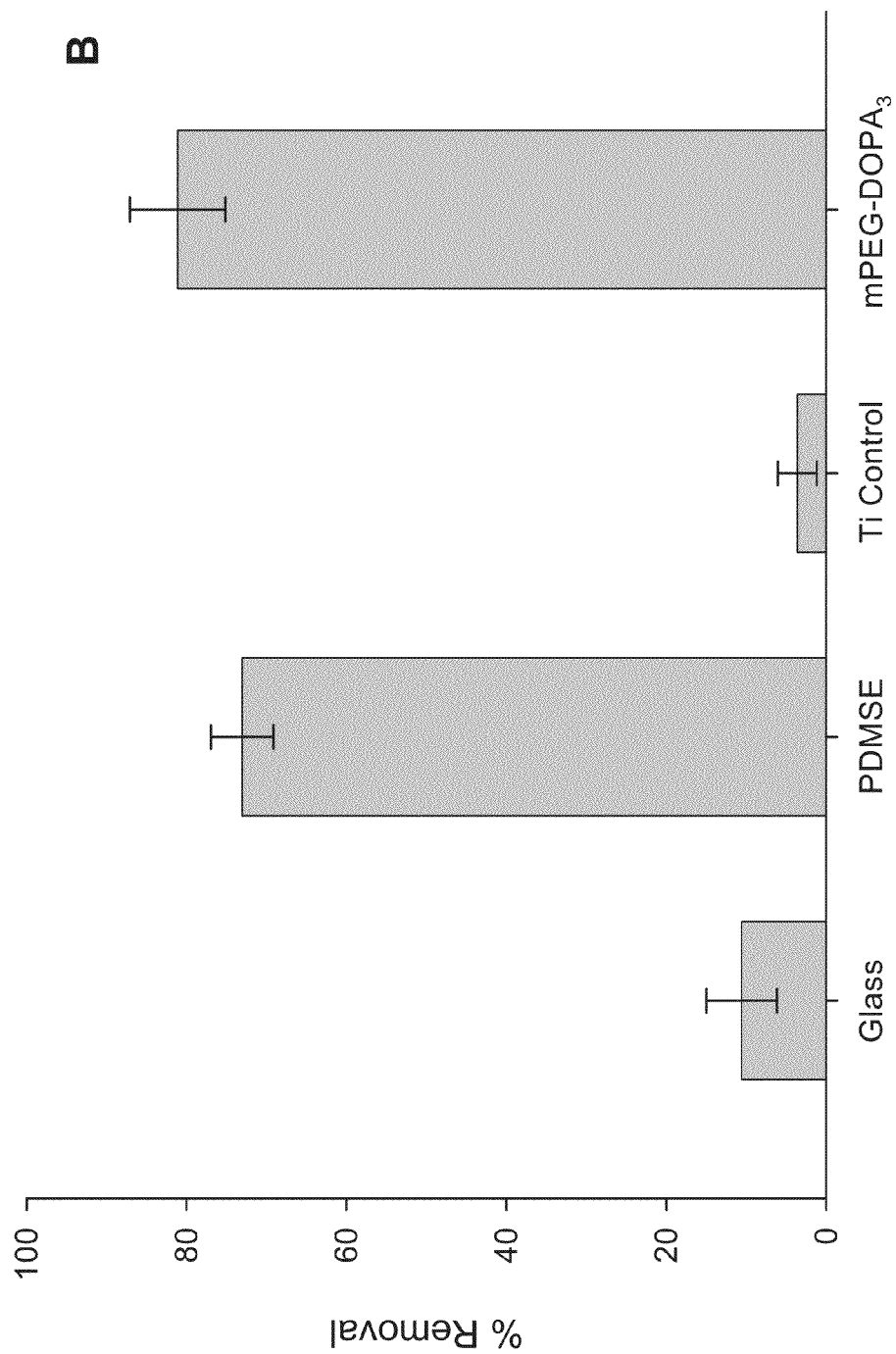

Zoospores readily settled and attached to the titanium-coated control slides, the settlement density being similar to that on the PDMSE standards, but less than on the glass slides. However, levels of spore settlement on the mPEG-DOPA$_3$ coated slides were extremely low (one-way analysis of variance $F_{3, 356}$=294 P<0.05) compared to either glass and titanium controls, or the PDMSE standard (FIG. 30).

While some spores did settle on the surface of the mPEG-DOPA$_3$ samples, the attachment strength was so weak that the cohesive forces of water removed the spores during removal of the slide from the dish and passage through the air/water interface. On removal from the dish, the displaced spores could be seen as concentrated floating green rafts of cells on the surface of the seawater.

Figure 31:
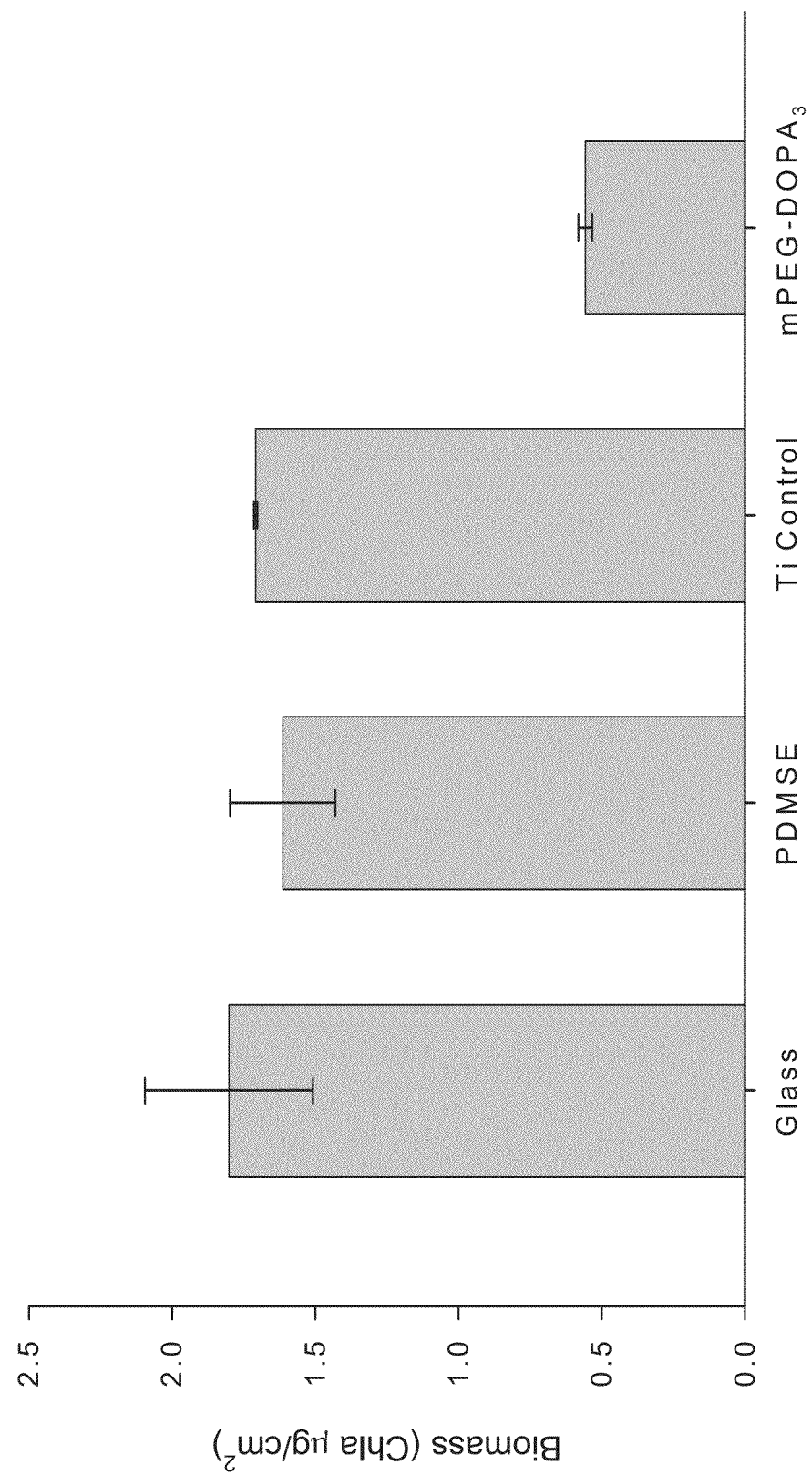
FIG. 31. Growth of *U. linza* sporelings after 8 days culture on control and mPEG-DOPA3-coated slides. Bars show the standard error of the mean from three replicate slides.

The few spores that remained attached to the mPEG-DOPA$_3$ surface following removal from the dish were only weakly adhered compared to the other surfaces (FIG. 31). Spore removal exceeded 80% on the mPEG-DOPA$_3$ surfaces, similar to that from PDMSE standards, but significantly different to glass and titanium controls, from which <10% of the spores were removed (one-way analysis of variance on arc-sine transformed data $F_{3, 356}$=218 P<0.05).

Growth and Attachment Strength of *Ulva* Sporelings.

Figure 32:
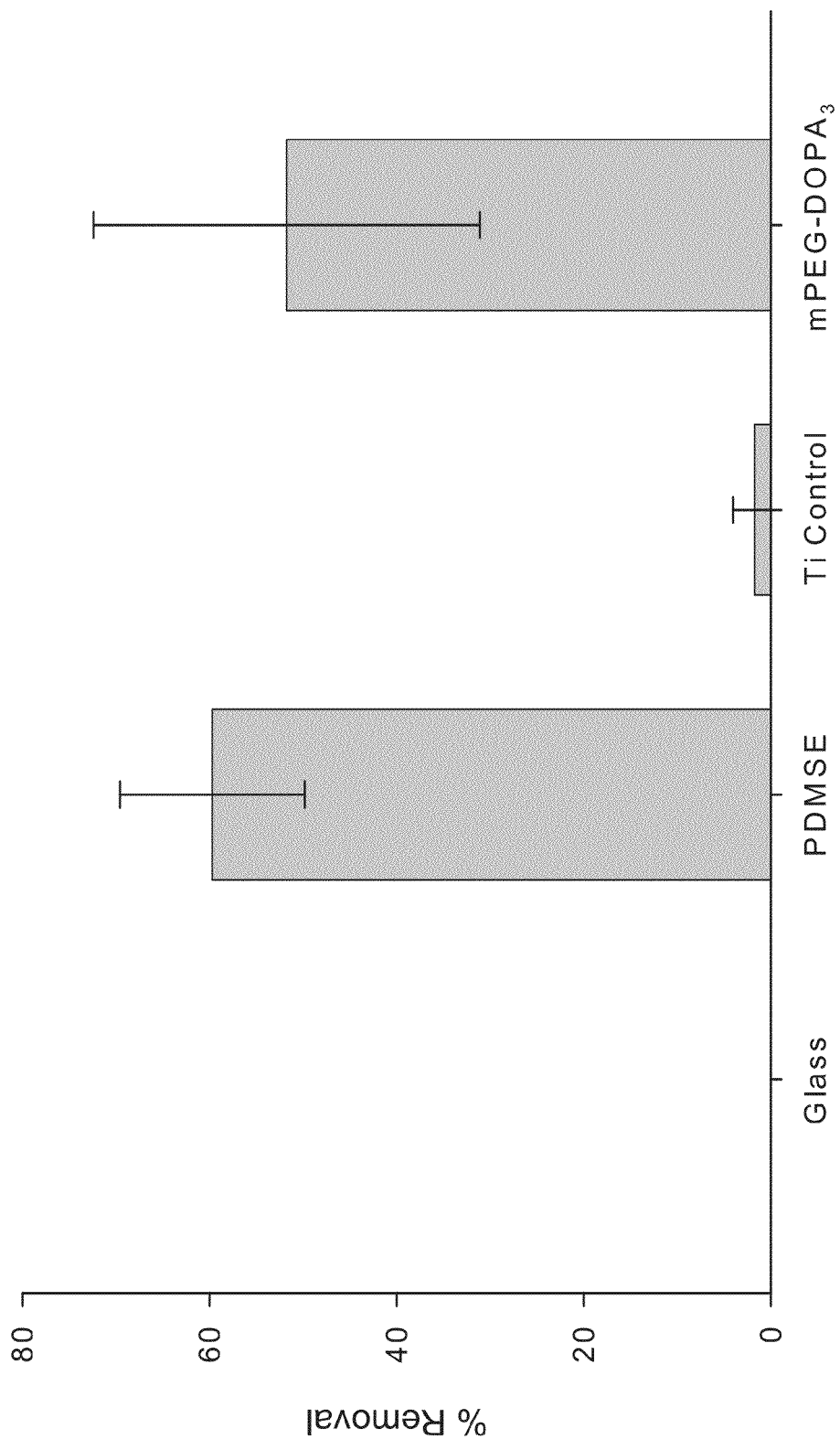
FIG. 32. Percent removal of *U. linza* sporelings after exposure to shear stress of 53 Pa in water channel. Bars show the standard error of the mean derived from arcsine transformed data from three replicate slides.

After 8 days in culture, the growth of sporelings was similar on the glass, PDMSE and titanium-coated surfaces, while growth was significantly reduced (<40% of the level on glass) on the mPEG-DOPA$_3$ modified substrates (one-way analysis of variance $F_{3, 12}$=7.3 P<0.05) (FIG. 32). Exposure to a shear stress of 53 Pa, caused very little of the *Ulva* biomass to be removed from the glass and titanium-coated controls (FIG. 33), but approximately 60% and 52% of biomass was removed from the PDMSE and the mPEG-DOPA$_3$ coatings respectively. There was no significant difference between these two treatments.

The antifouling and fouling-release properties of mPEG-DOPA$_3$ coatings were demonstrated through assays with the diatom *Navicula* and zoospores of the green seaweed *Ulva*. Diatoms are unicellular algae that readily form biofilms, often referred to as 'slime', on illuminated submerged surfaces (Callow et al. (2000) *Biofouling*, 16, 141-150; Kavanagh et al. (2005) *J Adhesion*, 81, 843-868). Attachment to the substrate is through the secretion of a range of complex proteoglycans (Chiovitti et al. (2006) Chapter 5, pages 77-99; Diatom adhesives: molecular and mechanical properties. In: *Biological Adhesives* (eds A Smith & J A Callow). Springer). The green algal genus *Ulva* comprises the most widespread species of alga that fouls man-made structures in the marine environment (Hayden et al. (2003) *European Journal of Phycology*, 38, 277-294). Fouling by *Ulva* occurs through the settlement of motile zoospores on available surfaces and secretion of adhesive glycoproteins (Stanley et al. (1999) *Planta*, 210, 61-71; Callow et al. (2000). *Biofouling*, 16, 141-150; Humphrey et al (2005) *Ulva J Adhesion*, 81, 791-803; Walker et al (2005) *Journal of Adhesion*, 81, 1101-1118; Krishnan et al (2006a) *Langmuir*, 22 (11), 5075-5086, 2006. Once anchored to a surface, the settled *Ulva* zoospores germinate into sporelings and ultimately grow into mature plants. The attachment strength of *Ulva* sporelings is low on fouling-release coatings (Schultz et al. (2003) *Biofouling*, 19 (supplement), 17-26; Chaudhury et al. (2005) *Biofouling*, 21, 41-48).

The weak attachment strength and high percentage of removal of *Navicula* cells on mPEG-DOPA$_3$ surfaces demonstrated a significant advantage for this hydrophilic coating over hydrophobic fouling-release silicone elastomers, from which diatoms were not readily released (Terlizzi et al. (2000) *Biofouling*, 15, 327-342; Holland (2004) *Biofouling*, 20, 323-329; Holm (2004) *Biofouling*, 20, 219-226).

The densities of attached *Ulva* zoospores and sporelings were lower on mPEG-DOPA$_3$ surfaces compared to the control surfaces, and the percentage removal of *Ulva* from mPEG-DOPA$_3$ surfaces was comparable to results for the PDMSE fouling-release standard used in this study.

The present example demonstrated that a non-toxic, polymer-based approach that exploits the adhesive behavior of marine mussels can paradoxically reduce marine algal fouling. The substantial reduction in initial settlement of both *Navicula* cells and *Ulva* zoospores on mPEG-DOPA$_3$-modified titanium establishes these coatings as novel remedies to marine fouling. Importantly, the fouling-release characteristics of the mPEG-DOPA₃ films appeared to be equivalent to a PDMS elastomer for *Ulva*, but surpassed the performance of the elastomer for the diatom *Navicula*. The nontoxic nature of the PEG films makes them especially attractive from an environmental standpoint, and the simple aqueous coating method provides for facile application.

Although the present invention has been described with reference to preferred embodiments, persons skilled in the art will recognize that changes may be made in form and detail without departing from the spirit and scope of the invention. All references cited throughout the specification, including those in the background, are incorporated herein in their entirety. Those skilled in the art will recognize, or be able to ascertain, using no more than routine experimentation, many equivalents to specific embodiments of the invention described specifically herein. Such equivalents are intended to be encompassed in the scope of the following claims.

REFERENCES

Love et al., *Chem. Rev.* 105, 1103 (2005).
Erli et al., *Biomed. Eng. Online* 2, 15 (2003).
Young et al., *Marine animals and adhesion*. W. K. Allen, Ed.
Waite et al, *Science* 212, 1038 (1981).
Yu et al., *Macromolecules* 31, 4739 (1998).
Statz et al., *J. Am. Chem. Soc.* 127, 7972 (2005).
Dalsin et al. *J. Am. Chem. Soc.* 125, 4253 (2003).
Bharathi et al., *Chem. Commun.*, 2303 (1997).
Ratner et al., *Biomaterials science: an introduction to materials in medicine*.
Alivisatos, *Nat. Biotech.* 22, 47 (2004).
Zeise et al., *Melanin: Its role in human photoprotection* (1995).
LaVoie et al., *Nature Med.* 11, 1214 (2005).
Burzio et al., *Biochemistry* 39, 11147 (2000).
Sugumaran et al., *Arch. Insect Biochem. Phys* 11, 127 (1989).
Gidanian et al., *J. Inorg. Biochem.* 89, 54 (2002).
Taylor et al., *J. Inorg. Chem.* 33, 5819 (1994).
Jo et al., *Biomaterials* 21, 605 (2000).
Pasche et al., *J. Phys. Chem. B* 109, 17545 (2005).
Li et al., *J. Phys. Chem. B* 109, 2934 (2005).
Ostuni et al., *Langmuir* 17, 5605 (2001).
Korobkova et al., *Nature* 428, 574 (2004).
Ho et al., *Adv. Mat.* 16, 957 (2004).
Li et al., *MRS Bulletin* 18, 18 (1993).
Sawada et al., *Langmuir* 22, 332 (2006).
Carmichael et al., *Langmuir* 20, 5593 (2004).
Nakagawa et al., *Biochem. Biophys. Res. Commun.* 272, 505 (2000).

What is claimed is:

1. A method of spontaneously modifying a substrate surface, the method comprising contacting at least a portion of the substrate with an alkaline solution comprising an oxidant selected from the group consisting of dissolved oxygen, triethylamine, hydrogen peroxide, sodium periodate, tertiary butylhydroperoxide, organic peroxides, quinines, nitroaryl compounds, $Cu^{2+}$, $Fe^{3+}$, $Co^{3+}$, $Mn^{3+}$, phenols, indoles, and aminobenzenes; the solution further comprising a surface-modifying agent according to Formula I:

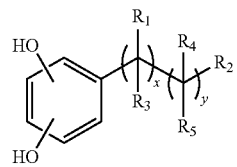

wherein each of $R_1$, $R_2$, $R_3$, $R_4$ and $R_5$ is independently selected from the group consisting of a thiol, a primary amine, a secondary amine, a nitrile, an aldehyde, an imidazole, an azide, a halide, a polyhexamethylene dithiocarbonate, a hydrogen, a hydroxyl, a carboxylic acid, an aldehyde, a carboxylic ester or a carboxamide, provided at least one of $R_1$, $R_2$, $R_3$, $R_4$ and $R_5$ is not a hydrogen atom;

wherein x ranges from 0 to 10 and wherein y ranges from 0 to 10, provided that x or y is at least 1;

wherein the substrate surface is spontaneously modified.

2. The method of claim 1 wherein x and y are both 1, and wherein $R_1$ and $R_4$ form a double bond when eliminated.

3. The method of claim 1 wherein $R_2$ is $NH_2$ or NHR, wherein R is an alkyl or aromatic group.

4. The method of claim 1 wherein one of $R_1$ or $R_4$ is a halide, a hydroxyl or a thiol, and wherein one of $R_3$ or $R_5$ is a hydrogen atom.

5. The method of claim 1 wherein x is 1, y is 1, $R_1$ is a hydroxyl, and wherein each of $R_3$, $R_4$ and $R_5$ are hydrogen atoms.

6. The method of claim 5 wherein $R_2$ is a $NH_2$.

7. The method of claim 1 wherein x and y are each 1 and wherein each of $R_1$, $R_3$, $R_4$ and $R_5$ are hydrogen atoms.

8. The method of claim 7 wherein $R_2$ is $NH_2$.

9. The method of claim 1 wherein $R_2$ is $NH_2$ or NHR, wherein R is an alkyl or aromatic group.

10. The method of claim 9 wherein one of $R_1$ or $R_4$ is a halide, a hydroxyl, or a thiol and wherein one of $R_3$ or $R_5$ is a hydrogen atom.

11. The method of claim 9 wherein $R_2$ is an amine.

12. The method of claim 1 wherein x+y is at least 2.

13. The method of claim 1 wherein x+y is at least 3.

14. The method of claim 1 wherein the hydroxyls of the phenyl moiety are positioned at the 3 and 4 positions of the phenyl group relative to the side chain.

15. The method of claim 1 wherein the surface-modifying agent forms a polymeric coat on the substrate surface.

16. The method of claim 1 wherein the surface-modifying agent is selected from the group consisting of 3,4-dihydroxy-L-phenylalanine (DOPA), 3,4-dihydroxyphenylalanine methyl ester dopamine, norepinephrine and epinephrine.

17. The method of claim 1 wherein the solution is aqueous.

18. The method of claim 1 wherein x+y ranges from 1 to 6.

19. A method of spontaneously modifying a substrate surface to provide a desired functionality, the method comprising:

a) contacting at least a portion of the substrate surface with an alkaline, aqueous solution comprising an oxidant selected from the group consisting of dissolved oxygen, triethylamine, hydrogen peroxide, sodium periodate, tertiary butylhydroperoxide, organic peroxides, quinines, nitroarl compounds, $Cu^{2+}$, $Fe^{3+}$, $Co^{3+}$, $Mn^{3+}$, phenols, indoles, and aminobenzenes; the solution further comprising a surface-modifying agent according to Formula I:

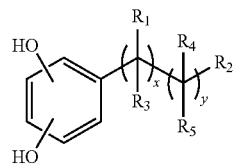

wherein each of $R_1$, $R_2$, $R_3$, $R_4$ and $R_5$ is independently selected from the group consisting of a thiol, a primary amine, a secondary amine, a nitrile, an aldehyde, an imidazole, an azide, a halide, a polyhexamethylene dithiocarbonate, a hydrogen, a hydroxyl, a carboxylic acid, an aldehyde, a carboxylic ester or a carboxamide, provided at least one of $R_1$, $R_2$, $R_3$, $R_4$ and $R_5$ is not a hydrogen atom;

wherein x ranges from 0 to 10 and wherein y ranges from 0 to 10, provided that x or y is at least 1; and wherein the substrate surface is spontaneously modified; and b) contacting the surface-modified substrate with a reactive moiety, wherein the reactive moiety reacts with and is bound to the modified surface.

20. The method of claim 19 wherein the reactive moiety comprises a nucleophile.

21. The method of claim 19 wherein the reactive moiety comprises a metal.

* * * * *

UNITED STATES PATENT AND TRADEMARK OFFICE
CERTIFICATE OF CORRECTION

| | | |
|---|---|---|
| PATENT NO. | : 8,911,831 B2 | Page 1 of 1 |
| APPLICATION NO. | : 12/793653 | |
| DATED | : December 16, 2014 | |
| INVENTOR(S) | : Phillip B. Messersmith et al. | |

It is certified that error appears in the above-identified patent and that said Letters Patent is hereby corrected as shown below:

In the Claims

Column 44, claim 19, line 64 "nitroarl" should be -- nitroaryl --

Signed and Sealed this
Sixteenth Day of June, 2015

Michelle K. Lee
*Director of the United States Patent and Trademark Office*